United States Patent
Kwok et al.

(10) Patent No.: US 12,385,057 B2
(45) Date of Patent: Aug. 12, 2025

(54) MODULATING LIGHT RESPONSE PATHWAYS IN PLANTS, INCREASING LIGHT-RELATED TOLERANCES IN PLANTS, AND INCREASING BIOMASS IN PLANTS

(71) Applicant: Ceres, Inc., Thousand Oaks, CA (US)

(72) Inventors: Shing Kwok, Alexandria, VA (US);
Kenneth Bounds, Tarzana, CA (US);
Ryan Miller, Sacramento, CA (US);
Sam Harris, Newbury Park, CA (US);
James Burns, Valley Village, CA (US);
Roger I. Pennell, Malibu, CA (US);
Vijay Sharma, Wildwood, MO (US);
Michael F. Portereiko, Thousand Oaks, CA (US); Han-Suk Kim, Pinole, CA (US); Gerard Magpantay, Woodland Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 36 days.

(21) Appl. No.: 18/470,831

(22) Filed: Sep. 20, 2023

(65) Prior Publication Data

US 2024/0102039 A1 Mar. 28, 2024

Related U.S. Application Data

(60) Division of application No. 17/481,090, filed on Sep. 21, 2021, now Pat. No. 11,926,836, which is a division of application No. 16/045,503, filed on Jul. 25, 2018, now Pat. No. 11,174,491, which is a division of application No. 13/630,902, filed on Sep. 28, 2012, now abandoned, which is a continuation-in-part of application No. 12/863,102, filed as application No. PCT/US2009/031292 on Jan. 16, 2009, now abandoned, said application No. 13/630,902 is a continuation-in-part of application No. 12/373,134, filed as application No. PCT/US2007/073154 on Jul. 10, 2007, now abandoned, said application No. 13/630,902 is a continuation-in-part of application No. 12/513,086, filed as application No. PCT/US2007/083495 on Nov. 2, 2007, now abandoned, said application No. 13/630,902 is a continuation-in-part of application No. 12/515,687, filed as application No. PCT/US2007/085237 on Nov. 20, 2007, now abandoned, said application No. 13/630,902 is a continuation-in-part of application No. 12/307,561, filed as application No. PCT/US2007/072877 on Jul. 5, 2007, now Pat. No. 8,344,210, said application No. 13/630,902 is a continuation-in-part of application No. 13/119,572, filed as application No. PCT/US2009/057116 on Sep. 16, 2009, now abandoned.

(60) Provisional application No. 61/021,943, filed on Jan. 18, 2008, provisional application No. 60/819,763, filed on Jul. 10, 2006, provisional application No. 60/856,613, filed on Nov. 3, 2006, provisional application No. 60/860,145, filed on Nov. 20, 2006, provisional application No. 60/818,569, filed on Jul. 5, 2006, provisional application No. 61/097,789, filed on Sep. 17, 2008.

(51) Int. Cl.
*C12N 15/82* (2006.01)
*C07K 14/41* (2006.01)
*C07K 14/415* (2006.01)

(52) U.S. Cl.
CPC ........ *C12N 15/8271* (2013.01); *C07K 14/415* (2013.01); *C12N 15/82* (2013.01); *C12N 15/8261* (2013.01); *Y02A 40/146* (2018.01)

(58) Field of Classification Search
CPC .................................................. C12N 15/8271
See application file for complete search history.

(56) References Cited

U.S. PATENT DOCUMENTS

| | | |
|---|---|---|
| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |

(Continued)

FOREIGN PATENT DOCUMENTS

| | | |
|---|---|---|
| EP | 0 534 858 | 3/1993 |
| WO | WO 97/01952 | 1/1997 |

(Continued)

OTHER PUBLICATIONS

Martinez-Garcia et al., 2023, Molecular mechanisms of shade tolerance in plants. New Phytologist; (Year: 2023).*

(Continued)

*Primary Examiner* — David H Kruse
*Assistant Examiner* — Santosh Sharma
(74) *Attorney, Agent, or Firm* — Dentons US LLP

(57) ABSTRACT

Methods and materials for modulating low light and/or shade tolerance, and red light specific responses in plants are disclosed. For example, nucleic acids encoding low light and/or SD+EODFR-tolerance polypeptides are disclosed as well as methods for using such nucleic acids to transform plant cells. Also disclosed are plants having increased low light and/or SD+EODFR tolerance. In addition, methods and materials involved in increasing UV-B tolerance in plants and methods and materials involved in modulating biomass levels in plants are provided.

11 Claims, 79 Drawing Sheets

Specification includes a Sequence Listing.

(56) References Cited

U.S. PATENT DOCUMENTS

| | | |
|---|---|---|
| 5,538,880 A | 7/1996 | Lundquist et al. |
| 5,766,847 A | 6/1998 | Jackle et al. |
| 5,878,215 A | 3/1999 | Kling et al. |
| 6,013,863 A | 1/2000 | Lundquist et al. |
| 6,326,527 B1 | 12/2001 | Kirihara et al. |
| 6,329,571 B1 | 12/2001 | Hiei |
| 6,423,885 B1 | 7/2002 | Waterhouse et al. |
| 6,452,067 B1 | 9/2002 | Bedbrook et al. |
| 6,573,099 B2 | 6/2003 | Graham |
| 6,753,139 B1 | 6/2004 | Baulcombe et al. |
| 6,777,588 B2 | 8/2004 | Waterhouse et al. |
| 6,906,244 B2 | 6/2005 | Fischer et al. |
| 7,173,121 B2 | 2/2007 | Fang |
| 7,196,245 B2 | 3/2007 | Jiang et al. |
| 7,214,789 B2 | 5/2007 | Pennell |
| 7,265,263 B1 | 9/2007 | Hannapel et al. |
| 7,312,376 B2 | 12/2007 | Apuya et al. |
| 7,378,571 B2 | 5/2008 | Apuya et al. |
| 7,402,667 B2 | 7/2008 | Cook et al. |
| 7,429,692 B2 | 9/2008 | Dang |
| 7,445,654 B2 | 11/2008 | Wong |
| 7,598,367 B2 | 10/2009 | Cook et al. |
| 8,344,210 B2 | 1/2013 | Kwok et al. |
| 11,174,491 B2 | 11/2021 | Kwok et al. |
| 11,926,836 B2 | 3/2024 | Kwok et al. |
| 2003/0175783 A1 | 9/2003 | Waterhouse et al. |
| 2003/0175965 A1 | 9/2003 | Lowe et al. |
| 2003/0180945 A1 | 9/2003 | Wang et al. |
| 2004/0214330 A1 | 10/2004 | Waterhouse et al. |
| 2005/0009187 A1 | 1/2005 | Shinozaki et al. |
| 2005/0032221 A1 | 2/2005 | Chang et al. |
| 2005/0160493 A9 | 7/2005 | Ratcliffe et al. |
| 2006/0021083 A1 | 1/2006 | Cook et al. |
| 2006/0021088 A1 | 1/2006 | Inze et al. |
| 2006/0041952 A1 | 2/2006 | Cook |
| 2006/0260004 A1 | 11/2006 | Fang et al. |
| 2006/0265788 A1 | 11/2006 | Rommens |
| 2006/0272060 A1 | 11/2006 | Heard et al. |
| 2007/0006335 A1 | 1/2007 | Cook et al. |
| 2007/0033671 A1 | 2/2007 | Jiang et al. |
| 2007/0056058 A1 | 3/2007 | Olivier et al. |
| 2009/0094717 A1 | 4/2009 | Troukhan et al. |
| 2010/0119688 A1 | 5/2010 | Kwok et al. |
| 2010/0192261 A1 | 7/2010 | Kwok et al. |
| 2010/0199378 A1 | 8/2010 | Kwok et al. |
| 2010/0205688 A1 | 8/2010 | Kwok et al. |
| 2011/0214199 A1 | 9/2011 | Coffin |
| 2013/0014292 A1 | 1/2013 | Pennell et al. |
| 2013/0117886 A1 | 5/2013 | Troukhan et al. |
| 2022/0073939 A1 | 3/2022 | Kwok et al. |

FOREIGN PATENT DOCUMENTS

| | | |
|---|---|---|
| WO | WO 98/36083 | 8/1998 |
| WO | WO 98/53083 | 11/1998 |
| WO | WO 99/32619 | 7/1999 |
| WO | WO 02/046449 | 6/2002 |
| WO | WO 05/011105 | 2/2005 |
| WO | WO 05/023639 | 3/2005 |
| WO | WO 05/034308 | 4/2005 |
| WO | WO 05/034343 | 4/2005 |
| WO | WO 2005/098007 | 10/2005 |
| WO | WO 2006/034479 | 3/2006 |
| WO | WO 06/038236 | 4/2006 |
| WO | WO 06/040572 | 4/2006 |
| WO | WO 2006/036864 | 4/2006 |
| WO | WO 2007/044988 | 4/2007 |
| WO | WO 2007/055826 | 5/2007 |
| WO | WO 07/062762 | 6/2007 |
| WO | WO 2007/0072877 | 6/2007 |
| WO | WO 2007/083495 | 7/2007 |
| WO | WO 2007/085237 | 8/2007 |
| WO | WO 07/103956 | 9/2007 |
| WO | WO 2007/120989 | 10/2007 |
| WO | WO 2008/008779 | 1/2008 |
| WO | WO 2009/057116 | 5/2009 |
| WO | WO 2009/092009 | 7/2009 |
| WO | WO 2010/033564 | 3/2010 |

OTHER PUBLICATIONS

Jiao et al., 2005, Conservation and divergence of light-regulated genome expression patterns during seedling development in rice and *Arabidopsis*, The plant cell, 17(12), 3239-3256 (Year: 2005).*

Boylan et al., 1991, Phytochrome a overexpression inhibits hypocotyl elongation in transgenic *Arabidopsis*. Proceedings of the National Academy of Sciences, 88(23), 10806-10810. (Year: 1991).*

Jiao et al., 2005, Conservation and divergence of light-regulated genome expression patterns during seedling development in rice and *Arabidopsis*, Supplemental Table 2, The plant cell, 17(12), 3239-3256 (Year: 2005).*

Somssich, M., 2019, A short history of *Arabidopsis thaliana* (L.) Heynh. Columbia-0 (No. e26931v5). PeerJ Preprints. (Year: 2019).*

Platt et al., 2010, The scale of population structure in *Arabidopsis thaliana*. PLOS genetics, 6(2), e1000843. (Year: 2010).*

Unknown protein [*Arabidopsis thaliana*] containing SAM domain (Sterile alpha motif), 2003, GenBank: AAP04089.1, NCBI protein database; https://www.ncbi.nlm.nih.gov/protein/. (Year: 2003).*

Jiao et al., 2005, Conservation and divergence of light-regulated genome expression patterns during seedling development in rice and *Arabidopsis*, Supplemental Table 2 summary, The plant cell, 17(12), 3239-3256 (Year: 2005).*

Sessa et al., 2005, A dynamic balance between gene activation and repression regulates the shade avoidance response in *Arabidopsis*. Genes & development, 19(23), 2811-2815. (Year: 2005).*

Sessa et al., 2005, A dynamic balance between gene activation and repression regulates the shade avoidance response in *Arabidopsis*, Supplementary Figure 1. Genes & development, 19(23), 2811-2815. (Year: 2005).*

*Arabidopsis* Locus: AT2G45700, The *Arabidopsis* Information Resource (TAIR). https://www.arabidopsis.org/, Accessed Jul. 9, 2024 (Year: 2023).*

U.S. Appl. No. 60/505,689, filed Sep. 23, 2003, Cook et al..
U.S. Appl. No. 60/518,075, filed Nov. 6, 2003, Pennell et al..
U.S. Appl. No. 60/544,771, filed Feb. 13, 2004, Cook et al..
U.S. Appl. No. 60/558,869, filed Apr. 1, 2004, Cook et al..
U.S. Appl. No. 60/583,609, filed Jun. 30, 2004, Alexandrov.
U.S. Appl. No. 60/583,691, filed Jun. 30, 2004, Alexandrov et al..
U.S. Appl. No. 60/612,891, filed Sep. 23, 2004, Kwok.
U.S. Appl. No. 60/637,140, filed Dec. 16, 2004, Feldman.
U.S. Appl. No. 60/757,544, filed Jan. 9, 2006, Dang.
U.S. Appl. No. 60/766,307, Kwok.
U.S. Appl. No. 61/097,789, filed Sep. 17, 2008, Pennell.

Abler et al. "Isolation and characterization of a genomic sequence encoding the maize Cat3 catalase gene" *Plant Mol. Biol.*, 22:1031-1038 (1993).

Akashi et al., "Gene discovery by ribozyme and siRNA libraries," *Nature Reviews Mol. Cell Biology*, 2005, 6:413-422.

Alonso-Blanco et al., "The use of recombinant inbred lines (RILs) for genetic mapping," In *Methods in Molecular Biology* (J.M. Martinez-Zapater and J. Salinas, Humana Press, Totowa, NJ., 1998), 2: 137-146.

Baerson et al., "Developmental regulation of an acyl carrier protein gene promoter in vegetative and reproductive tissues" *Plant Mol. Biol.*, 22(2):255-267 (1993).

Bateman et al., "Pfam 3.1: 1313 multiple alignments and profile HMMs match the majority of proteins" *Nucl. Acids Res.*, 27(1):260-262 (1999).

Bechtold et al., "In planta Agrobacterium mediated gene transfer by infiltration of adult *Arabidopsis thaliana* plants" *C.R. Acad. Sci. Paris*, 316:1194-1199 (1993).

Burr et al., "Gene mapping with recombinant inbreds in maize," *Genetics*, 1988, 118: 519-526.

Burr et al., "Mapping Genes with Recombinant Inbreds," In Freeling and Walbot (Ed.), *The Maize Handbook*, (New York, Springer-Verlag, 1994), pp. 249-254.

(56) References Cited

OTHER PUBLICATIONS

Bustos et al., "Regulation of b-glucuronidase expression in transgenic tobacco plants by an A/T-rich, cis-acting sequence found upstream of a French bean b-phaseolin gene" *Plant Cell*, 1(9):839-854.

Cerdan and Chory, "Regulation of flowering time by light quality," *Nature*, 2003, 423:881-885.

Cerdan et al., "A 146 bp fragment of the tobacco Lhcb1*2 promoter confers very-low-fluence, low-fluence and high-irradiance responses of phytochrom to a minimal CaMV 35S promoter" *Plant Mol. Biol.*, 33:245-255 (1997).

Chen et al., "Functional analysis of regulatory elements in a plant embryo-specific gene" *Proc. Natl. Acad. Sci.* USA, 83:8560-8564 (1986).

Chenna et al., "Multiple sequence alignment with the Clustal series of programs" *Nucleic Acids Res.*, 31(13):3497-3500 (2003).

Conceicao, "A cotyledon regulatory region is responsible for the different spatial expression patterns of *Arabidopsis* 2S albumin genes" *The Plant Journal*, 1994, 5(4):493-505.

Conkling et al. "Isolation of transcriptionally regulated root-specific genes from tobacco" *Plant Physiol.*, 93:1203-1211, (1990).

Dai et al., "RF2b, a rice bZIP transcription activator, interacts with RF2a and is involved in symptom development of rice tungro disease" *Proc. Natl. Acad. Sci.* USA, 101(2):687-692 (2004).

De Feyter et al., Methods in Molecular Biology, vol. 74, Chapter 43, "Expressing Ribozymes in Plants", Edited by Turner, P.C., Humana Press Inc., Totowa, NJ, 1997, pp. 403-415.

Do et al., "ProbCons: Probabilistic consistency-based multiple sequence alignment," *Genome Res.*, 2005, 15(2): 330-340.

Durbin et al., "3-Markov chains and hidden Markov models; 4-Pairwise alignment using HMMS; 5-Profile HMMs for sequence families" In Biological Sequence Analysis: Probabilistic Models of Proteins and Nucleic Acids, (Cambridge University Press, Cambridge, UK, 1998), pp. 47-134.

Fejes et al., "A 268 bp upstream sequence mediates the circadian clock-regulated transcription of the wheat Cab-1 gene in transgenic plants" *Plant Mol. Biol.*, 15:921-932 (1990).

Fromm et al., "An octopine synthase enhancer element directs tissue-specific expression and binds ASF-1, a factor from tobacco nuclear extracts" *The Plant Cell*, 1:977-984 (1989).

Gardiner et al., "Development of a core RFLP map in maize using an immortalized F2 population," *Genetics*, 1993, 134: 917-930.

GenBank Accession No. AF096096, dated Jan. 25, 1999, 2 pages.
GenBank Accession No. AF129516, dated Apr. 6, 1999, 2 pages.
GenBank Accession No. L05934, dated Oct. 22, 1993, 3 pages.
GenBank Accession No. U93215, dated Feb. 27, 2002, 42 pages.

Green et al., "Binding site requirements for pea nuclear protein factor GT-1 correlate with sequences required for light-dependent transcriptional activation of the rbcS-3A gene" *Embo J.*, 7:4035-4044.

Guerois, Raphael, "Predicting Changes in the Stability of Proteins and Protein Complexes: A Study of More Than 1000 Mutations," *J. Mol. Biol.* (2002) 320, 369-387.

Hong et al., "Promoter sequences from two different *Brassica napus* tapetal oleosin-likegenes direct tapetal expression of B-glucuronidase in transgenic *Brassica* plants" Plant Mol Biol., 1997. 34(3):549-555.

Hwang et al, "Aleurone- and embryo-specific expression of the β-glucuronidase gene controlled by the barley Chi26 and Ltp1 promoters in transgenic rice" *Plant Cell Rep.* 20(7):647-654 (2001).

Hyrup et al., Peptide nucleic acids (PNA): synthesis, properties and potential applications *Bioorgan. Med. Chem.*, 4:5-23 (1996).

Jordano et al., "A sunflower helianthinin gene upstream sequence ensemble contains an enhancer and sites of nuclear protein interaction" *Plant Cell*, 1:855-866 (1989).

Kasuga et al., "Improving plant drought, salt, and freezing tolerance by gene transfer of a single stress-inducible transcription factor," *Nature Biotech*, 1999, 17: 287-291.

Kebrom et al., "The molecular analysis of the shade avoidance syndrome in the grasses has begun," *J. Exp. Bot.*, 2007, 58: 3079-3089.

Keller et al., "Vascular-specific expression of the bean GRP 1.8 gene is negatively regulated" *Plant Cell*, 3(10):1051-1061 (1991).

Kumar, Prateek, et al., "Predicting the effects of coding non-synonymous variants on protein function using the SIFT algorithm," Nature Publishing Group, vol. 4, No. 8, 2009, pp. 1073-1082.

Lam et al., "Site-specific mutations in alter in vitro factor binding and change promoter expression pattern in transgenic plants" *Proc. Natl. Acad. Sci.* USA, 86:7890-7894 (1989).

Luan et al., "A rice cab gene promoter contains separate cis-acting elements that regulate expression in dicot and monocot plants" *The Plant Cell*, 4:971-981 (1992).

Lubberstedt et al., "Promoters from genes for plastid proteins possess regions with different sensitivities toward red and blue light" *Plant Physiol.*, 104:997-1006 (1994).

Matsuoka et al., "Tissue-specific light-regulated expression directed by the promoter of a C4 gene, maize pyruvate, orthophosphate dikinase, in a C3 plant, rice" *Proc. Natl. Acad. Sci.* USA, 90:9586-9590 (1993).

Matzke et al., "RNAi-mediated pathways in the nucleus," *Nature Reviews Genetics*, 2005, 6:24-35.

Medberry et al., "The Commelina yellow mottle virus promoter is a strong promoter in vascular and reproductive tissues" *Plant Cell*, 4(2):185-192 (1992).

Meier et al., "Elicitor-inducible and constitutive in vivo DNA footprints indicate novel cis-acting elements in the promoter of a parsley gene encoding pathogenesis-related protein 1" *Plant Cell*, 3:309-316 (1991).

Mittal, "Improving the efficiency of RNA interference in mammals," *Nature Reviews Genetics*, 2004, 5: 355-365.

Nature reviews RNA interference collection [online]. Nature publishing group, 2005, [retrieved on Apr. 12, 2012]. Retrieved from the Internet: <URL: ttp://www.nature.com/focus/rnai/index.html>, 2 pages.

Ng, Pauline C., et al., "Predicting the Effects off Amino Acid Substitutions on Protein Function," *Annu. Rev. Genomics Hum. Genet.* 2006, pp. 61-80.

Parks et al., "Sequential and coordinated action of phytochromes A and B during *Arabidopsis* stem growth revealed by kinetic analysis," *Proc. Natl. Acad. Sci.*, 1999, 96:14142-14146.

Perriman et al., "Effective ribozyme delivery in plant cells" *Proc. Natl. Acad. Sci.* USA, 92(13):6175-6179 (1995).

Refseth et al., "Hybridization capture of microsatellites directly from genomic DNA" *Electrophoresis*, 18:1519-1523 (1997).

Reva, Boris, et al., "Predicting the functional impact of protein mutations: application to cancer genomics," *Nucleic Acids Research*, 2011, vol. 39, No. 17, pp. 1-14.

Riggs et al., "Cotyledon nuclear proteins bind to DNA fragments harboring regulatory elements of phytohemagglutinin genes" *Plant Cell*, 1(6):609-621 (1989).

Rivera et al., "*Genomic evidence for two functionally distinct gene classes*" *Proc. Natl. Acad. Sci.* USA,95:6239-6244 (1998).

Sandhya, Sankaran, "CUSP: an algorithm to distinguish structurally conserved and unconserved regions in protein domain alignments and its application in the study of large length variations," *BioMed Central*, May 2008, pp. 1-14.

Sheridan, "The mac1 Gene: Controlling the commitment to the meiotic pathway in Maize" *Genetics*, 142:1009-1020 (1996).

Slocombe et al., "Temporal and tissue-specific regulation of a *Brassica napus* stearoyl-acyl carrier protein desaturase gene" *Plant Physiol.*, 104(4):1167-1176 (1994).

Sonnhammer et al., "Pfam: A comprehensive database of protein domain families based on seed alignments" *Proteins*, 28:405-420 (1997).

Sonnhammer et al., "Pfam: multiple sequence alignments and HMM-profiles of protein domains" *Nucl. Acids Res.*, 26:320-322 (1998).

Summerton et al., "Morpholino antisense oligomers: design, preparation, and properties" *Antisense Nucleic Acid Drug Dev.*, 7:187-195 (1997).

(56) References Cited

OTHER PUBLICATIONS

Truernit et al., "The promoter of the *Arabidopsis thaliana* SUC2 sucrose-H+ symporter gene directs expression of β-glucuronidase to the phloem: Evidence for phloem loading and unloading by SUC2" *Planta.* 196:564-570 (1995).

Urao et al. "Molecular cloning and characterization of a gene that encodes a MYC-related protein in *Arabidopsis*" *Plant Mol. Biol.*, 32:571-576 (1996).

Wagner et al., "Overexpression of phytochrome B induces a short hypocotyl phenotype in transgenic *Arabidopsis*," *Plant Cell*, 1991, 3: 1275-1288.

Yamamoto et al., "The promoter of a pine photosynthetic gene allows expression of a βglucuronidase reporter gene in transgenic rice plants in a light-independent but tissue-specific manner" *Plant Cell Physiol.*, 1994, 35:773-778.

Yan et al., "New construct approaches for efficient gene silencing in plants," *Plant Physiology*, 2006, 141: 1508-1518.

Zhang et al., "DNA sequences that activate isocitrate lyase gene expression during late embryogenesis and during postgerminative growth," *Plant Physiology*, 110:1069-1079 (1996).

Zheng et al., "SPK1 Is an Essential S-Phase-Specific Gene of *Saccharomyces cerevisiae* that encodes a nuclear serine/threonine/ tyrosine kinase" *Mol. Cell Biol.*, 1993, 13:5829-5842.

Authorized Examiner Philippe Becamel, International Preliminary Report on Patentability in PCT/US2009/031292 mailed Jul. 20, 2010, 5 pages.

International Search Report and Written Opinion in International Application No. PCT/US2009/031292, mailed Sep. 1, 2009, 8 pages.

Tiwari et al., The flowering time regulator Constans is recruited to the Flowering Locus T promoter via a unique cis-elememt. *New Phytologist*. 2010. 187:57-66.

GenBank Accession No. NP_5683001.1. Unknown Protein. Published Apr. 24, 2008. pp. 1-2.

GenBank Accession No. NP_5683001.1. CCT motif family protein. Published May 26, 2011. pp. 1-2.

Jiang et al., "Assessment of low light tolerance of seashore paspalum and burmudagrass", Crop Science, 2004, 44:587-594.

Smith et al., "The shade avoidance syndrome: multiple responses mediated by multiple phytochromes", Plant, Cell, and Environment; 1997; 20:840-844.

GenBank Accession No. NM_001036413, *Arabidopsis thaliana* BLH1 (BEL1-like homeodomain 1) AT2G35940 (BLH1) transcript variant AT2G35940.3 mRNA, complete cds., Published Nov. 3, 2005, pp. 1-2.

GenBank Accession No. AAK43836, BEL1-like homeodomain 1 [*Arabidopsis thaliana*], Published Apr. 30, 2001, p. 1.

Martinez-Garcia et al., 2003, Molecular mechanisms of shade tolerance in plants. New Phytologist; (Year: 2023).

Jiao et al., 2005, Conservation and divergence of light-regulated genome expression patterns during seeding development in rice and *Arabidopsis*, The plant cell, 17(12), 3239-3256. (Year: 2005).

Jiao et al., 2005, Conservation and divergence of light-regulated genome expression patterns during seeding development in rice and *Arabidopsis*, Supplemental Table 2, The plant cell, 17(12), 3239-3256. (Year: 2005).

*Arabidopsis thaliana* uncharacterized protein (AT1G13360), mRNA—Nucleotide—NCBI. https://www.ncbi.nim.nih.gov/. Aug. 7, 2023. (Year:2023).

Jiao et al., 2005, Conservation and divergence of light-regulated genome expression patterns during seeding development in rice and *Arabidopsis*, Supplemental Table 2 summary, The plant cell, 17(12), 3239-3256. (Year: 2005).

*Arabidopsis* Locus: AT1G09570, The *Arabidopsis* Information Resource (TAIR). https://www.arabidopsis.org/servlets/TairObject?type=locus &name=At1909570, Accessed Aug. 10, 2023. (Year: 2023).

Guo et al., Protein tolerance to random amino acid change, PNAS 101(25):9205-9210, 2004.

Ng, et al., Predicting deleterious amino acid substitutions, Genome research 11(5):863-874, 2001.

* cited by examiner

Figure 1

```
SEQ-ID-NO-3   MSSEQGNGSN PSTSPEVEGT KTIPFRRRLQ RGQRVFAPKL MEA_RRSRVS  50
SEQ-ID-NO-49  ------MTSP STTPNIVTN  TDISRDTRRK KRKNKTQKHH QQDQIQINP-  43
SEQ-ID-NO-32  ------MASP ISLN--STPT DLVRRKKRQS ASSSAASPRR NNAASATAGD  42
SEQ-ID-NO-53  --MISIGGSS SSSSAAAGV  RMGGAKRRGK P--------- -CCAAAPGAA  38
SEQ-ID-NO-55  ------MAPS SIIAS-AAAD ERDRKRKRGA ---------- -GGEAGTEAD  32
SEQ-ID-NO-57  ------MAST SSSTPAAEVE ERCRKRKRA- ---------- -AGAAPTQPS  32
SEQ-ID-NO-60  ------MAST SGSA--AAVE ERGNSERKRK R--------- -GATGESEGS  32
SEQ-ID-NO-7   ------MASF TPNLE-PAPD TSLQFKPKKP RITLQTPSSC PPNQRIQRIK  43
SEQ-ID-NO-25  ------MVES LF----PSIE NTGESSRRKK PRISETAEAE IEARRVNEES  40
SEQ-ID-NO-22  ------MASN QSNCDVSSQQ EPNQQRKKRR KLTHETTESH LQNDGTGETK  44
SEQ-ID-NO-36  ------MASF DPSVDSSRSD TLRESNHKKR R--------K ICDHAAADQN  36

SEQ-ID-NO-3   SEEAPVRHLS RRWRATTAQK VYSLKLYDAL QRSR------ ----------  84
SEQ-ID-NO-49  ---------- -KWKSQEQQQ IYSTKLRQAI TRVNSSSTPR ----------  72
SEQ-ID-NO-32  GESHA----- -RWRSEKQQR NYSAKLVQAL QQVRLSSSAA ET--PSPTAK  84
SEQ-ID-NO-53  GTPQT----- -RWRSGTQER IYGRRLLDAL RATRSGAASS AQ----PP--  76
SEQ-ID-NO-55  AERAP----- -KWRTRREHE IYSTRLLDAL RLVRAGAGVA PS----PS--  70
SEQ-ID-NO-57  ---------- -EWRTRREHE IYSSRLLEAI RLVRAGPSSA AAAKAAPT--  69
SEQ-ID-NO-60  EAQPS----- -KWRTRRAHE IYSSKLLDAI RLVRSGSPSS SA--EAPP--  72
SEQ-ID-NO-7   ---------- -RWRTQRDQH IYSSKLFQAL RRSRRTSL-- ----------  69
SEQ-ID-NO-25  LK-------- -RWKTNRVQQ IYACKLVEAL RRVRQRSSTT SNNETDKLVS  81
SEQ-ID-NO-22  NQPTV----- -RWRTDTARR IYSSKLLEAL RRSCRITSHR GE--------  80
SEQ-ID-NO-36  SAAAS----- -PWRSDEEQR LYSRRLVEAL RRTASSAAKP R---------  71

SEQ-ID-NO-3   -RSATVRDTA DKMLATTARG ATRWSRAILV S-RFGTSLRR RRNTKPASAL  132
SEQ-ID-NO-49  -RGKAVREAA DRALAVTARG RTRWSRIT LM T-RLKIKFRK KKPNRVTALP  120
SEQ-ID-NO-32  KRGKAVREAA DRALAVSARG RTLWSRAILA N-RIKLKFRK QKRPRPAAIP  133
SEQ-ID-NO-53  -QPRAVKAAA DSALALTARG QSRWSRAILL A---GAASCR RRVLVKAGGK  122
SEQ-ID-NO-55  -PARQVREAA DRALAVAARG RSRWSRAILA S-RRAHRVHR VRLHAPAPAP  118
SEQ-ID-NO-57  -RSRAVREAA DRALAVAARG RTHWSRAILA SHRRRLQAAH RARLRAPASP  118
SEQ-ID-NO-60  -RSRAVRESA DRAIAVSARG RTRWSRAILA SHRRRIQAAR RARLREATSP  121
SEQ-ID-NO-7   -ASREVHETA DRMLAVLAKG TTRWCRAILT A-R----KVTK HKKAKLPTNN  114
SEQ-ID-NO-25  CAARFIRDTA DRVLAASARG TTRWSRAILA S-RVRAKLKK HRKAKKSTGN  130
SEQ-ID-NO-22  -K-REVRCTA DRVLAVAARG KTRWSRAILA K-RARLLRVK KVKKQRVA--  126
SEQ-ID-NO-36  -AAGQVRETA DRVLAATARG RTRWSRAILS RWRKLRIQHK KAKKKEASS  120
```

Figure 1 (continued)

| | | | | | | | | |
|---|---|---|---|---|---|---|---|---|
| SEQ-ID-NO-3 | | ----------|--AAAI RGSG|GSGRR---RK|LSAVGN----|--RVRVLGGL| 161 |
| SEQ-ID-NO-49 | | ----------|--STRSKKSR|VNVFRLKGKV|VPSMQR----|--KVRFLGGL| 152 |
| SEQ-ID-NO-32 | AVITTGSSSS|SNSGRWKKRR|VTVVKLNKKS|LPTVNR----|--KVRVLGRL| 177 |
| SEQ-ID-NO-53 | | ----------|--IRRHRRPP|ARAAAAASAG|EPPLLKERKV|KDRLRVLGRL| 160 |
| SEQ-ID-NO-55 | APA-------|--LTRPASPG|ASSSGSTSAQ|AQTLAR----|--KAKTLGRL| 153 |
| SEQ-ID-NO-57 | | ----------|----PPRHGA|SAAKG--TAA|LPPVAR----|--KAMVLGRL| 146 |
| SEQ-ID-NO-60 | | ----------|----PSRHPS|SSSCK--GPK|APALAR----|--KAKVLGRL| 149 |
| SEQ-ID-NO-7 | | ----------|----RLRKPD|IYRER---RK|TPAVER----|--KLKVLGRL| 141 |
| SEQ-ID-NO-25 | | ----------|---CKSRKGL|TETNR---IK|LPAVER----|--KLKILGRL| 158 |
| SEQ-ID-NO-22 | | ----------|----RDRKSP|GSEKR---RK|LPFVEK----|--KVKVLSRL| 153 |
| SEQ-ID-NO-36 | | ----------|--NCLKRTRI|GNGER--RNR|LPAVQK----|--KARVLSRL| 150 |

| | | | | | | |
|---|---|---|---|---|---|---|
| SEQ-ID-NO-3 | VPGCRRTALP|ELLDETADYI|AALEMQVRAM|TALSKILSEL|Q------PST| 205 |
| SEQ-ID-NO-49 | VPGCKKEPLP|VILEEADYI|PALEMQVRAM|SALFNLLSAS|T------SGA| 196 |
| SEQ-ID-NO-32 | VPGCKKESVP|VIXEEATDYI|QALEMQVRAM|KSLAELLS--|-------GSN| 218 |
| SEQ-ID-NO-53 | VPGCRKLQAP|DLLECTADYV|AALEMQVRAM|RALADALAAA|QLSSPPPPAA| 210 |
| SEQ-ID-NO-55 | VPGCRKLPFP|ALLSEASDYI|AAIEMQVRAM|AALAQALSAV|A---------| 194 |
| SEQ-ID-NO-57 | VPGCRKLSFP|ILLAETIDYI|AALQMQVRAM|TALAEALSAV|SSSSSGAGSS| 196 |
| SEQ-ID-NO-60 | VPGCRKLPFP|ALLAEASDYI|AALEMQVRAM|TALAEVLSTV|SGSGSASSSG| 199 |
| SEQ-ID-NO-7 | VPGCRKLSFS|NLIEETSDYI|AALEMQVRAM|TAITEFLCGG|TGGGPQPPAD| 191 |
| SEQ-ID-NO-25 | VPGCRKVSVP|NLLDEATDYI|AALEMQVRAM|EALAELLTAA|A------PRT| 202 |
| SEQ-ID-NO-22 | VPGCRKVSFV|NLLEEASDYI|AALEMQIKVM|TNLSEILTVA|GG------GGG| 198 |
| SEQ-ID-NO-36 | VPGCRKVSFP|NLLEEATDYI|SALEMQVRAM|TALAELLAVA|A------PAS| 194 |

| | | |
|---|---|---|
| SEQ-ID-NO-3 | NLGSAL---- | 211 |
| SEQ-ID-NO-49 | GVSSG----- | 201 |
| SEQ-ID-NO-32 | SAPPPI---- | 224 |
| SEQ-ID-NO-53 | AGDDEAEMER | 220 |
| SEQ-ID-NO-55 | --PPP----- | 197 |
| SEQ-ID-NO-57 | PSSSPA---- | 202 |
| SEQ-ID-NO-60 | GSSSPA---- | 205 |
| SEQ-ID-NO-7 | RLPSNV---- | 197 |
| SEQ-ID-NO-25 | TLTGT----- | 207 |
| SEQ-ID-NO-22 | GGGSSS---- | 204 |
| SEQ-ID-NO-36 | LAGGTLS--- | 201 |

Figure 2

```
SEQ-ID-NO-93   MGKYMKKSKV TN--------- ---------ND TEPTEP---- ---TSLGVRTR  28
SEQ-ID-NO-70   MGKYIRKSKI DGAGAGAGGG GGGGGGGESS IALMDVVSPS SSSSLGVLTR   50
SEQ-ID-NO-80   ----MRKAKT TN--------- ---------D LTVVDL---- ----SCGVRTR  22
SEQ-ID-NO-99   MGKYIRKTRK TE--------- ---------D V--------- --SPLGVLTR   22
SEQ-ID-NO-72   MGKYIRKAKI AG--------- ---------E VAVMEL---- SQASLGVRTR   29
SEQ-ID-NO-105  MGKYMRKPKV SG--------- ---------E VAVMEV---- AAAPLGVRTR   29
SEQ-ID-NO-119  MGKYMRKGKV SG--------- ---------E VAVMEV---- GGALLGVRTR   29
SEQ-ID-NO-115  MGKYMRKGKV SG--------- ---------E VAVMEV--P GGALLGVRTR   30
SEQ-ID-NO-103  MGKYMRKGKV SG--------- ---------E VAVMEV---P GGALLGVRTR   30
SEQ-ID-NO-109  MGKYMRKGKV SG--------- ---------E VAVMEV---P GGALLGVRTR   30
SEQ-ID-NO-96   MAQVKARART AL--------- ---------A MAASASSRKR   23
SEQ-ID-NO-101  ------MEV SD--------- ---------D VDLDVP---- ------TTTTK  17
SEQ-ID-NO-102  ----MRKCKG IE--------- ---------E VILMEV--SD VDLEVPTTTK  27

SEQ-ID-NO-93   AAKTLALK-- -------RLN SSASDSALAG DSS------- -----------  52
SEQ-ID-NO-70   -AKSLALQQQ QQRCLLQKPS SPSSLPPTSA SPNPPSKQKM KKKQQQMNDC  99
SEQ-ID-NO-80   -AKTLALKKQ QA-----LRLH ASSASPPPPS SPA------- -----------  50
SEQ-ID-NO-99   -AKALALN-- -------G-- ---------G DGG------- -----------  34
SEQ-ID-NO-72   -AKTLALQ-- -------RLQ KSSTSSPPTV VSAPATGDG- -----------  58
SEQ-ID-NO-105  -ARALAMQ-- -------RQP QGAAVAKDQG ---------- -----------  49
SEQ-ID-NO-119  -SRTLALQ-- -------RI-T TSSQKPPEKG EGDPGAGAGA GA---------  60
SEQ-ID-NO-115  -SRTLALQ-- -------R--- --AQRPPDKG EAGEAAG--- -----------  53
SEQ-ID-NO-103  -SRTLALQ-- -------R--- --AQRPLDKG DAEDAAA--- -----------  53
SEQ-ID-NO-109  -SRTLALQ-- -------R--- --AQRPLDKG DAEDAAA--- -----------  53
SEQ-ID-NO-96   --RKISIN--- -------N-- ---------- ---------- -----------  30
SEQ-ID-NO-101  -KRKISSD-- ---------- ---------- ---------- -----------  24
SEQ-ID-NO-102  -KRKLSSD-- ---------- ---------- ---------- -----------  34
```

Figure 2 (continued)

```
SEQ-ID-NO-93   -CYLQLRSRR LEKPM----- ---------- ---------- ALTEPKQPPR   76
SEQ-ID-NO-70   GSYLQLRSRR LQKKPPIVVI RSTKRRKQQR ------RNET CGRNPNPRSN  143
SEQ-ID-NO-80   -GYLQLRSRR LEKKPPPVPS LHHGSPRRQQ QRLGGQNNNK LGQQESPSPI   99
SEQ-ID-NO-99   -SYLELRSRR LVKPFTVLEC RRQKNGV--- -------PXNP NLVNPNPNQQ   74
SEQ-ID-NO-72   -SFLQLRSRR LEKPP---LV VHHHVSKRHK QQQQGSKKDS CVQNPNPNSY  104
SEQ-ID-NO-105  EYLELRSRK LEKLP----- ---------- ---------- ---PPPPAAR   70
SEQ-ID-NO-119  -EYLELRSRR LEKPP----- ---------- ---------- --PHTPPAKEK   83
SEQ-ID-NO-115  -EYLELRSRR LEKPP----- ---------- ---------- KEQAAAPAPK   77
SEQ-ID-NO-103  -EYLELRSRR LEKPH----- ---------- -------KDP LPPPSAPATK   80
SEQ-ID-NO-109  -EYLELRSRR LFKPH----- ---------- ---------- KEHPPPPAPA   77
SEQ-ID-NO-96   -NFVQIKSLS NAIVP----- ---------- -------ATGE RISGESPASC   58
SEQ-ID-NO-101  -GDVKLIS-- ---------- ---------- ---------- -----PALLR   36
SEQ-ID-NO-102  -GDVKLMS-- ---------- ---------- ---------- -----PPLLR   46

SEQ-ID-NO-93   IKESASKGRV NSGSGSVRVD GDDW------ ---------- ----FGKSDA  106
SEQ-ID-NO-70   LDSIRGDGSR SDSVSESVVF GKDK----DLI S--------- -----EINKDP  177
SEQ-ID-NO-80   LKPSSRVDKD SCSSQEREGG ESKEVEENNN S--------- -----NSKDLG  136
SEQ-ID-NO-99   IPNVCVNSEE GKGVKEMENQ KEKE------K S--------- -----CLGPED  106
SEQ-ID-NO-72   SRVRPCGGSN SEKKKGEDIV QEDNGNDNII NYSNLNNNHN ESNDFGGVEA  154
SEQ-ID-NO-105  ---------RR AAAAERVEAE AEAD------ ---------- --------EV   88
SEQ-ID-NO-119  ETARRASAAA AAAVRMPAAP QAAE-----E F--------- ----EAEVEV  115
SEQ-ID-NO-115  ----NGAATK AAAAASPAL AEDE------ ---------- --------VEV  100
SEQ-ID-NO-103  RGAGRKVATA AAAAAPHGL AEDD------ ---------- -------VEV  107
SEQ-ID-NO-109  TATKRGAGRK AVAAAAQHVL MEDE------ ---------- -------VEV  104
SEQ-ID-NO-96   CSSIGSVDDE NRITKFSDLE VEST------ ---------- ---RVVTSTC   89
SEQ-ID-NO-101  CRSHTGVGDT PAGNLVSPSG SVNL------ ---------- ---KENDDDS   67
SEQ-ID-NO-102  CRSHSGVGDT PACSLVSPSS SVNL------ ---------- ------NDAS   74
```

Figure 2 (continued)

| | | | | | | | |
|---|---|---|---|---|---|---|---|
| SEQ-ID-NO-93 | FCGENSPDF- | -----ESRQS | TRESTPCNFT | EDLET:VTPG | SSTKSMR--- | | 147 |
| SEQ-ID-NO-70 | TFGQNFFDIF | FFHTQSFNRT | TRESTPCSLI | RRPEIMTTPG | SSTKLNICVS | | 227 |
| SEQ-ID-NO-80 | SFGDNVLDI- | -E---SRDRS | TRESTPCNLT | RGTEDTRTPG | STTKPAS--- | | 178 |
| SEQ-ID-NO-99 | SFGENLLEF- | -E---GRKRT | TRESTPCSLI | RDSDNIQTPG | SSTRRTN--- | | 148 |
| SEQ-ID-NO-72 | SFGENILDM- | -E---ARERG | TRESTPCSLI | RDSESIRTPG | SATRPTN--- | | 196 |
| SEQ-ID-NO-105 | SFGENVLES- | -E---AMGRG | TRETTPCSLI | RDSGTISTPG | STTRPSH--- | | 130 |
| SEQ-ID-NO-119 | SFGDNVIDLD | GD---AMERS | TRETTPCSLI | RSSEMISTPG | STTKTNT--- | | 159 |
| SEQ-ID-NO-115 | SFGENVLDF- | -D---SMERN | TRETTPCSLI | RNSEMISTPG | STTKSKT-SS | | 144 |
| SEQ-ID-NO-103 | SFGFNVLDF- | -D---AMERS | TRETTPCSLI | RNPEMISTPG | STTKSKT-SN | | 151 |
| SEQ-ID-NO-109 | SFGDNVLDL- | -D---TMERS | TRETTPCSLI | RNPEMISTPG | STTKSKTSSN | | 149 |
| SEQ-ID-NO-96 | DCGE------ | -----QQQQI | RREISLTSEL | R------LTNS | SSQEVDSAEE | | 123 |
| SEQ-ID-NO-101 | NLDHDLASC- | -----CSRNG | STE------- | ENNVASAES | KEAKLSS--- | | 101 |
| SEQ-ID-NO-102 | NLDHDLASY- | -----CLRNC | SSE------- | ENSVLASAES | KEAKLSS--- | | 108 |

| | | | | | | |
|---|---|---|---|---|---|---|
| SEQ-ID-NO-93 | --TAFRDC-I | RDRDSSVPST | SLEEEXFAYA | FQQQQRLFMD | KYNFDLVNDM | 194 |
| SEQ-ID-NO-70 | ESNQREDS-L | SRSHRRRPTT | PEMDEFFSGA | EEEQQKQFIE | KYNFDPVNEQ | 276 |
| SEQ-ID-NO-80 | PTESSRRL-Q | NSMQRRIPTT | REMDEFFGPA | EEEQLRQFTE | KYNFDPVSDK | 227 |
| SEQ-ID-NO-99 | ANEANGRV-P | NSIQPTIPTD | LEMEEFFTRA | EKEQQRKFIE | KYNFDPVNEK | 197 |
| SEQ-ID-NO-72 | SADTNQRV-Q | NSTQRHTPTS | HEMDEFFSLT | EEDQQRQFIE | KYNFDPVKDK | 245 |
| SEQ-ID-NO-105 | -SNSHRRV-Q | APARHIPCS | AEMNEFFSAA | FQPQQQATID | KYNFDPVNDC | 178 |
| SEQ-ID-NO-119 | SISSRRRM-E | TSVCRYVPSS | LEMEEFFAAA | EQQQIQATRE | RYNFCPVNDC | 208 |
| SEQ-ID-NO-115 | SMTSRRRM-E | SSVCRFIPNS | LEMEEFFAAA | EQHEQHTFRE | KYNFCPVNDS | 193 |
| SEQ-ID-NO-103 | SMTSRRRM-E | TSICRFIPSS | HEMEEFFSAA | EKQEQQSFRE | KYNFCPVNDC | 200 |
| SEQ-ID-NO-109 | STTSRRRTEE | TPSCRFIPSS | LEMEEFFSAA | EQQEQHSFRE | KYNFCPVNDC | 199 |
| SEQ-ID-NO-96 | QITQTKSL-- | --PPQKMPTE | LELDEFFAAA | EKDIRKRFSD | KYNYDIVKGV | 169 |
| SEQ-ID-NO-101 | ---ERERT-- | ---PEKMPSF | KEIEDFFAVR | QKAILKRFRE | KYNFDFEKEE | 143 |
| SEQ-ID-NO-102 | ---ERQRT-- | ---PEKMPSF | KEIEEFFAAR | QKAILKRFRK | KYNFDFEKEE | 150 |

Figure 2 (continued)

| | | | |
|---|---|---|---|
| SEQ-ID-NO-93 | PLTGRYEWVQ | VSP | 207 |
| SEQ-ID-NO-70 | PLPGRFEWTK | VDD | 289 |
| SEQ-ID-NO-80 | PLPGRYEWEK | LDP | 240 |
| SEQ-ID-NO-99 | PLPGRYEWVK | VNH | 210 |
| SEQ-ID-NO-72 | PLPGRYQWEK | MDP | 258 |
| SEQ-ID-NO-105 | PLPGRYEWVK | LD- | 190 |
| SEQ-ID-NO-119 | PLPGRYEWTR | LDC | 221 |
| SEQ-ID-NO-115 | PLPGRYEWTR | LGC | 206 |
| SEQ-ID-NO-103 | PLPGRYEWAR | LDC | 213 |
| SEQ-ID-NO-109 | PLPGRYEWAR | LDC | 212 |
| SEQ-ID-NO-96 | SLEGRYEWVK | L-- | 180 |
| SEQ-ID-NO-101 | PSEGRYEWVR | GS | 156 |
| SEQ-ID-NO-102 | PLEGRYEWVR | GS | 163 |

Figure 3

```
SEQ-ID-NO-129   MGRGRSSSSS S1ESSSKSNP FGASSST RNI  S---TDLRLG LSFGTSS---         44
SEQ-ID-NO-247   --------MS PPLELDYIGL SAAAGGRPDD DLKGTELRLG LP-GCESPDR          41
SEQ-ID-NO-302   ---------- ---MSTDTGR SSTESEVSGL DYEETELKLG LP-GGSRTAG          36
SEQ-ID-NO-270   ---------- ----MDGGVG- YA-----DMD ALKAIELRLG LP-GSHPPEK          30
SEQ-ID-NO-236   ---------- ----MERTAT- YE-----KDL NLKATELRLG LP-GIDEPEK          30
SEQ-ID-NO-137   ---------- ----MV----- FE-----KDL NLDATELRLG LP-ASSKESL          26
SEQ-ID-NO-300   ---------- ----ME----- FE-----RDL NLDATELRLG LP-GTATRQS          26
SEQ-ID-NO-303   ---------- ----ME----- FE-----RDL NLEATELRLG LP-GTATQQL          26
SEQ-ID-NO-133   ---------- ----MEGSVG- YD-----NDL NLRATELRLG LP-GTEPVSI          30
SEQ-ID-NO-209   ---------- ----MENSLGK YG-----KEL NLEATELRLG LP-GSDEPEK          31
SEQ-ID-NO-201   ---------- ----MEK---- ------DGL ELETTELRLG LP-GRDVTEK          25
SEQ-ID-NO-231   ---------- ----MAR---- ------EGL GLEITELRLG LSCGEPK---          23
SEQ-ID-NO-234   ---------- ----MEK---- ------EDL GLEITELRLG LP-GAGGENN          25

SEQ-ID-NO-129   ---------- ---------- ---------- ---------- -GTQYFNGGY          53
SEQ-ID-NO-247   RPVAATTTLE LLPAKGAKRG FSDEVVPPAP ISAAGKGKEA SGDEKDKKVA          91
SEQ-ID-NO-302   S--------- ---ETEKKRG FAETVDLSLG AESRSGDLGD RSTCDFGSGA          74
SEQ-ID-NO-270   PLPTTTTT-- ---ARPTKRS LDEDRAA--- ---------- -RRETSEGGR          61
SEQ-ID-NO-236   QSSSASTSA- ---KYSKKRT SSEMD----- ---------- -NSSSGKENE          60
SEQ-ID-NO-137   ---------- ----RISNKRA LPDMNDDS-- ---------- -GVAAAKKCD          50
SEQ-ID-NO-300   EKQTPNSNL- ---AKSNKRS LPDMNEDPAG SSRENSSTVS -SNEEKSHDQ          71
SEQ-ID-NO-303   EKQTPSSNV- ---TKSNKRS LPDMNEDSAG RSESSSV--- -SSNDKKSDE          68
SEQ-ID-NO-133   ---------- ---VRSNKRS LQQVADDDCG VN-------- -GCRSDDDNL          58
SEQ-ID-NO-209   RSA------- ---VRSNKRS SPEASEEECI SKGNMNSSD- -GSDITSDDQ          69
SEQ-ID-NO-201   M--------- ------MKKRG FTEMMTSSG SHSEQCESSV VSSGVDVEKV           61
SEQ-ID-NO-231   ---------- ---KNEKKRM FSEIDG---- ---------- -GVEENGGSG          45
SEQ-ID-NO-234   TDKDK----- ---NKNKKRV FSDIE----- ---------- -GENSSSEED          51
```

Figure 3 (continued)

| | | | | | | | |
|---|---|---|---|---|---|---|---|
| SEQ-ID-NO-129 | GYSVAAPAVE | DAEYVAAVEE | EENECNSVG | S---------- | --------FYV | | 87 |
| SEQ-ID-NO-247 | APPQPAAKAQ | VVGWPPVRSY | RKNTMATTTN | QLKSSKEDSD | TKQGQFFLYV | | 141 |
| SEQ-ID-NO-302 | GKP-PAVKAQ | VVGWPPVRSF | RKNALKSCT- | ---------- | --------YV | | 104 |
| SEQ-ID-NO-270 | ATSTRATKAQ | VIGWPPIRSY | RKNSFQAMKA | T-AEAAG---- | --------LYV | | 100 |
| SEQ-ID-NO-236 | QDSAPAPKAQ | VVGWPPVRSY | RKNVLQIKKS | ESDNSSG---- | --------MYL | | 100 |
| SEQ-ID-NO-137 | QETAPPTKAQ | VVGWPPIRSY | RKNSLQTKKT | E-AETSG---- | --------MYV | | 89 |
| SEQ-ID-NO-300 | FTAPPPIKAQ | VVGWPPIRSY | RKNCLQAKKQ | E-AEAAG---- | --------LYV | | 110 |
| SEQ-ID-NO-303 | QETAPPTETR | VVGWPPIRSY | RKNCLQAKKL | E-AEAAG---- | --------LYV | | 107 |
| SEQ-ID-NO-133 | TAP-PPPKAQ | IVCWPPIRSY | RKNNIQTKKN | E-SEGGG---- | --------YV | | 96 |
| SEQ-ID-NO-209 | DNVVPPAKAQ | VVGWPPVRSY | RKNSLQQKKE | EQAEGAG---- | --------MYV | | 109 |
| SEQ-ID-NO-201 | NET-PAVKTQ | VVGWPPVCSY | RRKNSCKEVS | T-TKVGL---- | --------GYV | | 99 |
| SEQ-ID-NO-231 | DRKSVDKKNQ | VVGWPPVCSY | RKKNMNEGSK | ---------- | --------MYM | | 78 |
| SEQ-ID-NO-234 | GK---KETKNQ | VVGWPPVCSY | RKKNTVNEPK | ---------- | --------LYV | | 82 |

| | | | | | | | |
|---|---|---|---|---|---|---|---|
| SEQ-ID-NO-129 | KVNMEGVPLG | RKIDLMSLNG | YRDLIRTLDF | MF-NA----- | SILWAEEEDM | | 131 |
| SEQ-ID-NO-247 | KVSMDGAPYL | RKVDLKTYKN | YKDMVVALGK | MFIGF----- | RTGKDGASEN | | 186 |
| SEQ-ID-NO-302 | KVAVDGAPYL | RKVDLCMYGG | YQQFLTAIED | MF-SCFTVRN | CPNERRLVDP | | 153 |
| SEQ-ID-NO-270 | KVSMDGTPYL | RKIDLEVYKG | YRELREALED | MF-KC----- | --------FEG | | 137 |
| SEQ-ID-NO-236 | KVSMDGGTYL | RKIDLKVYNS | YPELLKALQN | MF-KC----- | TIGVYTEREG | | 144 |
| SEQ-ID-NO-137 | KVSMDGAPYL | RKIDLKVYKG | YPELFKALED | MF-KF----- | KVGKYSEREG | | 133 |
| SEQ-ID-NO-300 | KVSMDGAPYL | RKIDLKVYKG | YPELLKALEE | MF-KS----- | KVGEYSEREG | | 154 |
| SEQ-ID-NO-303 | KVSMDGAPYL | RKIDLKVYKG | YPELLEVVEE | MF-KF----- | KVGEPSEREG | | 151 |
| SEQ-ID-NO-133 | KVSMDGAPYL | RKIDLKIYSG | YPELLQAIEN | MF-KF----- | TIGEYSEREG | | 140 |
| SEQ-ID-NO-209 | KVSMDGAPYL | RKIDLKVYKS | YPELLKALEN | MF-KC----- | TFGQYSEREG | | 153 |
| SEQ-ID-NO-201 | KVSMDGVPYL | RKMDLGSSQG | YDDLAFALDK | LF-GF----- | II-GTGVALKD | | 142 |
| SEQ-ID-NO-231 | KVSMDGAPYL | RKIDLCLHKG | YLELALALEK | LF-DC----- | C-GIEEALKD | | 121 |
| SEQ-ID-NO-234 | KVSMDGAPFL | RKIDLAMHKG | YSDLAFALDK | FF-GC----- | Y-GICEALKD | | 125 |

Figure 3 (continued)

```
SEQ-ID-NO-129   CNEKSHVLTY ADKEGDWMMV GDVPWEMFLS TVRRLKISRA NYHY------   175
SEQ-ID-NO-247   RKDGEYVMTY EDKDGDWMLV GDVPWEMFTE ACRRIRVMKS SDV-VGLGVT   235
SEQ-ID-NO-302   VNGTEYVPTY EDKDCDWMLV GDVPWKMFVA SCKRLRLMKS SEAI NLAPRT   203
SEQ-ID-NO-270   CKGSEYATTY EDKDGDLMLV GDVPWEMFTS SCKKLRIIRG AEAI RGLCSS   187
SEQ-ID-NO-236   YNGSDYAPTY EDKDGDWMLV GDVPWDMFLN SCRRLRIMKG SEA-KGLHAY   193
SEQ-ID-NO-137   YNGSEFVPTY EDKDGDWMLA GDVPWEMFIN ACKRLRIVRG SEA-RGLGCV   182
SEQ-ID-NO-300   YNGSEHVPTY EDKDGDWMLV GDVPWDMFIN SCKRLRIMKE SEA-RGLGCA   203
SEQ-ID-NO-303   YNGSEYVPTY EDKDGDWMLV GDVPWEMFIN SCKRLRIMKE SEA-RGLGCA   200
SEQ-ID-NO-133   YKGSDYAPTY EDKDGDWMLV CDVPWEMFIT SCKRLRIMKG SEA-RGLGCG   189
SEQ-ID-NO-209   YNGSEYAPTY EDKDGDWMLV GDVPWNMFVS SCKRLRIMKG SEA-KGLGCF   202
SEQ-ID-NO-201   GDNCEYVTTY EDKDGDWMLA GDVPWGMFIE SCRRVRIMKR SEX-TGFGLX   191
SEQ-ID-NO-231   AENCEHVPIY EDKDGDWMLV GDVPWEMFLE SCKRLRIMKR SDA-KGFDLQ   170
SEQ-ID-NO-234   AENAEHVPIY EDKDGDWMLV GDVPWEMFRE SCKRLRIMKR SDA-KGFDLQ   174

SEQ-ID-NO-129   ---------- ----   175
SEQ-ID-NO-247   RAGVKSKNKN ----   245
SEQ-ID-NO-302   POGSTRAR-- ----   211
SEQ-ID-NO-270   Q--------- ----   188
SEQ-ID-NO-236   RL-------- ----   195
SEQ-ID-NO-137   V--------- ----   183
SEQ-ID-NO-300   V--------- ----   204
SEQ-ID-NO-303   V--------- ----   201
SEQ-ID-NO-133   V--------- ----   190
SEQ-ID-NO-209   ---------- ----   202
SEQ-ID-NO-201   PXGLDF---- ----   197
SEQ-ID-NO-231   PKGSLKRFI- ----   179
SEQ-ID-NO-234   PKGSLKGFIE GVRK   188
```

Figure 4

```
SEQ·ID·NO·319   MEAGSL--GE NNRLSN---- ---------- ---PNKNISS SNEGNAKPKR  31
SEQ·ID·NO·331   MDDGDGAAPA EGSAASTPPP APPAAAAAAA AAVSAGSTGA SGSGEKTVKR  50
SEQ·ID·NO·317   M--------- ---------- ---------- ---------- ----------   1
SEQ·ID·NO·321   MELSSEVHFG ENRVSP---- ---------- ---------- ----EKNLKR  22
SEQ·ID·NO·327   MEEVTELQSE ENKLSM---- ---------- ---------- ----EKNKKR  22
SEQ·ID·NO·330   MEESSELQPE ENKVSA---- ---------- ---------- ----EKFPKR  22

SEQ·ID·NO·319   QMKTPFQIEA LEKAYALETY PSEATRAELS EKLGLSDRQL QMWFCHRRLK  81
SEQ·ID·NO·331   MMKSPYQLEV LEKTYAVEQY PSETLRAELS AKIGLSDRQL QMWFCHRRLK 100
SEQ·ID·NO·317   ---------A LENFYNEHKY PTEEMKCKLA EEVGLTEKQV SGWFCHRRLK  42
SEQ·ID·NO·321   -VKTPAQVVA LENFYNEHKY PTEEMKSELA DQIGLTEKQI SSWFCHRRLK  72
SEQ·ID·NO·327   RLKTPAQLKA LEDFYNDNKY PTEEMKSELA DELELTEKQI SGWFCHRRLK  72
SEQ·ID·NO·330   KLKTPAQLKG LEKFYTEHKY PTEELKLALA EELELTEKQV SGWFCHRRLK  72

SEQ·ID·NO·319   F-----KKDN PTKKQRKGAA LPPESPVDEL RAVPGPDYGS GSCSGSSPYM 126
SEQ·ID·NO·331   DRKPPTKRQR REEEAAAVPL MAPPPVLPPP ALPLSSGFLL IGASSPYDEP 150
SEQ·ID·NO·317   D-----KRHV KEDGNALGSQ DRSSVVLQDR GSGLRQDSCG STKQTDYWNP  87
SEQ·ID·NO·321   D-----KR-L RDEVCTNGRQ DRSSGIIQDR GSGLRQDSCG STKQGDYRNL 116
SEQ·ID·NO·327   D-----KKML NDEVCANGRQ DRSSGVIQDR GSGLVQDSCG STKHVHYRYL 117
SEQ·ID·NO·330   D-----KRLL KEEANANGRQ DRSSGVIQDR GSGLGQDSCG SSKHCDYKYL 117

SEQ·ID·NO·319   DTRKLGGS-- ---------- ---------- SSRGMMEDAP TV-------- 146
SEQ·ID·NO·331   PLPPVHSR-- ---------- ---------- RGAGRSSAVP RLSAPDIG-- 176
SEQ·ID·NO·317   KPREVESQRL Y--------- --------MG NADG-EDSTS SDRSSSLRKN 119
SEQ·ID·NO·321   DPREVESQRL YGRDFHPADL TYDRTSRYTG NMTG-IDNIS SGSSSSLQDK 165
SEQ·ID·NO·327   DPKEVESHGL YNHGFSAADI TYGHKNHRYA ENDSATDNTS SESSSSLQDR 167
SEQ·ID·NO·330   DPKEVESNGL YNRDLSVADM TYGRRNHFSE NVSGMDDDTS SESSSFLQER 167

SEQ·ID·NO·319   ---------- ----RRYESQ QSIM------ ---------- ---------E 158
SEQ·ID·NO·331   ---------- ----RRYYEPL PVMLPPPPVA SMQL---MPS ---------E 201
SEQ·ID·NO·317   LVSSKDGIRD VESSRYVAHK DVIQ--HPQF MRSYGYNKPS GYLKVKGESE 167
SEQ·ID·NO·321   FVCQREDPYD AETSKYLAQN GAAMPLIPKG TDSFGY-KPS GYLKVKGEIE 214
SEQ·ID·NO·327   LLCQCQDPYD MEPSSHVTPN GSLLPPNTKG ANNMGH-KPS GYLKVKGEIE 216
SEQ·ID·NO·330   MYPQGQDPYE MEPSRY---S KALPPLNPKG AINMCY-KPS GYLKVKGEIE 213
```

Figure 4 (continued)

| SEQ-ID-NO-319 | LRAI ACVEAQ | LGEPLRDDGP | MLGI EFDPLP | PDAFGA---- | ----------- | 194 |
| SEQ-ID-NO-331 | LRVI HSVESQ | LGEPLRDDGP | VLGI DFDPLP | PGSFGAPI -- | ----------- | 239 |
| SEQ-ID-NO-317 | NFAI TAVKRQ | LGRQYQFDGP | PLGVEFDPLP | PGAFEPQTNP | I VHEPI YVGN | 217 |
| SFQ-ID-NO-321 | NAAI TAVKMQ | LGRHYKEDGP | PL GVEFDPLP | PGAFASPSRD | PVSGPI YVGD | 264 |
| SEQ-ID-NO-327 | HAAI TAVKKQ | LGKHYREDGP | LLSVEFDL PI | PEAFECQLAD | LANEAYYAAN | 266 |
| SEQ-ID-NO-330 | HAAI TAVKKQ | LGRNYQEDGP | LLGVEFDPLP | PGAFECQTEE | AVHEFYHIAD | 263 |

| SEQ-ID-NO-319 | ----------- | ----------- | ----------- | ----------- | ----------- | 194 |
| SEQ-ID-NO-331 | ----------- | ----------- | ----------- | ----------- | ----------- | 239 |
| SEQ-ID-NO-317 | QRRPHLPHLL | GTRKSFNPGP | ----------- | ----------- | ----------- | 237 |
| SEQ-ID-NO-321 | LAQMCSPDVS | CVRKQSSLGA | FEAQVLLVHA | GNLYI LQLSI | TSNDVCHPMF | 314 |
| SEQ-ID-NO-327 | PALPNSPEVS | AVKKQSSLSS | ----------- | ----------- | ----------- | 286 |
| SEQ-ID-NO-330 | PALLNSPEIS | TVKSRPGLSS | ----------- | ----------- | ----------- | 283 |

| SEQ-ID-NO-319 | ----------- | ----------- | ----------- | ----------- | ----------- | 194 |
| SEQ-ID-NO-331 | ----------- | ----------- | ----------- | ----------- | ----------- | 239 |
| SEQ-ID-NO-317 | ----------- | ----------- | ----------- | ----------- | ----------- | 237 |
| SEQ-ID-NO-321 | ITTVTFTLLL | LPIYHQSCTG | TTSNYAHNMF | PSSFRYVPKK | GSVRPENVME | 364 |
| SEQ-ID-NO-327 | ----------- | ----------- | ----------- | ----------- | ----------- | 286 |
| SEQ-ID-NO-330 | ----------- | ----------- | ----------- | ----------- | ----------- | 283 |

| SEQ-ID-NO-319 | ----------- | ----------- | ----------- | ----------- | ----------- | 194 |
| SEQ-ID-NO-331 | ----------- | ----------- | ----------- | SYEI ARKSKL | ----------- | 239 |
| SEQ-ID-NO-317 | ----------- | ----------- | ----------- | RYE-VYSTKM | HSPDPDSEDD | 257 |
| SEQ-ID-NO-321 | QGI FLYDSSD | SI PPSSI SCT | SNESLYI LAV | RYD-SYFTKI | SSHDSYI EGA | 413 |
| SEQ-ID-NO-327 | ----------- | ----------- | ----------- | RYD-SYYTKH | SSQDS------ | 300 |
| SEQ-ID-NO-330 | ----------- | ----------- | ----------- |  | GSQDTHMEGV | 302 |

| SEQ-ID-NO-319 | ----------- | ----------- | ----------- | ----------- | ----------- | 194 |
| SEQ-ID-NO-331 | ----------- | ----------- | ----------- | ----------- | ----------- | 239 |
| SEQ-ID-NO-317 | EHDDDDNI MV | GMEPGLRDKK | SFGEPRLKSP | STSFYNSVPR | HKSFKETFKC | 307 |
| SEQ-ID-NO-321 | NCNPE------ | ---PSDSHDR | KSHHHLEQKP | TYNGSNSNAC | GNSAMDMPDD | 455 |
| SEQ-ID-NO-327 | ----------- | ----------- | ----------- | ----------- | ---QMVRD | 305 |
| SEQ-ID-NO-330 | DFGSLHDVHV | ---QDKQDKK | ALHGTKHRQT | FQSNAGRFPG | RNSSLDLYED | 349 |

Figure 4 (continued)

```
SEQ-ID-NO-319                                                                                           194
SEQ-ID-NO-331                                                                                           239
SEQ-ID-NO-317  SPRE PVTNS  KKGW-I SSKS  WAEGSRNHLV  ANVQNLSGS-  NI CTNOS---                             352
SEQ-ID-NO-321  LAGET SAYVN  KRHYRMSSKH  GFEERRSDSL  STHLCPSGR-  RVNSEKTEAW                              504
SEQ-ID-NO-327  SI GEASAYNN  TKNCRKGTKH  GFDGTRYDSG  SNPSDHYEEN  NLVVNQTDSL                              355
SEQ-ID-NO-330  ST GEA-AYNF  TKNHRKDAKR  GVEGJ RSDSF  SNHSDRYEE-  NLPVKHSDFL                             397

SEQ-ID-NO-319                                                                                           194
SEQ-ID-NO-331                                                                                           239
SEQ-ID-NO-317  -HDYDNNL SN  GGR-------  ----------  ----KTGYLT  KSSKLLPPSR                              380
SEQ-ID-NO-321  LHDCDNDNPK  I VQ-------  ----------  ----RNNYTS  KHP-HLMRCS                              532
SEQ-ID-NO-327  LHCYENSNLK  NVQ--------  ----------  ----RGEYAK  SKPSNSVHKS                              384
SEQ-ID-NO-330  QYNYENTNQK  NVQRSVHADI  LQYDYDNVNP  KKAPRSEHI K  SKPSNSI HNS                             447

SEQ-ID-NO-319                                                                                           194
SEQ-ID-NO-331                                                                                           239
SEQ-ID-NO-317  SRSPESMD-R  GPSSGMA---G  I YHGERNQMK  MQREK----L  HSTDEPPVAK                             423
SEQ-ID-NO-321  GKSLDTEE-R  ARCTI MEKED  KLHGEMKRMK  GSHDPVRVKR  HPTDEI I VAK                            581
SEQ-ID-NO-327  QVYLDTGERR  GLNKRMAKEE  KFDGDRKI KK  QYRDPDEV-R  VLTNEMTVAK                              433
SEQ-ID-NO-330  RGSVDTEE-R  GL SSRMTKDC  LFKGDRKSKK  QYRDAGGA-G  MLSNET MVAK                             495

SEQ-ID-NO-319              -------IPE  PHNRT G----                                                      203
SEQ-ID-NO-331              -------WE   TK--------                                                      244
SEQ-ID-NO-317  RVKHGYI QQV  YAPKSSSYSF  I LERKS----                                                     449
SEQ-ID-NO-321  RFRVDFPQQ-  EHVAKASFSE  RRRTNLTKR   LNPENMATGI  AFTEVVGALD                               630
SEQ-ID-NO-327  WAKVDPLEQ-  YDVKQSSVAE  LEPRKS----                                                       458
SEQ-ID-NO-330  RLKANTFQP-  YNMKQVPVAE  LEPRKT----                                                       520

SEQ-ID-NO-319                                                  203
SEQ-ID-NO-331                                                  244
SEQ-ID-NO-317  ---QI NRSCV  ELPSSLSGDD  ETDESSSSMD              476
SEQ-ID-NO-321  VPI DI GRSAM  ERPSSFS-ED  ETPCTSSSAE             659
SEQ-ID-NO-327  -----QRSAA  FMPSSFS-ED  ETAETSSSAD               482
SEQ-ID-NO-330  -----QRSAA  EMPSSFS-ED  ETADTSSSLD               544
```

Figure 5

```
SEQ-ID-NO-401   MGLSNFPSAS EGVLPVLVIN TMLSVAVLKN MFRSMLQVV-  LGGSAAANGS   49
SEQ-ID-NO-370   MGISSMPAPK ESLLIYLLYH AVVSIAALAG LLRAALVFLG  LPAPPSLL--   48
SEQ-ID-NO-409   MGISSMPAPK ESLLIYLLYH AVVSIAALAG LLRAALVFLG  LPAPPSLL--   48
SEQ-ID-NO-349   MGISSMPAPK DSVVAYLLYN TAVSIAILAD MVRAALVFLG  LPVPPS---A   47
SEQ-ID-NO-357   MGISSMPTPK DSLMGFVLYN TAVSVAILAG LVRAALVFLG  LAAPS----P   46
SEQ-ID-NO-337   MGLSSLPGPS EGMLCVILVN TALSISIVKG VRSFLGFVG   ISLSPSSSSP   50
SEQ-ID-NO-339   MCLSSLPGPS EGMLCVILVN TALSISIFKG LRSVLQLIG   IRLSPSSAAA   50
SEQ-ID-NO-395   MGLSSLPAPS EGVLCVLLVN TVLSISIFKG IVRTLHIVG   IHLSSSSSTS   50
SEQ-ID-NO-417   MGLSSLPAPS EGVLCILLVN TALSISIVKG IIRSLHVVG   IHLPP----P   46
SEQ-ID-NO-437   MGLSSLPAPS EGVLCVLLVN TALSISIVKG VRSILHIVG   IRLSPSASLP   50
SEQ-ID-NO-355   MGFPV--GYP EVSMPNFLY  TLSLLSFLRS LTTSFLSLLH  LSDL------   42
SEQ-ID-NO-393   MGFPV--GYS ELLMPRLVLH MALLLGYVRR FLFRAFDAVG  LGDLLDADVP   48

SEQ-ID-NO-401   N----IEHDE SSSSSWERRV SI-------- TQYKSLCHSH DICR-----T    82
SEQ-ID-NO-370   -----AGEDA DCADQLTAAT PA---GPSLA ERFRSRFRPA RFGR---RRG    87
SEQ-ID-NO-409   -----AGEDA DGADQLTAAT PA---GPSLA ERFRSRFRPA RFGR--RRGAA   89
SEQ-ID-NO-349   WED--GDDQL AAIAAAAAAA AAAAGGPSLA DRFRSRFRPA RFGR--RRGCG   94
SEQ-ID-NO-357   WEGLAADEHH HHRQVVSSTS PL---GPSLA DRFRSRVRPS RFGR--RRGG    91
SEQ-ID-NO-337   SSVTVSSENS STSESFDFRV CQ---PESYL EEFRNRIPTL RFES-LCRCK    96
SEQ-ID-NO-339   AA---ASSEN QTSDSFDFRV CQ---PESFL EEFRNRIPTV KFES-ICKCK    93
SEQ-ID-NO-395   PSS--PDPSL TAPESFEFHL SP---SESYI EEFRSRIPTL RFDS-VCCCK    94
SEQ-ID-NO-417   S----SDYTE NLSESFDFHI NT---PESYI EEFRSRIPTI HFGAVVCSCK    89
SEQ-ID-NO-437   S----SDNAE DTRESLEFRL SP---PENYI EEFRSRMPSI RFNT-VCSCE    92
SEQ-ID-NO-355   -----LDIDF STTTLPDSHI HR---PITLSA ILIRQFLPII TFND-LAEGD    83
SEQ-ID-NO-393   W----PENSG HRNLDHQQLL QPPQSPSVSA MLLREALPVV RYEE-LGAAG    93

SEQ-ID-NO-401   SMAMVECCVC LCRFEANQEV SELP-CKHYF HRGCLDKWFD NKHTTCPLCR   131
SEQ-ID-NO-370   AAAVPDCRVC LVRFEADAVV NRLP-CGHLF HRACLETWLD YDHATCPLCR   136
SEQ-ID-NO-409   ASPTPDCRVC LVRFEADAVV NRLP-CGHLF HRACLETWLD YDHATCPLCR   138
SEQ-ID-NO-349   AG-AADCRVC LARFEPESVV NRLP-CGHLF IRACLETWLD YDHATCPLCR   142
SEQ-ID-NO-357   ACAGADCRVC LARFEPESVV NRLP-CGHLF HRACLETWLD YDHATCPLCR   140
SEQ-ID-NO-337   KQADNECSVC LSKFQGDSEI NKLK-CGHLF HKTCLEKWID YWNITCPLCR   145
SEQ-ID-NO-339   KQADNECSVC LSKFEEDSEI NKLK-CGHLF HKTCLEKWID YWNITCPLCR   142
SEQ-ID-NO-395   -QPEHDCSVC LTQFEPESEI NRLS CGHLF HKVCLEKWLD YWNITCPLCR   142
SEQ-ID-NO-417   -RPQHDCQVC LTQFEPKSEI NHLS-CGHLF HKVCLEKWLD YWNITCPLCR   137
SEQ-ID-NO-437   -QPEHDCSVC LTQFEPESEI NSLS-CCHIF HKMCLEKWLD YWNITCPLCR   140
SEQ-ID-NO-355   SSPPVGCAVC LNEFAGEFEI RCMANCRHMF HRTCVDRWID HDQKICPLCR   133
SEQ-ID-NO-393   QHVGDSCVVC LYEFEAAEEV RRLSNCRHVF HRGCLDRWLE HHQRTCPLCR   143
```

Figure 5 (continued)

| | | |
|---|---|---|
| SEQ-ID-NO-401 | S----D--- ---------- ---------- ---------- ---------- ---------- | 134 |
| SEQ-ID-NO-370 | SRL--LPAA- AAADESWSPP APTLT--AW ---------- ---------- ---------- | 161 |
| SEQ-ID-NO-409 | SRL--LPAAT TAADESWSPP APTLT--AW ---------- ---------- ---------- | 164 |
| SEQ-ID-NO-349 | HRL--LP--- -ATTESPSPS PATATPHFAR I--------- ---------- ---------- | 167 |
| SEQ-ID-NO-357 | LRL--LP--- PAADDDYAAV AAGLAARF-- ---------- ---------- ---------- | 163 |
| SEQ-ID-NO-337 | TPLVVVP--- --EDHQLSSN -------VW- ---------- ---------- ---------- | 162 |
| SEQ-ID-NO-339 | TPIVVVA--- --ADDQLVSS N------VW- ---------- ---------- ---------- | 160 |
| SEQ-ID-NO-395 | TPL--MP--- --EDDTPC-- -------FQ- ---------- ---------- ---------- | 155 |
| SEQ-ID-NO-417 | TPL--LP--- --EEEASC-- -------FL- ---------- ---------- ---------- | 150 |
| SEQ-ID-NO-437 | TPL--LP--- --EEDASC-- -------FW- ---------- ---------- ---------- | 153 |
| SEQ-ID-NO-355 | THF--VPYHK MEDYNQRLWN DAASEDDIDD DVSLFSHRHD YYYIANASL- | 180 |
| SEQ-ID-NO-393 | TPL--VPGEM PVAVDDQMWA AAGVPDSYYD DFFSFPFASA SPPSPTLLLP | 191 |

| | | |
|---|---|---|
| SEQ-ID-NO-401 | ------- | 134 |
| SEQ-ID-NO-370 | ------- | 161 |
| SEQ-ID-NO-409 | ------- | 164 |
| SEQ-ID-NO-349 | ------- | 167 |
| SEQ-ID-NO-357 | ------- | 163 |
| SEQ-ID-NO-337 | ------- | 162 |
| SEQ-ID-NO-339 | ------- | 160 |
| SEQ-ID-NO-395 | ------- | 155 |
| SEQ-ID-NO-417 | ------- | 150 |
| SEQ-ID-NO-437 | ------- | 153 |
| SEQ-ID-NO-355 | ------- | 180 |
| SEQ-ID-NO-393 | HQLFSAS | 198 |

Figure 6

```
SEQ-ID-NO-1842   MSSSCI PTGL  RLDLDMVKAA  ASPVGAHSSP  LRPAHYSSPS  STLSSEASNA   50
SEQ-ID-NO-456    ----------   ----MCSNK   ASPVVGEE--  ----------  -KQSTRSSKR   22
SEQ-ID-NO-511    ----------   ----MLMNC   DFNCDLFE--  -QEAKRRS--  -YPWARPCDG   29
SEQ-ID-NO-498    ----------   ----MFMNC   NFNSNLLE--  -NEAGRIS--  -FPWARPCDG   29
SEQ-ID-NO-478    ----------   ----MFKQE   SNNICNRE--  -N--------  -NRGARACDT   23
SEQ-ID-NO-481    ----------   ----MLKQE   SF--------  ----------  --NWAQACDT   14
SEQ-ID-NO-485    ----------   ----MIKQE   SL--------  ----------  --NWAQTCDT   14
SEQ-ID-NO-496    ----------   ----MLKKE   NSN-------  ----------  --NWARVCDS   16
SEQ-ID-NO-510    ----------   ----MLKKE   KSGGFDRS--  -S--------  -NNWARVCOS   23
SEQ-ID-NO-536    ----------   ----MLKEE   RTSGGETG--  -E--------  -NNWARICDT   23
SEQ-ID-NO-474    ----------   ----MLKQE   SSGGGGGD--  ----------  --NRARVCDT   21
SEQ-ID-NO-475    ----------   ----MLKQE   SSGSGGGD--  ----------  --NRARLCDT   21
SEQ-ID-NO-457    ----------   ----------  ----------  ----------  ---MPKPCDA    7
SEQ-ID-NO-532    ----------   ----MKVEE   QTVVGGGG--  -GAGQGGAGF  WGLAGRPCDT   32
SEQ-ID-NO-466    ----------   ----MVIDT   TNVKGLTG--  -R--------  WGMAAKTCDT   24
SEQ-ID-NO-508    ----------   ----MGIDR   GGLKSLRG--  -G--------  WSVPPKLCDS   24
SEQ-ID-NO-488    ----------   ----------  ----------  ----------  --MALKLCDS    8
SEQ-ID-NO-494    ----------   ----------  ----------  ----------  --MATKLCDS    8

SEQ-ID-NO-1842   SSSSATSVSL   KRARAPRKRP  NQAYNEAAAL  --LASLHPSV  FPVNKSPKTA   98
SEQ-ID-NO-456    IKKRKN----   REATTIMEDK  SSSNLDASRK  --RTKTKK-   ---------P   56
SEQ-ID-NO-511    CHAAPSAVYC   HADAAYLCAS  CDTQVHSANR  --LASSHERV  RVCVSCESAA   77
SEQ-ID-NO-498    CHAAPSTVYC   CADAAYLCAS  CDTQVHSANR  --VASRHERV  RVCETCESAP   77
SEQ-ID-NO-478    CGSTICTVYC   HADSAYLCNS  CDAQVHSANR  --VASRHKRV  RVCESCERAP   71
SEQ-ID-NO-481    CRSAACTVYC   RADSAYLCTS  CDAQIHAANR  --LASRHERV  RVCESCERAP   62
SEQ-ID-NO-485    CRSAACTVYC   RADSAYLCTN  CDAQVHAANR  --LASRHERV  RVCQSCERAP   62
SEQ-ID-NO-496    CHSATCTVYC   RADSAYLCAG  CDARIHTASL  --MASRHERV  WVCEACERAP   64
SEQ-ID-NO-510    CHSATCTVYC   RADSAYICAG  CDSRIHAASL  --MASRHERV  WVCEACERAP   71
SEQ-ID-NO-536    CRSAACTVYC   RADSAYLCTS  CDARVHAANH  --VASRHERV  WVCESCERAP   71
SEQ-ID-NO-474    CRAAPCTVYC   RADSAYLCAG  CDARVHAANR  --VASRHERV  SVCEACERAP   69
SEQ-ID-NO-475    CRAAACTVYC   RADSAYLCAG  CDARVHAANR  --VASRHERV  WVCESCERAP   69
SEQ-ID-NO-457    CHVSSAAVFC   RADAAYLCVG  CDGKVHGANK  --LASRHERV  WMCEVCEVAP   55
SEQ-ID-NO-532    CAVDAARLYC   RLDGAYLCAG  CDARAHGAGS  ----RHARV   WLCEVCEHAP   77
SEQ-ID-NO-466    CKSAAAAIFC   RSDSAFMCLS  CDSRIHSAND  KLYSCRHERV  WMCEVCEQAP   74
SEQ-ID-NO-508    CKLTPAALFC   RSDSAFLCIN  CDSTIHSANK  --LSSRHERV  WMCEVCEQAP   72
SEQ-ID-NO-488    CKSATGTLFC   RADSAFLCVN  CDSKIHAANK  --LASRHARV  WLCEVCEQAP   56
SEQ-ID-NO-494    CKSTKATLFC   RSDSAFLCIT  CDSNLQAANK  --LASRHHRV  TLCEVCEQAP   56
```

Figure 6 (continued)

```
SEQ-ID-NO-1842    PPRPPQLSVL  AAALDASPDL  LPPLPVLADS  AFLLRDQDTP  -SPKPRSPSG   147
SEQ-ID-NO-456     KFLSLKLE--  ---LNTSHEI  NE-NPRSK--  ----KSKKKN  NNKKQSKKKE    94
SEQ-ID-NO-511     AVLECHADSA  ALCITCDAQV  HSANPIAQ--  ----RHQRVP  VLPLPALA--   119
SEQ-ID-NO-498     AVLACHADAA  ALCTACDAQV  HSANPIAQ--  ----RHQRVP  VLPLPAVA--   119
SEQ-ID-NO-478     AAFMCEADDV  SLCTACDLEV  HSANPLAR--  ----RHQRVP  VVPIIGNSCS   115
SEQ-ID-NO-481     AAFFCKADAA  SLCTACDSQI  HSANPLAR--  ----RHQRVP  ILPISGCVAT   106
SEQ-ID-NO-485     AAFFCKADAA  SLCTACDSQI  HSANPLAR--  ----RHQRVP  ILPISGSMV-   105
SEQ-ID-NO-496     AAFLCKADAA  SLCASCDADI  HSANPLAR--  ----RHHRVP  IMPIPGTIYG   108
SEQ-ID-NO-510     AAFLCKADAA  SLCASCDAVI  HSANPLAR--  ----RHHRVP  IMPIPCTLYG   115
SEQ-ID-NO-536     AAFLCKADAA  SLCAACDAEI  HSANPLAR--  ----RHHRVP  ILPISGSMSG   115
SEQ-ID-NO-474     AALLCKADAA  SLCTACDADI  HSANPLAR--  ----RHQRVP  ILPISGCLHG   113
SEQ-ID-NO-475     AALLCKADAA  SLCTACDADI  HSANPLAR--  ----RHQRVP  ILPISGCLHG   113
SEQ-ID-NO-457     AVVTCKADAA  SLCVACDTDI  HSANPLAQ--  ----RHERVP  VTPLFES---    96
SEQ-ID-NO-532     AAVTCRADAA  ALCATCDADI  HSANPLAS--  ----RHLLLP  -TPFFGALAD   120
SEQ-ID-NO-466     AAVTCKADAA  ALCVACDSDI  HSANPLAR--  ----RHERVP  VQPFFDSA--   116
SEQ-ID-NO-508     ASVTCKADAA  ALCVTCDSDI  HSANPLAR--  ----RHERVP  VEPFFDSAES   116
SEQ-ID-NO-488     AHVTCKADDA  ALCVTCDRDI  HSANPLSH--  ----ADERVP  VTPFYDSVNS   100
SEQ-ID-NO-494     AHVTCKADAA  ALCVSCDHDI  HSANPPAS--  ----RHERIP  LNTFHHNS--    98

SEQ-ID-NO-1842    AKNCPSPAPV  ----SSAFRD  FRDPPSSASL  DAVGADELGE  IDFDDDGFNA   193
SEQ-ID-NO-456     PD--------  ----TTPFKE  KKRAETT---  TTLGGGEK--  --EEEQYDTV   125
SEQ-ID-NO-511     ----------  ----IPAASV  FAEAEAA---  TTMYG-----  --DKEEGEEV   145
SEQ-ID-NO-498     ----------  ----IPAASG  FAEAEAS---  VTAHG-----  --DKEEGEEV   145
SEQ-ID-NO-478     SLA-------  ----TANHTT  VTEPEKR---  VVL-------  --VQEDAKET   142
SEQ-ID-NO-481     ----------  ----NHHSSE  TTEPENI---  VVMGQ-----  --EEEDEAEA   132
SEQ-ID-NO-485     ----------  ----TNHSSE  TTETEDI---  VVMGQ-----  --EEEDEAEA   131
SEQ-ID-NO-496     PPAVHTITGG  SMMIGGTTGE  GTEDDGF---  ISLNQDADDT  TIDEEDEDEA   155
SEQ-ID-NO-510     PPAVHTVSGG  SMMIGGTTGE  GTEDDGF---  LSLTQDADDT  TIDEEDENEA   162
SEQ-ID-NO-536     PMA-------  ----NHHPSE  TAMTDTE---  NDMVGREEA   EDEDEDDEEA   151
SEQ-ID-NO-474     SP--------  ----VGPAAG  ETEDRFT---  TQEGEETI--  --SEEEEDEA   144
SEQ-ID-NO-475     SQ--------  ----VGPAAG  ETEDRFT---  -TQEGEETIS  FFFEEEEDEA   147
SEQ-ID-NO-457     ----------  ----ASPLRG  PDFCVLV---  SENGCHDLLK  GCEDASVVEA   129
SEQ-ID-NO-532     P---------  ----POPVPS  PSSAAAT---  ------QEDA  EDDGSNEAEA   148
SEQ-ID-NO-466     ----------  ----DSIVKS  SSFSFLV---  ----PTDPNTG SVCQQEDVET   146
SEQ-ID-NO-508     VVK-------  ----SSSAAA  AAAASFN---  FVVPTDDG--  --YCQDDAEA   148
SEQ-ID-NO-488     ATD-------  ----SVPAVK  SAVNFLN---  DRYFSDVDGE  IEARREEAEA   136
SEQ-ID-NO-494     ----------  ----KQQFFS  ESDPDAD---  ----------  --VSTEEAEA   119
```

Figure 6 (continued)

```
SEQ-ID-NO-1842   DSI LDVGDAA  AGGLDGI MGS  LTVDVESGTA  ARSDDSI LSS  SGI HPYLRRL           243
SEQ-ID-NO-456    AAYLFNSATD   STI SSI HDLL PSS---AATD  VDCGGERNNL   ---SPYDR--            167
SEQ-ID-NO-511    DSWLLLERDS   DDNN-------  --------CTNN I DQYXNLFGY  ---DMYYDKF            180
SEQ-ID-NO-498    DSWLLRRNSD   ----------   --------DNNC ANKI DRYYNL  VGYNMYYDNI            179
SEQ-ID-NO-478    ASWLFPKNSD   YH---------  --------NNNN NQNNELLFS-   ---DDYLDL-            173
SEQ-ID-NO-481    ASWLLPSSVK   NC---------  --------GDNN NNTENNRFSV   G--EEYLDL-            165
SEQ-ID-NO-485    ASWLLPSSLK   NSGDNN-----  --------NNNN NNNSENRFSV   G--DEYVD--            167
SEQ-ID-NO-496    ASWLLLNPPV   K----------  --------NNNK NNNYGMLFGG   EVVDDYLDL-            189
SEQ-ID-NO-510    ASWLLLNPPV   KNNNKNNI NN  N-------NNNQ NNNYGMLFGG   EVVDEYLDL-            206
SEQ-ID-NO-536    ASWLLLNPGK   NS---------  --------GNNN NQNNGFFFDG   EA-DEYLDL-            185
SEQ-ID-NO-474    ASWLLLNPVK   ----------   --------NSKN QNNNGFLFGG   EV-DEYLDL-            176
SEQ-ID-NO-475    ASWLLLNPVK   ----------   --------NSKN QNNNGFLFEG   EV-DEYLDL-            179
SEQ-ID-NO-457    VSWLLPHPKI   ----------   --------STNS I RGSAAADE   MGSSPFHD--            161
SEQ-ID-NO-532    ASWLLPEP--   ----------   --------GDSP EDSAATFFAD   S--DAYLD--            176
SEQ-ID-NO-466    GSWLLPNPKL   TM--------   --------ETNQ VKTGDFFFSD   M--DPFID--            178
SEQ-ID-NO-508    AAWLIPNPNF   GSKLN------  --------ETQD I KTREMFFSD   M--DPFLD--            183
SEQ-ID-NO-488    ASWLLPNPKA   M---------   --------FNPD LNSGQYLFPE   M--DPYMD--            167
SEQ-ID-NO-494    ASWLLQTPAN   P---------   --------KGPD LNSSHYSFTE   I DATDL----           150

SEQ-ID-NO-1842   MVVGLAGRFE   LGLGSQHGAR   PSLNRALKRR   DDDGAWWMWP   AVPVKDLTI A           293
SEQ-ID-NO-456    -------QD    HGSSSSSLLR   TAMRKGASEE   E---------   ----------            190
SEQ-ID-NO-511    S------CN    PGPGEEYRLQ   EQDVQNMYRE   N---------   ----------            204
SEQ-ID-NO-498    T------CD    PRPEEQYRMQ   EQHVQNRYIE   K---------   ----------            203
SEQ-ID-NO-478    -------AD    YNSSMDYKFT   SQYNQPRHKQ   D---------   ----------            196
SEQ-ID-NO-481    -------VD    YSSSIDKRFX   GQ--TNQYQQ   D---------   ----------            186
SEQ-ID-NO-485    ----------   ----------   -LVDYNKYQQ   D---------   ----------            177
SEQ-ID-NO-496    -------AE    YGG--DSQFN   DQYSVNQQQQ   H---------   ----------            210
SEQ-ID-NO-510    -------AE    YGG--DSQFN   DQYSVNQQQQ   H---------   ----------            227
SEQ-ID-NO-536    -------VE    YNSSMENQFS   DQYSQ--YHQ   D---------   ----------            206
SEQ-ID-NO-474    -------VE    Y----NSCTE   NQCSDQYNQQ   H---------   ----------            195
SEQ-ID-NO-475    -------VE    Y----NSCIE   NQCSDQYNQQ   H---------   ----------            198
SEQ-ID-NO-457    -------RP    FSPKPKKQKV   ELPADI FSDV   D---------  ----PFLDL             189
SEQ-ID-NO-532    ----------   ----------   -LDFVRS      M---------   ----------            183
SEQ-ID-NO-466    ----------   ----------   FEYQDSFQQH   D---------   ----------            189
SEQ-ID-NO-508    ----------   ----------   FDYSNFQNN    N---------   ----------            194
SEQ-ID-NO-488    ----------   LDYGHV       DPKLEDAQEQ   N---------   ----------            184
SEQ-ID-NO-494    ----------   ----NFVCV    DAKTDSPEQH   S---------   ----------            166
```

Figure 6 (continued)

| | | | | | | | |
|---|---|---|---|---|---|---|---|
| SEQ-ID-NO-1842 | PPAPPAPPAP | NAAVPQAAAA | AAP------- | -EKKKSKKKK | VVKAMAKGNF | | 335 |
| SEQ-ID-NO-456 | ETTEERWVSY | SEVVEEVMSR | SGT------- | ---------P | RCCGGGDGND | | 224 |
| SEQ-ID-NO-511 | -------EVC | EFAVPSQVGM | ASE------- | -------QPE | SSYGMIGAEQ | | 233 |
| SEQ-ID-NO-498 | -------EGC | ECVVPPQVVM | ASE------- | ------QQES | DYGIIGAGQA | | 233 |
| SEQ-ID-NO-478 | CIVPEKNYSG | DRVVPLQLEE | TRG------- | ------NLRN | KQQNITYGSS | | 233 |
| SEQ-ID-NO-481 | YNVPQRSYVA | DGVVPLQVGV | ANG------- | ------HMHH | EKHNFQFGFT | | 223 |
| SEQ-ID-NO-485 | YNVPQRSYVA | DGVVPLQVGV | LKS------- | ------HMHH | EEHNFQFGFT | | 214 |
| SEQ-ID-NO-496 | YSVPQKSYVE | DSVVPVQNGQ | RKS-----LI | LYQTPQQQQS | HHLNFQLGME | | 255 |
| SEQ-ID-NO-510 | YSVPQKSYVE | DSVVPVQNGQ | RKSLILYHQP | QQQQQQQQS | HHLNFQLGME | | 277 |
| SEQ-ID-NO-536 | CGVPQKSFGG | DGVVPLQVEE | SRG------- | ------QLHH | EQQSFQLAIT | | 243 |
| SEQ-ID-NO-474 | YCVPPKSYGG | DRAVPIQYGE | GKD------- | ------HQQQR | QYHNFQLGLE | | 233 |
| SEQ-ID-NO-475 | YCVPPKSYGG | DRVVPIQYGE | GKD------- | ------HQQQR | QYHNFQLGLE | | 236 |
| SEQ-ID-NO-457 | DDATVTGIQP | DSLVPVHMPE | CSE------- | ------DTDS | LAHSMDPSFT | | 226 |
| SEQ-ID-NO-532 | ---------- | DGIKAGVPV | APS------- | ---------- | -ELDLAGGTL | | 205 |
| SEQ-ID-NO-466 | -------GAM | DSVVPVQTKP | ATI------- | --------SM | INNENCFDVD | | 217 |
| SEQ-ID-NO-508 | ----CSNAMN | DSVVPVQTKP | TPA------- | ------PMVN | HNSECCFDID | | 227 |
| SEQ-ID-NO-488 | SCIT------ | DGVVPEQSKN | MQP------- | -------QLV | NDISFEDFS | | 214 |
| SEQ-ID-NO-494 | ------PGTA | DGVVPVQSHS | KTV------- | ---------- | TEHYSDINND | | 193 |

| | | | | | | |
|---|---|---|---|---|---|---|
| SEQ-ID-NO-1842 | ELLPNAKCKE | EEADASVDDA | AANGDGDSDS | APTNAPKAGL | GLKLDADEVL | 385 |
| SEQ-ID-NO-456 | GRPSLALKLD | YEQ--IMEAW | SDKGTLYVDG | EPF-QTVPDL | ---------- | 261 |
| SEQ-ID-NO-511 | DASMTAGTST | YTA--SISNG | IPFSSMEVGI | IPD-NTRPDV | ---------- | 270 |
| SEQ-ID-NO-498 | -ASVTAMTST | YTA--SISND | LSFSSMEVGI | VPD-NSRPDI | ---------- | 269 |
| SEQ-ID-NO-478 | GS-------Q | YNNNGSINHN | AYNPSMETDF | VPE-QEAPDT | ---------- | 265 |
| SEQ-ID-NO-481 | ---------- | -----NVSSE | ASPIHM-VSL | VPF-SVTSDA | ---------- | 246 |
| SEQ-ID-NO-485 | ---------- | -----NVSSE | ASPIHM-VSL | VPE-STLSET | ---------- | 237 |
| SEQ-ID-NO-496 | YDNSNTGY-G | YPA--SLSHS | VSISSMDVSV | VPF-SAQSET | ---------- | 291 |
| SEQ-ID-NO-510 | YDNSNTGY-G | YPA--SLSHS | VSISSMDVSV | VPE-SALSET | ---------- | 313 |
| SEQ-ID-NO-536 | YGSPGALYGS | YNG--SMNHS | VSMSSMDIVV | VPE-STASDM | ---------- | 280 |
| SEQ-ID-NO-474 | YEPSKAAC-S | YNG--SISQS | VSMSSMDVGV | VPE-STMSEI | ---------- | 269 |
| SEQ-ID-NO-475 | YEPSKAAY-S | YNG--DSQS | VSMSSMDVGV | VPE-STMSEI | ---------- | 272 |
| SEQ-ID-NO-457 | KFPLSAKSGY | SYGISTLTQS | ISCSSLDAAV | VPD-SSLSDI | ---------- | 265 |
| SEQ-ID-NO-532 | FYPEH----- | -----SMNHS | MSTSE-EVAV | VPDALSAGGA | ---------- | 233 |
| SEQ-ID-NO-466 | FCRSKFPTFS | YQTK-SQSHS | VSSSSLEVGV | VPDGNSVSDI | ---------- | 256 |
| SEQ-ID-NO-508 | FCRSKLSSFN | YPSH-SISHS | VSSSSLDVGV | VPDGNTVSEI | ---------- | 266 |
| SEQ-ID-NO-488 | AASKPFVY-G | YHHAQCLRQS | VSSSSMDVSI | VPDDNAMTDD | ---------- | 253 |
| SEQ-ID-NO-494 | FSTSKPFTYN | Y-------NHS | VSSSSLEVGV | VPDGNVMSEM | ---------- | 227 |

Figure 6 (continued)

```
SEQ-ID-NO-1842   KAWSDKGSMF AEGSGPE--L PTSAAEVRAK ---LADIDLF PENGAGGGGV  430
SEQ-ID-NO-456    ---HASADGF NDGGEAGNLW AVPEMETTER ---LWRGH-- ----------  293
SEQ-ID-NO-511    ---S-NTNIQ RTSEAME--L AGHSLQMPVH ---FSSMD-- ----------  299
SEQ-ID-NO-498    ---S-NSNIL TSSEAME--L SGHSLQMPVH ---FSSMD-- ----------  298
SEQ-ID-NO-478    ---T-VSHPK THKGKTA-QL PEPLIQI--- ---LSPMD-- ----------  292
SEQ-ID-NO-481    ---T-VSHPR SPKACTE-EL PFAPVQM--- ---LSPME-- ----------  273
SEQ-ID-NO-485    ---T-VSHPR SPKVATE-EL HDAPVQM--- ---LSPVE-- ----------  264
SEQ-ID-NO-496    ---S-NSHPR PPKGTID-LF SGPPIQIPPQ ---LTPMD-- ----------  321
SEQ-ID-NO-510    ---S-NSHPR PPKGTID-LF SGPPIQIPPQ ---LTPMD-- ----------  343
SEQ-ID-NO-536    ---AVVSQLR APKGTID-LL IGPPIQMMPQ ---LSPMD-- ----------  311
SEQ-ID-NO-474    ---S-ISQHR PPKGTME-LF SSTAIQMPSQ ---LSPMD-- ----------  299
SEQ-ID-NO-475    ---S-ISQHR TPKRIIE-LF SSTAIQMPSQ ---LSPMD-- ----------  302
SEQ-ID-NO-457    ---S-TPYLD SQSSQDM--S ARLPHQTGGP ---IDIVD-- ----------  294
SEQ-ID-NO-532    ---------- --------P APAPSVAVVA ---SKGKE-- ----------  249
SEQ-ID-NO-466    ---S-YTLGR TMGDPSAPIW AATANNQAPP QAQVGGMD-- ----------  290
SEQ-ID-NO-508    ---S-YNFGS ESMVSGGVNS SNQGVQGATQ ---LCGMD-- ----------  297
SEQ-ID-NO-488    ---S-NPYNK SMTSAVE--S SHPAVQ---- ---LSSAD-- ----------  278
SEQ-ID-NO-494    ---SYCGYGR TEAVQ----- ---------- ---ITAAD-- ----------  244

SEQ-ID-NO-1842   REASVLRYKE KRRIRLFSKK RYQVRKVNA DCRPRMKGRF VRSPSL----  476
SEQ-ID-NO-456    REASLLRYKE KRQNRLFSKR RYQVRKLNA EKRPRVKGRF VKREDS----  339
SEQ-ID-NO-511    RDARVLRYKE KKQARTFQKT RYATRXAYA EARPRIKGRF AKRSDIE--H  347
SEQ-ID-NO-498    REARVLRYKE KKQTRKFQKT RYATRKAYA EARPRIKGRF AKRSDIE--H  346
SEQ-ID-NO-478    REARVLRYRE KKKRRKFEKT RYASRKAYA ERRPRINGRF AKMSETE--V  340
SEQ-ID-NO-481    RKARVLRYRE KKKIRKFEKR RYASRKEYA EKRPRIKGRF AKRNEVD---  320
SEQ-ID-NO-485    RKARVMRYRE KKKKRKFEKR RYASRKEYA EKRPRIKGRF AKRNEVD--A  312
SEQ-ID-NO-496    REARVLRYRE KKKNRKFEKT RYASRKAYA ETRPRIKGRF AKRTDVE--A  369
SEQ-ID-NO-510    REARVLRYRE KKKNRKFEKT RYASRKAYA ETRPRIKGRF AKRTDVK--A  391
SEQ-ID-NO-536    REARVLRYRE KKKTRKFEKT RYASRKAYA ETRPRIKGRF AKRTDIE--A  359
SEQ-ID-NO-474    REARVLRYRE KKKTRKFEKT RYASRKAYA ETRPRIKGRF AKRKDVE--V  347
SEQ-ID-NO-475    REARVLRYRE KKKTRKFEKT RYASRKAYA ETRPRVKGRF AKRKDVE--V  350
SEQ-ID-NO-457    REARVLRYKE KRQKRKFFKT RYASRKAYA ESRPRIKGRH AKRTDSD--M  342
SEQ-ID-NO-532    REARLMRYRE KRKNRRFQKT RYASRKAYA ETRPRIKGRF AKRTAEDDAL  299
SEQ-ID-NO-466    REARVLRYRE KRKNRKFFKT RYASRKAYA ESRPRIKGRF AKRNETD--N  338
SEQ-ID-NO-508    REARVMRYRE KRKNRKFEKT RYASRKAYA ETRPRIKGRF AKRTEID--S  345
SEQ-ID-NO-488    REARVLRYRE KRKNRKFEKT RYASRKAYA ETRPRIKGRF AKRIEVE--I  326
SEQ-ID-NO-494    REARVMRYRE KRKNRRFEKT RYASRKAYA ETRPRIKGRF AKRTDLN--M  292
```

Figure 6 (continued)

```
SEQ-ID-NO-1842   --LRQALEEE I---------- ---------- ------   485
SEQ-ID-NO-456    ---------- ---------- ---------- ------   339
SEQ-ID-NO-511    E-LDQMLTI P ALP------- -D-SGHATVL WF----   369
SEQ-ID-NO-498    E-EDHMLSPP ALP------- -DTSSYNTVP WF----   369
SEQ-ID-NO-478    E--DQEYNTM LMY------- CD-TGYGI VP SFYGQK   366
SEQ-ID-NO-481    --ADHALSTM VMF------- -D-TGYGI VP SFS---   342
SEQ-ID-NO-485    EEADKAFSSM VMF------- -D-TGYGI VP SF----   335
SEQ-ID-NO-496    E-VDQMFSTQ LMT------- -D-SNYGI VP SF----   391
SEQ-ID-NO-510    E-VDQMFSTQ LMT------- -D-SSYGI VP SF----   413
SEQ-ID-NO-536    E-VDQAFSTT LMQ------- -E-SGYGI VP SF----   381
SEQ-ID-NO-474    E-DDQMFSST LMA------- -E-TGYGI VP SF----   369
SEQ-ID-NO-475    E-DDRTFSST LMA------- -G-TGCGI VP SF----   372
SEQ-ID-NO-457    E-Q---FGSV DSS------- ----FGVVP SF----   358
SEQ-ID-NO-532    E-QDGPFSPA SSA---HLA SD-GDYGVVP SF----   325
SEQ-ID-NO-466    E-VDHMYNSA SSAATAAAFM YD-NQYGI VP SF----   368
SEQ-ID-NO-508    D-VDRLYNPA DPLSVPSSML MD-CPYGVVP TF----   375
SEQ-ID-NO-488    E-AEPM---- ---------- ---CRYGI VP SF----   340
SEQ-ID-NO-494    N-VN-LI GED ESY------- ...DGYGVVP SC----   312
```

Figure 7

| | | | | | | | |
|---|---|---|---|---|---|---|---|
| SEQ·ID·NO·634 | ---------- | ---------- | -MEESKKY-- | ------KSM | VKQTMNKKKK | | 20 |
| SEQ·ID·NO·637 | MHVKLSLWLK | HFVVTILIYK | YRPPSRPLHH | NSVFISKKAM | EESRSNREQR | | 50 |
| | | | | | | | |
| SEQ·ID·NO·634 | NNNKKGHGSG | SRSGLLQMKV | RRLQILIPGG | QICNHPDLLL | SKTVDYIVHL | | 70 |
| SEQ·ID·NO·637 | KQTKKKTGRG | SGSGSIQIKM | RKLRVLIPGG | RRLNQPDLLL | TKTADYIMHL | | 100 |
| | | | | | | | |
| SEQ·ID·NO·634 | KLKLRFLKAI | SEMYSL- | 86 | | | | |
| SEQ·ID·NO·637 | ELRIRFLKAI | SDIYSLS | 117 | | | | |

Figure 8

```
SEQ-ID-NO-826                ----MDPF YTSFSDSFIS  IPDHRS---P  VSDSSECSPK  -----------  31
SEQ-ID-NO-813                ----MTSF SI--SEMLGS  --EYES---P  VTLGGEYCPK  -----------  28
SEQ-ID-NO-809                ----MNSF SA-FAEMFGS  --FYFS---P  VTVGGDYCPT  -----------  28
SEQ-ID-NO-811                ----MSSF SA-FSEMFGS  --DYES---M  LSSVGDYSPT  -----------  28
SEQ-ID-NO-808                ----MNSF SA-FSEMLGS  --DYE-----  -PQGGDYCPT  -----------  25
SEQ-ID-NO-804                ----MNSF SA-FSEMFGS  --DYES---P  VSSGGDYSPK  -----------  28
SEQ-ID-NO-644                ----MNST SA-FSEMFGS  --DYES---S  VSSGGDYIPT  -----------  28
SEQ-ID-NO-796                ----MNSF SA-FSEMFGS  --DYES---S  VSSGGDYIPT  -----------  28
SEQ-ID-NO-797                ----MNSF SA-FSEMFGS  --DYES---S  VSSGGYYIPT  -----------  28
SEQ-ID-NO-645                ----MNSF SA-FSEMFGS  --DYES---S  VSSGCDYIPT  -----------  28
SEQ-ID-NO-767                ----MDSL SLDYCSVSSP --MSDS----G SGNGASRPPN  ----FSDEDVM 36
SEQ-ID-NO-1843               ----MATL IQ-FNTPYTS LSADNIPTTE  SSSTSDYSTG  -TSFSDEEVM  42
SEQ-ID-NO-834                ----MNTT SPPYSDPHPL VCNWDSLNLP  DSDGGSEELM  -----------  34
SEQ-ID-NO-837     MSLLSVLDEQ ECSYSSVLSD ----SS-I---T SSVTKGVQPG  -AIFSDEEVI  43
SEQ-ID-NO-838                ----MDGC SNYYVDPPGE ----------S SSASDTSRPM  FLTLSDKEVL  35
SEQ-ID-NO-830                ----MNIF ETYNSDSLIS ----------T FSSSSSSSSS  SSLFSEEFII  35
SEQ-ID-NO-840                ----MNIF ETYYSDSLIL --TESS----S SSSSSSFSEE  -------EVI  32
SEQ-ID-NO-832                ----MNIF RSYYSDPLTE ---SSS----S FSDSSIYSPN  RAIFSDEEVI  38
SEQ-ID-NO-835                ----MNIF RSYYSDPLTE ---SSS----S FSDSSIYSPN  RAIFSDEEVI  38
SEQ-ID-NO-831                ----MDIF RSYYSDPLAE ----CS----S ISDSSSSSCN  RANLSDEEVI  37
SEQ-ID-NO-839                ----MDIF RSYYSDPLAE ---Y-S----S LSDSSSSSCN  RANHSDEEVM  37
```

Figure 8 (continued)

| SEQ ID | | | | | | | |
|---|---|---|---|---|---|---|---|
| SEQ-ID-NO-826 | LASSCPKKLA | GRKKFRETRH | PIYRGVRQRN | SGKWVCEVRE | PNKKSRIWLG | 81 |
| SEQ-ID-NO-813 | LAASCPKKPA | GRKKFRETRH | PVYRGVRLRN | SGKWVCEVRE | PNKKSRIWLG | 78 |
| SEQ-ID-NO-809 | LATSCPKKPA | GRKKFRETRII | PIYRGVRRRN | SGKWVCEVRE | PNKKSRIWLG | 78 |
| SEQ-ID-NO-811 | LATSCPKKPA | GRKKFRETRH | PVYRGVRQRN | SGKWVSLRE | PNKKTRIWLG | 78 |
| SEQ-ID-NO-808 | LATSCPKKPA | GRKKFRETRH | PIYRGVRQRN | SGKWVSEVRE | PNKKTRIWLG | 75 |
| SEQ-ID-NO-804 | LATSCPKKPA | GRKKFRETRH | PIYRGVRQRN | SGKWVCELRE | PNKKTRIWLG | 78 |
| SEQ-ID-NO-644 | LASSCPKKPA | GRKKFRETRH | PIYRGVRRRS | SGKWVCEVRE | PNKKTRIWLG | 78 |
| SEQ-ID-NO-796 | LASSCPKKPA | GRKKFRETRH | PIYRGVRRRN | SGKWVCEVRE | PNKKTRIWLG | 78 |
| SEQ-ID-NO-797 | LASSCPKKPA | GRKKFRETRH | PIYRGVRRRN | SGKWVCEVRE | PNKKTRIWLG | 78 |
| SEQ-ID-NO-645 | LASSCPKKPA | GRKKFRETRH | PIYRGVRRRN | SGKWVCEVRE | PNKKTRIWLG | 78 |
| SEQ-ID-NO-767 | LASCYPKKRA | GRKKFRETRH | PVFRGVRRRN | SGKWVCEVRE | PYKKSRIWLG | 86 |
| SEQ-ID-NO-1843 | LASKNPKKRA | GRKKFRETRH | PIYRGVRRRD | SGKWVCEVRE | PNKKTRVWLC | 92 |
| SEQ-ID-NO-834 | LASTHPKKRA | GRKKFRETRH | PVYRGVRRRN | SGKWVCEVRE | PNKTSRIWLG | 84 |
| SEQ-ID-NO-837 | LASRNPKKRA | GRKKFRETRH | PVYRGVRRRN | SGKWVCEVRE | PNKKSRIWLG | 93 |
| SEQ-ID-NO-838 | LASTCPKKRA | GRKKFRETRH | PVFRGVRRRN | SGKWVCEVRE | PNKKTRIWLG | 85 |
| SEQ-ID-NO-830 | LASNNPKRPA | GRKKFRETRH | PIYRGIRKRN | SCKWVCEVRF | PNKKTRIWLG | 85 |
| SEQ-ID-NO-840 | LASNNPKKPA | GRKKFRETRH | PIYRGIRKRN | SGKWVCEVRE | PNKKTRIWLG | 82 |
| SEQ-ID-NO-832 | LASNNPKKPA | GRKKFRETRH | PVYRGVRKRN | SGKWVCEVRE | PNKKSRIWLG | 88 |
| SEQ-ID-NO-835 | LASNNPKKPA | GRKKFRETRH | PVYRGVRKRN | SGKWVCEVRE | PNKKSRIWLG | 88 |
| SEQ-ID-NO-831 | LASNNPKKRA | GRKKFRETRH | PVYRGVRKRN | SDKWVCEVRE | PNKKSRIWLG | 87 |
| SEQ-ID-NO-839 | LASNNPKKRA | GRKKFRETRH | PVYRGVRKRN | SDKWVCELRE | PNKKSRIWLG | 87 |

Figure 8 (continued)

| | | | | | | | |
|---|---|---|---|---|---|---|---|
| SEQ-ID-NO-826 | TFPTVEMAAR | AHDVAALALR | GRSACLNFAD | SAWRLR PES | TCPKEI QRAA | 131 |
| SEQ-ID-NO-813 | TFLTAEI AAR | AHDVAAI AI R | GKSACLNFAD | SAWRLR PET | TCPKEI QKAA | 128 |
| SEQ-ID-NO-809 | TFPTAEMAAR | AHDVAAI ALR | GRSACLNFAD | SAWRLR PES | TCAKD QKAA | 128 |
| SEQ-ID-NO-811 | TFQTAEMAAR | AHDVAAI ALR | GRSACLNFAD | SVWRLR PES | ACAKD QKAA | 128 |
| SEQ-ID-NO-808 | THQI AEMAAR | AHDVAALALR | GRSACLNFAD | SAWRLR PES | TCAKD QKAA | 125 |
| SEQ-ID-NO-804 | TFQTAEMAAR | AHDVAAI ALR | DRSACLNFAD | SAWRLR PES | TCAKE QKAA | 128 |
| SEQ-ID-NO-644 | TFQTAEMAAR | AHDVAALALR | GRSACLNFAD | SAWRLR PES | TCAKDI QKAA | 128 |
| SEQ-ID-NO-796 | TFQTAEMAAR | AHDVAALALR | GRSACLNFAD | SAWRLR PES | TCAKDI QKAA | 128 |
| SEQ-ID-NO-797 | TFQTAEMAAR | AHDVAALALR | GRSACLNFAD | SAWRLR PES | TCAKDI QKAA | 128 |
| SEQ-ID-NO-645 | TFQTAEMAAR | AHDVAALALR | GRSACLNFAD | SAWRLR PES | TCAKDI QKAA | 128 |
| SEQ-ID-NO-767 | TFPTEEMAAR | AHDVAALALR | GRLACLNFAD | SAWRLPVPAS | TDPKDI QKAA | 136 |
| SEQ-ID-NO-1843 | TYPTADMAAR | AHDVAALAMR | GRSACLNFAD | SLWRLPI PES | SNVKDI QKAA | 142 |
| SEQ-ID-NO-834 | TFPTAEMAAR | AHDVAALALR | GRCACLNFAD | SAWRLHVPSS | RDAKDI QKAA | 134 |
| SEQ-ID-NO-837 | TFPTADMAAR | AHDVAALALR | GRSACLNFAD | SAWRLPTPAS | SDAKDI QKAA | 143 |
| SEQ-ID-NO-838 | TFPTAEMAAR | AHDVAALALR | GRSACLNFAD | SARRI PVPAS | SNAKDI QTAA | 135 |
| SEQ-ID-NO-830 | TFPTAEMAAR | AHDVAALALR | GRSACLNFSD | SAWRLPI PAS | SNSKDI QKAA | 135 |
| SEQ-ID-NO-840 | TFPTAFMAAR | AHDVAALALR | GRSACLNFSD | SAWRLPI PAS | SNSKDI QKAA | 132 |
| SEQ-ID-NO-832 | TFPTAEMAAR | AHDVAALALR | GRSACLNFAD | SAWRLPVPAS | SDTKDI QKAA | 138 |
| SEQ-ID-NO-835 | TFPTAEMAAR | AHDVAAI ALR | GRSACLNFAD | SAWRLPVPAS | SDTKDI QKAA | 138 |
| SEQ-ID-NO-831 | TFPSAEMAAR | AHDVAAI ALK | GRSACLNFAD | SAWKLPI PAS | TDAKDI QKAA | 137 |
| SEQ-ID-NO-839 | TFPSAEMAAR | AHDVAAI ALR | GRSACLNFAD | SAWKLPI PAS | TDAKDI QKAA | 137 |

Figure 8 (continued)

| | | | | | | | | |
|---|---|---|---|---|---|---|---|---|
| SEQ-ID-NO-826 | AEAAMAFQNK | TATTETTMVE | AVKPAEETVG | QTCCETMEFN | GVFYMAEEAV | 181 |
| SEQ-ID-NO-813 | AEAALAFQAE | I-NNTTTD-H | GLD-MEETIV | EAIFT-EENN | DVFYMDEESM | 174 |
| SEQ-ID-NO-809 | AEAAVAFQAE | M-SDTMTSDH | GLD-MEETTV | EVIVTEEEQS | EGFYMDEEAM | 176 |
| SEQ-ID-NO-811 | AEAALAFQNE | LMSDTATTDH | GLD-MEETLV | EAIVTAEQI- | DTFYIDEETM | 176 |
| SEQ-ID-NO-808 | AEAALAFQDE | T-CDTTTTNIH | GLD-MQETMV | EAIYTPEQSE | GAFYMDEEIM | 173 |
| SEQ-ID-NO-804 | AEAALNFQDE | M-CHMTTDAH | GLD-MEETLV | EAIYTPEQSQ | DAFYMDEEAM | 176 |
| SEQ-ID-NO-644 | AEAALAFQDE | M-CDATTD-H | GFD-MECTLV | EAIYTAEQSE | NAFYMHDEAM | 175 |
| SEQ-ID-NO-796 | AEAALAFQDE | M-CDATTD-H | GSD-MEETLV | EAIYTAEQSE | NAFYMHDEAM | 175 |
| SEQ-ID-NO-797 | AEAALAFQDE | M-CDATTD-H | GFD-MEETLV | EAIYTAEQSE | NAFYMHDEAM | 175 |
| SEQ-ID-NO-645 | AEAALAFQDE | M-CDATTD-H | GFD-MEETLV | EAIYTAEQSE | NAFYMHDEAM | 175 |
| SEQ-ID-NO-767 | AEAAEVFRPV | DSAGDSSK-- | ----TAEN-- | TAVEGTKESE | EVFFLDEEAV | 178 |
| SEQ-ID-NO-1843 | VKAAEAFRPT | E-TDVAV---- | ----IEES-- | -----NELTG | NVFCVDDESI | 177 |
| SEQ-ID-NO-834 | AEAALAFRPM | E-NDGVMQ--- | ----DER--- | REESEVRTPD | NVFVMDEEDV | 174 |
| SEQ-ID-NO-837 | ACAAEAFRPE | GSLGVELTRT | GDE-VEKV- | -----AGTAAG | DVFYMDDDAD | 186 |
| SEQ-ID-NO-838 | TEAAEAFRPT | EESDEVCG-- | ----SPVAAP | SESTSASEQQ | QVFYMDEEAV | 179 |
| SEQ-ID-NO-830 | AEAAEITRPL | KESEEVSG-- | ----ESDNST | SPETSENVQE | SSDFVDEEAI | 179 |
| SEQ-ID-NO-840 | AOAVEIFRSE | EVSGESPE-- | ----------- | ---TSENVQE | SSDFVDEEAI | 167 |
| SEQ-ID-NO-832 | AEAAEAFRPL | KLEGISKE-- | ----------- | ---SSSSTPE | SMFFMDEEAL | 173 |
| SEQ-ID-NO-835 | AEAAEALRPL | KLEGISKE-- | ----------- | ---SSSSTPE | SMFFMDEEAL | 173 |
| SEQ-ID-NO-831 | AEAAEAFRSS | E-AENMPEYS | GED-TKEV-- | -----NSTPE | NMFYMDEEAL | 178 |
| SEQ-ID-NO-839 | AEAAEAFRSS | E-AENMPEYS | GED-TKEV-- | -----NSTPE | NMFYMDEEAL | 178 |

Figure 8 (continued)

```
SEQ-ID-NO-826    LGMPRFLENM GEEMLLPPPE -LGWN----N -DLAG-DADV SLWSF--  220
SEQ-ID-NO-813    LEMPALLASM AEGMLLPPPS -VHFGH---N YDFDG-DADV SLWSY--  214
SEQ-ID-NO-809    FGMPRLLANM AEGMLLPPPS -VQWGI---N YDCDG-DADV SLWSY--  216
SEQ-ID-NO-811    FGMPSLVANM AEGMLLPLPS -IQWI N---N YDVEG-DADM PLWSY--  216
SEQ-ID-NO-808    FGMPTLLDNM AEGMLLPPPS -VQWNH---N YDGEG-DGEV PLWSY--  213
SEQ-ID-NO-804    LGMSSLLDNM AEGMLLPSPS -VQWNY---N FDVKG-DDDM SLWSY--  216
SEQ-ID-NO-644    FEMPSLLANM AEGMLLPLPS -VQWNH---N HEVDGDDDDV SLWSY--  216
SEQ-ID-NO-796    FEMPSLLANM AEGMLLPLPS -VQWNH---N HEVDGDDDDV SLWSY--  216
SEQ-ID-NO-797    FEMPSLLANM AEGMLLPLPS -VQWNH---N HEVDGDDDDV SLWSY--  216
SEQ-ID-NO-645    FEMPSLLANM AEGMLLPLPS -VQWNH---N HEVDGDDDDV SLWSY--  216
SEQ-ID-NO-767    FGREKFLANM AAGMMMSPPH -SGYEK--DE QELEFVDDCV QLWSYSI   222
SEQ-ID-NO-1843   FEMQGFLADM AEGMMLPPPR TIEYDN---C QDDLEFFVDA SLWSF--  219
SEQ-ID-NO-834    FGMPGLLVNM AEGLLMPPPH SVADGY---G GDDMAADADM SLWSYSI   218
SEQ-ID-NO-837    FGMPGLLANI AEGMLLPPPN CCGYSGGDSL DNMENNDTDM SLWSFSV   233
SEQ-ID-NO-838    FGMPGLLADM AEGMLLPPPH ---YSD---D DDVDV-CADV PLWSFSI   219
SEQ-ID-NO-830    FFMPGLLANM AEGLMLPPPQ -CAEMG---D HYVET DAYMI FLWNYSI   222
SEQ-ID-NO-840    FFMPGLLANM AEGLMLPPPQ -CAEMG---D HCVET DAYMI FLWNYSI   210
SEQ-ID-NO-832    FCMPGLLTNM AEGLMLPPPQ -CAFIG---D H-VETADADT PLWSYSI   215
SEQ-ID-NO-835    FCMPGLLTNM AEGLMLPPPQ -CAEIG---D H-VETADADT PLWSYSI   215
SEQ-ID-NO-831    FCMPGLLANM AEGLMLPPPQ -CSQIG---D HMED--DFDM PLWSYSI   219
SEQ-ID-NO-839    FFMPGLLVNM AEGLMLPPPQ -CSQIG---D HMEA--DVDM PLWSYSI   219
```

Figure 9

```
SEQ-ID-NO-850                 MEKS-----  ----------  PRYRD-----  ----------  -------KA    11
SEQ-ID-NO-881                 MEPCTKQ--  ------FLPM  P-PQDPNSPS  SSTSSSSSSS  TSPSHPYHRA   40
SEQ-ID-NO-895                 MEVSTKQ--  ------LLPM  PHQQDPNSPS  SSISSSSSSS  TSPSHPHHRA   41
SEQ-ID-NO-885                 MEVAPAV--  ------KQLL  PMARCPNSPS  SSTTSSSPSP  SAA.......   34
SEQ-ID-NO-898                 ---------  ----------  -MAHDPNSPS  SSTSSSPSS   AAAAAASSSPS  29
SEQ-ID-NO-876        MDSIS--  ---  ----------  PKPQENNNNN  NNNI------  ----------   19
SEQ-ID-NO-877        MDSTSSMRYQ  FFQKSSLTSL  PSPKTQSNGH  NHSHNQIPSP  RPISLPSPKT   50
SEQ-ID-NO-853                 METSPRQTT  NPN---FLAS  PKSLSPNSST  SSTSSGS---  --------NT   35
SEQ-ID-NO-857                 METSPRHRD  NQNPQSLFPS  PTSYSSSSNS  NSNSSSTTAT  TNNVALNNNI   49

SEQ-ID-NO-850        ------KNL  LPSPSSCF--  ------TTP-  --TRYVKDDM  YETTFIRTDP   43
SEQ-ID-NO-881        ------QPP  HPHNLPPS..  ....PRP---  -VPRTIETTP  FPTTFVQADT   73
SEQ-ID-NO-895        ------Q--  -PHNLPPS--  ------PRP-  -IPRTIDTTP  FPTTFVQADT   71
SEQ-ID-NO-885        ------APS  PPPRQQQS--  -----QAP--  -VPRIDTTP   FPTTFVQADT   67
SEQ-ID-NO-898        ------SHR  PPPPPPSSSS  QPALPPSPRT  VVPRTIDTTP  FPTTFVQADT   72
SEQ-ID-NO-876        ---------  ----------  -----PKP--  -MTRSEPANS  YPTTFVQADT   41
SEQ-ID-NO-877        QTQSNGHNHN  HNHNQIPS--  ------PRP-  -ITRSEPGNP  YPTTFVQADT   90
SEQ-ID-NO-853        ------NPP  PPTPPPQQ--  ------PKP-  -ITRSESANP  YPTTFVQADT   68
SEQ-ID-NO-857        ------NHP  PPLPS-----  ------PKP-  -ISRSESTNP  YPTTFVQADS   79

SEQ-ID-NO-850        SSFKQVVQLL  TGIPK-----  ----------N  PTHQPDPRFP  PFHSIPP KA   79
SEQ-ID-NO-881        TSFKQIVQML  TGSEQS----  ----------S  KSAAAATTNG  SAGNQAASGS  110
SEQ-ID-NO-895        TSFKQVVQML  TGAEQPTKND  ----------A  TTAAAAPAGN  GGGGQAA---G 110
SEQ-ID-NO-885        ASFKQVVQRL  TGSD------  ----------T  PPPAQKPAKT  HGHHHHH--G  100
SEQ-ID-NO-898        ASFKQVVQML  TGSD------  ----------T  TPPSQRPPAK  SNHHQHHHSG  107
SEQ-ID-NO-876        TSFKQVVQML  TGSSETAK--  ---QAAAAAA  AASSSSSSSK  PANPIPPMKS   86
SEQ-ID-NO-877        TSFKQVVQML  TGSSET----  ----------A  KQASTSTKAN  HNHNIPP---  124
SEQ-ID-NO-853        SSFKQVVQML  IGSSEIAK--  ----LASSTK  PTPSPLSDSN  LKTHIPPIKS  112
SEQ-ID-NO-857        SSFKQVVQML  TGSPKPKPTC  TTTTTTTTTT  PNTSQVDPLP  KTHNIPPIKS  129

SEQ-ID-NO-850        VTNKKDSSSF  -RLSERRNS-  --MKHYLNIN  PTH-------S  CP--------  111
SEQ-ID-NO-881        GPCRPKKPSF  -KLYERRSS-  LKNLKMIA    PLA-------M  GAPPSPRNAS  150
SEQ-ID-NO-895        GPCRPKKPSF  -KLYERRSS-  --MKNLKMIA  PLA-------M  CPPPSPRR--  148
SEQ-ID-NO-885        GGVGPKKPAF  -KLYERRIG-  ---KNNLKMIA PL--------A  CPSPSPRK--  137
SEQ-ID-NO-898        APCRPKKQAF  -KLYERRSGV  --HKNFKMIA  PLAMAAAAAA  GASSSPRK--  152
SEQ-ID-NO-876        IPNKKQQPHF  SKLYERRINS  INERNSLHIN  PLTSFF----S  NHTNSPRK--  131
SEQ-ID-NO-877        ----KKQQGI  -KLYERRNS-  --FHKNLNIN  PLLPPIF---S  NSTFSPRNK-  163
SEQ-ID-NO-853        IPKNKQNSGF  -RLYERRSS-  ---LKNLKIN  PLNPAFGS-N  NSCFSPRK--  154
SEQ-ID-NO-857        MPKKNQSSGF  -KLYERRNS-  --LKNLKIN   PLNPIFAQ-P  SSGFSSRK--  171
```

Figure 9 (continued)

| SEQ-ID-NO | | | | | | | |
|---|---|---|---|---|---|---|---|
| SEQ-ID-NO-850 | ------PEIL | TPTILNFPAL | DL-SPDTPLM | SDPFYRPGSF | SQSP---SDSK | | 152 |
| SEQ-ID-NO-881 | AA----PFII | SPSVLDFPSL | KLSSPVTPLT | GDPFFPSPAS | SSGD------ | | 190 |
| SEQ-ID-NO-895 | AA----PEIL | SPSVLDFPSL | RLSSPVTPLT | GDPFNRSPAS | TSSS------ | | 188 |
| SEQ-ID-NO-885 | AA----PEVL | SPSVLDFPSL | ALCSPVTPLL | ADPFNRSASA | SPGE------ | | 177 |
| SEQ-ID-NO-898 | AAQHQQQEAL | SPSVLDFPSL | AL-SPVTPLV | ADPFNRSPAS | ASSS------ | | 195 |
| SEQ-ID-NO-876 | ------ADIL | SPSILDFPAL | VL-SPVTPLI | PDPFDRSNAA | DSE------ | | 168 |
| SEQ-ID-NO-877 | -------QEIL | SPSILDFPSL | VL-SPVTPLI | PDPFNRSGSS | SSSAARNGS | | 206 |
| SEQ-ID-NO-853 | ------PEIL | SPSILDFPSL | AL-SPVTPLI | PDPFDRSCSC | NYTNCINNNV | | 197 |
| SEQ-ID-NO-857 | ------PEIL | SPSILDFPAL | VL-SPVTPLI | PDPFDRSGSA | KYIN------ | | 208 |

| SEQ-ID-NO-850 | PSFDDDQERS | IKEKGFYLRP | SPST--TPRD | TEPRLLSLFP | MTPIHSPAPS | 200 |
|---|---|---|---|---|---|---|
| SEQ-ID-NO-881 | ----AAERAA | IADKGFFFHP | SPRGA-EP-- | --PRLLPLFP | VSSPRMAAAS | 231 |
| SEQ-ID-NO-895 | ---EEAERAA | IAERGFFLHP | SPRGA-EP-- | --PRLLPLFP | VTSPRMAAPA | 230 |
| SEQ-ID-NO-885 | --QDEAFAAA | IAQRGFFLHP | SPRGAVEP-- | --PRLLPLFP | VTSPKMAQ-- | 219 |
| SEQ-ID-NO-898 | -ASPEEEAAA | IAQKGFFLHP | SPRSA-EP-- | --PRLLPLFP | VTSPRVASSS | 239 |
| SEQ-ID-NO-876 | -----AFVKA | KEKGFFLHP | SPRD-----K | AQPLLLPLFP | TTSPRASSGP | 208 |
| SEQ-ID-NO-877 | SLDSLACDKA | IREKGFFLHP | SPRAASTSRD | SEPRLLPLFP | TSSPRASGPS | 256 |
| SEQ-ID-NO-853 | NLDKEAEEKA | IKEKGFYLHP | SPAS--TPRD | SEPRLLPLFP | VTSPRVSGSS | 245 |
| SEQ-ID-NO-857 | -----KEKA | IKEKGFYLHP | SPGS--SPRE | TEPRLLPLFP | ITSPRISGSV | 250 |

| SEQ-ID-NO-850 | ----PHD--- | -----H | 204 |
|---|---|---|---|
| SEQ-ID-NO-881 | ATAAPAE--- | ------ | 238 |
| SEQ-ID-NO-895 | AA--PSE--- | ------ | 235 |
| SEQ-ID-NO-885 | ---------- | ------ | 219 |
| SEQ-ID-NO-898 | SSSAAAAVAV | ASPSFE | 255 |
| SEQ-ID-NO-876 | SSSAPPS--- | ------ | 215 |
| SEQ-ID-NO-877 | SSSKYSAS-- | ------ | 264 |
| SEQ-ID-NO-853 | TS-------- | ------ | 247 |
| SEQ-ID-NO-857 | N-- PSS--- | ------ | 254 |

Figure 10

```
SEQ-ID-NO-948                                                                                                     0
SEQ-ID-NO-950   ----------  ----------  ----------  ----------  ----------  ----------                            0
SEQ-ID-NO-932   ------MEG   E-------D   DGQ KLQQQQ  SPCSDNFSLA  AA------SS                                       29
SEQ-ID-NO-931   -------MDA  A---------  -GQ KLQQQH  QPPCSDNNFS  LLAAAADSSS                                       33
SEQ-ID-NO-1844  ------MER   V-------D   DCQ KLQQQ-  QPPCSD-NFS  LAGAA---SS                                       30
SEQ-ID-NO-911   M------WNP  KQTQE----E  DDSWEVRAFA  EDT-GN NG-  --------TT                                       30
SEQ-ID-NO-907   MNGGAWMWNP  NKI EELE-DD DESWEVKAFE  QDTKCN SC-  --------TT                                       40
SEQ-ID-NO-922   M------WNH  SKNEELE-DD  DESWEVKAFE  QDTKCN YG-  --------TT                                       34
SEQ-ID-NO-923   M------WNP  SKVERLE-DD  DFSWFVKAFE  QDTKCN SC-  --------TT                                       34
SEQ-ID-NO-929   ------MHE   M-------T   DPALS YNFL  SREGAKRHY-  --------PP                                       26
SEQ-ID-NO-936   ---------M  EQELSLELTL  LHPSAS----  --------PP                                                   19
SEQ-ID-NO-947   ------MKS   RLSSRLPWQQ  EEELDLELSL  LPGDSDTE--  ----------                                       31

SEQ-ID-NO-948   ----------  ----------  ----MSQETS  KDEVI GGRSP  SGDGDKAEEE                                       26
SEQ-ID-NO-950   ----------  ----------  ----MSQKTS  KDEVI GGRSP  SGDGDKAEEE                                       26
SEQ-ID-NO-932   W--LPPQVRS  -----SSSSY  TCGYCKKEFR  SAQGLGGHMN  IHRLDRA--R                                       70
SEQ-ID-NO-931   W--PPPQVRS  PPSSSSSSSY  TCGYCKKEFR  SAQGLGGHMN  VHRLDRA--R                                       79
SEQ-ID-NO-1844  WPAPPPQVRS  SP----SSSSY TCGYCKKEFR  SAQGLGGHMN  VHRLDRA--R                                       75
SEQ-ID-NO-911   W--PPR----  -----S---Y  TCTFCRREFR  SACALGGHMN  VHRRDRA--R                                       64
SEQ-ID-NO-907   W--PPR----  -----S---Y  TCNFCRREFR  SAQALGGHMN  VHRRDRASSR                                       76
SEQ-ID-NO-922   W--PPR----  -----S---Y  TCNFCRREFR  SAQALGGHMN  VHRRDRA--SK                                      69
SEQ-ID-NO-923   W--PPR----  -----S---Y  ACNFCRREFR  SAQALGGHMN  VHRRDRA--SK                                      69
SEQ-ID-NO-929   L--PPP----  -----STRTF  QCHFCHRKFY  SSQALGGHQN  AHKLERA--A                                       63
SEQ-ID-NO-936   E--PPC----  -----Y---F  VCMYCDRKFF  SSQALGGHQN  AHKYERS--L                                       53
SEQ-ID-NO-947   ---PPC----  -----F---F  RCTYCDRKFY  TSQALGGHQN  AHKYERT--L                                       64

SEQ-ID-NO-948   LREARSG---  ----------  ----------  ----------  ----------                                       33
SEQ-ID-NO-950   LREARSG---  ----------  ----------  ----------  ----------                                       33
SEQ-ID-NO-932   LI HQQCI---  SHRI-APHPN  PNPSCTVLDL  EL----SLSSL  LAHGAA-SSD                                     112
SEQ-ID-NO-931   LI HQQYVSSS  SHRTAPPPSN  PNPSCAVLDL  GL----SLSSL  LARGG--GDG                                     124
SEQ-ID-NO-1844  LI HQQYM---  SHRI DAPPPN PNPSCTVLDL  GL----SLSSL  LARGGAAGSN                                     119
SEQ-ID-NO-911   LHQTQPG---  SI NPNSSTSS S---------  ------SSSTF  I I PTQEFPPN                                    97
SEQ-ID-NO-907   AHQGSTV     AAAARSGHGG  -----MLENS  CAFPLPTTTI  I I QSTA-SNI                                    117
SEQ-ID-NO-922   AHQGPAV     -----RSGGCS GGGRTTFLSS  CVF---PSITL  I I QSTA-SNS                                   109
SEQ-ID-NO-923   AHQGPAA---  AVAARSGGRS  RGGKKTFLNS  CVI ---PTATL  I I QSTA-SNN                                  113
SEQ-ID-NO-929   ARRSTKP---  LHNFHHHH-H  NNNNGSHPS   SL----I IDL  RPKPKPQKES                                     107
SEQ-ID-NO-936   AKRRREI---  AAALRAHGAA  ATATGAPEDD  AAA--AMGSR  DVPARPQGTG                                       98
SEQ-ID-NO-947   AKRRREI---  AAAFNAGGAG  R---------  --------AI  SMAAGA-ETV                                       93
```

Figure 10 (continued)

| SEQ-ID-NO-948 | | | | | | 33 |
|---|---|---|---|---|---|---|
| SEQ-ID-NO-950 | | | | | | 33 |
| SEQ-ID-NO-932 | GGLPVPVAKL | AGN------- | ---------- | ---------- | ---RFSSASS | 132 |
| SEQ-ID-NO-931 | GGLPVPLEKQ | LGD------- | ---------- | ---------- | ---RFSSASS | 144 |
| SEQ-ID-NO-1844 | GGLPAVPLEK | MGN------- | ---------- | ---------- | ---RFSSTAS | 139 |
| SEQ-ID-NO-911 | AGLCLLYQLP | NPNGVFTPAT | MNACATDSPS | TLLSITPYPH | NNLIEKSLNF | 147 |
| SEQ-ID-NO-907 | EGLSHFYQLQ | NPSGIFG--- | -----NSGDMV | NLYGTTSFPP | SNLPFSMLNS | 160 |
| SEQ-ID-NO-922 | EGESHFNQLQ | NPNGMFG--- | -----NSSDMV | NFYGTTPFPS | SNLEFSLLNS | 152 |
| SEQ-ID-NO-923 | EGLSHFYQLQ | NPNSMFG--- | -----HSSDTV | NFYGSSSFPS | SNLDFSVLNS | 156 |
| SEQ-ID-NO-929 | ARFFHNYPLL | EVE------- | ---------- | ---------- | ---PFHQLH- | 126 |
| SEQ-ID-NO-936 | TGVVVEDES | ATR------- | ---------- | ---------- | ---MMDKQKA | 118 |
| SEQ-ID-NO-947 | GARPRLEDAL | APE------- | ---------- | ---------- | ---------- | 106 |

| SEQ-ID-NO-948 | | | -DDDDDEAG | TRQPYNCT-- | | 50 |
|---|---|---|---|---|---|---|
| SEQ-ID-NO-950 | | | -DDDDDEAG | TRQPYNCT-- | | 50 |
| SEQ-ID-NO-932 | SAA------- | ------TKDV | EGKNLELRIG | ACSH-GDGAE | ERLDLQLRLG | 168 |
| SEQ-ID-NO-931 | AAATN----- | ------DYYS | EVKNLELRMC | ACSHGGDGTE | ERLDLQLRLG | 183 |
| SEQ-ID-NO-1844 | AAT------- | ------NDYS | EGKTLELRMG | ACSHGGDGTE | ERLDLQLRLG | 176 |
| SEQ-ID-NO-911 | LVAPPEINTS | HCYSIKAFPS | ASIDNSNN N | SDNNFKELAH | EELDLELRLG | 197 |
| SEQ-ID-NO-907 | PVEVPP---- | ---RLIEYST | GDDESIGSMK | EATGTSVD-- | -ELDLELRLG | 200 |
| SEQ-ID-NO-922 | SVEVPP---- | ---RLIQYPT | GDDEKAGSMK | ETIRTSVN-- | -EPDLELRLG | 192 |
| SEQ-ID-NO-923 | PVEVPP---- | ---RFIEYST | GDDESIGSMK | ETKRTSVG-- | -LPDLELRLG | 196 |
| SEQ-ID-NO-929 | ---------- | --------A | GTSITSHEYD | TPPPAEPSDH | ANLDLTLRL- | 156 |
| SEQ-ID-NO-936 | PAA------- | ------DDDA | PATASSSNMK | RSSLYGYG-V | EELDLSLRL- | 153 |
| SEQ-ID-NO-947 | ---------- | --------RS | SRILLRDKKG | SSEHGGVERA | DELDLSLRL- | 137 |

| SEQ-ID-NO-948 | | | | | FCRRGFPTAQ | 60 |
|---|---|---|---|---|---|---|
| SEQ-ID-NO-950 | | | | | FCRRGFPTAQ | 60 |
| SEQ-ID-NO-932 | YS-------- | ---------- | ---------- | ---------- | ---------- | 170 |
| SEQ-ID-NO-931 | Y--------- | ---------- | ---------- | ---------- | ---------- | 184 |
| SEQ-ID-NO-1844 | Y--------- | ---------- | ---------- | ---------- | ---------- | 177 |
| SEQ-ID-NO-911 | HRS------- | ---------- | ---------- | ---------- | ---------- | 200 |
| SEQ-ID-NO-907 | HHPPMEANHL | EDSKSSSEET | DKSEQSIDDM | RTGRRSYECV | FCKRGFSTAQ | 250 |
| SEQ-ID-NO-922 | HKP------- | ---------- | ---------- | ---------- | ---------- | 195 |
| SEQ-ID-NO-923 | HNP------- | ---------- | ---------- | ---------- | ---------- | 199 |
| SEQ-ID-NO-929 | ---------- | ---------- | ---------- | ---------- | ---------- | 156 |
| SEQ-ID-NO-936 | ---------- | ---------- | ---------- | ---------- | ---------- | 153 |
| SEQ-ID-NO-947 | ---------- | ---------- | ---------- | ---------- | ---------- | 137 |

Figure 10 (continued)

| SEQ ID | 60 | 70 | 80 | 90 | 100 | |
|---|---|---|---|---|---|---|
| SEQ-ID-NO-948 | ALGGHMNVHR | KDRVGRATPS | SSSSTTAAAA | RRSVSYDTLV | GLFLPPASGG | 110 |
| SEQ-ID-NO-950 | ALGGHMNVHR | KDRVGRATPS | SSSSTTAAAA | RRSVSYDTLV | RLFRPPASGG | 110 |
| SEQ-ID-NO-932 | ---------- | ---------- | ---------- | ---------- | ---------- | 170 |
| SEQ-ID-NO-931 | ---------- | ---------- | ---------- | ---------- | ---------- | 184 |
| SEQ-ID-NO-1844 | ---------- | ---------- | ---------- | ---------- | ---------- | 177 |
| SEQ-ID-NO-911 | ---------- | ---------- | ---------- | ---------- | ---------- | 200 |
| SEQ-ID-NO-907 | ALGGHMNIHR | KDRVKSRPSS | VPIVSLSGNK | ADDKNYPSFR | PYSYPPIHSY | 300 |
| SEQ-ID-NO-922 | ---------- | ---------- | ---------- | ---------- | ---------- | 195 |
| SEQ-ID-NO-923 | ---------- | ---------- | ---------- | ---------- | ---------- | 199 |
| SEQ-ID-NO-929 | ---------- | ---------- | ---------- | ---------- | ---------- | 156 |
| SEQ-ID-NO-936 | ---------- | ---------- | ---------- | ---------- | ---------- | 153 |
| SEQ-ID-NO-947 | ---------- | ---------- | ---------- | ---------- | ---------- | 137 |

| SEQ ID | | | | | | |
|---|---|---|---|---|---|---|
| SEQ-ID-NO-948 | SEDAAASTAA | GGGCSLRSRT | AEPAPQELRL | FGRGAGRREE | GGGRDRRDRY | 160 |
| SEQ-ID-NO-950 | SEDAAASTAA | GGGASLRSRT | AEPAPQELRL | FGRGAGRREE | GGGRDRRDRY | 160 |
| SEQ-ID-NO-932 | ---------- | ---------- | ---------- | ---------- | ---------- | 170 |
| SEQ-ID-NO-931 | ---------- | ---------- | ---------- | ---------- | ---------- | 184 |
| SEQ-ID-NO-1844 | ---------- | ---------- | ---------- | ---------- | ---------- | 177 |
| SEQ-ID-NO-911 | ---------- | ---------- | ---------- | ---------- | ---------- | 200 |
| SEQ-ID-NO-907 | QPHYSIAPEV | --------HV | SYQAFLPVSG | WGFRLPPHTA | QLFVDNSKHR | 342 |
| SEQ-ID-NO-922 | ---------- | ---------- | ---------- | ---------- | ---------- | 195 |
| SEQ-ID-NO-923 | ---------- | ---------- | ---------- | ---------- | ---------- | 199 |
| SEQ-ID-NO-929 | ---------- | ---------- | ---------- | ---------- | ---------- | 156 |
| SEQ-ID-NO-936 | ---------- | ---------- | ---------- | ---------- | ---------- | 153 |
| SEQ-ID-NO-947 | ---------- | ---------- | ---------- | ---------- | ---------- | 137 |

| SEQ ID | | | | | |
|---|---|---|---|---|---|
| SEQ-ID-NO-948 | GCCSKDGDGN | GGHDHGEEEE | LDLELRLGGS | GSAGS | 195 |
| SEQ-ID-NO-950 | GCCSKDGDGN | GGHDHGEEEE | LDLELRLGGS | GSAGS | 195 |
| SEQ-ID-NO-932 | ---------- | ---------- | ---------- | ----- | 170 |
| SEQ-ID-NO-931 | ---------- | ---------- | ---------- | ----- | 184 |
| SEQ-ID-NO-1844 | ---------- | ---------- | ---------- | ----- | 177 |
| SEQ-ID-NO-911 | ---------- | ---------- | --------TT | PPPSS | 207 |
| SEQ-ID-NO-907 | NPFGEDDHEN | KKADGYNDKE | DELDLFIRLG | HDP-- | 375 |
| SEQ-ID-NO-922 | ---------- | ---------- | ---------- | --P-- | 196 |
| SEQ-ID-NO-923 | ---------- | ---------- | ---------- | --P-- | 200 |
| SEQ-ID-NO-929 | ---------- | ---------- | ---------- | ----- | 156 |
| SEQ-ID-NO-936 | ---------- | ---------- | ---------- | ----- | 153 |
| SEQ-ID-NO-947 | ---------- | ---------- | ---------- | ----- | 137 |

Figure 11

```
SEQ-ID-NO-1005   MESLS----- -----SKKRV RNSD------ ------ESVVD SVFAKRI---        26
SEQ-ID-NO-953    MEKKLLDITR TDSA-EKKRV RDESFD---- ------EAVLD SPLVKRLR-D        39
SEQ-ID-NO-971    MAEETLTRTD SALPTDKKRV RDES-D---- ------GAVLD SPEVKRLR-D        39
SEQ-ID-NO-963    MEELLN---- -----HKKRV RDGS-D---- ------ESDLD FPEVKKIR-D        30
SEQ-ID-NO-955    MDELN----- -----SKKRA RDDS-N---- ------ESGLD SPDVKRLR-D        29
SEQ-ID-NO-977    MD-------- -----CKKRV RDDS-D---- ------ESVLE SPEAKRLR-D        26
SEQ-ID-NO-979    MD-------- -----CKKRV RDDS-D---- ------ESILE SPEAKRLR-D        26
SEQ-ID-NO-999    MEDSR----- -----DRKRR RDEAEE---- ---------QE SPEAKRLRDD        28
SEQ-ID-NO-985    MESSSSSLLL SSYAGNNKRA RDADLE---- ------VCSSAE AEAAKRMRPE       42
SEQ-ID-NO-995    MESSSSSLLL SSYIGGNKRA READLD---- ------VASSAE AEAAKRIRPE       42
SEQ-ID-NO-1015   MDSSNNNN-- -----NNKRA RDAE-D---- ---------E ADEAKRLRAE        29
SEQ-ID-NO-1009   MESS------ -----SHKRA REAA-D---- LAAAGDCALP E---KRLRPE        31
SEQ-ID-NO-991    METS------ -----SHKRA REAV-D---L AAAAGEAVWP EADAKRLRPQ        35
SEQ-ID-NO-993    METS------ -----SHKRA REAV-DLAAA AAAAGEAVWP ESDAKR.RPQ        38

SEQ-ID-NO-1005   -LLDILDDSD VC-TPSHDLD SFMKTFQDEI SPSPAPEF-- -TG---SST         68
SEQ-ID-NO-953    DLFDVLDDSD PE-PVSQDLD SVMKSFEDEL STVTTTTA-- -QG---SSTA        82
SEQ-ID-NO-971    DLFDVFDDSD PE-PVSQDLD SVMKSFEDEL SS-------- ------AQPR        74
SEQ-ID-NO-963    DLFGLLDDSD PD-SLGQDLD SVMKSFEQEI SASSSSPV-- -PVVDLTSES       76
SEQ-ID-NO-955    DLF--LDDSD SL-PLNQDLA SVMKSFEEEI SAVPSTSTES MPVVDLTSDS        76
SEQ-ID-NO-977    DLLEFFDDAD DA-PSSQDLD SVMKSLQEEI SCV------- ------ASDS        62
SEQ-ID-NO-979    DLLEFFDDAD DA-ASTQDLD SVMKSLQEEI SGV------- ------TSDY        62
SEQ-ID-NO-999    LFLDILDDDA FA--GDQDIA SVMKSLEEEI ALSSPPPP-- -PPT--RALV        71
SEQ-ID-NO-985    DLLDLLADDT DA-AAAGDLA SVMRSLEEEI C--------- ------ADEL        76
SEQ-ID-NO-995    DLLDLLDDDA DA-AAAGDLA SVMRSLEEEI C--------- ------AGDL        76
SEQ-ID-NO-1015   DLLDMLDDDT DAGGAACDLA SVMRSFEEEI VAGDVA---- ------GDVA        69
SEQ-ID-NO-1009   DLLDLLDDDA DA-AAAGDLA SVMRSLEEEL GSFDEAGA-- -PDA--AAAP        75
SEQ-ID-NO-991    DLLDMLDDDI EA-AAAGDLA SVMRSLEEEI ASFDEA---- ------AEAA        74
SEQ-ID-NO-993    DLLDMLEDDT DA-AAAGDLA SVMRSLEEEI ASFDEA---- ------AEAA        77
```

Figure 11 (continued)

```
SEQ-ID-NO-1005   SGERPELGFL FEASDDELGL PPFE------ ---------IN ERVLA-----    99
SEQ-ID-NO-953    GETQPDLGYL LEASDDELGL PPPPSISPVP VAKEEVTTET VTDLVRASS-   131
SEQ-ID-NO-971    GETQPDLGYL LEASDDELGL PPPP---PPVS VVEEVETTET VADLVRASS-  121
SEQ-ID-NO-963    GESQPDLGFL LEASDDELGL PPSS----IN LSSGEVKGGV ETELARVDSA   122
SEQ-ID-NO-955    CDSQPDLGYL LEASDDELGL PPPI-----A STTDAEGRSE ATDLVRADS-   120
SEQ-ID-NO-977    GESQAQIGYL LEASDDELGL PPAG------ NSSAPEEKNV ETELVRVAS-   105
SEQ-ID-NO-979    CFSQAQIGYL LEASDDDLGL PPAG------ NSSAPQEKNV EAELVRVAS-   105
SEQ-ID-NO-999    KTDQPDLGFL LEASDDELGL PPPV----LS SSDDGGEAPA ADDPAAEGVA   117
SEQ-ID-NO-985    MPPQPELGFL LEASDDELGL PPAA------ GASSSSDDAG GWEPE-----   115
SEQ-ID-NO-995    AAPQPELGFL LEASDDELGL PPAA-----G AASSSSDDAG GWEPE-----   116
SEQ-ID-NO-1015   PTTQPELGFL LEASDDELGL PPAT------ -ASSSEEEAG AGEPE-----   107
SEQ-ID-NO-1009   PAHQPELGFL LEASDDELGL PPAG------ ASSSEEEAVA AGAPD-----   114
SEQ-ID-NO-991    PSQQPELGFL LEASDDELGL PPAG----SA AAASSEEAGL AGPPL-----   115
SEQ-ID-NO-993    PSQQPELGFL LEASDDELGL PPAG-----S AAASSEEAGL AGPPLPAAP-   121

SEQ-ID-NO-1005   ESVCL-SE-L WGLDDEFIK- --YDSFESGF VY--DGDNNI NNGEYVALDG   142
SEQ-ID-NO-953    DSSGI-DE-L WGFEDHVSN- -YGGLDFGS GV---GDGG- ---DYVAVEG   169
SEQ-ID-NO-971    DSSGI-DE-L WGFEDHVPD- -YGSLDFGS GV---GDCG- ---DYVTVEG   159
SEQ-ID-NO-963    QSSGVGE-L WGFEDQIPT- -YDSFGLGV GD--SNYSS- ---DYVCFDD   162
SEQ-ID-NO-955    NSSGIHD-L WGFEEQNPN- -YDSFEFGF VDNFNDGT-- ------VAYDG  158
SEQ-ID-NO-977    DSSGI-GE-L WEFEEQIPR- -YDSFDLGM GFGYECDTT- ---EYAAFGG   146
SEQ-ID-NO-979    DSSGI-GE-L WEFEDQIPR- -YDSFDLGM GFGYECDAT- ---EYAAFGE   146
SEQ-ID-NO-999    VEGVVFCQ-L WGLDDDITGY --YDGFDLGI GPDDRVDTTH AAEDGV-YDG  164
SEQ-ID-NO-985    EAAGLFGEQI WGFEDEIDGA YAFGGVAYSP EAAVAAAAAA AFWGDDGFDA   165
SEQ-ID-NO-995    EPAGVFGEQI WGFEDEIDGA YAFGGVASSP EAAAAAAAAA AEWGDDGFDA   166
SEQ-ID-NO-1015   DALGFGCQ-I WGFDFEIGGG G-YAGFALTS PEAVAAAAAA AEWDDDGFDA   155
SEQ-ID-NO-1009   VAAGLDGQ-I WGFEDEIDGG --FGGYSPEA AA---AAAAA AAWDDDGFDA   158
SEQ-ID-NO-991    PAAAIYGQ-I WGFDDEIDGG --FGGYSPEA AA---AAAAA AAWDDDVFGA   159
SEQ-ID-NO-993    AAAALYGQ-I WAFDDEIDGG --FGGYSPEA AA---AAAAA AAWDDDVFGA   165
```

Figure 11 (continued)

| | | | | |
|---|---|---|---|---|
| SEQ-ID-NO-1005 | LFDYTDVGF | GSSDLT---W | RPETLPAQ | 166 |
| SEQ-ID-NO-953 | LFEFSDDCF | DSGDLFS--W | RSESLPAE | 194 |
| SEQ-ID-NO-971 | LFDFSGECF | DSGDLFS--W | RPESLPAE | 184 |
| SEQ-ID-NO-963 | SLFEYSNVCF | DSSDFSDLSW | RLGGMPAE | 190 |
| SEQ-ID-NO-955 | LFEYSDVYY | DSSDISGQLW | RPETLSAK | 185 |
| SEQ-ID-NO-977 | LFDHSDLYY | DS------W | RHETLPTQ | 166 |
| SEQ-ID-NO-979 | LFDHSDVYY | DS------W | RQ------ | 160 |
| SEQ-ID-NO-999 | GLFDYADVLC | APPDFLD--- | -------- | 181 |
| SEQ-ID-NO-985 | GLFGFGDFSF | GPSDLDV--L | RQETMPAV | 191 |
| SEQ-ID-NO-995 | GLFGFGDESF | GPSDLAV--L | RQETMPAV | 192 |
| SEQ-ID-NO-1015 | GLFGFGDEVS | A-------L | RHETMPAV | 175 |
| SEQ-ID-NO-1009 | GLFAFGDDAC | GASDLAA--L | RHETMPAV | 184 |
| SEQ-ID-NO-991 | GLFAFGDDAC | APSDLAA--L | RHESMPAV | 185 |
| SEQ-ID-NO-993 | GLFAFGDDAC | GPSDLAA--L | RHETMPAV | 191 |

Figure 12

```
SEQ-ID-NO-1024  MSRVLTCPPL VFARNHVGVQ NLVESTKLKR  LDSKKAHR  EKKEKKEKR  50
SEQ-ID-NO-1039  MSRYFTSPPP VYARNWANGQ NLVESTK ER OIVTSKKVHP KEKKERKKDK  50
SEQ-ID-NO-1042  MSRCFPYPPP VYLGNPV--- AVAEAESTAK LQKERERAHK --KKDKRSDK  45
SEQ-ID-NO-1043  MSRCFPYPPP GYVRNPVVAV AAALAQATTK LQKEREKAEK --KKEKRSDR  48
SEQ-ID-NO-1040  MSRCFPFPPP GYMKLRFDL DTPKKDRKKK NRKE-DKNER KEKREKRKRE  49
SEQ-ID-NO-1029  MSRCFPYPPP GYQIE----- STKTRKEKEK STTESHKDIK KEKKERRKHR  45

SEQ-ID-NO-1024  KEKKETKREK SHKHSKAT- -DNHKLFL PSKKVS-DES DSLEKSGLTD  97
SEQ-ID-NO-1039  KQKNEKTIEH ---------- ------VYL PLKQVS-DES EQLEKSCLTE  82
SEQ-ID-NO-1042  KAPQLGETSK HSKHNHKKRK LEDVSTGDQE PKKVFK-ESA ELLEKSGLSE  94
SEQ-ID-NO-1043  KALPHGESK HSKR-HKKRK HEDINNADQK SRKVSSMEPG EQLEKSGLSE  98
SEQ-ID-NO-1040  KELKQKDSTT SHASFGGAMK LKDINGKLLM GED----YEN EQLERSC TE  95
SEQ-ID-NO-1029  KENKDQTCYT VGKSHQKGK- -------TFL PR-----EKK EEAEKSDLTE  82

SEQ-ID-NO-1024  ELEEP--QKH LGYLSDGSQN SKKRI RDDSP PAVESLIKAA PVACKPLRIR  145
SEQ-ID-NO-1039  EHEK------ --YLSDGSQS SKKR-RREAS PSVESNIKAT PVTGNP-RIR  123
SEQ-ID-NO-1042  EHGAPCFVQM FRDSPFSSQD SSKR-RKAVL PSPSQA---- -KNGNITRIK  138
SEQ-ID-NO-1043  EHGAPCFTQT VHGSPLSSQU SSKR-RKVVL PSPSQA---- -KNGNILRIK  142
SEQ-ID-NO-1040  ELEQPVSSPQ EPYSSDSTQS SKRK-RCTLL PNQDHE---- ---DALKTR  136
SEQ-ID-NO-1029  EHNEPVCLDN TCYLSDDGTR SNKK-RKLEQ ATNDDK---- --PRNVFRIR  125

SEQ-ID-NO-1024  M --------- VFKKPKEEVP TLPR-FAVVC STTVAKSLS- ----------  174
SEQ-ID-NO-1039  F --------- VFKKPKLAEF VVPQ-EDLVC STS------- ----------  146
SEQ-ID-NO-1042  LKSNQDPQSV LLEKPRVIFQ PLVQ-QMSSV SSLSSKQNSI ---NRKVNVR  184
SEQ-ID-NO-1043  IRRDQDSSAS LSEKSNVVQT PF-VH-QMGSV SSLPSKKNSM QPHNTEMMVR  190
SEQ-ID-NO-1040  L --------- PLTKHSEPEK SKQGFQFGSC STSVGIGDSL TQETRRIDRP  177
SEQ-ID-NO-1029  L --------- PLTRHKEPDV PLN--SEGLC STS-GRADSV SGQNEGVHLS  163

SEQ-ID-NO-1024  ---------- ---------- ---------- ---------- ----------  174
SEQ-ID-NO-1039  ---------- ---------- ---------- ---------- ----------  146
SEQ-ID-NO-1042  S-TAGQQWVN GDSQAVQKSL VTETLSRAMQ RTVPQPAVKV TRRADPQLSV  233
SEQ-ID-NO-1043  TASTQQQSIK GDFQAV---- -------LK QGMPTPA-KV MPRVDVPPSM  227
SEQ-ID-NO-1040  L -------- ---------- ---------- ---------- ----------  178
SEQ-ID-NO-1029  ---------- ---------- ---------- ---------- ----------  163
```

Figure 12 (continued)

| SEQ ID | | | | | | | |
|---|---|---|---|---|---|---|---|
| SEQ-ID-NO-1024 | ---------- | ---------- | ---------- | --------HQ | DVITSSISSS | | 186 |
| SEQ-ID-NO-1039 | ---------- | ---------- | ---------- | --------GT | EISSSVSGHD | | 158 |
| SEQ-ID-NO-1042 | KAPVGRSDL- | PPKFSGSVGP | SPARVTGRFC | PAPVKTQQRT | EHPPSMVSQR | | 282 |
| SEQ-ID-NO-1043 | RASKERVGLR | PAEMLANVGP | SPSKAKQIVN | PAAAKVTQRV | DPPPAKASQR | | 277 |
| SEQ-ID-NO-1040 | ---------- | ---------- | ---------- | -------TKV | ETPNQQLHRN | | 191 |
| SEQ-ID-NO-1029 | ---------- | ---------- | ---------- | --------HQ | ETVNSKACTV | | 175 |

| SEQ-ID-NO-1024 | KTS------- | ---------- | ---------- | ----ELEKNL | PSTSIAAIDE | | 205 |
| SEQ-ID-NO-1039 | ENL------- | ---------- | ---------- | ----LPASL | ESVETAILSE | | 176 |
| SEQ-ID-NO-1042 | VDP--QAKVS | QKEMGSAVCL | PQAP-----H | PPVLQKPKDL | PVPKQREPIN | | 325 |
| SEQ-ID-NO-1043 | IDPLLPSKVH | IDATRSFTKL | SQTEIKPEVQ | PPIPKVPVAM | PTINRQQIDT | | 327 |
| SEQ-ID-NO-1040 | SAS------- | ---------- | ---------- | -KMCKPLQNL | VPVDALLANK | | 213 |
| SEQ-ID-NO-1029 | VGE------- | ---------- | ---------- | ---LASPEKM | PCLSMSCKKS | | 195 |

| SEQ-ID-NO-1024 | TKKRK----- | ---------- | ---------- | --KHRSSKED | QYNALFDGWT | | 228 |
| SEQ-ID-NO-1039 | SKKKK----- | ---------- | ---------- | --KHKTSKES | RYSSLFDEPV | | 199 |
| SEQ-ID-NO-1042 | SLPKEEPCFS | GRTVEADQGK | EAKLSRSDRK | KIHKTEKKNK | KFRDLFVTWN | | 375 |
| SEQ-ID-NO-1043 | SQPKEEPCSS | GRNAEAASVS | VEKQSKSDRK | KSRKALKKEK | KFKDLFVTWD | | 377 |
| SEQ-ID-NO-1040 | TVDDE----- | ---------- | ---------- | ---SRCVES | LYKSLL---H | | 231 |
| SEQ-ID-NO-1029 | TVCHESGISR | FKLPN----- | ---------- | --KKMRKADS | PYKVLIEDWV | | 228 |

| SEQ-ID-NO-1024 | PPSMCIADAS | SNDNGDYWLF | GNKTQEVLKP | KA-----AVKV | DDDTMMRPGD | | 274 |
| SEQ-ID-NO-1039 | LPCLSIEEDD | GNS--DDWLL | SGRRQENSST | KS----TMDED | MVMNLQKSGE | | 244 |
| SEQ-ID-NO-1042 | PLLMENEGSD | LCG--QDWLF | SSTRSSDGSM | AQPTVPDGLG | PIHPMVQQQP | | 423 |
| SEQ-ID-NO-1043 | PPSMEMDDMD | LGD--QDWLL | GSTRKPDAGI | GN--CREIVD | PLTSQSAEQF | | 423 |
| SEQ-ID-NO-1040 | TQPIAYELFD | ALD--QDWLF | SSVKIEAKHV | SK-------K | QKTDAFRCSK | | 272 |
| SEQ-ID-NO-1029 | SPPPQFELND | SDD--QEWLS | EASKRERHGN | KI------LN | ACRDVLCHES | | 270 |

| SEQ-ID-NO-1024 | SSWPRAQFLS | EVCLYSLPYT | VPF | 297 |
| SEQ-ID-NO-1039 | SCFPSSQFLS | EVCTFSLPYT | VLF | 267 |
| SEQ-ID-NO-1042 | YLQPRATFLP | DLHIYQLPYV | VPF | 446 |
| SEQ-ID-NO-1043 | SLQPRALHLP | DLFVYQLPYV | VPF | 446 |
| SEQ-ID-NO-1040 | SLWPRAQFMP | EVNILALPYT | IPF | 295 |
| SEQ-ID-NO-1029 | SIFPRGHYLP | EADVYALPYT | LPF | 293 |

Figure 13

```
SEQ-ID-NO-1099   MAFLQDQFQR H-YQQQQQPQ P--------- ---------- --QTKSFRNL  28
SEQ-ID-NO-1139   MALPHHHIQL H-IQQPQQQ  S--------- ---------- ---KSYRDIY  27
SEQ-ID-NO-1100   MALPHHHLQL H-IQQQPHQQ Q--------- ---------- QQSKSYRDLY  30
SEQ-ID-NO-1101   MALPHHHLQL HIQQQPHQQ  Q--------- ---------- --SKSYRDLY  29
SEQ-ID-NO-1105   MAVQAQHLSH A-FPHDLHAY N--------- ---------- --------SV  22
SEQ-ID-NO-1134   MAVQAQYLSH ASFPHDLYGL R--------- ---------- ----------  21
SEQ-ID-NO-1111   MAVEAHSLLD A-GGHKQLTS A---GWPWTT GDEARC---- ATARPSHQQA  42
SEQ-ID-NO-1131   MAVEAHHLLH A-GGQRPQLL APHEGWAW-A GDAACCEAPA ATAAGQGQRR  48
SEQ-ID-NO-1047   MAVQAHHMND --FSQFISPN R--------- ---------- --------DC  21
SEQ-ID-NO-1083   MPVQARHMND --FSPQLLSN R--------- ---------- ----------  19
SEQ-ID-NO-1085   MAVEASYMNL --LPSQLLTN R--------- ---------- ELIKSNQQLQ  29
SEQ-ID-NO-1053   -----MH--- --EGSQLLPL Y--------- ---------- ----------  11
SEQ-ID-NO-1057   MAVEAPHTND N-FPSHLLTN R--------- ---------- DFAKVNQANM  30

SEQ-ID-NO-1099   QTIEGQMSQQ MAFYNPT--D LQDQSQHPPY PPFL---GFA PGPVIPA--D  71
SEQ-ID-NO-1139   NNMDGQISTP VAYFNGS--N LPEQSQIIPPY PPFQVVGLA  PG-------L  68
SEQ-ID-NO-1100   NNMDGQITNP VVYFNGS--N LPEQSQHPPY PPFQVVGLA  PG-------T  71
SEQ-ID-NO-1101   NNMDGQITTP VVYFNGS--N LPEQSQHPPY PPFQVVGLA  PG-------T  70
SEQ-ID-NO-1105   GALEDEMTGG SLFF------ -PENLKRGPE LEGAGNTVFG DIPRVDP--T  63
SEQ-ID-NO-1134   -ALEGATAAG SLHLDDH--G GCAPATPAAA AAGIGHTVLS DLPRSELT-C  67
SEQ-ID-NO-1111   FQLQQASCVG VGVGLPA--A APVSSAAAAP PAPMIAQQYA ACCRLFVG-D  89
SEQ-ID-NO-1131   LAGKQQQQQH YRFQQPC--A A-TPAAAAGP RLVAPTGRYA PGPQLCAA-D  94
SEQ-ID-NO-1047   VKFQENMNHG EFEFTGG--- ----EVPLIT GESFAVEPLA AKANF----N  60
SEQ-ID-NO-1083   VNFKQDMNHG EFITGET--L AVDPLSNAAA KPSF------ ---------N  52
SEQ-ID-NO-1085   HQLNSDYMYN TTTQMDSSSA LPQPATMPFS LSFYQSNF-  CDP------N  72
SEQ-ID-NO-1053   ---------- ---------- ---------- -----QPL   CHPNISA--N  23
SEQ-ID-NO-1057   SLYNTQMDSG LVFNEP---- ------MPFT LSFYQSSLG  CDPVSAKASN  70
```

Figure 13 (continued)

```
SEQ-ID-NO-1099   GSDGGV-DLH WNFGLE---- --PERKRLKE QDFLENNSQ- ISSVDFLQPR  113
SEQ-ID-NO-1139   VDDGGL-DLQ WNYGLE---- --PKRKRPKE QDFINNNSQ  ISSIDFLQPR  111
SEQ-ID-NO-1100   ADDGGL-DLQ WNYGLE---- --PKKKRPKE QDFMENNNSQ ISSVDLLQRR  114
SEQ-ID-NO-1101   ADDGGL-DLQ WNYGLE---- --PKKKRPKE QDFMENNNSQ ISSVDLFQRR  113
SEQ-ID-NO-1105   WHDNTTRSHG F--------- --AQRKRARV VPEAPSYLE- ----------  91
SEQ-ID-NO-1134   NDNNGA-GYG F--------- --VPRKRARL -DADESAGAL MAAAAAQQQR  104
SEQ-ID-NO-1111   AAESGV-TFG GGGAV-QQE- --APRKRKRA ---------- ----------  114
SEQ-ID-NO-1131   ASESGV-TFG GGGGG-AQQQ AMAPRKRKRA ---------- ----------  122
SEQ-ID-NO-1047   KAESGL-SYN FTVPP----- --LSTKRQRD FQFSDSNAPV ----------  92
SEQ-ID-NO-1083   KSESGL-TYN FNSFNVVP-- --PPRKRPRV SQYLDSDARF ASAV------  91
SEQ-ID-NO-1085   KADSGL-TYH IP-------- --LQRKRSRD FITELTSL-- ----------  99
SEQ-ID-NO-1053   KADSGLTTYN MSIPVS---- --APRKRSRD SFTNGFDS-- ----------  55
SEQ-ID-NO-1057   KDDSGL-TYN VPAVV----- --APRKRSRD SINDNFDAF- ----------  101

SEQ-ID-NO-1099   SVSTGLGLSL DNTRLASTGD SALLSLIG-- -------DDI DRELQ-QQDL  153
SEQ-ID-NO-1139   SVSTGLGLSL DNGRLASSGD SAFLGLVG-- -------DDI ERELQ-RQDA  151
SEQ-ID-NO-1100   SVSTGLGLSL DNGRLASSCD SAFLGLVG-- -------DDI ERELQ-RQDA  154
SEQ-ID-NO-1101   SVSTGLGLSL DNGRLASSCD SAFLGLVG-- -------DDI ERELQ-RQDA  153
SEQ-ID-NO-1105   -NQRGQGLVP VGDVLTRAVG SGTASTSGRM :NAAGPPQDL LSQLY-RQGM  139
SEQ-ID-NO-1134   MVLPPHCLVF PGDVQSRAVG CGAASTSGRA GNAAGLSQGL LSQLY-HQGV  153
SEQ-ID-NO-1111   ---------- ----EQGQTP PPVLGTGA-- -------ADV AAQFQ-QQLV  140
SEQ-ID-NO-1131   ---------- ----GEGQ-P APALRLAS-- -------ADV AARFQ-QQLV  147
SEQ-ID-NO-1047   ---------- --KRRSVAFD SSSPSLIN-- -------VEL VSQIQNQQQS  121
SEQ-ID-NO-1083   ---------- --KLGSGPFG SPS-SLIN-- -------AEL VSHIQNQQQL  119
SEQ-ID-NO-1085   ---------- --PAHQKNKI SSDPSFLN-- -------QEI LYQFQ-NQQS  127
SEQ-ID-NO-1053   ---------- --YSLPQNNN ISGASSDV-- -------DDV FSQIQ--QQH  82
SEQ-ID-NO-1057   ---------- --HASQKTKV CPFSSFID-- -------QDI IFQIQ-QQQS  129
```

Figure 13 (continued)

| SEQ-ID-NO | | | | | | |
|---|---|---|---|---|---|---|
| SEQ-ID-NO-1099 | EVDRFLKLQG | EQLRQTILEK | VQATQLQSVS | IIEDKVLQKL | REKETEVENI | 203 |
| SEQ-ID-NO-1139 | EIDRYIKVQG | DRLRQAILEK | VQANQIQTVT | YVEEKVIQKL | REKETEVEDI | 201 |
| SEQ-ID-NO-1100 | EIDRYIKVQG | DRLRQAVLEK | VQANQIQAIT | YVEEKVLQKL | RERDTEVDDI | 204 |
| SEQ-ID-NO-1101 | EIDRYIKVQG | DRLRQAVLEK | VQANQIQAIT | YVEEKVLQKL | RERDTEVDDI | 203 |
| SEQ-ID-NO-1105 | EIDAVLRLET | DRMRAGLEEA | RQQHVRALVS | AAERAAARRL | RAAEAALELA | 189 |
| SEQ-ID-NO-1134 | EIDALVRLES | ERMRAGLEEA | RRRHVRAVVS | TVERAAAGRL | RAAEAELERA | 203 |
| SEQ-ID-NO-1111 | DVDRLVLQHT | AKMWAGLTEQ | RRRHARQVVA | TVEAAAAPRL | RAKEEEIQRM | 190 |
| SEQ-ID-NO-1131 | DVDRLVLQHT | SKMWADLREQ | RRRHAGQVVA | AVEAAAAKRI | RAKDEEIEHI | 197 |
| SEQ-ID-NO-1047 | EIDRFVAQQT | EKLRIEIEAR | QQTQTRMLAS | AVQNVIAKKL | KEKDDEIVRI | 171 |
| SEQ-ID-NO-1083 | EIDRFVAQQT | EKLRIEIEAR | QQTQTQMLAS | AVQNALAMKL | KEKDDEILRM | 169 |
| SEQ-ID-NO-1085 | EIDRVLAHHT | EKVRMELEEQ | KMRQSRMFVS | AIQEAMAKKL | KEKDQEIQRM | 177 |
| SEQ-ID-NO-1053 | DIDRFISDHT | EKLRLEVEER | RKRQSRMFIT | AIQERVMKKL | KEKDEEIQRI | 132 |
| SEQ-ID-NO-1057 | EIDRFIAEHN | QKVRMELEDR | RKRQSRMLVS | AIQGGMVRKL | TEKDECIQRM | 179 |

| SEQ-ID-NO | | | | | | |
|---|---|---|---|---|---|---|
| SEQ-ID-NO-1099 | NKRNMELEDQ | MEQLSVEAGA | WQQRARYNEN | MIAALKFNLQ | DAYLQCRDSK | 253 |
| SEQ-ID-NO-1139 | NKKNMELELR | TEQLALEANA | WQQRAKYNEN | LINTLKVNLQ | HVYAQSRDSK | 251 |
| SEQ-ID-NO-1100 | NKKNMELELR | VEQLALEANA | WQQRAKYNEN | LINTLKVNLQ | HVYAQSRDSK | 254 |
| SEQ-ID-NO-1101 | NKKNMELELR | MEQLDLEANA | WQQRAKYNEN | LINTLKVNLQ | HVYAQSRDSK | 253 |
| SEQ-ID-NO-1105 | RCRNAKLSER | LTQICAECQA | MIRVAKSHEA | VAAGLQATLD | QIIQSPCAAV | 239 |
| SEQ-ID-NO-1134 | RCRNMELEER | LRQMTAECQA | MLSVAKSHEA | VAAGLRAILD | QLLQSPCAAL | 253 |
| SEQ-ID-NO-1111 | RRVNWALEER | VKSMYVEAHM | WRDLAQSNDA | AVTALRCELQ | QALDAQQTRR | 240 |
| SEQ-ID-NO-1131 | GRLNWALEER | VRSLYVEAQV | WRDLAQSNEA | AANALRGELQ | QALDAQQAR- | 246 |
| SEQ-ID-NO-1047 | RNLNWVLQER | VKSLYVENQI | WRDIAQTNEA | NANTLRTNLD | QVLAQLETFP | 221 |
| SEQ-ID-NO-1083 | RNLNCVLQER | VKSLFVENQI | WRDIAQTNEA | QANNLRTNLD | QVLAQIETLP | 219 |
| SEQ-ID-NO-1085 | GKLNWALQER | VKSLCMENQI | WRELAQTNES | TANYLRSNLE | QVLAHVGEER | 227 |
| SEQ-ID-NO-1053 | GKLNWVLQFR | VKSLYVENQL | WRDLAQTNEA | TANSLRNNLE | QVLAHAGDSI | 181 |
| SEQ-ID-NO-1057 | GKLNWVLQEK | VKSLYVETQI | WRDLAQANEA | TANSLRSNLE | QVIAHVSEDR | 229 |

Figure 13 (continued)

```
SEQ-ID-NO-1099   EGCG------ -DSEVDDTAS -CCNGRSLD- ---FHLLSNE NSNMKDLMK-  290
SEQ-ID-NO-1139   EGCG------ -DSEVDDTAS -CCNGRATD- ---LHLLCRD SNEMKELMT-  288
SEQ-ID-NO-1100   EGCG------ -DSFVDDTAS -CCNGRATD- ---LHLLCRD SKEMKELMT-  291
SEQ-ID-NO-1101   EGCG------ -DSEVDDTAS -CCNGRATD- ---LHLLCRD SKEMKELMT-  290
SEQ-ID-NO-1105   AATGADG--- -DCDAEDARS -CCFETPAG- ---------D DAAASKASA-  273
SEQ-ID-NO-1134   AVAGAAGAGG AEGDAEDAQS -CCYETPCG- ---GDNAGAD DAASKTPAA-  297
SEQ-ID-NO-1111   ---------- ---RADDACS CCCGENDVFI TEAGAAENEE EAGTSSSSG-  276
SEQ-ID-NO-1131   --CG--GGVL ADGGAGDAES CCCGENDVA- ---AGGTGAG DEGEDEAGT-  287
SEQ-ID-NO-1047   TAS------- -AVVEDDAES -SCGSC---- ----CGDGGG EAVTAVGGG-  253
SEQ-ID-NO-1083   ---------- -TAVENDVES -SCGSCVEG- --------G  EAITAVSGG-  246
SEQ-ID-NO-1085   ---------- -ATVADDAQS -SCGSNDAA- ---EACNDTA ASAAATGRG-  260
SEQ-ID-NO-1053   --CG--GG-- -AALADDAES -SCGSSDQGW REVVTPQAQG SCGAQDNNKA  223
SEQ-ID-NO-1057   YING--GG-- -ATVADDAES -SCGSSDHG- ---RCPLAGG EEGAVKDKLV  269

SEQ-ID-NO-1099   ---------- ------CKAC RVNEVTMVLL PCKHLCLCKD C-ESK-LSFC  322
SEQ-ID-NO-1139   ---------- ------CKVC RVNEVSMLLL PCKHLCLCKE C-ESK-LSLC  320
SEQ-ID-NO-1100   ---------- ------CRVC RTNEVCMLLL PCKHLCLCKE C-ESK-LSLC  323
SEQ-ID-NO-1101   ---------- ------CRVC RTNEVCMLLL PCKHLCLCKE C-ESK-LSLC  322
SEQ-ID-NO-1105   ---------- ----AACRAC GEGESCVLLL PCRHLCLCSA C-DAA-VDTC  307
SEQ-ID-NO-1134   ---------- ----ALCKAC GAGEASMLLL PCRHLCLCRG C-EAA-VDAC  331
SEQ-ID-NO-1111   ---------- -HVI RACAVC GDNAADVLLL PCRHLCACAP C-AAA-ARAC  313
SEQ-ID-NO-1131   ---PGT---- ---RRMCTVG GEGAAEVLML PCRHLCACAP C-AGA-ARAC  325
SEQ-ID-NO-1047   ---------- ------CKRC GEREASVLVL PCRHLCLCTV CGGSALLRTC  287
SEQ-ID-NO-1083   ---------- ------CKRC GEREASVLVL PCRHLCLCTV C-GSAL-RTC  279
SEQ-ID-NO-1085   ---------- ------RLCKNC GLRESVVLLL PCRHLCLCTM C-GST-VRNC  294
SEQ-ID-NO-1053   VVVGNN---- ---NRKCRKC GEKESSVLLL PCRHICICTM C-GSTMVGTC  265
SEQ-ID-NO-1057   VVKDNNSSKN INHNRMCKKC GERESSVLLL PCRHLCLCTL C-GSNLIGTC  318
```

Figure 13 (continued)

| | | |
|---|---|---|
| SEQ-ID-NO-1099 | PLCQSSKFIG MEVYM-- | 337 |
| SEQ-ID-NO-1139 | PLCQSTKYIG MEIYM-- | 335 |
| SEQ-ID-NO-1100 | PLCQSTKYIG MEVYM-- | 338 |
| SEQ-ID-NO-1101 | PLCQSTKYIG MEVYM-- | 337 |
| SEQ-ID-NO-1105 | PLCATTKNAS LHVLLS- | 323 |
| SEQ-ID-NO-1134 | PVCAATKNAS LHVLLS- | 347 |
| SEQ-ID-NO-1111 | PACGCAKNGS VCVNFS- | 329 |
| SEQ-ID-NO-1131 | PACGCAKNGS VCVNFS- | 341 |
| SEQ-ID-NO-1047 | PVCDMVMNAS VHVNMSS | 304 |
| SEQ-ID-NO-1083 | PVCDSVMNAS VHVNMSS | 296 |
| SEQ-ID-NO-1085 | PICDSDMDAS VHVNLS- | 310 |
| SEQ-ID-NO-1053 | PVCLSLTNAS VHVNML- | 281 |
| SEQ-ID-NO-1057 | PVCDSVMDAS VHVNMA- | 334 |

Figure 14

```
SEQ-ID-NO-1258                         ----------  ---MDVTGDG  GGG-------  ---GQRPNFP  LQLLGKKE--   25
SEQ-ID-NO-1263                         ----------  ----------  ----------  ----------  ----------    0
SEQ-ID-NO-1211                         ----------  ---MELEADH  QNG-------  ---RSRLNFP  LQLLEKKDID   28
SEQ-ID-NO-1215                         ---------M  DGGDDLHHHH  HHQHHQHHHQ  HQQQQRQNFP  FQLLEKKEDN   41
SEQ-ID-NO-1264                         ---------M  EGGDDHHHHH  HHHN------  ---QSRPNFP  FQLLEKKTTN   32
SEQ-ID-NO-1209                         ----------  -------MSN  NDGV------  ----------  ----------    7
SEQ-ID-NO-1223                         ----------  ----MTTRPDG  GGG-------  ----------  ----------   10
SEQ-ID-NO-1246                         ----------  ---MTTRPAA  EGG-------  ----------  ----------   10
SEQ-ID-NO-1151             --MDLSDIRN  NNNDTAAVAT  GGGAR-----  ----------  ----------   23
SEQ-ID-NO-1155                         ----------  ----------  ----------  ----------  ----------    0
SEQ-ID-NO-1172             MESQRNTANQ  QSNSSGNKDH  HGQKQESVAA  SLQLVPLESR  PSQLQQQHGS   50

SEQ-ID-NO-1258             --------EQ  TCSTSQTAGA  GGGGVVGANG  SA--------  ------AAAP   53
SEQ-ID-NO-1263             ----------  MTTSSSDAPC  VDHNQKSKNQ  DK--------  ------KQQA   26
SEQ-ID-NO-1211             DVT------EQ  PCSTTSVVTA  TTTATTTTT   SDNNDLHLAE  QS----KKPP   69
SEQ-ID-NO-1215             QEAASCSTSS  PYPSLAI SPT  EPSTSNSNRS  NQLVPASTPT  TSDPANKKPP   91
SEQ-ID-NO-1264             --------NP  PSSALAI SAD  I ASNPSTTTS  TTTLTAASAE  TS----KKPP   70
SEQ-ID-NO-1209             --------MI  SNGSLI EHQR  QQQQQNLKQS  SD--------  ------GALV   35
SEQ-ID-NO-1223             --------GV  GGDGAEGKQL  VPVAAAASNG  AN--------  ------GALA   38
SEQ-ID-NO-1246             ----------  -AAAAAAAAD  NKQLVPTSNG  TV--------  ----------   31
SEQ-ID-NO-1151             --------QL  VDASLSI VPR  STPPEDSTLA  TTSST-----  ------ATAT   54
SEQ-ID-NO-1155             ----------  --MCSI SNQI G  VPSSSPTSTS  SL--------  ------AKPP   25
SEQ-ID-NO-1172             TTTTPTSQGP  SMGSI SCQI G  THPSTSTSNS  AV--------  -------TKS   85

SEQ-ID-NO-1258             PKRTSTKDRH  TKVDGRGRRI  RMPALCAARV  FQLTRELGHK  TDCETI EWLL  103
SEQ-ID-NO-1263             KKPTTTKDRH  TKVDGRGRRI  RMPATCAARV  FQLTRELGHK  SDGETI EWLL   76
SEQ-ID-NO-1211             PKRSSTKDRH  TKVDGRGRRI  RMPAACAARV  FQLTRELGHK  SDGETI EWLL  119
SEQ-ID-NO-1215             PKRTSTKDRH  TKVEGRGRRI  RMPALCAARV  FQLTRELGHK  SDGETI EWLL  141
SEQ-ID-NO-1264             PKRTSTKDRII  TKVDGRGRRI  RMPALCAARV  FQLTRELGHK  SDGETI EWLL  120
SEQ-ID-NO-1209             VKKPPAKDRH  SKVDGRGRRI  RMPI I CAARV  FQLTRELGHK  SDGQTI EWLL   85
SEQ-ID-NO-1223             VRKAPSKDRH  SKVDGRGRRI  RMPI I CAARV  FQLTRELGHK  SDGQTI EWLL   88
SEQ-ID-NO-1246             -RKAPSKDRH  SKVDGRGRRI  RMPI I CAARV  FQLTRELGHK  SDGQTI EWLL   80
SEQ-ID-NO-1151             TTKRSTKDRH  TKVDGRGRRI  RMPALCAARV  FQI TRELGHK  SDGETI EWLL  104
SEQ-ID-NO-1155             AAKRPTKDRH  TKVDGRGRRI  RMPAVCAARV  FQLTQELGIIK  SDGETI EWLL   75
SEQ-ID-NO-1172             TTKRPSKDRH  TKVDGRGRRI  RMPAMCAARV  FQLTRELGHK  SDGETI EWLL  135
```

Figure 14 (continued)

| SEQ-ID-NO-1258 | QQAEPAVI AA | TGTGTI PANF | TSLN-I SLRS | SGSSLSI PSH | LRLAGLAGP- | 151 |
| SEQ-ID-NO-1263 | QQAEPAVI AA | TGTGTI PANY | SSLN-I SLRS | S---RHHSASN | YLAHNNI NNF | 123 |
| SEQ-ID-NO-1211 | QQAEPAVI AA | TGTGTI PANF | TSLN-I SLRS | SGSTMSAPSH | YFRGNYFNPS | 168 |
| SEQ-ID-NO-1215 | QQAEPAVI AA | TGTGTI PANF | TSLN-I SLRS | SGSSMSVPSQ | -LRSSYFNPN | 189 |
| SEQ-ID-NO-1264 | QQAEPSVI AA | TGTGTI PANF | TSLN-I SLRS | SGSSMSVPSQ | -LRSSYFNPS | 168 |
| SEQ-ID-NO-1209 | RQAEPSI I AA | TGTGTTPASF | STAS-VSVRG | SSTTI STSIN | CTLSSSLDHK | 134 |
| SEQ-ID-NO-1223 | RQAEPSI I AA | TGSGTTPASF | STSSPSSLRP | PGAPHPQHPH | AIIAQPLAVSP | 138 |
| SEQ-ID-NO-1246 | RQAEPSI I AA | TGTGTIPASF | STSSPSSLRS | SSQTTPTAAA | ----PFI ---- | 123 |
| SEQ-ID-NO-1151 | QQAEPAI VAA | TGTGTI PANF | STLS-VSLRS | SGSTLSAPPS | -KSVPLYGAL | 152 |
| SEQ-ID-NO-1155 | QQAEPAI I AA | TGTGTI PANF | STLN-VSLRS | SGSTI SAPPS | -KSAPLSFHS | 123 |
| SEQ-ID-NO-1172 | QQAEPAI I AF | TGTGTI PANF | STLN-VSLRS | SGATI SAPAS | -KSAPLSFHG | 183 |

| SEQ-ID-NO-1258 | --------RF | GGGARAADAW | DRVVGLGFGG | A --------- | -----ADAPS | 179 |
| SEQ-ID-NO-1263 | GHVYHDRNYF | NG--------- | ---VGLFSSE | N--------- | -----NSFFP | 148 |
| SEQ-ID-NO-1211 | TFSTSAAAAA | AAQLRSRAEW | DRSMSMVMED | SRRSMLENTS | SI SAI LNFNP | 218 |
| SEQ-ID-NO-1215 | FSLQQRRTLF | PG--------- | ---I GLSPSD | N------NSN | NNTSMLLNFQ | 222 |
| SEQ-ID-NO-1264 | NYTMMSQPRR | GFSFPG----- | ---I GLSSSE | S------SSSG | TI I NFQQAAA | 206 |
| SEQ-ID-NO-1209 | PFI ------- | ----------- | ---LG----- | ---------- | ---------- | 139 |
| SEQ-ID-NO-1223 | HHHHLPHAAP | FI -------- | ---LG----- | ---------- | ---------- | 152 |
| SEQ-ID-NO-1246 | ---------- | ----------- | ---LG----- | ---------- | ---------- | 125 |
| SEQ-ID-NO-1151 | GLTFHQYDEQ | GGGGVFAAHT | SPLLGFHHQL | Q -------HH | QNQNQNQDPV | 195 |
| SEQ-ID-NO-1155 | ALGFYNSN-- | GDEARRI GNS | TAMLGFHHQL | Y---------P | QLLNPETHI R | 163 |
| SEQ-ID-NO-1172 | GLAFYDANNA | SETRRAMASN | PPMLGFHHQL | Y---------- | ----------P | 215 |

| SEQ-ID-NO-1258 | SATSSSSSPL | LLSFHSGSVG | LDVSPPSAST | SPA-------- | ---AADLSRKR | 220 |
| SEQ-ID-NO-1263 | SGNLNMLQ-A | KEELCDDDDN | DNDN------- | ---------- | --NNNTGRDK | 179 |
| SEQ-ID-NO-1211 | MGNVNVI QQA | KQELREESGG | GGGLESVASD | S--------- | --DGSLGRKR | 257 |
| SEQ-ID-NO-1215 | SNNLTNMLQA | KQEVRDGNTN | SNANANAPSS | STTLDLSETS | GEESMGGRKR | 272 |
| SEQ-ID-NO-1264 | NLNPSLMHQA | KQEMRENSNN | NNNSLE----S | E--------- | --EENMGRKR | 242 |
| SEQ-ID-NO-1209 | ---------- | -KRLREDSGG | GK--------- | ---- ----- | ---------- | 150 |
| SEQ-ID-NO-1223 | ---------- | -KRVRDDDCG | GNGNGNGQAA | A--------- | ---------- | 172 |
| SEQ-ID-NO-1246 | ---------- | -KRARDDAGA | DA--------- | ---------- | ---------- | 136 |
| SEQ-ID-NO-1151 | ETI PEGENFS | RKRYRSVDLS | KENDDRKQ-- | ---------- | --NENKSLKE | 231 |
| SEQ-ID-NO-1155 | SGGNPNDNYA | TKPFRDDLFK | ETSQHNTETG | AI -------- | --DANSPKPE | 203 |
| SEQ-ID-NO-1172 | QNLVSDDNYM | RKTFREDLFK | ETTQQQSIEI | I --------- | --EASNSAKS | 254 |

Figure 14 (continued)

```
SEQ-ID-NO-1258      R---WEQEM-  ------QQQQQ  YQQQ-MAGYT  QSQI PAG---  --TVWMVPSS   255
SEQ-ID-NO-1263      R---RSEDKD  LQHNNYHMSN   MLQSSTYGST  PASHQIGHI P  ATTLYMMTNN   226
SEQ-ID-NO-1211      R---PEQEL-  -----SQMGS   YLIQSSTGSL  PASHASN---   TAAFWMVAGH   295
SEQ-ID-NO-1215      RTSSGGSEQD  LSSLQHQMGS   YLMQSSAGSI  PASHTQI---   PANFWMVANS   319
SEQ-ID-NO-1264      R---AEQELQ  QHQ-HHQI GN  YLVQSSTGPM  AASHASI---   PANFWTLANS   285
SEQ-ID-NO-1209      ----------  -----DEMGS   FATPACFWAV  PARPDFG----  --QVWSFASH   180
SEQ-ID-NO-1223      ----------  -----VTAAM   APAP-CFWAL  PARGDFG----  --QLWSFAPP   201
SEQ-ID-NO-1246      ----------  -----EPTVA   APAP-CFWAL  PCRADLG---   --QLWSFAAA   165
SEQ-ID-NO-1151      S---------  -----ETSGP   TAAP-MWAVA  PPSRSGA---   GNTFWMLPVP   263
SEQ-ID-NO-1155      RTGMPEQEPG  LF---QTTNV   MPAPAMWAVA  PATTNGG---   -NAFWMLPVG   246
SEQ-ID-NO-1172      RAGVQDQETA  GSI-RPTTNM   LPTP-MWAVA  PAATTNG---   GNTFWMLPVG   299

SEQ-ID-NO-1258      ---NAQAAGG  GAPPGGGG--  ------ESIWT  FPQSG-SGGG   GGAATVYRGV   294
SEQ-ID-NO-1263      ---NNNTSHH  DPNN------  ------CSMWA  SPSNS-----   ------NIENS  252
SEQ-ID-NO-1211      ---GNQAMSG  GGSVGGGNNG  SSDN-NPIWA   IPSVG-----   ---NSGVYRGA  334
SEQ-ID-NO-1215      ---NNQIMSG  G---------  ----DPIWT    FPSVN-----   NSAAALYRGA   347
SEQ-ID-NO-1264      ---SNNNNNN  NNNNNNQGMG  S----DPIWT   FPSVN NNSA   AAAAXLYRGT   328
SEQ-ID-NO-1209      ---QEMFLQQ  QQQQQQQPAA  AALFVHQQQQ   QQAAM-----   ----------   212
SEQ-ID-NO-1223      ---P------  ----------  ------EMMAA  APAMA-----   ----------   212
SEQ-ID-NO-1246      ---PEMM---  ----------  -----VAAAA   TPAMA-----   ----------   179
SEQ-ID-NO-1151      TTAGNQMESS  SNNNTAAGHR  A-----PPMWP  FVNSAGGGAG   GGGGAATHFM   309
SEQ-ID-NO-1155      ----GGATAAS  ATVPE-----  -----AQMWT   FPAHY-----   ----------   268
SEQ-ID-NO-1172      ---GGATPTS  SVQE------  -----PQMWT   FPAAA-----   AGVPSMQRVN   330

SEQ-ID-NO-1258      --PSGLHFM   NFPATPM---  -------ALL   PGGQQLGLAG   AGGG-GEGHP   330
SEQ-ID-NO-1263      NIRGGLLNFM  NFHQPTL---  ----------   -GTRGGCGGG   TA---AECQW   285
SEQ-ID-NO-1211      MSAPCGIHFM  NF-ASPMNLM  PGGQLGSGIV   GGGGGGGGNG   GAQLLSESNL   383
SEQ-ID-NO-1215      VS-TSGLHFM  NF-PQPMALL  PGQQLG-NSS   GGCGGCGNIN   MNMNMNEGHL   394
SEQ-ID-NO-1264      V--SSGLHFM  NF-PAPV---  -------ALL   PSQQI GGNV-  ----LGEGQL   360
SEQ-ID-NO-1209      ----------  ----------  ----------   -GEASAARVG   NYLP---GHL   228
SEQ-ID-NO-1223      ----------  ----------  ----------   -GEASAARVG   NYLPMAQANL   231
SEQ-ID-NO-1246      ----------  ----------  ----------   -GEASAARVG   NYLPMAQGNL   198
SEQ-ID-NO-1151      AGTGFSFPMD  QYRGSPL---  ---QLG-SFL   AQPQPTQNLG   LSMP--DSNL   350
SEQ-ID-NO-1155      --SGGGR---  ---GNPV---  ---QLG-SMI   LQQQQAGGQQ   LGLGVTETNM   303
SEQ-ID-NO-1172      FGGGGGRV--  ---SSPV---  ---QLG-SMI   VQQQVGANQQ   LGLGISESNM   368
```

Figure 14 (continued)

```
SEQ-ID-NO-1258    GIL-AALNAY  RAQAAQPDAG  AAAQNGAQGS  SQHRQHQHHG  GGGGGGDERH  379
SEQ-ID-NO-1263    GML-TAAMNSY  RQ--------  ----SGG----  ----HASGSS  NQHNGGDDHQ  316
SEQ-ID-NO-1211    GML-AALNAY  RQIPAN----  ---GVS----  ----EPPGSA  GQHHGGDDGR  417
SEQ-ID-NO-1215    SML-AGLSPY  RPVSDHHQQH  HQPSGS----  ----QSHHHR  SGSHEHDDRH  435
SEQ-ID-NO-1264    G---NFMNPY  RNIGG-----  ---GGG----  ----ASESQA  SCSHGGDDRH  391
SEQ-ID-NO-1209    NLL-ASLS--  ----------  ---GGA----  --------PG  SGRREDDQR-  249
SEQ-ID-NO-1223    NLL-ASFS--  ----------  ---GGP----  ----GGAGQA  TGRAEEETAH  257
SEQ-ID-NO-1246    NLL-AYFS--  ----------  ---GGP----  ------APTAT AGRAEEESAR  223
SEQ-ID-NO-1151    GMI-AALNSA  YSRGGNAN--  ---ANAEQAN  NAVEHQEKQQ  QSDHDDDSRE  394
SEQ-ID-NO-1155    GLL-GSGMNVY  SN--------  ---NNRVGLK  MNLEQQHHHE  NQTQGSDSGD  342
SEQ-ID-NO-1172    GMI-GGVNPY  SSSRVGLG--  ---MNL----  ----EHHNQD  NQPQGSDSGD  405

SEQ-ID-NO-1258    ESMSASDS    387
SEQ-ID-NO-1263    HHS-----    319
SEQ-ID-NO-1211    DSTSQHS-    424
SEQ-ID-NO-1215    DN------    437
SEQ-ID-NO-1264    DSTSHHS-    398
SEQ-ID-NO-1209    --------    249
SEQ-ID-NO-1223    --------    257
SEQ-ID-NO-1246    --------    223
SEQ-ID-NO-1151    ENSNSSE-    401
SEQ-ID-NO-1155    ENPATDSQ    350
SEQ-ID-NO-1172    ENPNDSQ-    412
```

Figure 15

```
SEQ-ID-NO-1301   --------MH PKARIHADP- ----------A APEPDRIDGL PDSLVLLILN  32
SEQ-ID-NO-1317   --------MH PKARIHADP- ---------- VLEVDQFDCL PDSLVLLILN  31
SEQ-ID-NO-1303   MSED---PACS RRSRCDLGGD ER-WLS---G PACDDHFDRL PDALLLVIFN  44
SEQ-ID-NO-1326   MAED---PACS RRWRCDACDE HGCWLSSSAG GCCDDHFDRL PDPLLLVIFN  48
SEQ-ID-NO-1279   MSSV---YSD PIHGTHPEP ---------- ---IDHFDRL PDSLLLLVFN  33
SEQ-ID-NO-1285   MSSL--RADP PISKIHPEAE AEATTSCFCS SSKIDHFDRL PDSLLLFVFN  48
SEQ-ID-NO-1294   MAIILRSSDP LLSRIHPEP- ---------- -QEIDHFDNL PDSILLLIFN  38
SEQ-ID-NO-1277   MAVIIPRSDP P-SRIHPEPP ---------Q TLEIDHFDHL PDSILLLVFN  40

SEQ-ID-NO-1301   KLEDVHSLGR CAAVSRRFND LVPLVHDVYV KIDRVVAVDG DPDDALNLSS  82
SEQ-ID-NO-1317   KVEDVRSLGR CSAVSKRFCG LVSLVHDVYV KIDRVVAVDG DAEDTLNLSS  81
SEQ-ID-NO-1303   RICDVKALGR CSLVSLRFHE LVPLVDSVFV RVDCVIP-DE PPSSSSSPST  93
SEQ-ID-NO-1326   RICDVKALGR CSLVSRRFHD LVPLVDSVLV RVDCVIP-DD PASSSSSSSS  97
SEQ-ID-NO-1279   MIGDVKVLGR CCVVSRRFHS LVPQVENVVV RVDCVIS-DD DCSPSSSVKS  82
SEQ-ID-NO-1285   KIGDVKALGR CCVVSRRFHS LVPQVDNVVV RVDCVIS-DD DTSSSSSSIK  97
SEQ-ID-NO-1294   NIGDVKALGR CSVVSKRFHS LIPQVENVFV RVDCVIS-DD DSSSLLSDKP  87
SEQ-ID-NO-1277   KIGDVKALGR CCVVSRRFHS LVPQVDNVVV RVDCVIS-DD DSSSLSSIKS  89

SEQ-ID-NO-1301   ---------- -PKPRHIFSH LFKLMLFTIA KPFQGM---- --------RG 109
SEQ-ID-NO-1317   ---------- -PKPRNIFSH FLKLMLETII KPFHSM---- --------RN 108
SEQ-ID-NO-1303   ----PFSPTA SVRARGVFSQ IARIVLGGIV KPIQALGQIL SPANSA--SC 137
SEQ-ID-NO-1326   PSAAPSSPTA SARARIVFSQ IARIVLGGIV KPIQALGQIL SPANSA--SV 145
SEQ-ID-NO-1279   ---------- --RADGPFST LFRLVFGGIV KPLQALGQFL GPERPSLYKT 120
SEQ-ID-NO-1285   ---------S HSSSSSGFSS FRLVFGGIS KPIQALSQMF CTKVNS--RN 136
SEQ-ID-NO-1294   ---------R SASAASPFSA FRLVF----- KPIQALGQFL KRSGSS--SL 122
SEQ-ID-NO-1277   ---------R SGSSAGSFSA FRLVVGGIV KPLQALGQFL GTKRSS--SS 128

SEQ-ID-NO-1301   PGCAG----- ---------G RPLFPRLAQH SPVQVLRGFS HVRNLRVELP 145
SEQ-ID-NO-1317   PNCN------ ---------G RPLFAQLSQH SPAQVLRNFT HIRNLRVELP 143
SEQ-ID-NO-1303   FPASSDSSPS SSSSS----S PLPPADVSHH SPSEVLRSFK ELRHLRIELP 183
SEQ-ID-NO-1326   LAASVTSSPS SSSSSSSS-S PPLPGDVSHH SPSEVLRSFK ELRRLRIELP 194
SEQ-ID-NO-1279   LNISSSSSLS VGIGGGED-G ERDQGGVIHH SPTQVLRNEN ELRFLRIELP 169
SEQ-ID-NO-1285   GNC------PS LSVAADDD-M ELDQAGVTHH SPTQVLKNFN EIRFLRIELP 180
SEQ-ID-NO-1294   PSGS--SPSS LLISGDDD-G EIEQGGVTHH SPTQVLKNFD EIKFLKIELP 169
SEQ-ID-NO-1277   CGCSGSSSSS LSISGDDDGG EIEQGGVTHH SPTQVLKNFD EIRYLRIELP 178
```

Figure 15 (continued)

| SEQ-ID-NO-1301 | SGDVGI EEGV | LLKWRARYGS | TLQSCVI LGG | TLVDR----- | ---------- | 180 |
| SEQ-ID-NO-1317 | SGDVGI EEGV | LLKWRAEYGS | TLQSCVI LGG | TRVDR----- | ---------- | 178 |
| SEQ-ID-NO-1303 | AGELDMDDGV | MLKWKADFGS | TLGSCVI LGA | SSASASPSPS | SAGSDSTSTA | 233 |
| SEQ-ID-NO-1326 | AGELSMEEGV | LLKWKADFGS | TLGSCVI LGA | SSAGK----- | ---DCGACAA | 236 |
| SEQ-ID-NO-1279 | GGELGI DDGV | LLKWRADFGS | TLDSCVI LGA | ASVFNNVHFQ | VPDHGNDGFC | 219 |
| SEQ-ID-NO-1285 | SGELGI DDGV | LLKWRADFGS | TLDNCVI LGA | ASVI TNN--K | I SSAMQQENA | 228 |
| SEQ-ID-NO-1294 | SGELGI DDGV | LLKWRAEFGS | TLENCVI LGA | SSVI P----- | -PTNSDKTEA | 213 |
| SEQ-ID-NO-1277 | SGELGI DDGV | LLKWRAEFGS | TLDNCVI LGA | SSVI PPNPMR | VSQACDTTTV | 228 |

| SEQ-ID-NO-1301 | ----KPAGGH | EPSAAEDGGS | MPESFYTNGG | LKLRVVWTI S | SLI AASTRHY | 226 |
| SEQ-ID-NO-1317 | ----RPVGCE | HEPSLEDNGS | MPESFYTNGG | LKLRVVWTI S | SLI AASTRHY | 224 |
| SEQ-ID-NO-1303 | PS--VDCGRT | EPDECVDSGS | I PESFYTNGG | FKLRVVWTI S | SLI AAARHY | 281 |
| SEQ-ID-NO-1326 | PA--VDCGES | D-----ETGS | I PESFYTNGG | LKLRVVWTI S | SLI AASARHY | 279 |
| SEQ-ID-NO-1279 | I NNCSNVGNG | D-----DNGS | I PESFYTSGG | LKLRVVWTI S | SLI AASARHY | 264 |
| SEQ-ID-NO-1285 | AA---AAAADD | D-----DNGS | I PESFYTNGG | LKLRVVWTI S | SLI AASARHY | 271 |
| SEQ-ID-NO-1294 | SS---APVAAV | F-----DNGS | I PESFYTNGG | LKLRVVWTI S | SLI AASARHY | 256 |
| SEQ-ID-NO-1277 | VE---APGSGS | D-----DNGS | I PESFYTNGG | LKLRVVWTI S | SLI AASARHY | 271 |

| SEQ-ID-NO-1301 | LLRSI I KEHP | TLRSLVLADA | DGQGTLCMGA | EQLAEFRESR | LSASACSNRT | 276 |
| SEQ-ID-NO-1317 | LLRSI I KDHP | TLTSLVLTDA | DGQCTLCMGA | EQLKEFRENQ | LSASACSNRT | 274 |
| SEQ-ID-NO-1303 | LLQPI I ADHK | TLERLDLTDA | DGQGVLTMDK | CQLQELRVRP | VSI SRGSHRT | 331 |
| SEQ-ID-NO-1326 | LLQPI I ADHT | TLESLDLTDA | DGQGVLTMDK | WQLQELRVKP | VSASGCSHRT | 329 |
| SEQ-ID-NO-1279 | LLQSI I AEHK | TLDSLVLTDA | DGQGVLCMNG | EQLQELRVKP | LSASSASKRT | 314 |
| SEQ-ID-NO-1285 | LLQPI I AEHK | TLDSLVLADA | DGQGVLCMNR | EQLEELRVKP | LSASSASKRT | 321 |
| SEQ-ID-NO-1294 | LLQPI I AEHK | TLDSLVLTDV | DGQGVLCMNR | DQLEELRVKP | LSASSASKRT | 306 |
| SEQ-ID-NO-1277 | LLQPI I AEHK | TLDSLVLTDS | DGQGVLCMNR | DQLEELRVKP | LAASSASKRT | 321 |

| SEQ-ID-NO-1301 | QVPACSMKLK | YAPYLELPGG | LGLQGATLVV | I KPSGDGACG | CHVCRKETEA | 326 |
| SEQ-ID-NO-1317 | QVPACNMKLK | YAPYLELPGG | I ALQCATLVA | KPSTEGSNC | GHTSRKETDA | 324 |
| SEQ-ID-NO-1303 | LMPELSMWLW | YAPCI ELPGG | LVLNGATLVA | KPSEEGTGD | TVWNGAAGAA | 381 |
| SEQ-ID-NO-1326 | LMPALSMRLW | YAPHI ELPGG | I VLNGATLVA | KPTEEATRD | TVGSCI AGSA | 379 |
| SEQ-ID-NO-1279 | LVPALNMRLW | YAPHLDLPDG | VVI QGATLVA | RPSEQSASK | KEVSDAS--- | 361 |
| SEQ-ID-NO-1285 | LVPALNMRLW | YAPHLELPDG | VVLKGATLVA | RPSEQAATK | KDVSDVS--- | 368 |
| SEQ-ID-NO-1294 | LVPALNMRLW | YAPSLELPDG | TVLKGATI VA | RPSE---SK | KEVCDVS--- | 350 |
| SEQ-ID-NO-1277 | LVPALNMRLW | YAPTLELPDG | TVLKGATLVA | RPSE---SK | KEVSDI S--- | 365 |

Figure 15 (continued)

```
SEQ-ID-NO-1301    ---FVSGAFD GPFRFAAKAL MKRRTYLLEM NGF    356
SEQ-ID-NO-1317    ---FISGAFD GPFKVAVKAL TKRRIYLLEM NGF    354
SEQ-ID-NO-1303    ---WVLDAFE EPYRTAVRML LKQRIYSLEM NSF    411
SEQ-ID-NO-1326    GGCWVSDAFE EPYRTAVGMI LKRRTYSLEM NSF    412
SEQ-ID-NO-1279    ---WLSSAFE EPYGTAAKML VKRRTYCLEM NSF    391
SEQ-ID-NO-1285    ---WVSTIFE EPYGTAAKML VKRRTYCLEM NSF    398
SEQ-ID-NO-1294    ---WVSSAFD EPYGVAAKML VKRRTYCLEM NSF    380
SEQ-ID-NO-1277    ---WVSSAFE EPYETAAKML VKRRTYCLEM NSF    395
```

Figure 16

```
SEQ ID NO 1427   ----------  ----------  ---MEFKATE  LRLGL-P---  ---C T----     16
SEQ ID NO 1430   ----------  ----------  ---MEFKATE  LRLGL-P---  ---C T----     16
SEQ ID NO 1419   MSPPLDLDYI  GLSPAAAAAA  A-HDDLKGTE  LRLGL-P---  ---GSG----     38
SEQ ID NO 1422   MSPPLELDYI  GLSPPAAAAA  AENDELKCTE  LRLGL-P---  ---GSG----     39
SEQ ID NO 1347   ----------  ----------  ---MEL---D  LGLSLSPHKS  SKLGFN---F     21
SEQ ID NO 1431   ----------  ----------  ---MEL---Q  SGLAL-PIHS  SIEGFD--PY     21
SEQ ID NO 1429   ----------  ----------  ---MEL---Q  LGLGL-PSEK  TMKGLDLNSY     23

SEQ ID NO 1427   EEEKKIIHG   S---------  -SVVKNNNKR  QL--------  ------PQTSE    43
SEQ ID NO 1430   FFEKKIIHG   S---------  -SVVKNNNKR  QL--------  ------PQTSE    43
SEQ ID NO 1419   -SPDRRVVAA  TATTLD----  -LLPAKGAKR  GFSDEA----  -----PTPSP     73
SEQ ID NO 1422   -SPDRRVVAA  TATTLD----  -LLPAKGAKR  GFSDEA----  -----PPPSP     74
SEQ ID NO 1347   DLNKHCAIEG  A---------  -ASCLGTEKL  RFEATFGLGN  VEENCYMPKQ     61
SEQ ID NO 1431   NSDLNNHIRG  SE--------  -NIKYVKNKR  SFDESF----  --GDFSKPLP     56
SEQ ID NO 1429   VSEPKELLCS  GQLILGSYSW  FSTNDNDKKR  SFIDASEESS  RNEDVPRTLP     73

SEQ ID NO 1427   ESVSISKVTN  DE--------  ---HIVESSS  AAPPAKAKIV  GWPPIR----    78
SEQ ID NO 1430   ESVSISKVTN  DE--------  ---HIVESSS  AAPPAKAKIV  GWPPIR----    78
SEQ ID NO 1419   GAASGKGKKV  AEEED-----  ---DKKVAAT  PQPVAKAQVV  GWPPIR----   111
SEQ ID NO 1422   VATAGKGKKV  AEEEYD----  ---EKKVAAT  PQPAAKAQVV  GWPPVC----   113
SEQ ID NO 1347   RLFALNGQPN  EEDEDPLE--  ---SESSIVY  DDEEENSEVV  GWPPVKTCMI   106
SEQ ID NO 1431   -LLVWSCQPN  EEDGRSEKK-  ---NRSIHTS  NNECENH-IV  GWPPIK----    96
SEQ ID NO 1429   -LLVWNNQPN  EEDDPPKDLD  NHCNYSFSSN  KSDGESDGLV  GWPPIK----   118

SEQ ID NO 1427   ---SYRKNSL  HE--------  --------AD  V---------  ----------    90
SEQ ID NO 1430   ---SYRKNSL  HE--------  --------AD  V---------  ----------    90
SEQ ID NO 1419   ---SYRKNTM  ST--------  --------TQ  LKGSKEDAEA  K-------QD   135
SEQ ID NO 1422   ---NYRKNTM  TT--------  --------TQ  LEGSKEDGDA  K-------QG   137
SEQ ID NO 1347   KYGSYHHRH   RNHHHCPYHH  RGRRITAMNN  NISNPTTATV  GSSSSSSISS   156
SEQ ID NO 1431   ---SWRKKEF  HD--------  --------QQ  LPEHIRKANE  N-----QNRR   122
SEQ ID NO 1429   ---FKRKKLS  RQ--------  --------NS  RVLEVNRAVD  NGCEDCQARS   149
```

Figure 16 (continued)

```
SEQ-ID-NO-1427  -GGI FVKVSM DGAPYLRKI D LRVYGGYSEL LKALETMFK- LTI GEYSERE  138
SEQ-ID-NO-1430  -GGI FVKVSM DGAPYLRKI D IRVYGGYSEL LKALETMFK- LTI GEYSERE  138
SEQ-ID-NO-1419  OGFLYVKVSM DGAPYLRKI D LKTYKNYKDL STALEKMFSG FSTCKDCLSE  185
SEQ-ID-NO-1422  OGFLYVKVSM DGAPYLRKI D LKTYKNYKDL STALEKMFSG FSTCKDCSXE  187
SEQ-ID-NO-1347  RSSMYVKVKM DGVAI ARKVD I KLFNSYESL TNSLI TMFT- -----EYFDC  200
SEQ-ID-NO-1431  SKPLYVKVNM EGVGMGRQI N LRLYNSYQTL KDSLI SMFV- -----KCQNF  166
SEQ-ID-NO-1429  SNSMYI KVKM EGVGI ARKI D VSVYRCFPTL KHTLLDMFG- -----ICQ--  191

SEQ-ID-NO-1427  GYKGSEYAPT YEDKDGDWML VGDVPWDMFV TSCKRLRI MK GTEAKGLGCG  188
SEQ-ID-NO-1430  GYKGSEYAPT YEDKDGDWML VGDVPWD---V TSCKRLRI MK GTEAKGLGCG  186
SEQ-ID-NO-1419  YRKDGEYVLT YEDKDGDWML VGDVPWEMFA DSCRRLRI MK GSDAI GLAPR  235
SEQ-ID-NO-1422  YRKDGEYVLT YEDKDGDWML VGDVPWEMFA GSCRRLRI MK GSDAI GLAPR  237
SEQ-ID-NO-1347  DREDFNYTFT FQGKEGDWLL RGDVTWKI FA ESVHRI SI IR DRPCAYTRCL  250
SEQ-ID-NO-1431  EETGANYTLT FQNKQGEWKL TSHI TWQSFT GTVRRLAI LR NGECETI---  213
SEQ-ID-NO-1429  -ENSSNYRLT YQDREGDWLL AEDVPWRNFL GSVQRLKLMR SSN-------  233

SEQ-ID-NO-1427  V--------       189
SEQ-ID-NO-1430  V--------       187
SEQ-ID-NO-1419  AADKSKNRN       244
SEQ-ID-NO-1422  AADKSKNRN       246
SEQ-ID-NO-1347  F--------       251
SEQ-ID-NO-1431  ---------       213
SEQ-ID-NO-1429  ---------       233
```

Figure 17

```
SEQ-ID-NO-1480    ---------- ---MAAAPSA GGVGEGSSSS AAAAAAAAAA -TIGPHVVDE  36
SEQ-ID-NO-1475    ---------- --MA APS---GGGG GGAGEGSSSA AAAM------ -TIGAHGVDQ  32
SEQ-ID-NO-1477    ---------- --MA APSAGAGGGS GGAGEGSSSS AAAAAAAA-- -TIGAHGVDQ  39
SEQ-ID-NO-1471    MDEAGRASAP AVVTVTASAA APSPPPPPPP AIATAAAADP PSPDPDALYE  50
SEQ-ID-NO-1457    ---------- --------MD FNAGVPMS-- ---------- -SLSPLMNQ   18
SEQ-ID-NO-1467    ---------- --------MD FNAGVPMS-- ---------- -SLSP-LMNQ  18
SEQ-ID-NO-1460    ---------- ------MGFS FDAGIPMSRI ATAAVPVTEG SSLSP-SLNQ  33
SEQ-ID-NO-1462    ---------- --------MD FDAGIPMSRS GVGLPAVTEG TSMSP-SLSE  31*

SEQ-ID-NO-1480    --EAMW-QMN L--GEAMEAG PYPERIGEPD CSYYMRTGLC RFGMTCKFNH  81
SEQ-ID-NO-1475    VTEAMW-QMN L--GDAMELG PYPERVGDPD CSYYMRTGMC RFGMTCKFNH  79
SEQ-ID-NO-1477    VAEAMW-QMN L--GEAVELG PYPERVGEPD CSYYMRTGMC RFGMTCKFNH  86
SEQ-ID-NO-1471    --LGMWQQMA MSSGATMQSG PYPVRPGEPD CTYYLRTGLC RFGMSCRFNH  98
SEQ-ID-NO-1457    --DAMW-QMN LSSDETMETG SYPERPGEPD CSYYIRTGLC RFCSTCRFNH  65
SEQ-ID-NO-1467    --DAMW-QMN LSSDETMETG SYPERPGEPD CSYYIRTGLC RFGSTCRFNH  65
SEQ-ID-NO-1460    --DAMW-QMN LRSSETMESS PYPERPGEPD CSYYIRTGLC RFGATCHFNH  80
SEQ-ID-NO-1462    --DAMW-QMN LRSSETMEAG PYPFRPGEPD CSYYIRTGLC RFGATCRFNH  78

SEQ-ID-NO-1480    PADRKMAVAA ARMKGEYPQR IGQPECQYYL KTGTCKFGAT CKFHHPREKA 131
SEQ-ID-NO-1475    PADRKLAVAA ARMKGEYPQR LGQPECQYYL KTCTCKFGAT CKFHHPREKA 129
SEQ-ID-NO-1477    PADRKLAVAA ARMKGEYPQR NGQPECQYYL KTGTCKFGAT CKFHHPREKA 136
SEQ-ID-NO-1471    PQDRNTAIAS ARMKCEYPER VGQPECEYYL KTGTCKFGPT CKFHHPREKA 148
SEQ-ID-NO-1457    PRDRELVIAE ARMRGEYPER IGQPECEYYL KTGTCKFGVT CKFHHPRNKA 115
SEQ-ID-NO-1467    PRDRELVIAE ARMRGEYPER IGQPECEYYL KTGTCKFGVT CKFHHPRNKA 115
SEQ-ID-NO-1460    PPNRKLAIAA ARMKGEFPGR VGQPECQYYL KTGTCKFGAT CKFHHPRDKA 130
SEQ-ID-NO-1462    PPNRKLAIAA ARMKGEFPER IGQPECQYYL KTGTCKFGAT CKFHHPRDKA 128

SEQ-ID-NO-1480    ALATRVQLNA LGYPLRPNEK ECAYYLRTGQ CKFGSTCKFH H--PQPSNIM 179
SEQ-ID-NO-1475    AMATRVQLNE LGYPLRLNEK ECAYYLRTGQ CKFGSTCKFH H--PQPSIMM 177
SEQ-ID-NO-1477    AMALRVQLNE LGYPFRPSEK ECAYYLRTGQ CKFGSTCKFH H--PQPSEMM 184
SEQ-ID-NO-1471    GIAGMVQLNT LGYPLRPNER ECAYYLKTGQ CKYCNTCKFN H--PEIFNAV 196
SEQ-ID-NO-1457    GIAGRVSLNM LGYPLRSNEV DCAYFLRTGH CKFGGTCKFN HPQPQPTNMM 165
SEQ-ID-NO-1467    GIAGRVSLNM LGYPLRSNEV DCAYFIRTGH CKFGGTCKFN HPQPQPTNMM 165
SEQ-ID-NO-1460    GIAGRVSLNI LGYPLRPNEI ECAYYLRTGQ CKFGSTCKFH H--PQPTNMM 178
SEQ-ID-NO-1462    GISGRVSLNI LGYPLQFNEI ECAYYLRTGQ CKFGSTCKFH H--PQPTNMM 176
```

Figure 17 (continued)

| SEQ ID NO | | | | | | | |
|---|---|---|---|---|---|---|---|
| SEQ-ID-NO-1480 | VAVRGS-VYS | PGQSVTSPSQ | HTYPGAV-TN | MPLSRSASFI | ASPRWPGHSS | | 227 |
| SEQ-ID-NO-1475 | VAVRGS-VYS | PGQSATSPGH | HAYQGAV-TS | MPLSRSASFI | ASPRWPGHSS | | 225 |
| SEQ-ID-NO-1477 | VAVRCS-GYS | PGQSATSPGQ | HAYQGAV-TS | MPLSRSTSFI | ASPRWPGHSS | | 232 |
| SEQ-ID-NO-1471 | ASSRGSPIYP | PVHNSGSFCP | HSYTCTM-AS | WTYPR-GSFI | PSPRWQSPSN | | 244 |
| SEQ-ID-NO-1457 | VP-------- | -------TSGQ | QSYP------ | WS--R-ASFI | ASPRWQDPSS | | 192 |
| SEQ-ID-NO-1467 | VP-------- | -------TSCQ | QSYP------ | WS--R-ASFI | ASPRWQDPSS | | 192 |
| SEQ-ID-NO-1460 | VSLRGSPIYQ | TVPSPATPGQ | QSHPGGI-TN | WS--R-ASFI | PSPRWQGPSS | | 224 |
| SEQ-ID-NO-1462 | VPLRGSPIYP | TVSSPTTPGQ | QSYPGGLATT | WS--R-ASFI | TSPRWQAPSS | | 223 |
| | | | | | | | |
| SEQ-ID-NO-1480 | YAQVIVPPGL | VQVPGWNPYA | AQIGSSSSDD | QQ-RTAGGAQ | YYTGSRHSET | | 276 |
| SEQ-ID-NO-1475 | YAQVIVPPGL | VQVPGWSPYA | AQIGSSSSDD | QQ-RTPGAAQ | YYTGSRQSCT | | 274 |
| SEQ-ID-NO-1477 | YAQVLVPPGL | VQVPGWNPYT | AQIGSSSSED | QQ-QTPGAAQ | YYTGSRQSGT | | 281 |
| SEQ-ID-NO-1471 | YTPMIVPQGL | VQVPNWNSYP | GQMVPVSSPE | SRLQSPGAQQ | YYGTSRQGEA | | 294 |
| SEQ-ID-NO-1457 | YASIIMPRGV | VPVQGWNPYS | GQLGSVSPSG | ------TGNDQ | NYRNLQQNET | | 237 |
| SEQ-ID-NO-1467 | YASLIMPQGV | VPVQGWNPYS | GQLGSVSPSG | ------TGNDQ | NYRNLQQNET | | 237 |
| SEQ-ID-NO-1460 | YASIILPQGM | VSVPGWNAYS | GQ-ASVSSSE | NLQQTNVNHQ | IHGTSRQNES | | 274 |
| SEQ-ID-NO-1462 | YTPLILPQGV | VSVPGWNAYS | GQ-GSVSSPE | SQ-QDTGNSQ | IYGTSRHSES | | 272 |
| | | | | | | | |
| SEQ-ID-NO-1480 | PNMG---DQGM | FSSYQAG-SV | PL-GLYTVQR | ESIFPERPDQ | PECQFYMKTG | | 322 |
| SEQ-ID-NO-1475 | PGIG---DRGM | FSSYQAG-SV | PV-GLYAVQT | ENVFPERPDQ | PECQFYMKTG | | 320 |
| SEQ-ID-NO-1477 | PCIG---DQGM | FSSYQAG-SV | PV-GLYAVQR | ENVFPERPDQ | PLCQFYMKTG | | 327 |
| SEQ-ID-NO-1471 | -SAG---NQGM | QSPYRSS-SF | PA-PQYALQR | ENVFPERPDQ | PLCIYYIKTG | | 339 |
| SEQ-ID-NO-1457 | IESGSQSQGS | FSGYNPGSSV | PLGGYYALPR | ENVFPERPGQ | PECQFYMKTG | | 287 |
| SEQ-ID-NO-1467 | IESGSQSQGS | FSGYNPCSSV | PIGGYYALPR | ENVFPERPGQ | PECQFYMKTG | | 287 |
| SEQ-ID-NO-1460 | ATAG---SQAS | FSELRSG-SV | PV-GVYALQR | ENVFPERPGE | PECQFYMKTG | | 320 |
| SEQ-ID-NO-1462 | VNAG---SQGT | FSPYRSG-SA | PL-GFYALQR | ESVFPFRPGQ | PECQFYMKTG | | 318 |
| | | | | | | | |
| SEQ-ID-NO-1480 | DCKFGAVCKF | HHPKERIIPT | PNCALSSLGL | PLRPGEPICT | FYSRYGICKF | | 372 |
| SEQ-ID-NO-1475 | DCKFGSVCKF | HIPRERIIPT | PNCALSPLGL | PLRPGEPICS | FYNRYGMCKF | | 370 |
| SEQ-ID-NO-1477 | DCKFCMVCKF | HHRERIIPA | PNCALSSLGL | PLRPGEPICS | FYSRYGMCKF | | 377 |
| SEQ-ID-NO-1471 | DCKFGAVCKF | HHPRVRSQPP | PDCILSPMGL | PLRPGEELCK | FYSRYGICKF | | 389 |
| SEQ-ID-NO-1457 | DCKFGTVCKF | HHPRDRQAPP | PDCLLSSIGL | SLRPGEPLCV | FYTRYGICKF | | 337 |
| SEQ-ID-NO-1467 | DCKFGTVCKF | HHPRDRQAPP | PDCLLSSIGL | PLRPGEPLCV | FYTRYGICKF | | 337 |
| SEQ-ID-NO-1460 | DCKFGAVCKF | HHPRERVLPA | PDCVLSPIGL | PLRPGEPLCI | FYSRYGICKF | | 370 |
| SEQ-ID-NO-1462 | DCKFGAVCRF | HHPRERLIPA | PDCVLSPIGL | PLRPGEPLCI | FYSRYGICKF | | 368 |

Figure 17 (continued)

```
SEQ-ID-NO-1480  GPNCKFDH-- --PMCTVMYG LATSPTGDVS ARRML----- -APVPAHSEV  412
SEQ-ID-NO-1475  GPNCKFHH-- --PMCNPMYG HASSPTSEAQ TSRRM----- LAHVPSHPEV  411
SEQ-ID-NO-1477  GPNCKFDH-- --PIGTVMYG HVSSPTSEVP TSRRM----- LAYVPSHPEV  418
SEQ-ID-NO-1471  GVNCKFDHPM AAPMGVYAYG YSASASPNAP M--------- ----------  420
SEQ-ID-NO-1457  GPSCKFDH-- --PMRVFTYD NTASETDEV- ---------- ----------  362
SEQ-ID-NO-1467  GPSCKFDH-- --PMRVFTYD NTASETDFV- ---------- ----------  362
SEQ-ID-NO-1460  GPSCKFNH-- --PMGIFTYS YSPSSPSDAP VIICFLGSSSG TAGLNLSSEG  416
SEQ-ID-NO-1462  GPSCKFDH-- --PMGVFTYN LTASSSADAP VRRLLGSSSG SPGLTLSSEG  414

SEQ-ID-NO-1480  SPDNVSGRSR RITHSDSQQI PSGERGILRE AS----  444
SEQ-ID-NO-1475  SPDSGSGRSR RIVHSDSQQI PSVERITERE AS----  443
SEQ-ID-NO-1477  LPDNGSGRSR RITHSDSQQI PSGERSILRE AS----  450
SEQ-ID-NO-1471  ----------GR RLLESPSGSA YAS--- ------  435
SEQ-ID-NO-1457  -VETSTGKSR RLSVSETRQA ATTSSGKDIT IDNTQQ  397
SEQ-ID-NO-1467  -VETSTGKSR RLSVSETRQA ATTSSGKDTT IDNTQQ  397
SEQ-ID-NO-1460  LVEAVPTKPR RLSLSENRQI SPSDD-IDAE G-----  446
SEQ-ID-NO-1462  LVEAGPTKPR RLSLSEPRQM PPGDDNIDTG G-----  445
```

Figure 18

```
SEQ-ID-NO-1512    MSVSSSMGG GGGGDAGGRT VVWFRRDLRV EDNPALAAAA RAGGEVVPAY  50
SEQ-ID-NO-1499    ------MSG ------GGCS IVWFRRDLRV EDNPALAAGV RA-GAVVAVF  36
SEQ-ID-NO-1506    ---MSNSCSG G-----GGCS IVWFRRDLRV EDNPALAAAV RA-CPVIAVF  41
SEQ-ID-NO-1497    MSCSVSGCGS ------GGCS IVWFRRDLRV EDNPALAAAV RA-GPVIALF  43
SEQ-ID-NO-1502    MSGSVSGCGS ------GGCS IVWFRRDLRV EDNPALAAAV RA-GPVNALF  43

SEQ-ID-NO-1512    VWAPEEDGPY YPGRVSRWWL SQSLKHLDAS LRRLGACKLV TRRSADAVMA  100
SEQ-ID-NO-1499    VWAPEEEGHY YPGRVSRWWL KQSLAHLDSS LRSLCTS-LV TKRSTDSVST  85
SEQ-ID-NO-1506    VWAPEEEGHY QPGRVSRWWL KNSLAQLDSS LRSLGTC-LI TKRSTDSVAS  90
SEQ-ID-NO-1497    VWAPEEEGHY HPGRVSRWWL KNSLAQLDSS LRSLGTC-LI TKRSTDSVAS  92
SEQ-ID-NO-1502    VWAPEEEGHY HPGRVSRWWL KNSLAQLDSS LRSLGTC-LI TKRSTDSVAS  92

SEQ-ID-NO-1512    LLQLVRDIGA TRLFFNHLYD PISLVRDHRL KEMMAAEGIL VQSFNADLLY  150
SEQ-ID-NO-1499    LLEVIKSTGA TQLFFNHLYD PLSLVRDHRA KEVLTAQGIA VRSFNADLLY  135
SEQ-ID-NO-1506    LLEVVKSTGA SQIFFNHLYD PLSLVRDHRA KDALTAEGIA VKSFNADLLY  140
SEQ-ID-NO-1497    LLDVVKSTGA SQIFFNHLYD PLSLVRDHRA KDVLTAQGIA VRSFNADLLY  142
SEQ-ID-NO-1502    LLDVVKSTGA SQIFFNHLYD PLSLVRDHRA KDVLTAQGIA VRSFNADLLY  142

SEQ-ID-NO-1512    EPWEVVDDEG QSFTMFAPFW NRCLSMPYDP AAPLLPPKRI NSGDLSMCPS  200
SEQ-ID-NO-1499    EPWDVNDAQG RPFTLFATFW DRCLSMPFDP EAPLLPPKRI ISGDASRCPS  185
SEQ-ID-NO-1506    EPWEVTDELG RPFSMFAAFW ERCLSMPYDP ESPLLPPKKI ISGDVSKCVA  190
SEQ-ID-NO-1497    EPWEVTDELG RPFSMFAAFW ERCLSMPYDP ESPLLPPKKI ISGDVSKCVA  192
SEQ-ID-NO-1502    EPWEVTDELG RPFSMFAAFW ERCLSMPYDP ESPLLPPKKI ISGDVSKCVA  192

SEQ-ID-NO-1512    DDLIFEDDSE RGSNALLARA WSPGWQNADK ALIAFLNGPL HYSVNRKKA  250
SEQ-ID-NO-1499    EMLVFEDCLE KGSNALLARA WSPGWSNADR ALTTFINGPL EYSKNRRKA  235
SEQ-ID-NO-1506    DTLIFEDESE KGSNALLARA WSPGWSNADK ALTTFINGPL EYSKNRRKA  240
SEQ-ID-NO-1497    DPLVFEDDSE KGSNALLARA WSPGWSNGDK ALTTFINGPL LEYSKNRRKA 242
SEQ-ID-NO-1502    DPLVFEDDSE KGSNALLARA WSPGWSNGDK ALTTFINGPL LEYSKNRRKA 242

SEQ-ID-NO-1512    DSASTSLLSP YLHFGELSVR KVFHLVRMKQ LVWSNEGNRA AEESCTLFLR  300
SEQ-ID-NO-1499    DSATTSFLSP HLHFGEVSVR KVFHLVRIKQ VLWANEGNKA GEESVNLFLK  285
SEQ-ID-NO-1506    DSATTSFLSP HLHFGEVSVR KVFHLLRIKQ VAWANEGNQA GEESVNLFLK  290
SEQ-ID-NO-1497    DSATTSFLSP HLHFGEVSVR KVFHLVRIKQ VAWANEGNEA GEESVNLFLK  292
SEQ-ID-NO-1502    DSATTSFLSP HLHFGEVSVR KVFHLVRIKQ VAWANEGNEA GEESVNLFLK  292
```

Figure 18 (continued)

| | | | | | | | |
|---|---|---|---|---|---|---|---|
| SEQ-ID-NO-1512 | SIGLREYSRY | LSFNHPCSHE | KPLLAHLRFF | PWVINECYFK | IWRQGRTGYP | | 350 |
| SEQ-ID-NO-1499 | SIGLREYSRY | LSFNHPYSHE | RPLLGHLKFF | PWMVDGGYFK | AWRQGRTGYP | | 335 |
| SEQ-ID-NO-1506 | SIGLREYSRY | ISFNHPYSHE | RPLLGHLKFF | PWAVDENYFK | AWRQGRTGYP | | 340 |
| SEQ-ID-NO-1497 | SIGLREYSRY | ISFNHPYSHE | RPLLGHLKFF | PWAVDENYFK | AWRQGRTGYP | | 342 |
| SEQ-ID-NO-1502 | SIGLREYSRY | ISFNHPYSHE | RPLLGHLKFF | PWAVDENYFK | AWRQGRTGYP | | 342 |

| | | | | | | | |
|---|---|---|---|---|---|---|---|
| SEQ-ID-NO-1512 | LVDAGMRELW | ATCWLHDRIR | VVVSSFFVKV | LQLPWRWGMK | YFWDTLLDAD | | 400 |
| SEQ-ID-NO-1499 | LVDAGMRELW | ATGWLHDRIR | VVVASFFVKV | LQLPWRWGMK | YFWDTLLDAD | | 385 |
| SEQ-ID-NO-1506 | LVDAGMRELW | ATGWLHDRIR | VVVSSFFVKV | LQLPWRWGMK | YFWDTLLDAD | | 390 |
| SEQ-ID-NO-1497 | LVDAGMRELW | ATGWLHDRIR | VVVSSFFVKV | LQLPWRWGMK | YFWDTLLDAD | | 392 |
| SEQ-ID-NO-1502 | LVDAGMRELW | ATGWLHDRIR | VVVSSFFVKV | LQLPWRWGMK | YFWDTLLDAD | | 392 |

| | | | | | | | |
|---|---|---|---|---|---|---|---|
| SEQ-ID-NO-1512 | LESDALGWQY | ISGSLPDGRE | LDRIDNPQLE | GYKFDPHGEY | VRRWLPELAR | | 450 |
| SEQ-ID-NO-1499 | LESDALGWQY | ITGTLPDGRE | FDRIDNPQFE | GYKFDPNGEY | VRRWLPELAR | | 435 |
| SEQ-ID-NO-1506 | LFSDALGWQY | ITGTLPDSRE | FDRIDNPQFE | GYKFDPNGEY | VRRWLPELSR | | 440 |
| SEQ-ID-NO-1497 | LESDALGWQY | ITGTLPDSRE | FDRIDNPQFE | GYKFDPNGFY | VRRWLPELSR | | 442 |
| SEQ-ID-NO-1502 | LESDALGWQY | ITGTLPDSRE | FDRIDNPQFE | GYKFDPNGEY | VRRWLPELSR | | 442 |

| | | | | | | | |
|---|---|---|---|---|---|---|---|
| SEQ-ID-NO-1512 | LPTEWIHHPW | DAPASVLQAA | CVELGSNYPL | PIVGLDAANA | RLQEALSEMW | | 500 |
| SEQ-ID-NO-1499 | LPTEWIHHPW | NAPESVLQAA | GIELGSNYPL | PIVGIDAAKV | RLEEALSEMW | | 485 |
| SEQ-ID-NO-1506 | LPTEWIHHPW | NAPESVLQAA | GIELGSNYPR | PIVGIDEAKA | RLHEALSQMW | | 490 |
| SEQ-ID-NO-1497 | LPTDWIHHPW | NAPESVLQAA | GIELGSNYPL | PIVGLDEAKA | RLHEALSQMW | | 492 |
| SEQ-ID-NO-1502 | LPTDWIHHPW | NAPESVLQAA | CIELGSNYPL | PIVGLDEAKA | RLHEALSQMW | | 492 |

| | | | | | | | |
|---|---|---|---|---|---|---|---|
| SEQ-ID-NO-1512 | QLEAASRAAM | DNGMEEGLGD | SSE--VPPIE | FPRELQMEVD | REPARVTANV | | 548 |
| SEQ-ID-NO-1499 | QQEAASRAAI | ENGTEEGLGD | SSE--SAPIA | FPQDINMEEN | HEPVRN--NP | | 531 |
| SEQ-ID-NO-1506 | QLEAASRAAI | ENGSEEGLGD | STEFVEAPIE | FPRDITMEET | -EPTRL--NP | | 537 |
| SEQ-ID-NO-1497 | QLEAASRAAI | ENGSEEGLGD | SAEVEEAPIE | FPRDITMEET | -EPIRL--NP | | 539 |
| SEQ-ID-NO-1502 | QLEAASRAAI | ENGSEEGLGD | SAEVEEAPIE | FPRDITMEET | -EPTRL--NP | | 539 |

| | | | | | | | |
|---|---|---|---|---|---|---|---|
| SEQ-ID-NO-1512 | LTTARRREDQ | MVPTMTSSLN | RA--ELELSA | DFMNSV-DSR | AEVPTR-VNF | | 594 |
| SEQ-ID-NO-1499 | PATNRRYEDQ | MVPSMTSSFL | RI-EDEETSS | DVRNSTGDGR | AEVPRD-VNV | | 579 |
| SEQ-ID-NO-1506 | ---VRRYEDQ | MVPSITTSL' | RPEEDQESSL | SLRNSGGDSR | AEVPRNMVNT | | 584 |
| SEQ-ID-NO-1497 | ---NRRYEDQ | MVPSITSSL' | RPEEDEESSL | NLRNSVGDSR | AEVPRNMVNT | | 586 |
| SEQ-ID-NO-1502 | ---NRRYEDQ | MVPSITSSL: | RPEEDEESSL | NLRNSVGDSR | AEVPRNMVNT | | 586 |

Figure 18 (continued)

```
SEQ-ID-NO-1512    EPATEREENF RTTAGNVARI NGIHEHNNFQ QPQHRMRNVL APSVSEASSG    644
SEQ-ID-NO-1499    NQQPRRDTLN QGFVQSVHND NSLPPFN---  -VVRGLANVE DSTAESSSSS    625
SEQ-ID-NO-1506    NQARQQEARA DPVSNQV--T AMIPEFN--- -IRIVAENTE ESTAESSSSG    628
SEQ-ID-NO-1497    NQAQQR--RA EPASNQV--T AMIPEFN--- -IRIVAESTE DSTAESSSSG    628
SEQ-ID-NO-1502    NQAQQR--RA EPASNQV--T AMIPEFN--- -IRIVAFSTE DSTAESSSSG    628

SEQ-ID-NO-1512    WTGREGGVVP VWSPPAASDH SEIFASDEAD I----SSRSY DRHPQSHRL    690
SEQ-ID-NO-1499    RRERDGGIVP VWSPPASS-Y SFQFVGDENG IG---AITSSY LPRHPQSHQI    671
SEQ-ID-NO-1506    RRERDGGIVP EWSG-----Y SEQFASEENG IGGGSTTSSY LQNH---HEI    670
SEQ-ID-NO-1497    RRERSGGIVP EWSPG----Y SEQFPSEENG IGGGSTTSSY LQNH---HEI    671
SEQ-ID-NO-1502    RRERSGGIVP EWSPG----Y SEQFPSEENG IGGGSTTSSY LQNH---IEI    671

SEQ-ID-NO-1512    MNWSQLSQSL    700
SEQ-ID-NO-1499    LNWRRLPQTG    681
SEQ-ID-NO-1506    VNWRRLSQTG    680
SEQ-ID-NO-1497    INWRRLSQTG    681
SEQ-ID-NO-1502    LNWRRLSQTG    681
```

Figure 19

```
SEQ-ID-NO-1612   MDEAL-----  ----------  ----------  ----------  ----------              5
SEQ-ID-NO-1597   MDGASGGSGG  GEGST-----  ----------  ----------  -------TQIP            19
SEQ-ID-NO-1609   MAAEHATAAV  GEPPP-----  ----------  ----------  ---AISQPAEG            25
SEQ-ID-NO-1614   MGEPSPPPPA  PAAEA-----  ----------  ----------  ---------AG            17
SEQ-ID-NO-1589   -MAPPPVEQN  GDATT-----  ----------  ----------  ----------             14
SEQ-ID-NO-1587   ----MPGEQT  GEPPTVAGVG  GGGAGCSAGN  SGCSSGCGAG  GGGGGSGGGG             46
SEQ-ID-NO-1596   -MAPLPAEQT  GESAP-----  ----------  ----------  ----------             14
SEQ-ID-NO-1591   -MPPLPVEQT  GESPA-----  ----------  ----------  --AC GGGAAAGGPP        26
SEQ-ID-NO-1603   ----------  ----------  ----------  ----------  ---------M              1
SEQ-ID-NO-1605   ----------  ----------  ----------  ----------  ----------              0
SEQ-ID-NO-1606   ----------  ----------  ----------  ----------  ----------              0

SEQ-ID-NO-1612   ----GSSCSL  PLPFLAKTYE  MVDDLSTNSI  VSWSVSSKSF  VWNPPCFAR              50
SEQ-ID-NO-1597   APTPMLNANA  PPPFLSKTYD  MVDDPSTDAI  VSWSATNNSF  VVWDPPEFAR             69
SEQ-ID-NO-1609   VTAAAGQRSV  PTPFLSKTYQ  LVDDPAVDDI  SWNDDGSAF   VWRPAEFAR              73
SEQ-ID-NO-1614   VGVGQQQRTV  PTPFLTKTYQ  LVDDPAVDDV  SWNDDGSTF   VVWRPAEFAR             67
SEQ-ID-NO-1589   -GTAESQRSI  PTPFLTKTYQ  LVDDHIIDDV  SWNDDGSTF   VWNPTVFAR              63
SEQ-ID-NO-1587   GGCGDSQRSI  PTPFLTKTYQ  LVEDPVYDEL  SWNEDGTTF   VWRPAEFAR              96
SEQ-ID-NO-1596   ---TEDQRSI  PIPFLTKTYQ  LVDDPSADDL  SWNEDGTSF   VWRPAEFAR              61
SEQ-ID-NO-1591   SGSGDSQRSL  PTPFLTKTYQ  LVDDPSVDDL  SWNDDGSTF   VWRPAEFAR              76
SEQ-ID-NO-1603   VFTMESQKSV  PAPFLTKTYQ  LVDDPLTDHI  VSWSDDETTF  VVWRPPEFAR             51
SEQ-ID-NO-1605   ----MSQRTA  PAPFLLKTYQ  LVDDAATDDV  SWNETGTTF   VVWKTAEFAK             46
SEQ-ID-NO-1606   ----MSQRTV  PAPFLTKTYQ  LVDDATTDDV  VSWNESGTTF  VVWKTAEFAK             46

SEQ-ID-NO-1612   DLLPRFFKHN  NFSSFIRQLN  TYGFKKIDPE  QWEFANDDFV  RGQPHLMKNI            100
SEQ-ID-NO-1597   DLLPKFFKHN  NFSSFVRQLN  TYGFRKVDPD  RWEFANEGFL  RGQKQLLKSI            119
SEQ-ID-NO-1609   DLLPKYFKHN  NFSSFVRQLN  TYGFRKIVPD  RWEFANDCFR  RGEKRLLCDI            123
SEQ-ID-NO-1614   DLLPKYFKHN  NFSSFVRQLN  IYGFRKIVPD  RWEFANDCFR  RGERRLLCEI            117
SEQ-ID-NO-1589   DLLPKYFKIN  NFSSFVRQLN  TYGFRKVVPD  RWEFSNDYFR  RGEKRLLCEI            113
SEQ-ID-NO-1587   DLLPKYFKHN  NFSSFVRQLN  TYGFRKVVPD  RWEFSNDCFK  RGEKILLRDI            146
SEQ-ID-NO-1596   DLLPKYFKHN  NFSSFVRQLN  TYGFRKVVPD  RWFFANDCFR  RGERALLRDI            111
SEQ-ID-NO-1591   DLLPKYFKHN  NFSSFVRQLN  TYGFRKVVPD  RWEFANDCFR  RGEKALLRDI            126
SEQ-ID-NO-1603   DLLPNFFKHN  NFSSFVRQLN  TYGFKKVVAD  RWEFANDYFK  KGAKHLLCEI            101
SEQ-ID-NO-1605   DLLPKYFKHN  NFSSFVRQLN  TYGFRKIVPD  KWEFANENFK  RGQKELLTAI             96
SEQ-ID-NO-1606   DLVPTYFKHN  NFSSFVRQLN  TYGFRKIVPD  KWEFANENFK  RGQKELLTAI             96
```

Figure 19 (continued)

| SEQ ID | seq1 | seq2 | seq3 | seq4 | seq5 | # |
|---|---|---|---|---|---|---|
| SEQ-ID-NO-1612 | HRRKPVHSHS | LQNLQAQGPL | GDSERQGFTD | GIEKLKRDKE | RLLVELQ-KF | 149 |
| SEQ-ID-NO-1597 | SRRKPAHGHT | QQQAQQPHGQ | SSSVGACVEV | GKFGLEEEVE | RLKRDKNVIM | 169 |
| SEQ-ID-NO-1609 | HRRKV----- | ----SPATGA | VIVAAAAAAA | IP-------- | ---------MA | 148 |
| SEQ-ID-NO-1614 | HRRKV----- | ----TPPAPA | ATIAAVA-AA | IP-------- | ---------MA | 141 |
| SEQ-ID-NO-1589 | QRRKL----- | ---SSPFAAA | VTVAPVTVAA | IP-------- | ---------MA | 139 |
| SEQ-ID-NO-1587 | QRRKISQPAM | AAAAAAAAAA | VAASAVTVAA | VP-------- | ---------VV | 180 |
| SEQ-ID-NO-1596 | QRRKL----- | -LPVPPAAAA | PAAVTANTVT | VA-------- | ---------VA | 139 |
| SEQ-ID-NO-1591 | QRRKL----- | ---STMAASA | VTSASVTVAA | LP-------- | ---------TV | 152 |
| SEQ-ID-NO-1603 | HRRKT----- | ---------- | ---------- | ---------- | -------PQ | 108 |
| SEQ-ID-NO-1605 | RRRKT----- | -VTSTPAGGK | SVAAGAS--- | ---------- | ---------- | 117 |
| SEQ-ID-NO-1606 | RRRKT----- | -VTPTPAGGK | SVVPGTS--- | ---------- | ---------- | 117 |

| SEQ ID | seq1 | seq2 | seq3 | seq4 | seq5 | # |
|---|---|---|---|---|---|---|
| SEQ-ID-NO-1612 | QHEWQTYEIQ | IHCSNDRLEK | L------EQK | QHKMVSSISH | VLQKPVLAVN | 193 |
| SEQ-ID-NO-1597 | QELVRLRQQQ | QTTDGQLQTM | VQRLQGMEQR | QQQMMSFLAK | AVQSPGFFAQ | 219 |
| SEQ-ID-NO-1609 | LPV-----GS | PVYSGEEQ-- | V--------- | -------LSS | SSPEPPSLQQ | 175 |
| SEQ-ID-NO-1614 | LPVTTTRDGS | PVLSGEEQ-- | V--------- | --------IS | SSSSPEPPLV | 172 |
| SEQ-ID-NO-1589 | KPI-----IS | PSNSGDEQSP | V--------- | --------IS | SASSP----- | 162 |
| SEQ-ID-NO-1587 | AHI-----VS | PSNSGEEQ-- | V--------- | --------IS | SNSSPAAAAA | 206 |
| SEQ-ID-NO-1596 | APAVRI--VS | PTTSGDEQ-- | V--------- | --------LS | SNSSP----- | 163 |
| SEQ-ID-NO-1591 | ARA-----VS | PANSGDDQ-- | G--------- | --------IS | STSSP----- | 173 |
| SEQ-ID-NO-1603 | HYQCQYYEQS | PQIFQPDE-- | S--------- | --------LC | WIDSP----- | 134 |
| SEQ-ID-NO-1605 | -------AS | PDNSGDDI-- | G--------- | -------SS | STSSP----- | 135 |
| SEQ-ID-NO-1606 | -------AS | PDNSGEDL-- | G--------- | -------SS | STSSP----- | 135 |

| SEQ ID | seq1 | seq2 | seq3 | seq4 | seq5 | # |
|---|---|---|---|---|---|---|
| SEQ-ID-NO-1612 | IIPITFIMDR | KRRLPRSGHY | YDESSIEDAI | ETSQMLPREN | AENTTVLTLN | 243 |
| SEQ-ID-NO-1597 | FVQQQNDSNR | RITEVNKKRR | ---LKQDGIA | EITEQATPPD | GQIVKYQPMM | 266 |
| SEQ-ID-NO-1609 | HPPAPSGSG- | -------SGG | ---VVSGDVG | EENERLRREN | ARLARELGQM | 214 |
| SEQ-ID-NO-1614 | LPQAPSGSG- | -------SGG | ---VASGDVG | DENERLRREN | AQLARELSQM | 211 |
| SEQ-ID-NO-1589 | ---SRLNQAG- | ---------- | ---TVMAELM | KENEKLRKEN | VQLNKQLSEM | 196 |
| SEQ-ID-NO-1587 | AIGGVVGGG- | --SLQRTTSC | ---TTAPELV | EENERLRKDN | ERLRKEMTKL | 250 |
| SEQ-ID-NO-1596 | -IAGNNNNN- | --TVHRTTSC | ---TTAPELL | EENERLRKEN | IQLSNELSQL | 206 |
| SEQ-ID-NO-1591 | --GGAGTAGG | ANSFLRTTSC | ---TTTPEIL | EENERLRKEN | SALSHELTQL | 218 |
| SEQ-ID-NO-1603 | -LPSPKSNT- | ---------- | ---DILTALS | EDNQRLRRKN | FMLLSELSIM | 169 |
| SEQ-ID-NO-1605 | ---DSKNPG- | --SVDTPCKL | ---SQFTDLS | DENEKLKKDN | QMLSSELVQA | 176 |
| SEQ-ID-NO-1606 | ---DSKNPG- | --SVDTPGK- | ---SQFADLS | DENEKLKKDN | QMLSSELAQA | 175 |

Figure 19 (continued)

```
SEQ-ID-NO-1612   VERLDQLESS VAFWEAIAHD IGDNFAQIQS NMDFDESTSC ADSPSISCAQ                      293
SEQ-ID-NO-1597   NETAKAMIRK IMKWDIPRVE SFNKNPDNYL IGDGTSPSSA MDSSSSTSWN                      316
SEQ-ID-NO-1609   KKLCNNILLL MSKYAATQQP DAAKEAAAG- ------NCTG CSSDAAAAPP                      257
SEQ-ID-NO-1614   RKLCNNIILL MSKYASTQQL DAANASSAAC NNNNNNNCSG ESAEAATPLP                      261
SEQ-ID-NO-1589   KSLCNNIFSL MSNYASSQSE ---------- ---------- ------NISP                      220
SEQ-ID-NO-1587   KGLYANIYTL MANFTPGQED ---------- ---------- ----CAHLLP                      276
SEQ-ID-NO-1596   KGLCNNILSL MTNYASGFSR QQLESSTSA- ---------- --VRTVPVPD                      243
SEQ-ID-NO-1591   RGLCNNIMVL MNNYASPQLE GNSGNSNN-- ---------- ------NLAE                      250
SEQ-ID-NO-1603   KNLYNDIIYF IQNHVSPASP FEQRSNNSA- ---------- ---TILKLVE                      205
SEQ-ID-NO-1605   KKQCNELVAF LSQYVKVAPD MINRIMSQG- ---------- ----------TP                     207
SEQ-ID-NO-1606   KKQCDELVAF LNQYVKVAPD MINRIISQG- ---------- -----------T                     205

SEQ-ID-NO-1612   LDVDVRPK-- -SSGIDMNSE PTAAAVPDPL ASKDQPAGIT ----VAATCV                        336
SEQ-ID-NO-1597   SGVTLQEV-- -PPSSVQSTQ IPMSTGTQGH IPSAEK---- ----PETLSV                        355
SEQ-ID-NO-1609   LPSILELL-- -PSCRADPAP AAAGTDHEDD EKAC------ ----ARLFGV                        294
SEQ-ID-NO-1614   LPAVLDLM-- -PSCPGAASA AAPVSDNEEG MMS------- ----AKLFGV                        297
SEQ-ID-NO-1589   VHKPLDFL-- -PAKRLSCGE SVEEETS--- ---------- ----PRIFGV                        250
SEQ-ID-NO-1587   EGKPLDLL-- -PLERQEMSE AIMASEIETG IGLKLGEDLT ----PRLFGV                        318
SEQ-ID-NO-1596   GKAPLELL-- -PAKHVSSAD DALHVGGAAG AAACATGNAA EAEVPKIFGV                        290
SEQ-ID-NO-1591   VKAALELL-- -PL----VAD EVAVSGRPRG GAAATESEVS ----PRLFGV                        288
SEQ-ID-NO-1603   LDSSSPQL-- -PNDKDCNSS S--------- ---------- ----VKLFGV                        229
SEQ-ID-NO-1605   SGSSLEELVK EVGGVKDLEE QGSYNDNDDK EDDDEKGDT- ----LKLFGV                        252
SEQ-ID-NO-1606   SGSSYGEL-- -VKEVIGGVN DLEAQGSDDD EKGDT----- ----LKLFGV                        243

SEQ-ID-NO-1612   NDVFWEQFLT EDPG------ ---------- ---------- ----------                        350
SEQ-ID-NO-1597   PQAAASANVM KDCTHAASTI PTSQADVIMP DIPSVPEIVP KSILDIPEDN                        405
SEQ-ID-NO-1609   SIG--RKRMR DESDHHA--- ---------- ---------- ----------                        309
SEQ-ID-NO-1614   SIG--RKRMR HDGGGD---- ---------- ---------- ----------                        311
SEQ-ID-NO-1589   PIGCAAKRAR EEGEGVATEA ATAADEI--- ------QLQLQ Q---------                        283
SEQ-ID-NO-1587   SIG--VKRAR REEELGAAEE EDDDRR---- ------EAAAQ E---------                        348
SEQ-ID-NO-1596   SIG--LKRCR TECE---AEP EGEDQNQMQT RAQTQSQSSQ E---------                        326
SEQ-ID-NO-1591   SIG--FKRVR IDEE---EEE EGN------- ------RQQTE G---------                        312
SEQ-ID-NO-1603   PLCG--KKRVH ---------- ---------- ---------- ----------                       238
SEQ-ID-NO-1605   LLK--EKKKK RG-------- ---------- ---------- ----------                        262
SEQ-ID-NO-1606   LLK--ENKKK RG-------- ---------- ---------- ----------                        253
```

Figure 19 (continued)

```
SEQ-ID-NO-1612    --ASETQEVQ SER------- --KDCDGRKN EGKPNDHSKF WWNIRNANNL  389
SEQ-ID-NO-1597    YMAPETDDGF MDPSSLGSLP IDLDCLSPGA DIDDLLSNSI WDDLLQTPIP  455
SEQ-ID-NO-1609    --GVCAAEVK AEP------- --VDARPDQQ RQRNATEPQS WPIYRPRPVY  348
SEQ-ID-NO-1614    --DDIAATVK AEP------- --MDGRPHCK DEQSA-ETQA WPIYRPRPVY  349
SEQ-ID-NO-1589    --PGGSEIIK LEP------- --LDCQNRGR DDDRGIQDAP WLRQFHRANQ  322
SEQ-ID-NO-1587    --GEQSSDVK AEP------- --ME------ ENNSGNHNGS WLELGK----  377
SEQ-ID-NO-1596    --PDHGSDVK SEP------- --LD----GD DSDYQDHDPH WLEL------  355
SEQ-ID-NO-1591    --KEHESDVK AEP------- --LD----GS SGNSDHQDQR ----------  337
SEQ-ID-NO-1603    --PSN----- ---------- --LD------ ---------- ----------  243
SEQ-ID-NO-1605    --PDENLETC GGR------- --------GK MMKFVDYNGP WMKMSSPAGE  295
SEQ-ID-NO-1606    --PDENADIS GSR------- --------GK MMKTMDYNLP WMKMSSAPGE  286

SEQ-ID-NO-1612    SEPMGHVGQA EKT------- ---------- ---------- --------    402
SEQ-ID-NO-1597    EDFEANIDEI SRGNFVQPTE NGWDNNIOPL DQLTEQMGLL SSDAKRI     502
SEQ-ID-NO-1609    HPLRACNGSG SAGSDHDCSN DSR------- ---------- --------    371
SEQ-ID-NO-1614    QPIRACNGYE YDRAGSDQDG SNST------ ---------- --------    373
SEQ-ID-NO-1589    RVCN------ ---------- ---------- ---------- --------    326
SEQ-ID-NO-1587    ---------- ---------- ---------- ---------- --------    377
SEQ-ID-NO-1596    ---------- ---------- ---------- ---------- --------    355
SEQ-ID-NO-1591    ---------- ---------- ---------- ---------- --------    337
SEQ-ID-NO-1603    ---------- ---------- ---------- ---------- --------    243
SEQ-ID-NO-1605    SSKVCN---- ---------- ---------- ---------- --------    301
SEQ-ID-NO-1606    SNKVCN---- ---------- ---------- ---------- --------    292
```

Figure 20

```
SEQ-ID-NO-1646                                                    -----MVAA  AGDAETDLTL   15
SEQ-ID-NO-1648                                                               MATVDCPLPS   10
SEQ-ID-NO-1650                                              ----------MA    TADGDPPQPF   12
SEQ-ID-NO-1642                                              -----MDFSD      EDDDENCFGS   15
SEQ-ID-NO-1644                          --MSFPTAAS PPAASEAGTL               HDDGDSYNV    28
SEQ-ID-NO-1651  MPANPKLAAK PSPSPPTAAA -AASRPKATA KPPLGAGYRD NDDDDDDFQS                    49
SEQ-ID-NO-1653  MPANPKLAAK PSPSTAEPPP QTASRPKATA KPPLGAGYRD NDDDDDDFQS                    50
SEQ-ID-NO-1637  MSSKFN----  ---------- ---------- ----SSQFSS LDDDDDDFQI                   22
SEQ-ID-NO-1635                                              ------MSNT     VEDDDDDFQI   14

SEQ-ID-NO-1646  P---------                                                                16
SEQ-ID-NO-1648  P---------                                                                11
SEQ-ID-NO-1650  P---------                                                                13
SEQ-ID-NO-1642  R---------                                                                16
SEQ-ID-NO-1644  N---------                                                                29
SEQ-ID-NO-1651  P----PRASS RAARALKPSG NGAASRRPSK RLKPSSSCCS GKENLPAAAG                    95
SEQ-ID-NO-1653  P----PRASS RAARALKPSG NGAASRRPSK RLKPSSSCCS GKENRPAAAG                    96
SEQ-ID-NO-1637  PLSQTPKQTL SIRN--KPAD ----NPRRPS K-KPKKPPNP GKENI-----                    60
SEQ-ID-NO-1635  P----PSSQL SIRKPLHPTN ANNISHRPPN K-KPRLCRYP GKENV-----                    54

SEQ-ID-NO-1646                                                                            16
SEQ-ID-NO-1648                                                                            11
SEQ-ID-NO-1650                                                                            13
SEQ-ID-NO-1642                                                                            16
SEQ-ID-NO-1644                                                                            29
SEQ-ID-NO-1651  SGRAPAGRAA SKGAGVGETL GVVSRVSSGV PGGDKARGGG ICGLLRCGSD                   145
SEQ-ID-NO-1653  SGRAPAGRAA SKGAGVGETL GVVSRVSSGV PGGDKARGGG ICGLLRCGSD                   146
SEQ-ID-NO-1637                                                                            60
SEQ-ID-NO-1635                                                                            54

SEQ-ID-NO-1646                                                                            16
SEQ-ID-NO-1648                                                                            11
SEQ-ID-NO-1650                                                                            13
SEQ-ID-NO-1642                                                                            16
SEQ-ID-NO-1644                                                                            29
SEQ-ID-NO-1651  DFSSVSNGKK GLDRYWRRDG GLHSRPNPMD STVSMPDATC DLENGGSQVA                   195
SEQ-ID-NO-1653  DFSSVSNGKK GLDRYWRRDG GLHSRPNPMD STVSMPDATC DLENGGSQVA                   196
SEQ-ID-NO-1637                                                                            60
SEQ-ID-NO-1635                                                                            54
```

Figure 20 (continued)

| SEQ ID NO | | | | | | |
|---|---|---|---|---|---|---|
| SEQ-ID-NO-1646 | ---------- | ---------- | ---------- | ---------- | ---------- | 16 |
| SEQ-ID-NO-1648 | ---------- | ---------- | ---------- | ---------- | ---------- | 11 |
| SEQ-ID-NO-1650 | ---------- | ---------- | ---------- | ---------- | ---------- | 13 |
| SEQ-ID-NO-1642 | ---------- | ---------- | ---------- | ---------- | ---------- | 16 |
| SEQ-ID-NO-1644 | ---------- | ---------- | ---------- | ---------- | ---------- | 29 |
| SEQ-ID-NO-1651 | QMLSSNDRIS | VQLEGNAKVE | LGKSESDPTT | MRKERNGSGA | CESDHPARLI | 245 |
| SEQ-ID-NO-1653 | QMLSSNDRIS | VQLEGNAKVE | LGKSESDPTT | MRKERNGSGA | CESDHPARLI | 246 |
| SEQ-ID-NO-1637 | ---------- | ---------- | ----DPNSLL | LYQKTESGAN | DFNLDF---- | 82 |
| SEQ-ID-NO-1635 | ---------- | ---------- | ----TPPP-- | ---SPDPDLF | CSSSTP---- | 71 |

| SEQ-ID-NO-1646 | ---------- | ---------- | ---------- | ---------- | ---------- | 16 |
|---|---|---|---|---|---|---|
| SEQ-ID-NO-1648 | ---------- | ---------- | ---------- | ---------- | ---------- | 11 |
| SEQ-ID-NO-1650 | ---------- | ---------- | ---------- | ---------- | ---------- | 13 |
| SEQ-ID-NO-1642 | ---------- | ---------- | ---------- | ---------- | ---------- | 16 |
| SEQ-ID-NO-1644 | ---------- | ---------- | ---------- | ---------- | ---------- | 29 |
| SEQ-ID-NO-1651 | EPRLLTLVTN | CDFGGADSMD | SKELGSAIHP | SVSKDRNVEN | ESGGASVCTF | 295 |
| SEQ-ID-NO-1653 | EPRLLTLVTN | CDFGGADSMD | SKELGSAIHP | SVSKDRNVEN | ESGGASVCTF | 296 |
| SEQ-ID-NO-1637 | ---------- | ---------- | ---------- | ---------- | ---------- | 82 |
| SEQ-ID-NO-1635 | ---------- | ---------- | ---------- | ---------- | ---------- | 71 |

| SEQ-ID-NO-1646 | ---------- | ---------- | ---------- | ---------- | ---------- | 16 |
|---|---|---|---|---|---|---|
| SEQ-ID-NO-1648 | ---------- | ---------- | ---------- | ---------- | ---------- | 11 |
| SEQ-ID-NO-1650 | ---------- | ---------- | ---------- | ---------- | ---------- | 13 |
| SEQ-ID-NO-1642 | ---------- | ---------- | ---------- | ---------- | ---------- | 16 |
| SEQ-ID-NO-1644 | ---------- | ---------- | ---------- | ---------- | ---------- | 29 |
| SEQ-ID-NO-1651 | ALHNRNCHSS | CVESELELLN | AKYDLGPRDC | KESQEGPGLC | SLISEERTVA | 345 |
| SEQ-ID-NO-1653 | ALHNRNCHSS | CVESELEMLN | AKYDLGPRDC | KESQEGPGLC | SLISEERTVA | 346 |
| SEQ-ID-NO-1637 | ----NCSLD | FIESSID--- | ---------- | ---------C | TVS------S | 99 |
| SEQ-ID-NO-1635 | ----HCILD | CIPSSVD--- | ---------- | ---------C | SLGDFNGPIS | 94 |

| SEQ-ID-NO-1646 | ---------- | ---------- | ---------- | ---------- | ---------- | 16 |
|---|---|---|---|---|---|---|
| SEQ-ID-NO-1648 | ---------- | ---------- | ---------- | ---------- | ---------- | 11 |
| SEQ-ID-NO-1650 | ---------- | ---------- | ---------- | ---------- | ---------- | 13 |
| SEQ-ID-NO-1642 | -------FN | DGVNE----- | ---------- | ---------- | --------EE | 25 |
| SEQ-ID-NO-1644 | ---------- | ---------- | ---------- | ---------- | ---------- | 29 |
| SEQ-ID-NO-1651 | AEGDATFTFE | ERGNTSSGLE | ACKGSHCLDP | VEPKLMDSCA | TH----ALEG | 391 |
| SEQ-ID-NO-1653 | AEGDATFTFE | ERGNTSSGLE | ACKGSHCLDP | VEPKLMDSCA | TH----ALEG | 392 |
| SEQ-ID-NO-1637 | KVGNEKF--D | SGSGKKEKLE | VS-GGYLCNS | IEARLMKSRV | DY---SGVNV | 143 |
| SEQ-ID-NO-1635 | SLGEEDK--E | D---KDDCIK | VNREGYLCNS | MEARLLKSRI | CLGFDSGIHE | 139 |

Figure 20 (continued)

| | | | | | | | |
|---|---|---|---|---|---|---|---|
| SEQ-ID-NO-1646 | | -------I SD | DLDD------ | ---------- | -------- | ------NC | FPA-------- | 28 |
| SEQ-ID-NO-1648 | | --------A | DLDD------ | ---------- | -------- | ------NG | FPA-------- | 21 |
| SEQ-ID-NO-1650 | | --------A | DLDD------ | ---------- | -------- | ------NG | FPD-------- | 23 |
| SEQ-ID-NO-1642 | | EDEEGFVFND | DVEE------ | ---------- | -------- | ------NE | EEE-------- | 44 |
| SEQ-ID-NO-1644 | | -DDDASFDAI | RLDD------ | ---------- | -------- | ------EG | FPS-------- | 47 |
| SEQ-ID-NO-1651 | | DGCDDFEIGT | QLNELINLCM | E-DYTEGPLS | NKVACLEGNG | MDCGSFNSSC | 440 |
| SEQ-ID-NO-1653 | | DGCDDFFIGT | QLNELINLCM | E-DYTEGPLS | NKVACLEGNG | MDCGSFNSSC | 441 |
| SEQ-ID-NO-1637 | | GNEEDFEENS | ELDAIKLCT | EEEESEAREK | IKVNC---NG | DEC------C | 184 |
| SEQ-ID-NO-1635 | | DDEGFVESNS | ELDVLINLCS | ESEGRSG--- | -EFSL---GK | DDS------- | 175 |

| | | | | | | |
|---|---|---|---|---|---|---|
| SEQ-ID-NO-1646 | ---------- | ---------- | ---------- | SPPTAPAT-- | ---------- | 36 |
| SEQ-ID-NO-1648 | ---------- | ---------- | ---------- | -LPSSPAA-- | ---------- | 28 |
| SEQ-ID-NO-1650 | ---------- | ---------- | ---------- | -LPSSPAA-- | ---------- | 30 |
| SEQ-ID-NO-1642 | ---------- | ---------- | ---------- | ---------- | ---------- | 44 |
| SEQ-ID-NO-1644 | ---------- | ---------- | --------QQ | LPIESPSP-- | ---------- | 57 |
| SEQ-ID-NO-1651 | EVQCPLCGSN | ISDLSEELRL | VHTNSCLDGD | KPAKEPNS-- | ---------- | 478 |
| SEQ-ID-NO-1653 | EVQCPLCGSN | ISDLSEELRL | VHTNSCLDGD | KPAKEPNS-- | ---------- | 479 |
| SEQ-ID-NO-1637 | FVLCPLCGTD | ISDLSEEFRL | VHTNECLDKE | ENSVTYVSVF | RILVVLGGDD | 234 |
| SEQ-ID-NO-1635 | -IQCPLCSMD | ISSLSEEQRQ | VHSNTCLDKS | YNQPSEQDSL | RKCENLSS-- | 222 |

| | | | | | | |
|---|---|---|---|---|---|---|
| SEQ-ID-NO-1646 | ---------- | ---------- | ---------- | -----SSFAD | DFYRSGIDWS | 51 |
| SEQ-ID-NO-1648 | ---------- | ----CSSG-- | ---------- | -------FAE | DFYRSGTDWS | 45 |
| SEQ-ID-NO-1650 | ---------- | ---------- | ---------- | ATTSSGFAE | DFYRSGIDWS | 50 |
| SEQ-ID-NO-1642 | ---------- | ---------- | ---------- | -------GFAS | DFYKAGSDWS | 58 |
| SEQ-ID-NO-1644 | ---------- | ----NGSFKS | S--------- | -------FAA | DFYRCGSDCS | 77 |
| SEQ-ID-NO-1651 | -------DNQ | NEP-CGESNV | E-KRRVMEWL | RNLGLSKYEE | IFIKEEVDWE | 519 |
| SEQ-ID-NO-1653 | -------DNQ | NEP-CGESNV | E-KRRVMEWL | RNLGLSKYEE | IFIKEEVDWE | 520 |
| SEQ-ID-NO-1637 | GRPLVVPRGV | EGPVCGPKKV | V-VSPVVKWL | RNLGLERYEE | DFVREEIDWE | 283 |
| SEQ-ID-NO-1635 | ----LIKESI | DDPVQLPQLV | TDLSPVLKWL | RSLGLAKYED | VFIREELDWD | 268 |

| | | | | | | |
|---|---|---|---|---|---|---|
| SEQ-ID-NO-1646 | SLQ------- | --------AP | PSHRRRPADG | TTEKF--CGP | LVQKNLFQAW | 84 |
| SEQ-ID-NO-1648 | SLR------- | --------APP | PLGPPRRAPG | VKERG--GGS | AVQSSLFQAW | 79 |
| SEQ-ID-NO-1650 | SLR------- | --------APP | PRRPPEGAAG | VKEKGKEGGS | LVQSSLFQAW | 86 |
| SEQ-ID-NO-1642 | CL-------- | --------VED | EETVSSSVKK | MKQSN----- | -----LFQIW | 83 |
| SEQ-ID-NO-1644 | SL-------- | --------LTP | ERDSLSSGKK | LKQAN----- | -----LFQIW | 102 |
| SEQ-ID-NO-1651 | TLQWLTEEDL | LGMGITSLGP | RKKIAHALCE | LRKKN----D | DANDLAADML | 565 |
| SEQ-ID-NO-1653 | TLQWLTEEDL | LGMGISLGP | RKKIAHALCE | LRKKN----N | DANDLAADML | 566 |
| SEQ-ID-NO-1637 | TLQWLTEEDL | FGIGVTALGP | RKKIVHALSE | LRKGS-NHAI | EAHGDAHAFG | 332 |
| SEQ-ID-NO-1635 | TLQSLTEEDL | LSIGITSLGP | RKKIVNALSG | VRDPF-ASSA | EVQAQSHCTS | 317 |

Figure 20 (continued)

| | | | | | | | |
|---|---|---|---|---|---|---|---|
| SEQ-ID-NO-1646 | GIEKP---AS | GMIEKVC--- | -----GPPVQ | KNLFQAWGLQ | KPPREEAAQG | | 123 |
| SEQ-ID-NO-1648 | GIEKPRR-DG | RGAGDSS--- | --------LVQ | RSLFQAWGLE | RPQRE----- | | 113 |
| SEQ-ID-NO-1650 | GIERPRREEG | AGAGDSS--- | --------LVQ | RSLFQAWGLE | RPKRE----- | | 121 |
| SEQ-ID-NO-1642 | GLQENSPDTT | KKMK------ | ----------Q | TDLFQSWGLQ | KP-------- | | 110 |
| SEQ-ID-NO-1644 | GFKRNVEHES | PNOGGYCDVV | GEGSVSSEKK | SMKRGNWGSI | LRD------- | | 145 |
| SEQ-ID-NO-1651 | NLENTKKAKI | PMNG------ | ---------N | KLITEYFRCP | SSDQ------ | | 594 |
| SEQ-ID-NO-1653 | NLENTKKAKI | PMNG------ | ---------N | KLITEYFRCP | SSDQ------ | | 595 |
| SEQ-ID-NO-1637 | EVGSRRSHGA | EMQVEASKII | GDDTSKPTAN | KLITDYFPGS | VPIK------ | | 376 |
| SEQ-ID-NO-1635 | GHVTERQRDK | STTRKAS--- | --EPKKPTAN | KLITEFFPGQ | AT-------- | | 354 |

| | | | | | | | |
|---|---|---|---|---|---|---|---|
| SEQ-ID-NO-1646 | VPVGAGASSS | SPSPSVAGS | -GRKRRWGGS | DEN--GASRK | PVACPFYKQI | | 169 |
| SEQ-ID-NO-1648 | ---GLGAGDS | SPSSSLSGSL | LARKRRRGST | EEERVAAK-K | PLACPFYKKI | | 159 |
| SEQ-ID-NO-1650 | ---GGGAGDA | SPSPSRSGSW | SGRKRRRGGP | EEEVAAAAMN | PRTCPFYKKI | | 168 |
| SEQ-ID-NO-1642 | ---SPFTSPA | SNSAKKTTSA | LGKRRRDSSF | SND------S | PRPCPFYKKL | | 151 |
| SEQ-ID-NO-1644 | ---TGKVVEN | SKSTGKRKSF | HGEKR----- | ---------V | TRSCPFYKKM | | 178 |
| SEQ-ID-NO-1651 | ---RQKKACK | VNTPSNLNSQ | KNSNAKATGG | RRTVKG---K | VKDTPIWCCI | | 638 |
| SEQ-ID-NO-1653 | ---RQKKACK | VNTPSNLNSQ | KKSNAKATGG | RRTVKG---K | VKDTPIWCCI | | 639 |
| SEQ-ID-NO-1637 | ---KKTSMIS | KEQRGAEKSQ | PGYVRKQGVK | NYTKKG---K | FKDIPLWCSI | | 420 |
| SEQ-ID-NO-1635 | ---EGTKIRT | APKPVAEKSP | SDSSSRRAVR | RNGNNG---K | SKVIPHWNCI | | 398 |

| | | | | | | | |
|---|---|---|---|---|---|---|---|
| SEQ-ID-NO-1646 | PGTPFTVDAF | RYCAVEWCSA | YFLSHFHYDH | YGGLTKKWCH | GPIYCTALTA | | 219 |
| SEQ-ID-NO-1648 | PGTPFTVDAF | RYGQVEGCSA | YFLSHFHHDH | YGGLTKKWCH | GPIYCSAITA | | 209 |
| SEQ-ID-NO-1650 | PGTPFTVDAF | RYGEVEGCSA | YFLSHFHHDH | YGGLTKKWCH | GPIYCSALTA | | 218 |
| SEQ-ID-NO-1642 | PGTPFTVDAF | RYGCVQGCSA | YFLTHFHADH | YIGLTKAWSH | GPIYCSSLTS | | 201 |
| SEQ-ID-NO-1644 | PGTNFTVDAF | RYGCVEECSA | YFLSHFHADH | YGGLSKKWSH | GPIYCSPLTG | | 228 |
| SEQ-ID-NO-1651 | PGTPFRVDAF | RYF-LRGDCCH | WFLTHFHVDH | YQGLTKSFCH | GKIYCSSVTA | | 687 |
| SEQ-ID-NO-1653 | PGTPFRVDAF | RYF-LRGDCCH | WFLTHFHVDH | YQGLTKSFCH | GKIYCSSVTA | | 688 |
| SEQ-ID-NO-1637 | PGTPFRVDAF | KYF-LRGDCSII | WFLTHFHMDH | YQGLTRSFCH | GKIYCSLITA | | 469 |
| SEQ-ID-NO-1635 | PGTPFRVDAF | KYF-LTRDCCH | WFLTHFHLDH | YQGLTKSFSH | GKIYCSLVTA | | 447 |

| | | | | | | | |
|---|---|---|---|---|---|---|---|
| SEQ-ID-NO-1646 | RLVKMLSID | SAYVCPLELD | TEYV-DGVKV | TFIFANHCPG | AALIFFRPSD | | 269 |
| SEQ-ID-NO-1648 | RLVKMCLSVN | SEYICPLELD | TEYV-EGVTV | TLLEANHCPG | AALIFFRLSD | | 259 |
| SEQ-ID-NO-1650 | RLVKMCLSVN | SDYICPLELD | TEYV-EGVTV | TLLEANHCPG | AALIFFRLSD | | 268 |
| SEQ-ID-NO-1642 | RLLRLSLSVN | PSSIHPLELD | VLYII-NGIKV | TLIEANHCPG | AALIFFRLLD | | 251 |
| SEQ-ID-NO-1644 | RLVQMCLYVN | PSYICPLEFD | TEYV-DGIKV | TLIDANHCPG | AALIHFELPN | | 278 |
| SEQ-ID-NO-1651 | NLVHYKIGIP | WDRLHVLPLN | EKITIAGVNL | TCFDANHCPG | AVIILFEPSN | | 737 |
| SEQ-ID-NO-1653 | NLVHYKIGIP | WDRLHVLPLN | EKITIAGVNL | TCFDANHCPG | AVIILFEPSN | | 738 |
| SEQ-ID-NO-1637 | KLVNLKIGIP | WDSLHVLPLN | QKICIAGVDV | TCLDANHCPG | SIIILFEPPN | | 519 |
| SEQ-ID-NO-1635 | KLVNMKLGIP | WERLQVLDLG | QKVNLSGIDV | TCFDANHCPG | SIMILFEPAN | | 497 |

Figure 20 (continued)

```
SEQ-ID-NO-1646   GKTYLHTGDF RASKSMQLHP LLQTGCISLL YLDTTYCNPK YKFPPQEDVI   319
SEQ-ID-NO-1648   GKTCLHTGDF RASKTMQSHP LLQRGRVNLV YLDTTYCNPK YKFPPQEDVI   309
SEQ-ID-NO-1650   GKTYLHTGDF RASRSMQLHP LLQRGRINLL YLDTTYCNPK YKFPPQEDVI   318
SEQ-ID-NO-1642   GTCYLHTGDF RASKQMQTHP LLFNQRVHVL YLDTTYCNPR YKFPSKEDVL   301
SEQ-ID-NO-1644   GQCYLHTGDF RACKLMQDYH LFVNKRVNVL YLDTTYCNPR YKFPSKDDVL   328
SEQ-ID-NO-1651   GKAVLHTGDF RFSSEMANNR VLQSSPIHTL ILDTTYCNPR YDFPTQEIVI   787
SEQ-ID-NO-1653   GKAVLHTGDF RFSSEMANNR VLQSSPIHTL ILDTTYCNPR YDFPTQEIVI   788
SEQ-ID-NO-1637   GKAVLHTGDF RFSEKMVTMP VIQMSSIHTL ILDTTYCN-- ----AQEAVI   563
SEQ-ID-NO-1635   GKAVLHTGDF RYSEEMSNW- -LTGSHLSSL ILDTTYCNPQ YDFPKQEAVI   545

SEQ-ID-NO-1646   DFVVRTAQRY LKKQPKTLIV VGAYSIGKEN VYLAISQALE VPIYTDASRR   369
SEQ-ID-NO-1648   DFVVRIIQRY LKKQPKTLIV VGAYSIGKEN VYLAISQALE AHIYTDASRR   359
SEQ-ID-NO-1650   DFVVSTARRY LKKQPKTLIV VGAYSIGKEN VYLAISQALE VPIYTDASRR   368
SEQ-ID-NO-1642   SYVVRITKDF LRKQPKTLIV VGSYSIGKEC VYLAIAKALG VKITANASRR   351
SEQ-ID-NO-1644   NYVVKITNNH LKKYPRTLVV VGAYSIGKEC VYLAISKAIG VKIHVNASRR   378
SEQ-ID-NO-1651   QFVIEAIQAE AFN-PKTLFL IGSYTIGKER LYMEVARLLQ KKIYVGAAKL   836
SEQ-ID-NO-1653   QFVIEAIQAE AFN-PKTLFL IGSYTIGKER LYMEVARLLQ KKIYVGAAKL   837
SEQ-ID-NO-1637   QFVIEAIQAE AFN-PKTLFL IGSYTIGKER LFLEVARVLH KKVYVNMAKF   612
SEQ-ID-NO-1635   QFVVEAIQAE AFN-PKTLFL ICSYTIGKER LFLEVARVLR EKIYINPAKL   594

SEQ-ID-NO-1646   RILHSFGWP- DLSKRISSCN QSSPLHVLPL ASLQHENLKK YLET-LDQRF   417
SEQ-ID-NO-1648   RILYSFGWP- DLSKRLCSCN QSSPLHVLPI GSINHENLKK YMFT-INGRF   407
SEQ-ID-NO-1650   RILHSFGWK- DLSKRICSCN QSSALHVLPL GSVNHENWKK YLGT-LNQQF   416
SEQ-ID-NO-1642   RILQSFGWD- DISKNLSTDG KATCLHVLPM SSLKVERIDE HLKI-YREQY   399
SEQ-ID-NO-1644   RILLAYDCP- DYSDRLCTNG NNTLLHVLPM SSLRIETLKE YLKT-YKEQF   426
SEQ-ID-NO-1651   QILKHLGLPQ EIMHWFTANE AESHIHVVPM WTIASFKRMK YLSTQYADRF   886
SEQ-ID-NO-1653   QILKHLGLPQ EIMHWFTANE AESHIHVVPM WILASFKRMK YLSTQYADRF   887
SEQ-ID-NO-1637   RLLECLGFPE EDMRWITLNE QESHIHVVPM WTLASFKRLK HLSSQYAGRF   662
SEQ-ID-NO-1635   KLLECLGFSK DDIQWFIVKE EESHIHVVPL WILASFKRLK HVANRYTNRY   644

SEQ-ID-NO-1646   LAVLAFRPTG WTFSEAAGKE LDLIKPSSRG RVTIYGVPYS FHSSFSELRD   467
SEQ-ID-NO-1648   LAVLAFRPTG WTFSEATGKH LDLIKPSSNA NVTIYGVPYS EHSSFTELRD   457
SEQ-ID-NO-1650   LAVLAFRPTG WTFSEATCKQ LDLIKPNSNG SVTIYGVPYS EHSSFTE---   463
SEQ-ID-NO-1642   GAVLAFRPTG WTYSEKIGEH LDLIKPTSRG KITIYGVPYS EHSSFTELRE   449
SEQ-ID-NO-1644   TSVLAFRPTG WTFSEKICND LALIKPVSNG NITIYGVPYS EHSSFTELRD   476
SEQ-ID-NO-1651   DLIVAFCPTG WSFGK---GKK RIPGRKWQQG AIIRYEVPYS EHSSFTELRE   934
SEQ-ID-NO-1653   DLIVAFCPTG WSFGK---GKK RTPGRKWQQG AIIRYEVPYS EHSSFTELRE   935
SEQ-ID-NO-1637   TLIVAFSPTG WTFGK---CKK KSPGRRCQQG TIIRYEVPYS LHCSFTELRE   710
SEQ-ID-NO-1635   SLIVAFSPTG WTSGK---TKK KSPGRRLQQG TIIRYEVPYS EHSSFTELKE   692
```

Figure 20 (continued)

| | | | | | | |
|---|---|---|---|---|---|---|
| SEQ-ID-NO-1646 | FLKFLRPQKV | IPTVNVGNAA | NRDKMQAYFR | EWLKGT | 503 |
| SEQ-ID-NO-1648 | FVMLLKPQKI | IPTVNVGNAT | SRDKMQAHFR | EWLKSP | 493 |
| SEQ-ID-NO-1650 | ---------- | ---------- | ---------- | ------ | 463 |
| SEQ-ID-NO-1642 | FVQFLRPDKI | IPTVNNGNAG | TREKMQSCFR | EWLRP- | 484 |
| SEQ-ID-NO-1644 | FVQFLRPDKI | IPTVNVGNAA | NREKMQSYFR | DWLKG- | 511 |
| SEQ-ID-NO-1651 | FVRFISPEHI | IPSVNNDGPD | SANAMLAQLL | ND---- | 966 |
| SEQ-ID-NO-1653 | FVRFISPEHI | IPSVNNDGPD | SANAMLAQLL | ND---- | 967 |
| SEQ-ID-NO-1637 | FVKFVSPENI | IPSVNNDGPD | SANDMVSLLL | S----- | 741 |
| SEQ-ID-NO-1635 | FVQKVSPEVI | IPSVNNDGPD | SAAAMVSLLV | T----- | 723 |

Figure 21

```
SEQ-ID-NO-1561   -MATYYSS-P GSERDSQ--- ------TMYS AESGNVSYPV PS-ALGNFLY  38
SEQ-ID-NO-1563   MMATYYSS-P GSERDSQ--- ------NMYS RDLGNASYPM PS-ALGNLLY  39
SEQ-ID-NO-1565   -MAAYYHGGA GTDIQ----- ------SGT DGLQTLYLMN PS-YAG---Y  33
SEQ-ID-NO-1556   ---MYYQGTS CNNQADHHQ QQHNNLGNSN NNIQTLYLMN PNSYMQCYTT  47
SEQ-ID-NO-1540   -MAAYFHG-N PPEIS----- ------AGSD GGLQTLTLMN PTTYVQ---Y  34
SEQ-ID-NO-1567   -MATYFHN-- NSEIQ----- ------GGSA DGLQTLIFMN PSGYIN---Y  33
SEQ-ID-NO-1543   -MSTYFHG-- NPEIQ----- ---------AST DGLQTLVLMN PA-YVQ---Y  31
SEQ-ID-NO-1547   -MATYFHG-- NPEIQAA--- ------AASA EGLQTLVLMN PT-YVQ---Y  34

SEQ-ID-NO-1561   TNNASSGPYT EFSG-IVQPQ -QNFMEL---T GHPSAMSHDS S--SNEATNM  82
SEQ-ID-NO-1563   LNNSISGPYT EFSG-ILQSQ -QNCMEMPDP GHPSVMSQDS S--ARESDML  85
SEQ-ID-NO-1565   GDAAAAAAAP GAAANMMLLN -SAVTSMTPV SFGHQPSPSS S--SAAQHFV  80
SEQ-ID-NO-1556   TDTQQHLQQQ QNQHQLLFLN -SAPAGGNAL SHANI--QHA P--LQQQHFV  92
SEQ-ID-NO-1540   TQQDNDSNNN NNSNNSNNNN -TNTNTNNNN SSFVFLDSHA PQPNASQQFV  83
SEQ-ID-NO-1567   SDTPQPPPHA GN---LVFLN -SAATLAGNG NTSIQQQHNL S--HAPPQFV  77
SEQ-ID-NO-1543   SDTPPPPPAN N----LLFFN -PNSL------ ---------S P--PQTQQLV  60
SEQ-ID-NO-1547   SETPPPPQSN N----LVFLN AAASAAANSL SPPPHLSGHA P--SNTQQFV  78

SEQ-ID-NO-1561   GSSLTEQRSF GPLKDMRNEM LMHLMDGAHS SGSDLI---- ----------  118
SEQ-ID-NO-1563   GSHQ-GQRSF GPVKDMKNEM LMHMMDGSQS STADLI---- ----------  120
SEQ-ID-NO-1565   GIPL------ ---------- ---QAPPAS- ---------- ----------   90
SEQ-ID-NO-1556   GVPL------ -PAVSLHDQI NHHGLLQRMW NNQDQSQQVI VPSSTVVSAT  135
SEQ-ID-NO-1540   GIPL-SGHEA ASTTAADNIS VLHGYPPRV- ---------- ----------  111
SEQ-ID-NO-1567   GVPL---SAE QSVQAHHDIS ALHGFPPRM- ---------- ----------  103
SEQ-ID-NO-1543   GIPLPATSAA NQGPTSHDIS PLHGLVQRV- ---------- ----------   89
SEQ-ID-NO-1547   GIPL------ --DPNSHEAS TLHGLIPRV- ---------- ----------   99

SEQ-ID-NO-1561   ---------- -HNDAHSTVQ LE-FGMLNNH --NSTSVPLA PGQGLSLSLN  154
SEQ-ID-NO-1563   ---------- -HDDDHNGAQ LD-FGVLNNH --SSSNIPSV QGQGLSLSLN  156
SEQ-ID-NO-1565   ---------- -GYNLWTPAA ATGAGDMSPP --TPQHQHQQ AHGGGAAGVS  127
SEQ-ID-NO-1556   SCGGTTTDLA SQLAFQRPIV -------VSPT --PQHRQQQQ QQGGLSLSLS  177
SEQ-ID-NO-1540   ---------- -QYSLYGSHQ ------VDPT HQQAACETPR AQQGLSLTLS  144
SEQ-ID-NO-1567   ---------- -QYNMWNA-- ------ADPN --SAAREATR ATQGLSLSLH  132
SEQ-ID-NO-1543   ---------- -HYNLYNP-- ------IDPS --GSARETPR SQQGLSLTLS  118
SEQ-ID-NO-1547   ---------- -HYNFYNP-- ------IDST --STARETPR AQQGLSLSLS  128
```

Figure 21 (continued)

```
SEQ-ID-NO-1561  THI LAPSYPH WSAKQDLL TP NSYQG----- ----DDNRMK NMQSEASHAI  195
SEQ-ID-NO-1563  TQI LAPSLPY WSVKPDML SP HSYHD----- SLRVDDI RMK SMQSEASRAI  201
SEQ-ID-NO-1565  AVLS--LSSR EAAPPVTMAA VVAAG----- DEGKYLQAMA QGAASHGQMV  170
SEQ-ID-NO-1556  PQQQQQI SFN NNI SS----- -SSPR----- TNNVT RGTM DGCSS---NMI  214
SEQ-ID-NO-1540  SQQQQQQQHH QQHQPI HVGF GSGHGEDI RV GSGSTGSGVT NGI AN-----L  190
SEQ-ID-NO-1567  AQ------GSG EDARV----- --SAG----- GSCSSAS--N NGVSGI QSVL  163
SEQ-ID-NO-1543  SLQQ--PGYG SQAQA----- --VSD----- CSASSGSGVH NRVSGVQSVF  154
SEQ-ID-NO-1547  SQQQ--GGFG SCAQAVSGED I RVSG----- GLVSPGSGVT NGVPGMQGVL  171

SEQ-ID-NO-1561  RNSKYLKAAQ ELLDEI VSVW KCM----KQKT DKGPAEAGK- -------ADGK  235
SEQ-ID-NO-1563  WNSRYLKAAQ ELLDEVVNVW KNI----KQKA QKEQVEAGK- -------TDAK  241
SEQ-ID-NO-1565  MSSKYLKAAQ ELLDEVVSVS KGMDDVKAAA AAKSPASVK- ---------KK  211
SEQ-ID-NO-1556  LGSKYLKAAQ ELLDEVVNIV GKSN--KGDD QKKDNSMNKE LI -----PLVS  258
SEQ-ID-NO-1540  VSSKYLKAAQ ELLDEVVNAD SDDMNAKSQL FSSKKGSCGN D------KPVG  235
SEQ-ID-NO-1567  LNSKYLKATQ ELLDEVVNVN GGI----KVES VKKSFEKN-- ------KVWG  202
SEQ-ID-NO-1543  LSSKYLKAAQ ELLDEVVNVN TTGI -TKSEL LAKKGGGGNN HSNSSSKAVG  203
SEQ-ID-NO-1547  LSSKYLKATE ELLDEVVNVN SNGI --KSEL SKKSNGI SSN NSN---KVLG  216

SEQ-ID-NO-1561  ETDGGI KSEG V--SSNPQES GANAAAELST AEKQELQNKM AKLMTMLDEV  283
SEQ-ID-NO-1563  ETEGGLKSEG V--SSNPQES AANAAPELST AERQELQNKM AKLMAMLDEV  289
SEQ-ID-NO-1565  EDSEGVSGGG TEDCGGAKSG GAPPPPEMST AERQELQMKK GKLI NMLDEV  261
SEQ-ID-NO-1556  DVNI NSSGCG G--GESSSRQ KNEVAI ELTT AQRQELQMKK AKLLAMLEEV  306
SEQ-ID-NO-1540  ESSAGAGCEG SI--CGGAEAA CKR-PVELGT AKLSNMLHEV  282
SEQ-ID-NO-1567  ESSTAVSGDG G--SVGCDGS GKR-STELST TERQEVQMKK AKLI NMLDEV  249
SEQ-ID-NO-1543  ESS-VVAGDG SI--G-GGEAG EKH-AAELTT AEKQEI QMKK AKLI NMLDEV  248
SEQ-ID-NO-1547  ESS---TCEG SI--G-EGEAS GKR-GPELST AERQEI FMKK AKLMSMLDEV  259

SEQ-ID-NO-1561  DRKYKHYYHQ MQLVMSSFNM VAGAGAAKPY TAVALQTI SR HFRCLKDAI N  333
SEQ-ID-NO-1563  DRKYKHYYHQ MQSVVSSFDV VAGPGAAKPY TAVALQTI SR HFRCLKDAI N  339
SEQ-ID-NO-1565  EQRYRQYHQQ MQVVVASFEA VAGGGSARTY TALALRTI SR QFRCLRDAI A  311
SEQ-ID-NO-1556  EQRYRQYHHQ MQI I VSSFEQ VAGVGSAKSY TDLALHA SK QFRCLKDAI S  356
SEQ-ID-NO-1540  EQRYRQYHQQ MQMVI SSFEQ AAGI GSAKSY TSLALKTI SR QFRCLKEAI A  332
SEQ-ID-NO-1567  EQRYRQYHNQ MQMVI SSFEQ VAGI GSARTY TALALQTI SK QFRCLKDAI T  299
SEQ-ID-NO-1543  EQRYRQYHHQ MQI VTSSFEQ AAGI GSAKTY TALALKTI SK QFRCLKDAI S  298
SEQ-ID-NO-1547  EQRYRQYHHQ MQI VI SSFEQ AAGI GSAKTY TALALKTI SK QFRCLKDAI T  309
```

Figure 21 (continued)

```
SEQ-ID-NO-1561   DQTSVIRKKL GEDDNTSGKE GKL--TRLRY IDQQIRQQRA FQQYGMLQQ-    380
SEQ-ID-NO-1563   DQINVIRKKL GEEENSSGKE GKL--TRLRY IDQQLRQQRA FQQYGMIPQ-    386
SEQ-ID-NO-1565   GQVRAASRAL GEAVDADGGC GRTVGSRLRY IDHQLRQQRA LQQLGMMQS-    360
SEQ-ID-NO-1556   EQVKATSKSL G-EDEGLGG- -KIEGSRLKF VDHHLRQQRA LQQLGMMQP-    402
SEQ-ID-NO-1540   GQIKAANKSL G-EEDSVSGV GRFEGSRLKF VDHHLRQQRA LQQLGMIQHP    381
SEQ-ID-NO-1567   GQIRAANKSL G-EDDSFGG- -KIEGSRLKY VDHHLRQQRA IQQLGMMHH-    345
SEQ-ID-NO-1543   DQIRAANKSL GEEEDGVGGA AKIEGSRLKF VDHHLRQQRA LQQLGMIQH-    347
SEQ-ID-NO-1547   GQIKAANKSL G-EEDCLGG- -KIEGSRLKF VDHHLRQQRA LQQLGMIQH-    355

SEQ-ID-NO-1561   --NAWRPQRG LPENSVSILR AWLFEHFLHP YPKDSEKLML SRQTGLTRSQ    428
SEQ-ID-NO-1563   --NAWRPQRG LPENSVTILR AWLFEHFLHP YPKDSDKIML ARQTGLTRSQ    434
SEQ-ID-NO-1565   --SAWRPQRG LPERSVSILR AWLFEHFLHP YPKDSDKIML AKQTGLTRSQ    408
SEQ-ID-NO-1556   --NAWRPQRG LPERAVSVLR AWLFEHFLHP YPKDSDKIML AKQTGLTRSQ    450
SEQ-ID-NO-1540   SNNAWRPQRG LPERAVSVLR AWLFEHFLHP YPKDSDKHML AKQTGLTRSQ    431
SEQ-ID-NO-1567   --NAWRPQRG LPERSVSVLR AWLFEHFLHP YPKDSDKHML AKQTGLTRSQ    393
SEQ-ID-NO-1543   --NAWRPQRG LPERSVSVLR AWLFEHFLHP YPKDSDKHML AKQTGLTRSQ    395
SEQ-ID-NO-1547   --NAWRPQRG LPERSVSVLR AWLFEHFLHP YPKDSDKHML AKQTGLTRSQ    403

SEQ-ID-NO-1561   ISNWFINARV RLWKPMIEDM YKEEIGEAEL DS----NSSS DNGQRNKDKA    474
SEQ-ID-NO-1563   ISNWFINARV RLWKPMIEDM YKEEIGDLEQ DS----NSSS DNAPRSKGKM    480
SEQ-ID-NO-1565   VSNWFINARV RLWKPMVEEM YLEETKDQDG GG---GAGAG DEGSKPGGSK    455
SEQ-ID-NO-1556   VSNWFINARV RLWKPMVEEM YLEEVKNQEQ NS---SNTSG DNKNKETNLS    497
SEQ-ID-NO-1540   VSNWFINARV RLWKPMVEEM YMEEMKEQAK NMGSMEKTPL DQSNEDSASK    481
SEQ-ID-NO-1567   VSNWFINARV RLWKPMVEEM YTEEMKEQEM NG-SEDNKSS KHIDEDTSMK    442
SEQ-ID-NO-1543   VSNWFINARV RLWKPMVEEM YLEEIKEQEQ NGTSDDKTSK TENHEDSASK    445
SEQ-ID-NO-1547   VSNWFINARV RLWKPMVEEM YMEEIKEQEQ NG-SEDKTSK SEHNEDAASR    452

SEQ-ID-NO-1561   PSPEENEDL- ---------- ---------- ---QPTSQA CQTSQLGESK    500
SEQ-ID-NO-1563   ASSEDKEDL- ---------- ---------- ---KSSTPRV CESSQLSFSR    506
SEQ-ID-NO-1565   GGGAGVNGGV VDSAAKM--- -DSKAAH--M ESGGGVHPSL LELAGDHQAQ    499
SEQ-ID-NO-1556   APNEEKQPI TSSLLQD--- -GTTQAE--I SITSTI STSPIT AGASLHHAHN    541
SEQ-ID-NO-1540   STSNQEK--- ---------- ---------- ------SPM ADTNYHMNPN    501
SEQ-ID-NO-1567   STTPQQVPTS ETESKSF--- -NSKQDIPIV SVSTQSTSPI GVNVRNNNSG    488
SEQ-ID-NO-1543   STAPSCQNPG ENQKVSL--- ----------M SISTASTSPL AG-NAHQQSR    482
SEQ-ID-NO-1547   SVLQEKGSVN GNLTRSFKSL DNSPDAPSAI SIPTSSTSPV GG-NLRNQSG    501
```

Figure 21 (continued)

| | | | | | | | | |
|---|---|---|---|---|---|---|---|---|
| SEQ-ID-NO-1561 | AIVGGVMGFS | GVL------A | GGFHTEANPD | D------SFM | SLMLK----- | | | 533 |
| SEQ-ID-NO-1563 | ASI-GTMNVG | GAA------- | VGFQNEANPD | D------SFM | NLMLK----- | | | 537 |
| SEQ-ID-NO-1565 | AGFYDDDDFD | GGA---AAALQ | QKLKKARTEE | Q---QQAAFHV | SDMATLHAHA | | | 545 |
| SEQ-ID-NO-1556 | FSFLGSFNME | NTITTVDHIE | NNAKKPRNID | MHKFSPSSL | SSVEM----- | | | 586 |
| SEQ-ID-NO-1540 | HN-----CDLE | GVT----GMQ | GSPKRLRTSD | E--------- | --TMMQ----- | | | 528 |
| SEQ-ID-NO-1567 | FSF----TELD | CIT------Q | ASPKRTRNHE | I---LQSPNHV | KSNET----- | | | 522 |
| SEQ-ID-NO-1543 | FSLIGSSELE | GIT------Q | GSPKKPRSNE | L---LQSPTSV | PSMNM----- | | | 519 |
| SEQ-ID-NO-1547 | FSFMGSSELD | GIT------Q | GSPKKPRSHD | L--IQSPTSV | PSINM----- | | | 538 |

| | | | | | | | |
|---|---|---|---|---|---|---|---|
| SEQ-ID-NO-1561 | ----AQRPGE | TEGTGLLHDA | VAHH----SD | DGARFM---- | ---------A | 562 |
| SEQ-ID-NO-1563 | ----DQRSNE | GDGGLLVHNA | VAHH----QD | ENARFM---- | ---------A | 566 |
| SEQ-ID-NO-1565 | AAAAAARHDE | VSHRELLMKF | MESGSA-GAG | AGAAARDHHH | EHHGGVGYSL | 594 |
| SEQ-ID-NO-1556 | ----EAKARE | SINKGFTNPL | ---------- | ---------- | -----MA--A | 605 |
| SEQ-ID-NO-1540 | ----PINADF | SSNEKLTMKI | LEERQGIRSD | GCYPFMCN-- | ------FG--Q | 565 |
| SEQ-ID-NO-1567 | --------NN | NNNEQISMKF | GDDRQ----SR | DGYCFMGNQT | NFIAGFG--Q | 559 |
| SEQ-ID-NO-1543 | ----DMNQSE | ASNDL-VSMKF | --------SK | DGYSFMGTNT | DFMGGLG--Q | 554 |
| SEQ-ID-NO-1547 | ----DIKPGE | ANNEQVSMKF | GDERQ----SR | DGYSFIGGQT | NFIGGFG--Q | 579 |

| | | | | | | | |
|---|---|---|---|---|---|---|---|
| SEQ-ID-NO-1561 | YHLAEFGRY- | ---------- | --------GNSS | NVSLTLGLQH | AENSLAVPPN | 595 |
| SEQ-ID-NO-1563 | YHLAELGRY- | ---------- | --------GN-G | NVSLTLGLQH | SGSSLSV-HN | 597 |
| SEQ-ID-NO-1565 | FAPAPYGQFA | T--EQ--FAF | AGHGGGGGG | GVSLTLGLPH | G-------AE | 633 |
| SEQ-ID-NO-1556 | YAMGDFGRFD | PHDQQ--MTA | NFH---GN-N | GVSLTLGLPP | SEN-LAM-PV | 647 |
| SEQ-ID-NO-1540 | YQMDEMSRFD | VVSDQELMAQ | RYS---GNNN | GVSLTLGLPH | CDS-LSF-ST | 609 |
| SEQ-ID-NO-1567 | YPMEEIGRFD | A--EQ--FTP | RFS---GNNN | GVSLTLGLPH | CDT-L---SG | 598 |
| SEQ-ID-NO-1543 | YPIGEIGRFD | A--EQ--FAP | RFP---GN-- | GVSLTLGLPH | CEN-LSL-SG | 593 |
| SEQ-ID-NO-1547 | YPMGEIGRFD | G--EQ--FTP | RFS---GN-- | GVSLTLGLPH | CEN-LSL-SG | 618 |

| | | | | | | | |
|---|---|---|---|---|---|---|---|
| SEQ-ID-NO-1561 | TQPCF----- | -------PGV | RDQDMYNAIA | --------PP | LNVASTSSEY | 625 |
| SEQ-ID-NO-1563 | AQQSF----- | -------AGV | GDDDIYNAIA | ---------P | LGVSVTSSDY | 626 |
| SEQ-ID-NO-1565 | QTASFLMTSS | ---------- | NGSDGAGHVA | ---------- | -----GGGGY | 658 |
| SEQ-ID-NO-1556 | SQQNYLSNE- | ---LGSRPEI | GSH------- | ---------- | ----YNRMGY | 672 |
| SEQ-ID-NO-1540 | HHQGFMQTHH | GIPIGRRVKI | GETEEYGPAT | INGGSSTTTA | HSSAAAAAAY | 659 |
| SEQ-ID-NO-1567 | THQSFMPNQN | -IQLGRRLDI | SEQNEFGL-- | ---------- | ----DSSAAF | 630 |
| SEQ-ID-NO-1543 | THQNFLPNQT | -MQMGRRLDI | DEPNEFGAIN | ---------- | PPTPHSSAAY | 632 |
| SEQ-ID-NO-1547 | THQTFLPNQN | -IQLGRRVEI | GEPNEYGALN | ---------- | TSTPHSSTAY | 657 |

Figure 21 (continued)

| | | | | | |
|---|---|---|---|---|---|
| SEQ-ID-NO-1561 | DSASQ DQQQ | QRQRF EPSPL | MHDFVA ---- - | | 651 |
| SEQ-ID-NO-1563 | ES--- MNQMD | QRQRF EQSPL | LHDFVA ---- - | | 649 |
| SEQ-ID-NO-1565 | D---- MNMQS | -TKSF -AAQL | MRDFVA ---- - | | 678 |
| SEQ-ID-NO-1556 | EN--- DFQS | GNKRF -PTQL | LPDFV TGNLG | T | 699 |
| SEQ-ID-NO-1540 | NG--- MNI QN | -QKRY -VAQL | LPDFVA ---- - | | 680 |
| SEQ-ID-NO-1567 | ES--- MNMQN | -PKRF -AAQL | LPDFVA ---- - | | 651 |
| SEQ-ID-NO-1543 | ES--- NL QN | -RKRF -VAQL | LPDFVA ---- - | | 653 |
| SEQ-ID-NO-1547 | ES--- DI QN | -RKRF -I AQL | LPDFVA ---- - | | 678 |

Figure 22

| | | | | | | |
|---|---|---|---|---|---|---|
| SEQ-ID-NO-544 | MSNSCSGGGG | CSIVWFRRDL | RVEDNPALAA | AVRAGPVLAV | FVWAPEEEGH | 50 |
| SEQ-ID-NO-539 | --------MAA | CTIVWFRRDL | RLEDNPALTA | AAHAGTVVPV | FVWSPAEDGQ | 43 |
| SEQ-ID-NO-549 | -----MAGSE | RTVVWFRRDL | RIDDNPALAS | AARDGAVLPV | FIWCPADEGQ | 45 |
| SEQ-ID-NO-543 | -----MSTNK | KTIVWFRRDL | RIEDNPALAA | AAHEGSVFPV | FIWCPEEEGQ | 45 |
| SEQ-ID-NO-538 | -----MKMDK | KTIVWFRRDL | RIEDNPALAA | AAHEGSVFPV | FIWCPEEEGQ | 45 |
| SEQ-ID-NO-542 | -----MTTNK | KTIVWFRRDL | RIEDNPALAA | AAHQGSVFPV | FIWCPEEEGQ | 45 |
| SEQ-ID-NO-547 | -----MESNY | KTIVWFRRDL | RIEDNPALAA | AARNGSVFPV | FIWCPKEEGQ | 45 |
| SEQ-ID-NO-548 | -----MESNS | KTIVWFRRDL | RIEDNPALAA | AARNGSVFPV | FIWSPKEEGQ | 45 |
| SEQ-ID-NO-541 | ------MDRS | KTIVWFRRDL | RIEDNPALAA | AARDGCVFPV | FIWCPKEEGQ | 44 |
| SEQ-ID-NO-545 | --------MN | RTIVWFRRDL | RIEDNPALAA | AARDGSVFPV | FICCPKEEGQ | 42 |
| SEQ-ID-NO-546 | ------MGSN | RTIVWFRRDL | RIEDNPALAA | AARDGSVFPV | FIWCPKEEGQ | 44 |
| | | | | | | |
| SEQ-ID-NO-544 | YQPGRVSRWW | LKNSLAQLDS | SLRSLGTCLI | TKRSTDSVAS | LLEVVKSTGA | 100 |
| SEQ-ID-NO-539 | FHPGRVSRWW | LKQSLTHLEL | SLKKLGSPLI | LRKSPDTLSV | LLEIAEATGA | 93 |
| SEQ-ID-NO-549 | FYPGRCSRWW | LKQSLPHLSQ | SLESLGCPLV | LIRAESTLEA | LLRCIDSVGA | 95 |
| SEQ-ID-NO-543 | FYPGRASRWW | MKQSLAHLTQ | SLKALGSEPT | LIKTHNTVSA | ILDCVRATGA | 95 |
| SEQ-ID-NO-538 | FYPGRASRWW | MKQSLAHLSQ | SLKALGSDLT | LIKTHNTISA | ILDCIRVTGA | 95 |
| SEQ-ID-NO-542 | FYPGRASRWW | MKQSLAHLSQ | SLKALGSELT | LIKTHNTVSA | ILDCIRVTGA | 95 |
| SEQ-ID-NO-547 | FYPGRVSRWW | LKQSLIHLKQ | SLKSLGAELV | LMKAQSTLSA | LTECVDAVGA | 95 |
| SEQ-ID-NO-548 | FYPGRVSRWW | LKQSLIHLEQ | SLKSLGAELV | LIKAQSTLSA | LLDCIEAVGA | 95 |
| SEQ-ID-NO-541 | FYPGRVSRWW | LKQSLAHLGQ | SLKSLGAELV | LIKTHSTVAA | LLDCIETIGA | 94 |
| SEQ-ID-NO-545 | FYPGRVSRWW | LKQSLYHLDQ | SLKSLGAGLV | MIKTDSTLKA | LLECVNAVQA | 92 |
| SEQ-ID-NO-546 | FYPGRVSRWW | LKQSLAHLDQ | SLKSLGAKLV | LIKTDSTLNA | LLECVNAIQA | 94 |
| | | | | | | |
| SEQ-ID-NO-544 | SQIFFNHLYD | PLSLVRDHRA | KDALTAEGIA | VKSFNADLLY | EPWEVTDELG | 150 |
| SEQ-ID-NO-539 | TQVFYNHLYD | PVSLVRDHRV | KQGLSQRGIV | VHTFNGDLLY | EPWEVYDEEG | 143 |
| SEQ-ID-NO-549 | TRLVYNHLYD | PVSLVRDDKI | KKELSALGIS | QSFNGDLLY | EPWEIYDDSG | 145 |
| SEQ-ID-NO-543 | TKVVFNHLYD | PVSLVRDHTV | KEKLVERGIS | VQSYNGDLLY | EPWEIYCEKG | 145 |
| SEQ-ID-NO-538 | TKVVFNHLYD | PVSLVRDHTV | KEKLVERGIS | VQSYNGDLLY | EPWEIYCEKG | 145 |
| SEQ-ID-NO-542 | TKVVFNHLYD | PVSLVRDHTV | KEKLVELGIS | VQSFNGDLLY | EPWEIYCEKG | 145 |
| SEQ-ID-NO-547 | TKVVYNHLYD | PVSLVRDHNI | KQKLGDLGIS | VQSYNGDLLN | EPWEVYDDDG | 145 |
| SEQ-ID-NO-548 | TKVVYNHLYD | PVSLVRDHNI | KQKLGELGIS | VQSYNGDLLN | EPWEVYDDDG | 145 |
| SEQ-ID-NO-541 | TRVVFNHLYD | PVSLVRDHNI | KEKLVELGIS | VQSYNGDLLY | EPWEIYDERG | 144 |
| SEQ-ID-NO-545 | KKVVFNHLYD | PVSLVRDHNI | KEKLVELGIS | VQSYNGDLLH | EPWDIYDESG | 142 |
| SEQ-ID-NO-546 | TKVVFNHLYD | PVSLVRDHNI | KEKLVELGIS | VKSYNGDLLY | EPWELYDEKG | 144 |

Figure 22 (continued)

```
SEQ-ID-NO-544   RPFSMFAAFW ERCLSMPYDP ESPLLPPKKI ISGLLLHHTL SEIVSYPLLI  200
SEQ-ID-NO-539   QAFTVYEAFW KKCMSMPFEP EAPLLPPRR- ---------- ---------LI  174
SEQ-ID-NO-549   LAFTTFNMYW EKCMELPIDA -SPSLAPWK- ---------- ---------LV  175
SEQ-ID-NO-543   KPFTNFNSYW KKCLDMPVES -VVIPPPWR- ---------- ---------LI  175
SEQ-ID-NO-538   KPFTSFNSYW KKCLDMSIES -VMLPPPWR- ---------- ---------LM  175
SEQ-ID-NO-542   KPFTSFSSYW KKCLDMSIES -VMLPPPWR- ---------- ---------LI  175
SEQ-ID-NO-547   KVFTTFDAYW EKSLSIQNEP -VSQLPPWR- ---------- ---------LI  175
SEQ-ID-NO-548   KVFTTFDAYW EKSLRLQKEP -VSHLPPWK- ---------- ---------LI  175
SEQ-ID-NO-541   HAFTTFEAYW DRCLHMQMEP -VSHLPPWR- ---------- ---------LV  174
SEQ-ID-NO-545   HAFTTFDPFW SRCLQMQMKT -YSTIPPCQ- ---------- ---------LI  172
SEQ-ID-NO-546   HAFTTFDPFW ERCLHKQMEP -VSLIPPWQ- ---------- ---------LI  174

SEQ-ID-NO-544   TLFVLAGDVS KCVADILLFE -DESEKGSNA LLARAWSPGW SNADKALTIF  249
SEQ-ID-NO-539   G---PIGKIV GCNAEELGLE -DEFEKSSNA LLARAWCPGW GFANKSLDSF  220
SEQ-ID-NO-549   PVP-GLESVR SCSVDDLGLE SSKDEESSNA LLMRAWSPGW RNAEKMLEEF  224
SEQ-ID-NO-543   PLT-AAGTVW ACSIEELGLE -NEAEKPSNA LLTRAWSPGW SNADKILTEF  223
SEQ-ID-NO-538   PITAAAFAIW ACSIEELGLE -NEAEKPSNA LLTRAWSPGW SNADKLLNEF  224
SEQ-ID-NO-542   PITAAVEAVW ACSIEELGLE -NDAEKPSNA LLTRAWSPGW SNADKILNEF  224
SEQ-ID-NO-547   Q---AAGSVK MCSVEELGLE -NESEKSSNA LLGKGWAPGW SNADKALTEF  221
SEQ-ID-NO-548   P---AAGSVK MCSVEELGLE -NESEKSSNA LLGKGWAPGW SNADKALTEF  221
SEQ-ID-NO-541   P---AAGTVM KCSVEELGLE -DEAEKSSNS LLGRGWSPGW SNADKALTEF  220
SEQ-ID-NO-545   P---AQGKVE KHSIEQLGLE -DELEISSNA LLSRAWSPGW SKSDKALTEF  218
SEQ-ID-NO-546   P---AKGKVE RCSIEDLGLE -NELEKPSNA LLGRAWSPGW GNANKALTEF  220

SEQ-ID-NO-544   INGPLIEYSK NRRKADSAT- --TSFLSPHL HFGEVSVRKV FHLLRIKQVA  296
SEQ-ID-NO-539   LRSPLIDYAR DRQKADGASG TPTSLLSPHL HFGELSVRKI FHEVRKRQIT  270
SEQ-ID-NO-549   VSHGLLEYSK HGMKVEGAT- --TSLLSPYL HFGEVSVRKV YQLVRMQQIK  271
SEQ-ID-NO-543   IEKQLIDYAK NSKKVVGNS- --TSLLSPYL HFGEISVRRV FQCARMKQII  270
SEQ-ID-NO-538   IEKQLIDYAK NSKKVVGNS- --TSLLSPYL HFGEISVRHM FQCARMKQII  271
SEQ-ID-NO-542   IDKQLIYYAK NSNKVVGNA- --TSLLSPYL HYGEISVRRV FQCARMKQII  271
SEQ-ID-NO-547   VESNLLAYSK DRLRVGGNS- --TSLLSPYL HFGEVSVRKV FNSVRLKQIL  268
SEQ-ID-NO-548   VENQLLAYSK DRLRVGGNS- --TSLLSPYL HFGEVSVRKV FNSVRLKQIL  268
SEQ-ID-NO-541   AEQHLIDYME SRLKVG-TS- --TSLLSPYL HFGELSVRKV FQCVQLKQLL  266
SEQ-ID-NO-545   VENHLIHYSK NRLNLGVDS- --TSLLSPYI HFGELSVRKV FQLVRTKQIL  265
SEQ-ID-NO-546   MDKQLLNYSK NRQKVGGDS- --TSLLSPYL HFGELSVRKV FQMARVKQIS  267
```

Figure 22 (continued)

| SEQ-ID-NO-544 | WANEGNQAGE ESVNLFLKST GLREYSRYIS FNHPYSHERP LLGHLKFFPW | 346 |
| --- | --- | --- |
| SEQ-ID-NO-539 | WAREGNAGGE ASVNMFLRAL GFREYSRYLS FHFPFTHERS LLANLKSFPW | 320 |
| SEQ-ID-NO-549 | WENEGTSEAE ESIHFFMRSI GLREYSRYLC FNFPFTHEKS LLGNLKHYPW | 321 |
| SEQ-ID-NO-543 | WARDKNGQGV ESAVLFLRGI GLRDYSRYIC FNFPFTHEQS LLSHLRFFPW | 320 |
| SEQ-ID-NO-538 | WARDKNSEGE ESADLFLRGI GLREYSRYIC FNFPFTHEQS LLSHLRFFPW | 321 |
| SEQ-ID-NO-542 | WARDKNSEGE ESTDLFLKGI GLREYSRYIC FNFPFTHEQS LLSHLRFFPW | 321 |
| SEQ-ID-NO-547 | MTKEGNSVGK DSATIYLRAI GLREYSRYIC FNFPFTHERS LLNNLRFFPW | 318 |
| SEQ-ID-NO-548 | MTKEGNSVGD ESASLYLRAI GLREYSRYIC FNFPFTHERS LLNNLKFFPW | 318 |
| SEQ-ID-NO-541 | WAKEENLMGK ESVTLFLRSI GLREYSRYLC FNFPFTHERS LLRNLKYFPW | 316 |
| SEQ-ID-NO-545 | WKNEGNIVGE ESATFFLRAI GFREYSRYLC FSFPFTMERP LLGNLKFFPW | 315 |
| SEQ-ID-NO-546 | WGNEGNSVGK ESVTLFLRAI GLREYSRYLC FNFPFTHERA LLGHLSFFPW | 317 |

| SEQ-ID-NO-544 | AVDENYFKAW RQGRTGYPLV DAGMRELWAT GWLHDRIRVV VSSFFVKMLQ | 396 |
| --- | --- | --- |
| SEQ-ID-NO-539 | RADEGYFKAW RQGRTGYPLV DAGMRELWAT GWAHNRIRVV VASFSVKFLQ | 370 |
| SEQ-ID-NO-549 | KVDEERFKSW RQGMTGYPLV DAGMRELWAT GWTHNRIRVI ISSFAVKFLL | 371 |
| SEQ-ID-NO-543 | DADVEKFKAW RQGRTGYPLV DAGMRELWAT GWMHNRIRVI VSSFAVKFLL | 370 |
| SEQ-ID-NO-538 | DADVDKFKAW RQGRTGYPLV DAGMRELWAT GWMHNRIRVI VSSFAVKFLL | 371 |
| SEQ-ID-NO-542 | DADVDKFKAW RQGRTGYPLV DAGMRELWAT GWMHNRIRVI VSSFFVKFLL | 371 |
| SEQ-ID-NO-547 | NADQAHFKAW RQGRTGYPLV DAGMRELWAT GWVHNKIRVI VSSFFVKFLL | 368 |
| SEQ-ID-NO-548 | NADQARFKAW RQGRTGYPLV DAGMRELWAT GWIHNKIRVI VASFFVKFLL | 368 |
| SEQ-ID-NO-541 | NDNQVHFKAW RQGRTGYPLV DAGMRELWAT GWIHNKIRVI VSSFAVKMLL | 366 |
| SEQ-ID-NO-545 | NTDPSKFKAW RLGRTGYPLV DAGMRELWAT GWIHNKMRVI VSSFAVKMLL | 365 |
| SEQ-ID-NO-546 | NADPSNFKTW RQGRTGYPLV DAGMRELWAT GWMHNRIRVI VSSFAVKMLL | 367 |

| SEQ-ID-NO-544 | LPWRWGMKYF WDTLLDADLE SDALGWQYIT GTLPDSREFD RIDNPQFEGY | 446 |
| --- | --- | --- |
| SEQ-ID-NO-539 | LPWRWGMKYF WDVLLDADLE CDVLGWQYIS GSLPDGHELD RIENPEVEGY | 420 |
| SEQ-ID-NO-549 | IPWTWGMKYF WDVLLDADLE SDILGWQYIS GSLPDGHELS RLDNPEVDGQ | 421 |
| SEQ-ID-NO-543 | LPWKWGMKYF WDTLLDADLE CDIIGWQYIS GSLPDGHELD RLDNPAIQGA | 420 |
| SEQ-ID-NO-538 | LPWKWGMKYF WDTLLDADLE CDILGWQYIS GSIPDGHELD RLDNPALQGA | 421 |
| SEQ-ID-NO-542 | LPWKWGMKYF WDTLLDADLE CDILGWQYIS GSLPDGHELD RLDNPAIQGA | 421 |
| SEQ-ID-NO-547 | LPWQWGMKYF WDTLLDADLE SDIIGWQYIS GSLPDGHELE RLDNPEVQGF | 418 |
| SEQ-ID-NO-548 | LPWQWGMKYF WDTLLDADLE SDIIGWQYIS GSLPDGHELE RLDNPEVQGF | 418 |
| SEQ-ID-NO-541 | LPWRWGMKYF WDTLLDADLE SDILGWQYIS GSLPDAHELE RLDNPEIQGS | 416 |
| SEQ-ID-NO-545 | IPWKWGMKYF WDTLLDADLE SDILGWQYIS GSLPDGHELE RLDDPEIQGT | 415 |
| SEQ-ID-NO-546 | LPWKWGMKYF WDTLLDADLE CDILGWQYIS GCLPDGHELE RLDDPEILGA | 417 |

Figure 22 (continued)

| SEQ ID | col1 | col2 | col3 | col4 | col5 | col6 | num |
|---|---|---|---|---|---|---|---|
| SEQ-ID-NO-544 | KFDPNGEYVR | RWLPELSRLP | TEWIHHPWNA | PESVLQAAGI | ELGSNYPRPI | | 496 |
| SEQ-ID-NO-539 | RFDPDGDYVR | RWIPELARLP | NEWVHHPWDA | PPSALRAAGV | ELGTNYPRPI | | 470 |
| SEQ-ID-NO-549 | KYDPDGVYVR | TWIPELARMP | TEWIHHPWDA | PSCILEVAGV | ELGFNYPKPI | | 471 |
| SEQ-ID-NO-543 | KYDPEGEYIR | QWLPELARLP | TEWIHHPWDA | PLTVLKASGV | ELGTNYAKPI | | 470 |
| SEQ-ID-NO-538 | KYDPEGEYIR | QWLPELARLP | TEWIHHPWDA | PLTVLKASGV | ELGTNYAKPI | | 471 |
| SEQ-ID-NO-542 | KFDPEGEYIR | QWLPELARLP | TEWIHHPWDA | PLTVLKASGV | ELGTNYVKPI | | 471 |
| SEQ-ID-NO-547 | NYDPEGEYVR | HWLPELARMP | AEWIHHPWDA | PLNVLKAAGV | ELGMNYPNPI | | 468 |
| SEQ-ID-NO-548 | NYDPEGEYVR | HWLPELARMP | AEWIHHPWDA | PLTVLKAAGV | ELGMNYPNPI | | 468 |
| SEQ-ID-NO-541 | KFDPEGEYVR | RWLPELARMP | AEWIHHPWDA | SIAVLKAAGV | ELGINYPKPI | | 466 |
| SEQ-ID-NO-545 | KYDPEGEYIR | QWLPELARIP | TEWIHHPWNA | PLTVLKASGI | ELGQNYPKPI | | 465 |
| SEQ-ID-NO-546 | KFDPEGEYVR | QWLPELARMP | IEWIHHPWNA | PLSVLRASGV | ELGQNYPNPI | | 467 |

| SEQ ID | col1 | col2 | col3 | col4 | col5 | col6 | num |
|---|---|---|---|---|---|---|---|
| SEQ-ID-NO-544 | VGLDEAKARL | HEALSQMWQL | EAASRAAIEN | GSEEGLGDSI | EFVE------ | | 540 |
| SEQ-ID-NO-539 | VEIGAARERL | QASLAEMWER | DAAMKAALAN | GLEEGLGEIV | EVAGTGGPEH | | 520 |
| SEQ-ID-NO-549 | VDLHIARECL | DDSISTMWQL | DIAEKLAFID | G--EVVEDNL | SNI------- | | 512 |
| SEQ-ID-NO-543 | VDIDTARELL | TKAISRTREA | QIMIGAA--- | -PDEIVADSF | ---------- | | 505 |
| SEQ-ID-NO-538 | VDIDTARELL | AKAISRTREA | QIMIGAA--- | -PDEIVADSF | ---------- | | 507 |
| SEQ-ID-NO-542 | VDIDTARELL | TKAISRTREA | QIMIGAA--- | -PDEIVADSF | ---------- | | 507 |
| SEQ-ID-NO-547 | IDVDVARDRL | MQAIIIMREK | EAAVNTSHAN | GTVEVVFDNS | ENVG------ | | 512 |
| SEQ-ID-NO-548 | IDVDVARDRL | MQAIFIMREK | EAAANAADAN | GTNEVVFDNS | ENVG------ | | 512 |
| SEQ-ID-NO-541 | IDIDLARERL | MEAIFKMWEM | EAAARASNTN | GTNEVVVDNT | DDT------- | | 509 |
| SEQ-ID-NO-545 | IEIDLAREQL | TQAIFKMWED | EAASKASTSE | NKHEVVDDS- | ---------- | | 504 |
| SEQ-ID-NO-546 | IDIDLAREKL | TQAIFKMWEI | QAASKASCSE | ARDEVVVDN- | ---------- | | 506 |

| SEQ ID | col1 | col2 | col3 | col4 | col5 | num |
|---|---|---|---|---|---|---|
| SEQ-ID-NO-544 | APIEFPRDIT | MEETEPTRL- | NPVRRYEDQM | VPSITTSLIR | PEEDQESSLS | 589 |
| SEQ-ID-NO-539 | ERMDVPR-VM | VHMQRDADM- | SCNSSRRDQL | VPEIVPN--- | ---------- | 555 |
| SEQ-ID-NO-549 | KTFDIPK-VV | L---REISP- | CA--LPIDQR | VPHA------ | ---------- | 539 |
| SEQ-ID-NO-543 | EALEAAN--T | V---KEHGY- | CPL-SSNDQQ | VPSDV----- | ---------- | 532 |
| SEQ-ID-NO-538 | EALGANT--- | I---KEPGL- | CPSVSSNDQQ | VPSAV----- | ---------- | 535 |
| SEQ-ID-NO-542 | GALEGNT--- | V---KEIGL- | CPSVSSNDQQ | VPSAV----- | ---------- | 535 |
| SEQ-ID-NO-547 | DSASIPKDDV | V---KGKEP- | CPSSSSVDQR | VPSMQ----- | ---------- | 543 |
| SEQ-ID-NO-548 | DSVNIPK--V | V---KGKVP- | CPSSSSYDQR | VPSMQ----- | ---------- | 540 |
| SEQ-ID-NO-541 | ENLAIPK-VV | L---KDKVT- | CPTNSSNDQR | VPTNQN---- | ---------- | 540 |
| SEQ-ID-NO-545 | ENLSIPK-VF | L---KDKAPR | GATSSSNDQK | VPILQNP--- | ---------- | 537 |
| SEQ-ID-NO-546 | ENQDIPK-VI | L---KDKGP- | CVTISANDQK | VPALPDP--- | ---------- | 538 |

Figure 22 (continued)

```
SEQ-ID-NO-544                LRNSGGDSRA EVPRNMV-NT NQARQQEARA DPVSNQVTA-  ----------            627
SEQ-ID-NO-539                -QFH RAHES I MNRSAA-MV EDGEEAGRAA VPMVFASVRR GMGGNYGGHH            603
SEQ-ID-NO-549                ---SSKDHN- --LKSKV-LK ASNRSSI--- -----CVDM- ----------            563
SEQ-ID-NO-543                -RYSGS---- --KRVKPAEE EEEREMKKLR GFNEVI---- ----------            561
SEQ-ID-NO-538                -RYNGS---- --KRVKP-EE EEERDMKKSR GFD------- ----------            560
SEQ-ID-NO-542                -RYNGS---- --KRVKH-VE EEERDMKKSR GFDE------ ----------            561
SEQ-ID-NO-547                ---NVGTYR- --KRPKP-EE ETKKLNDNKL SYKNERI K- ----------            574
SEQ-ID-NO-548                ---KGSTNK- --KRPNP-VE EEKKFKDNWL SCKI KTEGK- ----------           572
SEQ-ID-NO-541                -SKN PAYR- --KRSKY-ME F.ERPQPDKLH NDGNVVG--- ----------            572
SEQ-ID-NO-545                -KI DDPPNR- --KKQKC-MD KEDREQDSLS NLSKRTDTG- ----------            571
SEQ-ID-NO-546                -KNELPVR-- --KRKKG-ME EKGKEQESSV NNEKDSK--- ----------            569

SEQ-ID-NO-544                ---------- --MI PEFNI R IVAENTEEST AESSSSGRRE RDGGI ---VP           662
SEQ-ID-NO-539                VEGNGGEVAQ ASAPI QWPTV TAVDYELDST AESASVTGRG GSEGGT--VP            651
SEQ-ID-NO-549                ---------- ---------I RSSKMEATSS VANSPVSRKR SFCFTAFHVP            594
SEQ-ID-NO-543                ---------- ---------R EEEERGLFST AESSS----S SSVRSVFMVS            588
SEQ-ID-NO-538                ---------- ---------- ---ERELFST AESSS----- --SSSVFFVS            580
SEQ-ID-NO-542                ---------- ---------V MREERDLFST AESSS----- SSTTVRFLVS            587
SEQ-ID-NO-547                ---------- ---------M SNVDGDLCST AESSSMKKQM TVSRNSFSVP            605
SEQ-ID-NO-548                ---------- ---------I SKADDDLCST AESSSMKKQM TTSRNSFSVP            603
SEQ-ID-NO-541                ---------- ---------T TRKDEDLCST AESSS-AKKQ ATSSCSFSVP            602
SEQ-ID-NO-545                ---------- ---------V SCVDQEVCST AESSS--KRQ SSSTCSFYVP            600
SEQ-ID-NO-546                ---------- ---------V SSPDQEFCST ADSSACKKQC STSTYTFSVP            600

SEQ-ID-NO-544                EWSGYSEQFA SEENGIGG-- ---------- ------GSTT STYLQNHHE)            694
SEQ-ID-NO-539                VWS----QSV SARTPI QVRE GLVPEVRRGP GLSRRQLQAS VQRVNLEGMT            697
SEQ-ID-NO-549                SYS----SSA EVHSHI QDHG GSL------V GPSRYLLQEA GRNYVDEVED            634
SEQ-ID-NO-543                HSC----SLV SEGKNLEG-- ---------- -------I QDS SDQIA------           611
SEQ-ID-NO-538                QSC----SLA SEGKNLEG-- ---------- -------I QDS SDQIT------           603
SEQ-ID-NO-542                HSC----SLV SEGKNLEG-- ---------- -------I QDP SDQIT------           610
SEQ-ID-NO-547                RTI ----TMS HDRKSFDD-- ---------- ------EASS HVKLQKEEE)            633
SEQ-ID-NO-548                QAI ----SMS YDI KSFDG-- ---------- ------EASS HVKLQNEEE)            631
SEQ-ID-NO-541                QYC-----SS SEGKPLQE-- ---------- ------SESS DLRQPLQAQ)            629
SEQ-ID-NO-545                ---------- ---------- ---------- ---------- ----------            600
SEQ-ID-NO-546                QQC------- ---------- ---------- -----SSSS NLKWSWQEQ)            617
```

Figure 22 (continued)

| SEQ-ID-NO-544 | VNWRRLSQTG | | | 704 |
|---|---|---|---|---|
| SEQ-ID-NO-539 | SNKQAEEEDF | YVPKLVKWTQ | PRKRRVKQDG | 727 |
| SEQ-ID-NO-549 | SSTADSGSSL | SRQRKAA--- | ---------- | 651 |
| SEQ-ID-NO-543 | ---TSLGKNG | ---------- | ---------- | 618 |
| SEQ-ID-NO-538 | ---TSLGKNG | CK-------- | ---------- | 612 |
| SEQ-ID-NO-542 | ---TKLGKNG | ---------- | ---------- | 617 |
| SEQ-ID-NO-547 | DT-------- | ---------- | ---------- | 635 |
| SEQ-ID-NO-548 | DMEINSCKNE | ---------- | ---------- | 641 |
| SEQ-ID-NO-541 | EMEQSSSKDG | KQLHFIV--- | ---------- | 646 |
| SEQ-ID-NO-545 | ---------- | ---------- | ---------- | 600 |
| SEQ-ID-NO-546 | DMEQSSGKDG | PT-------- | ---------- | 629 |

Figure 23

| SEQ-ID-NO-606 | ---MDYSSMHQ | -NVMGVSSCS | QDYQNQKKP | LSATRPAPPE | QSLRCPRCDS | 47 |
| SEQ-ID-NO-609 | ---MNPSSGQP | -QQMSSQSVE | ---------- | -KKPKP-HPE | QALKCPRCDS | 35 |
| SEQ-ID-NO-607 | MGMDSSSGQQ | -QQMSNQSLE | SMLTCSKGEQ | DKKPKPPQPE | -ALKCPRCDS | 48 |
| SEQ-ID-NO-608 | ---MDSSSFQQ | HQQMSNQSLE | SMLTCSKGEQ | DKKAKP-QPE | -ALKCPRCDS | 46 |

| SEQ-ID-NO-606 | TNTKFCYYNN | YSLSQPRYFC | KSCRRYWTKG | GLLRNIPIGG | AYRKHKRS-S | 96 |
| SEQ-ID-NO-609 | TNTKFCYYNN | YSLSQPRYFC | KSCRRYWTKG | GTLRNVPVGG | GCRKKR---S | 82 |
| SEQ-ID-NO-607 | NNTKFCYYNN | YSLSQPRYFC | KSCRRYWTKG | GTLRNVPVGG | GCRKNKRSSS | 98 |
| SEQ-ID-NO-608 | SNTKFCYYNN | YSLSQPRYFC | KSCRRYWTKG | GTLRNVPVGG | GCRKNKRSSS | 96 |

| SEQ-ID-NO-606 | SATKSLRTTP | EPTMTHDCKS | FPTASFGYNN | NNISNEQME- | -----LGLA- | 139 |
| SEQ-ID-NO-609 | SSLKRAQGQT | LTPNLNPLTT | LPHLSYDSND | FTLAVARFQK | QSSGQLGYN- | 131 |
| SEQ-ID-NO-607 | ASSKRSQDQP | FQTNPNPLTC | FPSLSYDSND | LTLALARLQK | ---GHLGFDH | 145 |
| SEQ-ID-NO-608 | SVSRRTQDQA | FVNNPNPVTC | FPSLSYDSND | LTLALARLQK | ---GQLGFDH | 143 |

| SEQ-ID-NO-606 | ---YALLNKQ | P--------- | --LGVSSHLG | FG-SSQSPMA | MDGV----YG | 170 |
| SEQ-ID-NO-609 | DRDLSTLGNP | T--------TG | SFCDILGNSG | MNPSSANPSF | LDAIRTGFLE | 174 |
| SEQ-ID-NO-607 | FHDFSILGNQ | T---------N | TSCGILNNHG | MNHSSNNQGF | FEAL----MG | 183 |
| SEQ-ID-NO-608 | EHDFSILGNH | ANSNININTN | TSCAVLNNHG | MNHSSNNHGF | FEAL----MG | 189 |

| SEQ-ID-NO-606 | TTSHQMENTG | YAFGNGCGG- | ---------- | VSGEMMLPYD | ---------- | 189 |
| SEQ-ID-NO-609 | TQNH-LQNLY | CMYGNGDLGE | VDNGNSGVVG | VSGEMMLPYD | QVIMSNATTQ | 223 |
| SEQ-ID-NO-607 | SQNN-VQNLY | Y------MGE | VDNGNANGNG | -NGEMMLPYD | HE-MSIATTQ | 224 |
| SEQ-ID-NO-608 | SQNN-VQNLY | YGYGNRDMGE | VDNGNV---- | -SGEMMLPYD | HE-MSIATTQ | 232 |

| SEQ-ID-NO-606 | ---------- | MEQMATSDPN | RVLMGFPWQM | NMGGCSCHGH | GHVDQID-SG | 228 |
| SEQ-ID-NO-609 | SVSV--MKQE | MCSRREQSER | RVLGGFPWQL | N-------AD | TNIGELD-SG | 263 |
| SEQ-ID-NO-607 | AVTVTTMKQE | MCNVREQNEN | RVLLGFPWQF | N------NGD | TNMAEMDHLG | 268 |
| SEQ-ID-NO-608 | AVTVTTMKQE | MCNVREQNES | RVLLGFPWQF | N------NGD | SNMDEIDHSG | 276 |

| SEQ-ID-NO-606 | REI--WSSTV | NYINTG---- | ALL | 245 |
| SEQ-ID-NO-609 | RTIASWNSFT | NSW-GELQS | PLM | 285 |
| SEQ-ID-NO-607 | RAG--WNGLT | SSWGHGLLNS | PLM | 289 |
| SEQ-ID-NO-608 | RAG--WNGLT | SPW-HGLLNS | PLM | 296 |

Figure 24

| | | | | | | | |
|---|---|---|---|---|---|---|---|
| SEQ-ID-NO-579 | MVRTL----- | ---------- | -PERSY--SC | SSAKEVAYSC | GYCGYALNLS | | 31 |
| SEQ-ID-NO-570 | MERSASVGVN | DGRFGGNQFY | SPSFSSSSSS | SSMRHVNYSC | GSCGYELNLS | | 50 |
| SEQ-ID-NO-578 | MDRSASVGLK | DGGFGGNHLY | SPSFSL--SS | SSMRHVNYSC | GSCGYELNLS | | 47 |
| SEQ-ID-NO-576 | MDDSA-FKRG | -----GH--- | -FNRIY--SC | SSQRDVCYSC | GTCGYELNLS | | 38 |
| SEQ-ID-NO-574 | MEKSK-VGKG | -AYLNCN--- | -PHHSFSSSS | ASQRHVSYSC | GICGYELNLS | | 44 |
| SEQ-ID-NO-572 | MEKSV-FVKD | VQQLNGN--- | -LHHSF--SS | VSQRDVTYSC | GSCGYELNLS | | 43 |
| | | | | | | | |
| SEQ-ID-NO-579 | SSIRNTANIG | SKYGKQIRKG | VISFFAIDES | RFTQIDEVSC | MPYFHSRRSW | | 81 |
| SEQ-ID-NO-570 | STNRITSTIG | SKYGKSMKSG | IISFFNIDEG | RFSQVDEFQC | MPHF-SRYSW | | 99 |
| SEQ-ID-NO-578 | STNRITSSIG | SKYGKSMKTG | IISFFNIDEG | RFSQVDEFQC | MPHF-SRYSW | | 96 |
| SEQ-ID-NO-576 | SSNRNTASIG | SKYGKSIKRG | IISFFSIDLS | RFTQVDCIQC | VPHF-DKHSW | | 87 |
| SEQ-ID-NO-574 | SSNRNTSSIG | SKYGKSIKRG | IISFFIDES | RFTQVDEFQC | LPFF-SRNSW | | 93 |
| SEQ-ID-NO-572 | SSSRNTATIG | SKYGKLIKRG | MISFFNIDET | RFTQVDEFQC | RPYFI-SKHSW | | 92 |
| | | | | | | | |
| SEQ-ID-NO-579 | GLFRKRTRLT | CRKCCGRIGN | AYEDEDSILY | DGSDDLHMSS | EGYSMSSGKK | | 131 |
| SEQ-ID-NO-570 | GLFRHRTKLL | CRKCNNYICN | ASQEKA-PEY | ALVTQNSDPT | SP-RLGSVTK | | 147 |
| SEQ-ID-NO-578 | GLFRRKTKLL | CRQCNNYICN | ASYDKAPPEY | ALVTQNSSPR | KG-VTDIVTK | | 145 |
| SEQ-ID-NO-576 | GLFRRRTKLL | CRKCGNHIGN | AYNGYT-SSF | PLVSDGAESS | PSSKVVSHTK | | 136 |
| SEQ-ID-NO-574 | GLFHRRTALL | CRKCGNNIGI | AYDDKA-SAY | PLVADGSDSS | SMSEVSKHRK | | 142 |
| SEQ-ID-NO-572 | GLFRHRTKLL | CRKCGNHIGD | AYDDKS-SGY | PHVLDGSDSS | SGTEPSNHRK | | 141 |
| | | | | | | | |
| SEQ-ID-NO-579 | YVIKINALQP | ST-DDSGVPF | TL | 152 | | | |
| SEQ-ID-NO-570 | YDIRIRSLQP | SS-----AV | AL | 163 | | | |
| SEQ-ID-NO-578 | YDIRIRALQP | SS-----GVA | SL | 162 | | | |
| SEQ-ID-NO-576 | YDIRICALQP | SSSEESGPV | FA | 158 | | | |
| SEQ-ID-NO-574 | YDVKIRALQP | SSVDQFSTPI | HT | 164 | | | |
| SEQ-ID-NO-572 | YDVRIRALQP | STAEGLGSPL | FA | 163 | | | |

MODULATING LIGHT RESPONSE PATHWAYS IN PLANTS, INCREASING LIGHT-RELATED TOLERANCES IN PLANTS, AND INCREASING BIOMASS IN PLANTS

CROSS-REFERENCE TO RELATED APPLICATIONS

This application is a divisional of U.S. patent application Ser. No. 17/481,090, filed Sep. 21, 2021, which is a divisional of U.S. patent application Ser. No. 16/045,503 filed Jul. 25, 2018 which application is a divisional of U.S. patent application Ser. No. 13/630,902 filed Sep. 28, 2012, which application is a continuation-in-part application of and claims priority to U.S. patent application Ser. No. 12/863,102, filed Apr. 11, 2011, which is a National Stage application under 35 U.S.C. § 371 of International Application No. PCT/US2009/031292, filed Jan. 16, 2009, which claims the benefit of priority under 35 U.S.C. § 119(e) to U.S. Provisional Patent Application Ser. No. 61/021,943, filed Jan. 18, 2008. U.S. patent application Ser. No. 13/630,902, filed Sep. 28, 2012, is also a continuation-in-part application of and claims priority to U.S. patent application Ser. No. 12/373,134, filed Apr. 6, 2010, which is a National Stage application under 35 U.S.C. § 371 of International Application No. PCT/US2007/073154, filed Jul. 10, 2007, which claims the benefit of priority under 35 U.S.C. § 119(e) to U.S. Provisional Patent Application Ser. No. 60/819,763, filed Jul. 10, 2006. U.S. patent application Ser. No. 13/630,902 filed Sep. 28, 2012, is also a continuation-in-part application of and claims priority to U.S. patent application Ser. No. 12/513,086, filed Apr. 23, 2010, which is a National Stage application under 35 U.S.C. § 371 of International Application No. PCT/US2007/083495, filed Nov. 2, 2007, which claims the benefit of priority under 35 U.S.C. § 119(e) to U.S. Provisional Patent Application Ser. No. 60/856,613, filed Nov. 3, 2006. U.S. patent application Ser. No. 13/630,902 filed Sep. 28, 2012, is also a continuation-in-part application of and claims priority to U.S. patent application Ser. No. 12/515,687, filed Apr. 6, 2010, which is a National Stage application under 35 U.S.C. § 371 of International Application No. PCT/US2007/085237, filed Nov. 20, 2007, which claims the benefit of priority under 35 U.S.C. § 119(e) to U.S. Provisional Patent Application Ser. No. 60/860,145, filed Nov. 20, 2006. U.S. patent application Ser. No. 13/630,902 filed Sep. 28, 2012, is also a continuation-in-part application of and claims priority to U.S. patent application Ser. No. 12/307,561, filed Nov. 23, 2009, which is a National Stage application under 35 U.S.C. § 371 of International Application No. PCT/US2007/072877, filed Jul. 5, 2007, which claims priority under 35 U.S.C. § 119(e) to U.S. Provisional Patent Application Ser. No. 60/818,569, filed Jul. 5, 2006. U.S. patent application Ser. No. 13/630,902 filed Sep. 28, 2012, is also a continuation-in-part application of and claims priority to U.S. patent application Ser. No. 13/119,572, filed Aug. 10, 2011, which is a National Stage application under 35 U.S.C. § 371 of International Application No. PCT/US2009/057116, filed Sep. 16, 2009, which claims the benefit of priority under 35 U.S.C. § 119(e) to U.S. Provisional Patent Application Ser. No. 61/097,789, filed Sep. 17, 2008. The disclosures of these prior applications are considered part of (and are incorporated by reference in their entirety in) the disclosure of this application.

INCORPORATION OF SEQUENCE LISTING

The Sequence listing contained in the file named CRES026USD4_ST26.xml, which is 6,805 kilobytes (size as measured in Microsoft Windows®), was created on Sep. 14, 2023, was filed herewith by electronic submission on Sep. 20, 2023, and is incorporated by reference herein.

TECHNICAL FIELD

This document relates to methods and materials involved in plant shade and/or low light tolerance, and red light specific responses. For example, this document provides plants having increased shade and/or low light tolerance as well as materials and methods for making plants having increased shade and/or low light tolerance. This document also relates to methods and materials involved in increasing UV-B tolerance in plants and methods and materials involved in modulating biomass levels in plants.

BACKGROUND

Light is the source of energy that fuels plant growth through photosynthesis. Light is also a developmental signal that modulates morphogenesis, such as de-etiolation and the transition to reproductive development. Since plants cannot choose their surroundings, they are forced to adapt their growth to ambient light conditions and have evolved complex mechanisms for monitoring the quantity and quality of the surrounding light. For example, many kinds of plants respond to growth under dense canopies or at high densities by growing faster and taller (Cerdan and Chory (2003) *Nature*, 423:881). Densely planted crops tend to place energy into stem and petiole elongation to lift the leaves into the sunlight rather than putting energy into storage or reproductive structures. The response to low light conditions and/or shade conditions negatively affects crop yields by reducing the amount of harvestable products such as seeds, fruits and tubers. In addition, tall spindly plants tend to be less wind resistant and lodge more easily, further reducing crop yield.

There is a continuing need for plants that can thrive under less than optimal environmental conditions. One strategy to improve a plant's ability to withstand suboptimal environmental conditions relies upon traditional plant breeding methods. Another approach involves genetic manipulation of plant characteristics through the introduction of exogenous nucleic acids conferring a desirable trait.

SUMMARY

The spectral energy distribution of daylight is dramatically altered by vegetation. Light reflected from neighboring vegetation is depleted in red (R) wavelengths, but remains rich in far-red (FR) wavelengths. It is desirable to have plants that exhibit increased shade tolerance. Plants having increased shade tolerance described herein exhibit an increased tolerance to shade conditions, in particular, Short Day plus End-of-Day Far-Red (SD+EODFR) conditions. Wild-type plants typically exhibit shade avoidance responses to SD+EODFR conditions, whereas the SD+EODFR-tolerant plants described herein display a reduction in the level of shade avoidance responses relative to the level of shade avoidance responses displayed by non-SD+EODFR-tolerant plants.

The quantity of light can dictate the eventual biomass and yield of plants. Wild-type plants typically exhibit low light responses, whereas the low light-tolerant plants described herein display a reduction in the level of low light responses relative to the level of low light responses displayed by non-low light-tolerant plants.

Increasing the SD+EODFR and/or low light tolerance of plants can increase the crop yields of such plants, which can benefit both food consumers and producers. This document provides methods and materials related to plants having increased shade and/or low light tolerance. For example, this document provides transgenic plants having increased SD+EODFR and/or low light tolerance, nucleic acids used to generate transgenic plants having increased SD+EODFR and/or low light tolerance, and methods for making plants having increased SD+EODFR and/or low light tolerance. Such plants may be useful to produce biomass which may be converted to a liquid fuel or other chemicals and/or to produce crops with increased yield and/or quality.

Methods of producing a plant are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 20, using an HMM generated from the amino acid sequences depicted in one of FIGS. 1-24. A plant produced from the cell has a difference in low light or SD+EODFR tolerance as compared to a control plant that does not comprise the exogenous nucleic acid.

In another aspect, the exogenous nucleic acid comprises a regulatory region operably linked to a nucleotide sequence encoding a polypeptide having 80 percent or greater sequence identity to an amino acid sequence set forth in SEQ ID NOs:3, 5, 7, 9, 10, 12, 14, 16, 18, 20, 22, 24, 25, 26, 28, 30, 32, 34, 36, 38, 40, 42, 44, 46, 48, 49, 51, 53, 55, 57, 59, 60, 61, 62, 63, 65, 67, 70, 72, 74, 76, 78, 80, 82, 84, 86, 88, 89, 90, 91, 93, 95, 96, 97, 98, 99, 100, 101, 102, 103, 105, 107, 109, 111, 113, 115, 116, 117, 118, 119, 120, 121, 122, 124, 126, 129, 130, 131, 132, 133, 135, 137, 139, 141, 143, 145, 147, 149, 151, 153, 155, 157, 159, 161, 163, 165, 167, 169, 171, 173, 175, 177, 179, 181, 183, 185, 187, 188, 189, 191, 193, 195, 197, 199, 201, 203, 205, 207, 209, 211, 213, 215, 217, 219, 221, 223, 225, 227, 229, 230, 231, 232, 233, 234, 235, 236, 237, 238, 239, 241, 243, 245, 247, 249, 251, 253, 255, 257, 259, 261, 262, 264, 266, 268, 270, 271, 273, 275, 277, 279, 281, 283, 285, 287, 289, 291, 292, 293, 294, 295, 296, 297, 298, 299, 300, 301, 302, 303, 304, 306, 308, 310, 312, 314, 317, 319, 321, 323, 325, 327, 329, 330, 331, 332, 334, 337, 339, 341, 343, 344, 346, 347, 348, 349, 350, 351, 352, 353, 354, 355, 357, 359, 361, 362, 364, 365, 366, 367, 368, 370, 372, 374, 376, 378, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 456, 457, 458, 459, 460, 462, 464, 466, 468, 470, 472, 474, 475, 477, 478, 479, 480, 481, 482, 483, 484, 485, 486, 487, 488, 489, 491, 493, 494, 495, 496, 497, 498, 499, 501, 503, 505, 507, 508, 509, 510, 511, 512, 514, 515, 516, 518, 520, 521, 522, 523, 524, 525, 526, 527, 528, 529, 530, 531, 532, 533, 534, 535, 536, 538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 634, 636, 637, 638, 639, 641, 644, 645, 647, 649, 651, 653, 655, 657, 659, 661, 663, 665, 667, 669, 671, 673, 675, 676, 678, 680, 682, 684, 686, 688, 690, 692, 694, 695, 697, 699, 701, 702, 704, 706, 708, 709, 711, 712, 713, 714, 716, 718, 720, 721, 723, 725, 726, 728, 730, 732, 734, 736, 738, 740, 741, 742, 743, 744, 745, 747, 749, 750, 751, 753, 755, 757, 759, 761, 762, 763, 764, 765, 767, 769, 771, 773, 774, 776, 778, 779, 780, 782, 783, 784, 786, 788, 790, 792, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 826, 827, 829, 830, 831, 832, 833, 834, 835, 837, 838, 839, 840, 841, 843, 845, 847, 850, 851, 853, 855, 857, 859, 861, 862, 863, 864, 865, 866, 868, 870, 872, 874, 876, 877, 879, 881, 883, 885, 887, 889, 891, 893, 895, 897, 898, 900, 902, 904, 907, 909, 911, 913, 915, 917, 919, 920, 922, 923, 924, 926, 928, 929, 930, 931, 932, 934, 936, 937, 938, 939, 940, 941, 943, 945, 947, 948, 949, 950, 953, 955, 957, 959, 961, 963, 965, 966, 967, 969, 971, 973, 975, 977, 979, 981, 983, 985, 987, 989, 991, 993, 995, 997, 999, 1001, 1003, 1005, 1007, 1009, 1011, 1013, 1014, 1015, 1016, 1018, 1024, 1025, 1027, 1029, 1030, 1032, 1033, 1035, 1037, 1039, 1040, 1042, 1043, 1044, 1047, 1049, 1051, 1053, 1055, 1057, 1059, 1061, 1063, 1065, 1067, 1068, 1069, 1071, 1072, 1073, 1074, 1075, 1077, 1078, 1080, 1081, 1083, 1085, 1087, 1089, 1091, 1093, 1095, 1097, 1098, 1099, 1100, 1101, 1103, 1105, 1107, 1109, 1111, 1113, 1115, 1117, 1119, 1121, 1123, 1125, 1127, 1129, 1131, 1133, 1134, 1135, 1136, 1137, 1138, 1139, 1141, 1143, 1145, 1147, 1149, 1151, 1153, 1155, 1157, 1159, 1160, 1161, 1162, 1164, 1166, 1168, 1170, 1172, 1174, 1176, 1178, 1180, 1182, 1184, 1186, 1188, 1190, 1192, 1194, 1196, 1198, 1199, 1200, 1201, 1202, 1203, 1204, 1206, 1208, 1209, 1211, 1213, 1214, 1215, 1216, 1217, 1219, 1221, 1223, 1225, 1227, 1229, 1230, 1232, 1234, 1236, 1238, 1240, 1242, 1244, 1246, 1248, 1250, 1252, 1254, 1255, 1256, 1257, 1258, 1259, 1260, 1261, 1262, 1263, 1264, 1266, 1268, 1270, 1272, 1274, 1277, 1279, 1281, 1283, 1285, 1287, 1289, 1291, 1293, 1294, 1295, 1297, 1298, 1299, 1301, 1303, 1305, 1307, 1309, 1311, 1313, 1315, 1317, 1319, 1321, 1322, 1323, 1324, 1325, 1326, 1327, 1328, 1329, 1330, 1331, 1332, 1334, 1336, 1338, 1340, 1342, 1344, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1457, 1458, 1460, 1462, 1464, 1466, 1467, 1468, 1469, 1471, 1473, 1475, 1477, 1478, 1479, 1480, 1481, 1482, 1483, 1484, 1485, 1486, 1488, 1490, 1492, 1494, 1497, 1499, 1501, 1502, 1503, 1504, 1505, 1506, 1508, 1510, 1511, 1512, 1513, 1514, 1515, 1516, 1518, 1519, 1520, 1521, 1522, 1523, 1524, 1525, 1527, 1528, 1529, 1531, 1532, 1533, 1534, 1535, 1536, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1587, 1589, 1591, 1593, 1594, 1596, 1597, 1598, 1599, 1600, 1601, 1602, 1603, 1604, 1605, 1606, 1607, 1609, 1611, 1612, 1613, 1614, 1615, 1616, 1617, 1618, 1619, 1620, 1621, 1623, 1625, 1630, 1631, 1632, 1635, 1637, 1639, 1641, 1642, 1643, 1644, 1646, 1648, 1650, 1651, 1652, 1653, 1654, 1655, 1657, 1659, 1661, 1663, 1665, 1667, 1669, 1671, 1673, 1675, 1677, 1679, 1681, 1682, 1684, 1686, 1688, 1690, 1692, 1694, 1696, 1698, 1699, 1700, 1701, 1702, 1703, 1704, 1705, 1707, 1709, 1711, 1713, 1715, 1717, 1719, 1720, 1721, 1722, 1723, 1725, 1727, 1729, 1730, 1732, 1734, 1736, 1738, 1739, 1740, 1741, 1742, 1743, 1744, 1745, 1746, 1748, 1750, 1751, 1752, 1754, 1756, 1758, 1760, 1762, 1764, 1766, 1767, 1768, 1769, 1770, 1771, 1772, 1773, 1774, 1775, 1776, 1777, 1778, 1780, 1782, 1784, 1786, 1788, 1790, 1792, 1794, 1796, 1798, 1800, 1802, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1842, 1843, 1844, 1845, 1846, 1847, 1848, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2069, 2070, 2072, 2074, 2076, 2078, 2080, 2081, 2083, 2084, 2085, 2087, 2089, 2091, 2093, 2095, 2097, 2099, 2101, 2103, 2105, 2107, 2109, 2111, 2113, 2114, 2115, 2116, 2117, 2118, 2119, 2120, 2121, 2123, 2125, 2127, 2129, 2131, 2133, 2135, 2136, 2137, 2138, 2139, 2140, 2141, 2142, 2143, 2144, 2146, 2148, 2150, 2152, 2154, 2156, 2158, 2160, 2162, 2164, 2166, 2168, 2170, 2172, 2174, 2176, 2178, 2180, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2266, 2268, 2269, 2270, 2271, 2272, 2273, 2274, 2275, 2276, 2277, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2350, 2352, 2354, 2356, 2358, 2360, 2362, 2364, 2366, 2368, 2370, 2372, 2374, 2375, 2376, 2377, 2378, 2379, 2380, or 2381. A plant produced from the plant cell has a difference in low light or SD+EODFR tolerance as compared to a control plant that does not comprise the exogenous nucleic acid.

In one aspect, the polypeptide further comprises a CDI domain having 70 percent or greater sequence identity to the CDI domain of SEQ ID NO:70. In another aspect, the polypeptide further comprises an AUX/IAA domain having 70 percent or greater sequence identity to the AUX/IAA domain of SEQ ID NO:129 or SEQ ID NO:1347. In another aspect, the polypeptide further comprises a homeobox domain having 70 percent or greater sequence identity to the homeobox domain of SEQ ID NO:317. In another aspect, the polypeptide further comprises a zf_C3HC4 domain having 70 percent or greater sequence identity to the zf_C3HC4 domain of SEQ ID NO:337. In another aspect, the polypeptide further comprises a B-box zinc finger domain having 70 percent or greater sequence identity to the B-box zinc finger domain of SEQ ID NO:456 and a CCT motif having 70 percent or greater sequence identity to the CCT motif of SEQ ID NO:456. In another aspect, the polypeptide further comprises a FAD_binding_7 domain having 70 percent or greater sequence identity to the FAD_binding_7 domain of SEQ ID NO:538 or SEQ ID NO:1497 and a DNA photolyase domain having 70 percent or greater sequence identity to the DNA photolyase domain of SEQ ID NO:538 or SEQ ID NO:1497. In another aspect, the polypeptide further comprises a zf_Dof domain having 70 percent or greater sequence identity to the zf_Dof domain of SEQ ID NO:606. In another aspect, the polypeptide further comprises an AP2 domain having 70 percent or greater sequence identity to the AP2 domain of SEQ ID NO:645. In another aspect, the polypeptide further comprises a VQ motif having 70 percent or greater sequence identity to the VQ motif of SEQ ID NO:850. In another aspect, the polypeptide further comprises a zf_C2H2 domain having 70 percent or greater sequence identity to the zf_C2H2 domain of SEQ ID NO:907. In another aspect, the polypeptide further comprises a TCP domain having 70 percent or greater sequence identity to the TCP domain of SEQ ID NO:1151. In another aspect, the polypeptide further comprises an F-box domain having 70 percent or greater sequence identity to the F-box domain of SEQ ID NO:1277. In another aspect, the polypeptide further comprises a zf_CCCH domain having 70 percent or greater sequence identity to the zf_CCCH domain of SEQ ID NO:1457. In another aspect, the polypeptide further comprises a POX domain having 70 percent or greater sequence identity to the POX domain of SEQ ID NO:1540 and a homeobox domain having 70 percent or greater sequence identity to the homeobox domain of SEQ ID NO:1540. In another aspect, the polypeptide further comprises an HSF-type DNA-binding domain having 70 percent or greater sequence identity to the HSF-type DNA-binding domain of SEQ ID NO:1587. In another aspect, the polypeptide further comprises a SAM_1 domain having 70 percent or greater sequence identity to the SAM_1 domain of SEQ ID NO:1635 and a DRMBL domain having 70 percent or greater sequence identity to the DRMBL domain of SEQ ID NO:1635.

In another aspect, a method of producing a plant comprises growing a plant cell comprising an exogenous nucleic acid, where the exogenous nucleic acid comprises a regulatory region operably linked to a nucleotide sequence having 80 percent or greater sequence identity to a nucleotide sequence, or a fragment thereof, set forth in SEQ ID NOs:1, 2, 4, 6, 8, 11, 13, 15, 17, 19, 21, 23, 27, 29, 31, 33, 35, 37, 39, 41, 43, 45, 47, 50, 52, 54, 56, 58, 64, 66, 68, 69, 71, 73, 75, 77, 79, 81, 83, 85, 87, 92, 94, 104, 106, 108, 110, 112, 114, 123, 125, 127, 128, 134, 136, 138, 140, 142, 144, 146, 148, 150, 152, 154, 156, 158, 160, 162, 164, 166, 168, 170, 172, 174, 176, 178, 180, 182, 184, 186, 190, 192, 194, 196, 198, 200, 202, 204, 206, 208, 210, 212, 214, 216, 218, 220, 222, 224, 226, 228, 240, 242, 244, 246, 248, 250, 252, 254, 256, 258, 260, 263, 265, 267, 269, 272, 274, 276, 278, 280, 282, 284, 286, 288, 290, 305, 307, 309, 311, 313, 315, 316, 318, 320, 322, 324, 326, 328, 333, 335, 336, 338, 340, 342, 345, 356, 358, 360, 363, 369, 371, 373, 375, 377, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 455, 461, 463, 465, 467, 469, 471, 473, 476, 490, 492, 500, 502, 504, 506, 513, 517, 519, 537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 632, 633, 635, 640, 642, 643, 646, 648, 650, 652, 654, 656, 658, 660, 662, 664, 666, 668, 670, 672, 674, 677, 679, 681, 683, 685, 687, 689, 691, 693, 696, 698, 700, 703, 705, 707, 710, 715, 717, 719, 722, 724, 727, 729, 731, 733, 735, 737, 739, 746, 748, 752, 754, 756, 758, 760, 766, 768, 770, 772, 775, 777, 781, 785, 787, 789, 791, 793, 825, 828, 836, 842, 844, 846, 848, 849, 852, 854, 856, 858, 860, 867, 869, 871, 873, 875, 878, 880, 882, 884, 886, 888, 890, 892, 894, 896, 899, 901, 903, 905, 906, 908, 910, 912, 914, 916, 918, 921, 925, 927, 933, 935, 942, 944, 946, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1019, 1020, 1021, 1022, 1023, 1026, 1028, 1031, 1034, 1036, 1038, 1041, 1045, 1046, 1048, 1050, 1052, 1054, 1056, 1058, 1060, 1062, 1064, 1066, 1070, 1076, 1079, 1082, 1084, 1086, 1088, 1090, 1092, 1094, 1096, 1102, 1104, 1106, 1108, 1110, 1112, 1114, 1116, 1118, 1120, 1122, 1124, 1126, 1128, 1130, 1132, 1140, 1142, 1144, 1146, 1148, 1150, 1152, 1154, 1156, 1158, 1163, 1165, 1167, 1169, 1171, 1173, 1175, 1177, 1179, 1181, 1183, 1185, 1187, 1189, 1191, 1193, 1195, 1197, 1205, 1207, 1210, 1212, 1218, 1220, 1222, 1224, 1226, 1228, 1231, 1233, 1235, 1237, 1239, 1241, 1243, 1245, 1247, 1249, 1251, 1253, 1265, 1267, 1269, 1271, 1273, 1275, 1276, 1278, 1280, 1282, 1284, 1286, 1288, 1290, 1292, 1296, 1300, 1302, 1304, 1306, 1308, 1310, 1312, 1314, 1316, 1318, 1320, 1333, 1335, 1337, 1339, 1341, 1343, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1453, 1454, 1455, 1456, 1459, 1461, 1463, 1465, 1470, 1472, 1474, 1476, 1487, 1489, 1491, 1493, 1495, 1496, 1498, 1500, 1507, 1509, 1517, 1526, 1530, 1537, 1538, 1539, 1542, 1544, 1546, 1548, 1550, 1552, 1560, 1562, 1569, 1571, 1573, 1575, 1577, 1579, 1581, 1583, 1585, 1586, 1588, 1590, 1592, 1595, 1608, 1610, 1622, 1624, 1626, 1627, 1628, 1629, 1633, 1634, 1636, 1638, 1640, 1645, 1647, 1649, 1656, 1658, 1660, 1662, 1664, 1666, 1668, 1670, 1672, 1674, 1676, 1678, 1680, 1683, 1685, 1687, 1689, 1691, 1693, 1695, 1697, 1706, 1708, 1710, 1712, 1714, 1716, 1718, 1724, 1726, 1728, 1731, 1733, 1735, 1737, 1747, 1749, 1753, 1755, 1757, 1759, 1761, 1763, 1765, 1779, 1781, 1783, 1785, 1787, 1789, 1791, 1793, 1795, 1797, 1799, 1801, 1803, 1841, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2068, 2071, 2073, 2075, 2077, 2079, 2082, 2086, 2088, 2090, 2092, 2094, 2096, 2098, 2100, 2102, 2104, 2106, 2108, 2110, 2112, 2122, 2124, 2126, 2128, 2130, 2132, 2134, 2145, 2147, 2149, 2151, 2153, 2155, 2157, 2159, 2161, 2163, 2165, 2167, 2169, 2171, 2173, 2175, 2177, 2179, 2181, 2265, 2267, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2349, 2351, 2353, 2355, 2357, 2359, 2361, 2363, 2365, 2367, 2369, 2371, or 2373. A plant produced from the plant cell has a difference in low light or SD+EODFR tolerance as compared to a control plant that does not comprise the exogenous nucleic acid.

Methods of modulating low light tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 1-24. A plant produced from the plant cell has a difference in low light tolerance as compared to a control plant that does not comprise the exogenous nucleic acid.

In another aspect, a method comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NOs:3, 5, 7, 9, 10, 12, 14, 16, 18, 20, 22, 24, 25, 26, 28, 30, 32, 34, 36, 38, 40, 42, 44, 46, 48, 49, 51, 53, 55, 57, 59, 60, 61, 62, 63, 65, 67, 70, 72, 74, 76, 78, 80, 82, 84, 86, 88, 89, 90, 91, 93, 95, 96, 97, 98, 99, 100, 101, 102, 103, 105, 107, 109, 111, 113, 115, 116, 117, 118, 119, 120, 121, 122, 124, 126, 129, 130, 131, 132, 133, 135, 137, 139, 141, 143, 145, 147, 149, 151, 153, 155, 157, 159, 161, 163, 165, 167, 169, 171, 173, 175, 177, 179, 181, 183, 185, 187, 188, 189, 191, 193, 195, 197, 199, 201, 203, 205, 207, 209, 211, 213, 215, 217, 219, 221, 223, 225, 227, 229, 230, 231, 232, 233, 234, 235, 236, 237, 238, 239, 241, 243, 245, 247, 249, 251, 253, 255, 257, 259, 261, 262, 264, 266, 268, 270, 271, 273, 275, 277, 279, 281, 283, 285, 287, 289, 291, 292, 293, 294, 295, 296, 297, 298, 299, 300, 301, 302, 303, 304, 306, 308, 310, 312, 314, 317, 319, 321, 323, 325, 327, 329, 330, 331, 332, 334, 337, 339, 341, 343, 344, 346, 347, 348, 349, 350, 351, 352, 353, 354, 355, 357, 359, 361, 362, 364, 365, 366, 367, 368, 370, 372, 374, 376, 378, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 456, 457, 458, 459, 460, 462, 464, 466, 468, 470, 472, 474, 475, 477, 478, 479, 480, 481, 482, 483, 484, 485, 486, 487, 488, 489, 491, 493, 494, 495, 496, 497, 498, 499, 501, 503, 505, 507, 508, 509, 510, 511, 512, 514, 515, 516, 518, 520, 521, 522, 523, 524, 525, 526, 527, 528, 529, 530, 531, 532, 533, 534, 535, 536, 538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 634, 636, 637, 638, 639, 641, 644, 645, 647, 649, 651, 653, 655, 657, 659, 661, 663, 665, 667, 669, 671, 673, 675, 676, 678, 680, 682, 684, 686, 688, 690, 692, 694, 695, 697, 699, 701, 702, 704, 706, 708, 709, 711, 712, 713, 714, 716, 718, 720, 721, 723, 725, 726, 728, 730, 732, 734, 736, 738, 740, 741, 742, 743, 744, 745, 747, 749, 750, 751, 753, 755, 757, 759, 761, 762, 763, 764, 765, 767, 769, 771, 773, 774, 776, 778, 779, 780, 782, 783, 784, 786, 788, 790, 792, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 826, 827, 829, 830, 831, 832, 833, 834, 835, 837, 838, 839, 840, 841, 843, 845, 847, 850, 851, 853, 855, 857, 859, 861, 862, 863, 864, 865, 866, 868, 870, 872, 874, 876, 877, 879, 881, 883, 885, 887, 889, 891, 893, 895, 897, 898, 900, 902, 904, 907, 909, 911, 913, 915, 917, 919, 920, 922, 923, 924, 926, 928, 929, 930, 931, 932, 934, 936, 937, 938, 939, 940, 941, 943, 945, 947, 948, 949, 950, 953, 955, 957, 959, 961, 963, 965, 966, 967, 969, 971, 973, 975, 977, 979, 981, 983, 985, 987, 989, 991, 993, 995, 997, 999, 1001, 1003, 1005, 1007, 1009, 1011, 1013, 1014, 1015, 1016, 1018, 1024, 1025, 1027, 1029, 1030, 1032, 1033, 1035, 1037, 1039, 1040, 1042, 1043, 1044, 1047, 1049, 1051, 1053, 1055, 1057, 1059, 1061, 1063, 1065, 1067, 1068, 1069, 1071, 1072, 1073, 1074, 1075, 1077, 1078, 1080, 1081, 1083, 1085, 1087, 1089, 1091, 1093, 1095, 1097, 1098, 1099, 1100, 1101, 1103, 1105, 1107, 1109, 1111, 1113, 1115, 1117, 1119, 1121, 1123, 1125, 1127, 1129, 1131, 1133, 1134, 1135, 1136, 1137, 1138, 1139, 1141, 1143, 1145, 1147, 1149, 1151, 1153, 1155, 1157, 1159, 1160, 1161, 1162, 1164, 1166, 1168, 1170, 1172, 1174, 1176, 1178, 1180, 1182, 1184, 1186, 1188, 1190, 1192, 1194, 1196, 1198, 1199, 1200, 1201, 1202, 1203, 1204, 1206, 1208, 1209, 1211, 1213, 1214, 1215, 1216, 1217, 1219, 1221, 1223, 1225, 1227, 1229, 1230, 1232, 1234, 1236, 1238, 1240, 1242, 1244, 1246, 1248, 1250, 1252, 1254, 1255, 1256, 1257, 1258, 1259, 1260, 1261, 1262, 1263, 1264, 1266, 1268, 1270, 1272, 1274, 1277, 1279, 1281, 1283, 1285, 1287, 1289, 1291, 1293, 1294, 1295, 1297, 1298, 1299, 1301, 1303, 1305, 1307, 1309, 1311, 1313, 1315, 1317, 1319, 1321, 1322, 1323, 1324, 1325, 1326, 1327, 1328, 1329, 1330, 1331, 1332, 1334, 1336, 1338, 1340, 1342, 1344, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1457, 1458, 1460, 1462, 1464, 1466, 1467, 1468, 1469, 1471, 1473, 1475, 1477, 1478, 1479, 1480, 1481, 1482, 1483, 1484, 1485, 1486, 1488, 1490, 1492, 1494, 1497, 1499, 1501, 1502, 1503, 1504, 1505, 1506, 1508, 1510, 1511, 1512, 1513, 1514, 1515, 1516, 1518, 1519, 1520, 1521, 1522, 1523, 1524, 1525, 1527, 1528, 1529, 1531, 1532, 1533, 1534, 1535, 1536, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1587, 1589, 1591, 1593, 1594, 1596, 1597, 1598, 1599, 1600, 1601, 1602, 1603, 1604, 1605, 1606, 1607, 1609, 1611, 1612, 1613, 1614, 1615, 1616, 1617, 1618, 1619, 1620, 1621, 1623, 1625, 1630, 1631, 1632, 1635, 1637, 1639, 1641, 1642, 1643, 1644, 1646, 1648, 1650, 1651, 1652, 1653, 1654, 1655, 1657, 1659, 1661, 1663, 1665, 1667, 1669, 1671, 1673, 1675, 1677, 1679, 1681, 1682, 1684, 1686, 1688, 1690, 1692, 1694, 1696, 1698, 1699, 1700, 1701, 1702, 1703, 1704, 1705, 1707, 1709, 1711, 1713, 1715, 1717, 1719, 1720, 1721, 1722, 1723, 1725, 1727, 1729, 1730, 1732, 1734, 1736, 1738, 1739, 1740, 1741, 1742, 1743, 1744, 1745, 1746, 1748, 1750, 1751, 1752, 1754, 1756, 1758, 1760, 1762, 1764, 1766, 1767, 1768, 1769, 1770, 1771, 1772, 1773, 1774, 1775, 1776, 1777, 1778, 1780, 1782, 1784, 1786, 1788, 1790, 1792, 1794, 1796, 1798, 1800, 1802, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1842, 1843, 1844, 1845, 1846, 1847, 1848, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2069, 2070, 2072, 2074, 2076, 2078, 2080, 2081, 2083, 2084, 2085, 2087, 2089, 2091, 2093, 2095, 2097, 2099, 2101, 2103, 2105, 2107, 2109, 2111, 2113, 2114, 2115, 2116, 2117, 2118, 2119, 2120, 2121, 2123, 2125, 2127, 2129, 2131, 2133, 2135, 2136, 2137, 2138, 2139, 2140, 2141, 2142, 2143, 2144, 2146, 2148, 2150, 2152, 2154, 2156, 2158, 2160, 2162, 2164, 2166, 2168, 2170, 2172, 2174, 2176, 2178, 2180, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2266, 2268, 2269, 2270, 2271, 2272, 2273, 2274, 2275, 2276, 2277, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2350, 2352, 2354, 2356, 2358, 2360, 2362, 2364, 2366, 2368, 2370, 2372, 2374, 2375, 2376, 2377, 2378, 2379, 2380, or 2381. A plant produced from the plant cell has a difference in low light tolerance as compared to a control plant that does not comprise the exogenous nucleic acid.

In another aspect, a method comprises introducing into a plant cell an exogenous nucleic acid, that comprises a regulatory region operably linked to a nucleotide sequence having 80 percent or greater sequence identity to a nucleotide sequence set forth in SEQ ID NOs:1, 2, 4, 6, 8, 11, 13, 15, 17, 19, 21, 23, 27, 29, 31, 33, 35, 37, 39, 41, 43, 45, 47, 50, 52, 54, 56, 58, 64, 66, 68, 69, 71, 73, 75, 77, 79, 81, 83, 85, 87, 92, 94, 104, 106, 108, 110, 112, 114, 123, 125, 127, 128, 134, 136, 138, 140, 142, 144, 146, 148, 150, 152, 154, 156, 158, 160, 162, 164, 166, 168, 170, 172, 174, 176, 178, 180, 182, 184, 186, 190, 192, 194, 196, 198, 200, 202, 204, 206, 208, 210, 212, 214, 216, 218, 220, 222, 224, 226, 228, 240, 242, 244, 246, 248, 250, 252, 254, 256, 258, 260, 263, 265, 267, 269, 272, 274, 276, 278, 280, 282, 284, 286, 288, 290, 305, 307, 309, 311, 313, 315, 316, 318, 320, 322, 324, 326, 328, 333, 335, 336, 338, 340, 342, 345, 356, 358, 360, 363, 369, 371, 373, 375, 377, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 455, 461, 463, 465, 467, 469, 471, 473, 476, 490, 492, 500, 502, 504, 506, 513, 517, 519, 537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 632, 633, 635, 640, 642, 643, 646, 648, 650, 652, 654, 656, 658, 660, 662, 664, 666, 668, 670, 672, 674, 677, 679, 681, 683, 685, 687, 689, 691, 693, 696, 698, 700, 703, 705, 707, 710, 715, 717, 719, 722, 724, 727, 729, 731, 733, 735, 737, 739, 746, 748, 752, 754, 756, 758, 760, 766, 768, 770, 772, 775, 777, 781, 785, 787, 789, 791, 793, 825, 828, 836, 842, 844, 846, 848, 849, 852, 854, 856, 858, 860, 867, 869, 871, 873, 875, 878, 880, 882, 884, 886, 888, 890, 892, 894, 896, 899, 901, 903, 905, 906, 908, 910, 912, 914, 916, 918, 921, 925, 927, 933, 935, 942, 944, 946, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1019, 1020, 1021, 1022, 1023, 1026, 1028, 1031, 1034, 1036, 1038, 1041, 1045, 1046, 1048, 1050, 1052, 1054, 1056, 1058, 1060, 1062, 1064, 1066, 1070, 1076, 1079, 1082, 1084, 1086, 1088, 1090, 1092, 1094, 1096, 1102, 1104, 1106, 1108, 1110, 1112, 1114, 1116, 1118, 1120, 1122, 1124, 1126, 1128, 1130, 1132, 1140, 1142, 1144, 1146, 1148, 1150, 1152, 1154, 1156, 1158, 1163, 1165, 1167, 1169, 1171, 1173, 1175, 1177, 1179, 1181, 1183, 1185, 1187, 1189, 1191, 1193, 1195, 1197, 1205, 1207, 1210, 1212, 1218, 1220, 1222, 1224, 1226, 1228, 1231, 1233, 1235, 1237, 1239, 1241, 1243, 1245, 1247, 1249, 1251, 1253, 1265, 1267, 1269, 1271, 1273, 1275, 1276, 1278, 1280, 1282, 1284, 1286, 1288, 1290, 1292, 1296, 1300, 1302, 1304, 1306, 1308, 1310, 1312, 1314, 1316, 1318, 1320, 1333, 1335, 1337, 1339, 1341, 1343, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1453, 1454, 1455, 1456, 1459, 1461, 1463, 1465, 1470, 1472, 1474, 1476, 1487, 1489, 1491, 1493, 1495, 1496, 1498, 1500, 1507, 1509, 1517, 1526, 1530, 1537, 1538, 1539, 1542, 1544, 1546, 1548, 1550, 1552, 1560, 1562, 1569, 1571, 1573, 1575, 1577, 1579, 1581, 1583, 1585, 1586, 1588, 1590, 1592, 1595, 1608, 1610, 1622, 1624, 1626, 1627, 1628, 1629, 1633, 1634, 1636, 1638, 1640, 1645, 1647, 1649, 1656, 1658, 1660, 1662, 1664, 1666, 1668, 1670, 1672, 1674, 1676, 1678, 1680, 1683, 1685, 1687, 1689, 1691, 1693, 1695, 1697, 1706, 1708, 1710, 1712, 1714, 1716, 1718, 1724, 1726, 1728, 1731, 1733, 1735, 1737, 1747, 1749, 1753, 1755, 1757, 1759, 1761, 1763, 1765, 1779, 1781, 1783, 1785, 1787, 1789, 1791, 1793, 1795, 1797, 1799, 1801, 1803, 1841, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2068, 2071, 2073, 2075, 2077, 2079, 2082, 2086, 2088, 2090, 2092, 2094, 2096, 2098, 2100, 2102, 2104, 2106, 2108, 2110, 2112, 2122, 2124, 2126, 2128, 2130, 2132, 2134, 2145, 2147, 2149, 2151, 2153, 2155, 2157, 2159, 2161, 2163, 2165, 2167, 2169, 2171, 2173, 2175, 2177, 2179, 2181, 2265, 2267, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2349, 2351, 2353, 2355, 2357, 2359, 2361, 2363, 2365, 2367, 2369, 2371, or 2373, or a fragment thereof. A plant produced from the plant cell has a difference in low light tolerance as compared to a control plant that does not comprise the exogenous nucleic acid.

Methods of modulating SD+EODFR tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIG. 16 or 24-27. A plant produced from the plant cell has a difference in SD+EODFR tolerance as compared to a control plant that does not comprise the exogenous nucleic acid.

In another aspect, a method comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NOs:538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1679, 1681, 1682, 1748, 1750, 1751, 1752, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 2268, 2269, 2270, 2271, 2272, 2273, 2274, 2275, 2276, 2277, or 2278. A plant produced from the plant cell has a difference in SD+EODFR tolerance as compared to a control plant that does not comprise the exogenous nucleic acid.

In another aspect, a method comprises introducing into a plant cell an exogenous nucleic acid, that comprises a regulatory region operably linked to a nucleotide sequence having 80 percent or greater sequence identity to a nucleotide sequence set forth in SEQ ID NOs:537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1537, 1538, 1539, 1542, 1544, 1546, 1548, 1550, 1552, 1560, 1562, 1569, 1571, 1573, 1575, 1577, 1579, 1581, 1583, 1678, 1680, 1747, 1749, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, and 2267, or a fragment thereof. A plant produced from the plant cell has a difference in SD+EODFR tolerance as compared to a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 20, using an HMM based on the amino acid sequences depicted in one of FIGS. 1-24. A plant produced from the cells has a difference in low light or SD+EODFR tolerance as compared to a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NOs:3, 5, 7, 9, 10, 12, 14, 16, 18, 20, 22, 24, 25, 26, 28, 30, 32, 34, 36, 38, 40, 42, 44, 46, 48, 49, 51, 53, 55, 57, 59, 60, 61, 62, 63, 65, 67, 70, 72, 74, 76, 78, 80, 82, 84, 86, 88, 89, 90, 91, 93, 95, 96, 97, 98, 99, 100, 101, 102, 103, 105, 107, 109, 111, 113, 115, 116, 117, 118, 119, 120, 121, 122, 124, 126, 129, 130, 131, 132, 133, 135, 137, 139, 141, 143, 145, 147, 149, 151, 153, 155, 157, 159, 161, 163, 165, 167, 169, 171, 173, 175, 177, 179, 181, 183, 185, 187, 188, 189, 191, 193, 195, 197, 199, 201, 203, 205, 207, 209, 211, 213, 215, 217, 219, 221, 223, 225, 227, 229, 230, 231, 232, 233, 234, 235, 236, 237, 238, 239, 241, 243, 245, 247, 249, 251, 253, 255, 257, 259, 261, 262, 264, 266, 268, 270, 271, 273, 275, 277, 279, 281, 283, 285, 287, 289, 291, 292, 293, 294, 295, 296, 297, 298, 299, 300, 301, 302, 303, 304, 306, 308, 310, 312, 314, 317, 319, 321, 323, 325, 327, 329, 330, 331, 332, 334, 337, 339, 341, 343, 344, 346, 347, 348, 349, 350, 351, 352, 353, 354, 355, 357, 359, 361, 362, 364, 365, 366, 367, 368, 370, 372, 374, 376, 378, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 456, 457, 458, 459, 460, 462, 464, 466, 468, 470, 472, 474, 475, 477, 478, 479, 480, 481, 482, 483, 484, 485, 486, 487, 488, 489, 491, 493, 494, 495, 496, 497, 498, 499, 501, 503, 505, 507, 508, 509, 510, 511, 512, 514, 515, 516, 518, 520, 521, 522, 523, 524, 525, 526, 527, 528, 529, 530, 531, 532, 533, 534, 535, 536, 538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 634, 636, 637, 638, 639, 641, 644, 645, 647, 649, 651, 653, 655, 657, 659, 661, 663, 665, 667, 669, 671, 673, 675, 676, 678, 680, 682, 684, 686, 688, 690, 692, 694, 695, 697, 699, 701, 702, 704, 706, 708, 709, 711, 712, 713, 714, 716, 718, 720, 721, 723, 725, 726, 728, 730, 732, 734, 736, 738, 740, 741, 742, 743, 744, 745, 747, 749, 750, 751, 753, 755, 757, 759, 761, 762, 763, 764, 765, 767, 769, 771, 773, 774, 776, 778, 779, 780, 782, 783, 784, 786, 788, 790, 792, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 826, 827, 829, 830, 831, 832, 833, 834, 835, 837, 838, 839, 840, 841, 843, 845, 847, 850, 851, 853, 855, 857, 859, 861, 862, 863, 864, 865, 866, 868, 870, 872, 874, 876, 877, 879, 881, 883, 885, 887, 889, 891, 893, 895, 897, 898, 900, 902, 904, 907, 909, 911, 913, 915, 917, 919, 920, 922, 923, 924, 926, 928, 929, 930, 931, 932, 934, 936, 937, 938, 939, 940, 941, 943, 945, 947, 948, 949, 950, 953, 955, 957, 959, 961, 963, 965, 966, 967, 969, 971, 973, 975, 977, 979, 981, 983, 985, 987, 989, 991, 993, 995, 997, 999, 1001, 1003, 1005, 1007, 1009, 1011, 1013, 1014, 1015, 1016, 1018, 1024, 1025, 1027, 1029, 1030, 1032, 1033, 1035, 1037, 1039, 1040, 1042, 1043, 1044, 1047, 1049, 1051, 1053, 1055, 1057, 1059, 1061, 1063, 1065, 1067, 1068, 1069, 1071, 1072, 1073, 1074, 1075, 1077, 1078, 1080, 1081, 1083, 1085, 1087, 1089, 1091, 1093, 1095, 1097, 1098, 1099, 1100, 1101, 1103, 1105, 1107, 1109, 1111, 1113, 1115, 1117, 1119, 1121, 1123, 1125, 1127, 1129, 1131, 1133, 1134, 1135, 1136, 1137, 1138, 1139, 1141, 1143, 1145, 1147, 1149, 1151, 1153, 1155, 1157, 1159, 1160, 1161, 1162, 1164, 1166, 1168, 1170, 1172, 1174, 1176, 1178, 1180, 1182, 1184, 1186, 1188, 1190, 1192, 1194, 1196, 1198, 1199, 1200, 1201, 1202, 1203, 1204, 1206, 1208, 1209, 1211, 1213, 1214, 1215, 1216, 1217, 1219, 1221, 1223, 1225, 1227, 1229, 1230, 1232, 1234, 1236, 1238, 1240, 1242, 1244, 1246, 1248, 1250, 1252, 1254, 1255, 1256, 1257, 1258, 1259, 1260, 1261, 1262, 1263, 1264, 1266, 1268, 1270, 1272, 1274, 1277, 1279, 1281, 1283, 1285, 1287, 1289, 1291, 1293, 1294, 1295, 1297, 1298, 1299, 1301, 1303, 1305, 1307, 1309, 1311, 1313, 1315, 1317, 1319, 1321, 1322, 1323, 1324, 1325, 1326, 1327, 1328, 1329, 1330, 1331, 1332, 1334, 1336, 1338, 1340, 1342, 1344, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1457, 1458, 1460, 1462, 1464, 1466, 1467, 1468, 1469, 1471, 1473, 1475, 1477, 1478, 1479, 1480, 1481, 1482, 1483, 1484, 1485, 1486, 1488, 1490, 1492, 1494, 1497, 1499, 1501, 1502, 1503, 1504, 1505, 1506, 1508, 1510, 1511, 1512, 1513, 1514, 1515, 1516, 1518, 1519, 1520, 1521, 1522, 1523, 1524, 1525, 1527, 1528, 1529, 1531, 1532, 1533, 1534, 1535, 1536, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1587, 1589, 1591, 1593, 1594, 1596, 1597, 1598, 1599, 1600, 1601, 1602, 1603, 1604, 1605, 1606, 1607, 1609, 1611, 1612, 1613, 1614, 1615, 1616, 1617, 1618, 1619, 1620, 1621, 1623, 1625, 1630, 1631, 1632, 1635, 1637, 1639, 1641, 1642, 1643, 1644, 1646, 1648, 1650, 1651, 1652, 1653, 1654, 1655, 1657, 1659, 1661, 1663, 1665, 1667, 1669, 1671, 1673, 1675, 1677, 1679, 1681, 1682, 1684, 1686, 1688, 1690, 1692, 1694, 1696, 1698, 1699, 1700, 1701, 1702, 1703, 1704, 1705, 1707, 1709, 1711, 1713, 1715, 1717, 1719, 1720, 1721, 1722, 1723, 1725, 1727, 1729, 1730, 1732, 1734, 1736, 1738, 1739, 1740, 1741, 1742, 1743, 1744, 1745, 1746, 1748, 1750, 1751, 1752, 1754, 1756, 1758, 1760, 1762, 1764, 1766, 1767, 1768, 1769, 1770, 1771, 1772, 1773, 1774, 1775, 1776, 1777, 1778, 1780, 1782, 1784, 1786, 1788, 1790, 1792, 1794, 1796, 1798, 1800, 1802, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1842, 1843, 1844, 1845, 1846, 1847, 1848, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2069, 2070, 2072, 2074, 2076, 2078, 2080, 2081, 2083, 2084, 2085, 2087, 2089, 2091, 2093, 2095, 2097, 2099, 2101, 2103, 2105, 2107, 2109, 2111, 2113, 2114, 2115, 2116, 2117, 2118, 2119, 2120, 2121, 2123, 2125, 2127, 2129, 2131, 2133, 2135, 2136, 2137, 2138, 2139, 2140, 2141, 2142, 2143, 2144, 2146, 2148, 2150, 2152, 2154, 2156, 2158, 2160, 2162, 2164, 2166, 2168, 2170, 2172, 2174, 2176, 2178, 2180, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2266, 2268, 2269, 2270, 2271, 2272, 2273, 2274, 2275, 2276, 2277, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2350, 2352, 2354, 2356, 2358, 2360, 2362, 2364, 2366, 2368, 2370, 2372, 2374, 2375, 2376, 2377, 2378, 2379, 2380, and 2381.

Also provided herein is a method of identifying whether a polymorphism is associated with variation in low light or SD+EODFR tolerance. The method includes the steps of: determining whether one or more genetic polymorphisms in a population of plants is associated with the locus for a polypeptide selected from the group consisting of the polypeptides depicted in FIGS. 1-24 and functional homologs thereof; and measuring the correlation between variation in the low light or SD+EODFR tolerance in plants of the population and the presence of the genetic polymorphisms in plants of the population, thereby identifying whether or not one or more genetic polymorphisms are associated with variation in low light or SD+EODFR tolerance. The population of plants can be a population of switchgrass, sorghum, sugar cane, or miscanthus plants.

A method of making a plant line is also provided herein. The method includes the steps of: determining whether one or more genetic polymorphisms in a population of plants is associated with the locus for a polypeptide selected from the group consisting of the polypeptides depicted in FIGS. 1-24 and functional homologs thereof; identifying one or more plants in the population in which the presence of at least one allele at the one or more genetic polymorphisms is associated with variation in low light or SD+EODFR tolerance; crossing each of the identified plants with itself or a different plant to produce seed; crossing at least one progeny plant grown from the seed with itself or a different plant; and repeating the crossing steps for an additional 0-5 generations to make the plant line, wherein the allele is present in the plant line. The population of plants can be a population of switchgrass plants.

In another aspect, this document provides a method of producing a plant. The method comprises growing a plant cell comprising an exogenous nucleic acid, wherein the exogenous nucleic acid is effective for down-regulating an endogenous nucleic acid in the plant cell. The endogenous nucleic acid can encode a polypeptide. The HMM bit score of the amino acid sequence of the polypeptide can be greater than about 210. The HMM can be based on the amino acid sequences depicted in one of FIGS. 6, 11, and 21. The plant produced from the cell can have an increase in hypocotyl length as compared to a control plant that does not comprise the exogenous nucleic acid.

In another aspect, a transgenic plant cell is provided. The plant cell comprises an exogenous nucleic acid. The exogenous nucleic acid is effective for down-regulating an endogenous nucleic acid in the plant cell. The endogenous nucleic acid can encode a polypeptide. The HMM bit score of the amino acid sequence of the polypeptide is greater than about 210. The HMM is based on the amino acid sequences depicted in one of FIGS. 6, 11, and 21.

A transgenic plant is also provided. The transgenic plant comprises a plant cell comprising an exogenous nucleic acid. The exogenous nucleic acid is effective for down-regulating an endogenous nucleic acid in the plant cell. The endogenous nucleic acid can encode a polypeptide. The HMM bit score of the amino acid sequence of the polypeptide is greater than about 210. The HMM is based on the amino acid sequences depicted in one of FIGS. 6, 11, and 21. The plant has an increase in hypocotyl length as compared to a control plant that does not comprise the plant cell.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is an alignment of At4g37295 (Ceres Seedline ME05268; SEQ ID NO:3) with homologous and/or orthologous amino acid sequences including Ceres CLONE ID no. 1844057 (SEQ ID NO:7), Ceres ANNOT ID no. 1469148 (SEQ ID NO:22), Public GI ID no. 18390998 (SEQ ID NO:25), Ceres CLONE ID no. 1065656 (SEQ ID NO:32), Ceres CLONE ID no. 1652677 (SEQ ID NO:36), Public GI ID no. 92874556 (SEQ ID NO:49), Ceres CLONE ID no. 1329161 (SEQ ID NO:53), Ceres CLONE ID no. 1030378 (SEQ ID NO:55), Ceres CLONE ID no. 1413787 (SEQ ID NO:57), and Public GI ID no. 125543598 (SEQ ID NO:60). In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIG. 2 is an alignment of At2g32710 (Ceres Seedline ME06120; SEQ ID NO:70) with homologous and/or orthologous amino acid sequences including Ceres CLONE ID no. 1975934 (SEQ ID NO:72), Ceres ANNOT ID no. 1529913 (SEQ ID NO:80), Ceres CLONE ID no. 977794 (SEQ ID NO:93), Public GI ID no. 42362378 (SEQ ID NO:96), Public GI ID no. 23899378 (SEQ ID NO:99), Public GI ID no. 15963346 (SEQ ID NO:101), Public GI ID no. 15963344+B816 (SEQ ID NO:102), Public GI ID no. 92429657 (SEQ ID NO:103), Ceres CLONE ID no. 746644 (SEQ ID NO:105), Ceres CLONE ID no. 623089 (SEQ ID NO:109), Ceres CLONE ID no. 1913678 (SEQ ID NO:115), and Public GI ID no. 115450609 (SEQ ID NO:119).

FIG. 3 is an alignment of At2g46990 (Ceres Seedline ME09503; SEQ ID NO:129) with homologous and/or orthologous amino acid sequences including Public GI ID no. 34550779 (SEQ ID NO:133), Ceres CLONE ID no. 1932235 (SEQ ID NO:137), Ceres CLONE ID no. 981738 (SEQ ID NO:201), Ceres CLONE ID no. 565974 (SEQ ID NO:209), Public GI ID no. 1352058 (SEQ ID NO:231), Public GI ID no. 11131101 (SEQ ID NO:234), Public GI ID no. 4887018 (SEQ ID NO:236), Public GI ID no. 4887018 (SEQ ID NO:236), Ceres CLONE ID no. 644455 (SEQ ID NO:247), Ceres CLONE ID no. 1731500 (SEQ ID NO:270), Public GI ID no. 20269063 (SEQ ID NO:300), Public GI ID no. 50404477 (SEQ ID NO:302), and Public GI ID no. 62125392 (SEQ ID NO:303).

FIG. 4 is an alignment of At4g03250 (Ceres Seedline ME10007; SEQ ID NO:317) with homologous and/or orthologous amino acid sequences including Ceres CLONE ID no. 1842125 (SEQ ID NO:319), Ceres ANNOT ID no. 1461360 (SEQ ID NO:321), Ceres CLONE ID no. 480906 (SEQ ID NO:327), Public GI ID no. 92889352 (SEQ ID NO:330), and Public GI ID no. 56201850 (SEQ ID NO:331).

FIG. 5 is an alignment of At2g04240 (Ceres Seedline ME10852; SEQ ID NO:337), Ceres CLONE ID no. 952050 (SEQ ID NO:339) with homologous and/or orthologous amino acid sequences including Public GI ID no. 115477050 (SEQ ID NO:349), Public GI ID no. 87162911 (SEQ ID NO:355), Ceres CLONE ID no. 1790901 (SEQ ID NO:357), Ceres CLONE ID no. 1460088 (SEQ ID NO:370), Ceres CLONE ID no. 1734065 (SEQ ID NO:393), Ceres CLONE ID no. 473509 (SEQ ID NO:395), Ceres CLONE ID no. 849918 (SEQ ID NO:401), Ceres CLONE ID no. 633470 (SEQ ID NO:409), Ceres CLONE ID no. 1808334 (SEQ ID NO:417), and Ceres ANNOT ID no. 1525600 (SEQ ID NO:437).

FIG. 6 is an alignment of At5g14370 (Ceres Seedline ME11939; SEQ ID NO:456) with homologous and/or orthologous amino acid sequences including Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 21655154 (SEQ ID NO:532), Public GI ID no. 90657642 (SEQ ID NO:536), and Ceres CLONE ID no. 1569555 (SEQ ID NO:1842).

FIG. 7 is an alignment of At1g70270 (Ceres Seedline ME13456; SEQ ID NO:634) with homologous and/or orthologous amino acid sequences including Public GI ID no. 98961985 (SEQ ID NO:637).

FIG. 8 is an alignment of At4g25480 (Ceres Seedline ME15935; SEQ ID NO:644) with homologous and/or orthologous amino acid sequences including SEQ ID NO:645, Ceres CLONE ID no. 1849479 (SEQ ID NO:767), Public GI ID no. 89275008 (SEQ ID NO:796), Public GI ID no. 120400525 (SEQ ID NO:797), Public GI ID no. 98980426 (SEQ ID NO:804), Public GI ID no. 71983373 (SEQ ID NO:808), Public GI ID no. 41351817 (SEQ ID NO:809), Public GI ID no. 76446191 (SEQ ID NO:811), Public GI ID no. 5616086 (SEQ ID NO:813), Ceres CLONE ID no. 1052602 (SEQ ID NO:826), Public GI ID no. 72068957 (SEQ ID NO:830), Public GI ID no. 71534113 (SEQ ID NO:831), Public GI ID no. 37147896 (SEQ ID NO:832), Public GI ID no. 92918850 (SEQ ID NO:834), Public GI ID no. 40647095 (SEQ ID NO:835), Ceres ANNOT ID no. 1527711 (SEQ ID NO:837), Public GI ID no. 71041116 (SEQ ID NO:838), Public GI ID no. 12003384 (SEQ ID NO:839), Public GI ID no. 18535580 (SEQ ID NO:840), and Public GI ID no. 115353971 (SEQ ID NO:1843).

FIG. 9 is an alignment of At2g33780 (Ceres SEEDLINE ID no. ME16594, SEQ ID NO:850) with homologous and/or orthologous amino acid sequences including Ceres CLONE ID no. 1833093 (SEQ ID NO:853), Ceres ANNOT ID no. 1502190 (SEQ ID NO:857), Ceres CLONE ID no. 565641 (SEQ ID NO:876), Public GI ID no. 87240507 (SEQ ID NO:877), Ceres CLONE ID no. 1325382 (SEQ ID NO:881), Ceres CLONE ID no. 1558265 (SEQ ID NO:885), Ceres CLONE ID no. 1823669 (SEQ ID NO:895), and Public GI ID no. 115464921 (SEQ ID NO:898).

FIG. 10 is an alignment of At4g17810 (Ceres SEEDLINE ID no. ME16597, SEQ ID NO:907) with homologous and/or orthologous amino acid sequences including Ceres CLONE ID no. 1940797 (SEQ ID NO:909), Ceres ANNOT ID no. 1538900 (SEQ ID NO:911), Ceres CLONE ID no. 1126868 (SEQ ID NO:922), Public GI ID no. 89257684 (SEQ ID NO:923), Public GI ID no. 124360460 (SEQ ID NO:929), Public GI ID no. 62865694 (SEQ ID NO:931), Public GI ID no. 62865692 (SEQ ID NO:932), Ceres CLONE ID no. 260368 (SEQ ID NO:936), Ceres CLONE ID no. 1873510 (SEQ ID NO:947), Public GI ID no. 125541662 (SEQ ID NO:948), Public GI ID no. 48716268 (SEQ ID NO:950), and Public GI ID no. 62865696 (SEQ ID NO:1844).

FIG. 11 is an alignment of At1g13360 (Ceres SEEDLINE ID no. ME16630, SEQ ID NO:953) with homologous and/or orthologous amino acid sequences including Ceres CLONE ID no. 1798705 (SEQ ID NO:955), Ceres ANNOT ID no. 1458907 (SEQ ID NO:963), Ceres CLONE ID no. 1090409 (SEQ ID NO:971), Ceres CLONE ID no. 479817 (SEQ ID NO:977), Ceres CLONE ID no. 1041793 (SEQ ID NO:979), Ceres CLONE ID no. 684633 (SEQ ID NO:985), Ceres CLONE ID no. 371815 (SEQ ID NO:991), Ceres CLONE ID no. 1686460 (SEQ ID NO:993), Ceres CLONE ID no. 1448595 (SEQ ID NO:995), Ceres CLONE ID no. 1734477 (SEQ ID NO:999), Ceres CLONE ID no. 1605693 (SEQ ID NO:1005), Ceres CLONE ID no. 1757400 (SEQ ID NO:1009), and Public GI ID no. 115434334 (SEQ ID NO:1015).

FIG. 12 is an alignment of At1g75860 (Ceres SEEDLINE ID no. ME17128, SEQ ID NO:1024) with homologous and/or orthologous amino acid sequences including Ceres ANNOT ID no. 1452905 (SEQ ID NO:1029), Ceres CLONE ID no. 956176 (SEQ ID NO:1039), Public GI ID no. 92870366 (SEQ ID NO:1040), Ceres CLONE ID no. 294166 (SEQ ID NO:1042), and Public GI ID no. 125543067 (SEQ ID NO:1043).

FIG. 13 is an alignment of At4g19700 (Ceres SEEDLINE ID no. ME17578, SEQ ID NO:1047) with homologous and/or orthologous amino acid sequences including Ceres CLONE ID no. 1837694 (SEQ ID NO:1053), Ceres ANNOT ID no. 1483367 (SEQ ID NO:1057), Ceres CLONE ID no. 1077781 (SEQ ID NO:1083), Ceres CLONE ID no. 471026 (SEQ ID NO:1085), Public GI ID no. 92888885 (SEQ ID NO:1099), Public GI ID no. 45544873 (SEQ ID NO:1100), Public GI ID no. 45758663 (SEQ ID NO:1101), Ceres CLONE ID no. 772927 (SEQ ID NO:1105), Ceres CLONE ID no. 895080 (SEQ ID NO:1111), Ceres CLONE ID no. 1806128 (SEQ ID NO:1131), Public GI ID no. 115458192 (SEQ ID NO:1134), and Public GI ID no. 82470795 (SEQ ID NO:1139).

FIG. 14 is an alignment of At1g58100 (Ceres SEEDLINE ID no. ME18158, SEQ ID NO:1151) with homologous and/or orthologous amino acid sequences including Ceres CLONE ID no. 1851526 (SEQ ID NO:1155), Ceres ANNOT ID no. 1486769 (SEQ ID NO:1172), Public GI ID no. 83032232 (SEQ ID NO:1209), Ceres CLONE ID no. 1620420 (SEQ ID NO:1211), Public GI ID no. 92892428 (SEQ ID NO:1215), Ceres CLONE ID no. 884742 (SEQ ID NO:1223), Ceres CLONE ID no. 1821559 (SEQ ID NO:1246), Public GI ID no. 51535021 (SEQ ID NO:1258), Public GI ID no. 113205304 (SEQ ID NO:1263), and Public GI ID no. 37719051 (SEQ ID NO:1264).

FIG. 15 is an alignment of At5g46170 (Ceres SEEDLINE ID no. ME18314, SEQ ID NO:1277) with homologous and/or orthologous amino acid sequences including Ceres CLONE ID no. 1926352 (SEQ ID NO:1279), Ceres ANNOT ID no. 1448905 (SEQ ID NO:1285), Public GI ID no. 15236865 (SEQ ID NO:1294), Ceres CLONE ID no. 934771 (SEQ ID NO:1301), Ceres CLONE ID no. 338386 (SEQ ID NO:1303), Ceres CLONE ID no. 1780691 (SEQ ID NO:1317), and Public GI ID no. 115464819 (SEQ ID NO:1326).

FIG. 16 is an alignment of At4g32280 (Ceres SEEDLINE ID no. ME18408, SEQ ID NO:1347) with homologous and/or orthologous amino acid sequences including Ceres CLONE ID no. 285028 (SEQ ID NO:1419), Ceres CLONE ID no. 100969565 (SEQ ID NO:1422), Public GI ID no. 1352057 (SEQ ID NO:1427), Ceres ANNOT ID no. 1453784 (SEQ ID NO:1429), Public GI ID no. 452777 (SEQ ID NO:1430), and Public GI ID no. 92873297 (SEQ ID NO:1431).

FIG. 17 is an alignment of At3g02830 (Ceres SEEDLINE ID no. ME19304, SEQ ID NO:1457) with homologous and/or orthologous amino acid sequences including Ceres CLONE ID no. 1924904 (SEQ ID NO:1460), Ceres ANNOT ID no. 1543346 (SEQ ID NO:1462), Public GI ID no. 18396338 (SEQ ID NO:1467), Ceres CLONE ID no. 833872 (SEQ ID NO:1471), Ceres CLONE ID no. 1579587 (SEQ ID NO:1475), Ceres CLONE ID no. 1786411 (SEQ ID NO:1477), and Public GI ID no. 108864370 (SEQ ID NO:1480).

FIG. 18 is an alignment of At4g08920 (Ceres SEEDLINE ID no. ME19738, SEQ ID NO:1497) with homologous and/or orthologous amino acid sequences including Ceres ANNOT ID no. 1443463 (SEQ ID NO:1499), Public GI ID no. 13605525 (SEQ ID NO:1502), Public GI ID no. 94965681 (SEQ ID NO:1506), and Public GI ID no. 28201254 (SEQ ID NO:1512).

FIG. 19 is an alignment of At4g11660 (Ceres SEEDLINE ID no. ME20871, SEQ ID NO:1587) with homologous and/or orthologous amino acid sequences including Ceres CLONE ID no. 1839577 (SEQ ID NO:1589), Ceres ANNOT ID no. 1491567 (SEQ ID NO:1591), Ceres CLONE ID no. 574505 (SEQ ID NO:1596), Public GI ID no. 56117815 (SEQ ID NO:1597), Public GI ID no. 92874021 (SEQ ID NO:1603), Public GI ID no. 123684 (SEQ ID NO:1605), Public GI ID no. 5821136 (SEQ ID NO:1606), Ceres CLONE ID no. 283366 (SEQ ID NO:1609), Public GI ID no. 16118447 (SEQ ID NO:1612), and Public GI ID no. 125562434 (SEQ ID NO:1614).

FIG. 20 is an alignment of At2g45700 (Ceres SEEDLINE ID no. ME21508, SEQ ID NO:1635) with homologous and/or orthologous amino acid sequences including Ceres ANNOT ID no. 1508307 (SEQ ID NO:1637), Public GI ID no. 1495267 (SEQ ID NO:1642), Public GI ID no. 87241310 (SEQ ID NO:1644), Ceres CLONE ID no. 938390 (SEQ ID NO:1646), Ceres CLONE ID no. 272338 (SEQ ID NO:1648), Ceres CLONE ID no. 1993510 (SEQ ID NO:1650), Public GI ID no. 125563862 (SEQ ID NO:1651), and Public GI ID no. 125605833 (SEQ ID NO:1653).

FIG. 21 is an alignment of At2g35940 (Ceres SEEDLINE ID no. ME19971, SEQ ID NO:1540) with homologous and/or orthologous amino acid sequences including Ceres CLONE ID no. 1943265 (SEQ ID NO:1543), Ceres ANNOT ID no. 1454522 (SEQ ID NO:1547), Public GI ID no. 31323447 (SEQ ID NO:1556), Ceres CLONE ID no. 1583941 (SEQ ID NO:1561), Ceres CLONE ID no. 1792942 (SEQ ID NO:1563), Public GI ID no. 77548772 (SEQ ID NO:1565), and Public GI ID no. 84453182 (SEQ ID NO:1567).

FIG. 22 is an alignment of At1g04400 (Ceres SEEDLINE ID no. ME12006, SEQ ID NO:538) with homologous and/or orthologous amino acid sequences including Public GI ID no. 5731739 (SEQ ID NO:539), Ceres ANNOT ID no. 1538045 (SEQ ID NO:541), Public GI ID no. 29467479 (SEQ ID NO:542), Public GI ID no. 133921974 (SEQ ID NO:543), Public GI ID no. 113197027 (SEQ ID NO:544), Public GI ID no. 92879277 (SEQ ID NO:545), Public GI ID no. 45935260 (SEQ ID NO:546), Public GI ID no. 8101444 (SEQ ID NO:547), Public GI ID no. 78217443 (SEQ ID NO:548), and Public GI ID no. 28372347 (SEQ ID NO:549).

FIG. 23 is an alignment of At3g45610 (Ceres SEEDLINE ID no. ME12899, SEQ ID NO:606) with homologous and/or orthologous amino acid sequences including Public GI ID no. 92873064 (SEQ ID NO:607), Public GI ID no. 37051125 (SEQ ID NO:608), and Public GI ID no. 112363376 (SEQ ID NO:609).

FIG. 24 is an alignment of At4g08330 (Ceres SEEDLINE ID no. ME12596, SEQ ID NO:570) with homologous and/or orthologous amino acid sequences including Ceres CLONE ID no. 1919714 (SEQ ID NO:572), Ceres ANNOT ID no. 1443290 (SEQ ID NO:574), Ceres CLONE ID no. 1042157 (SEQ ID NO:576), Ceres CLONE ID no. 1384304 (SEQ ID NO:578), and Public GI ID no. 115464375 (SEQ ID NO:579).

DETAILED DESCRIPTION

This document provides methods and materials related to modulating tolerance of plants to Short Day plus End-of-Day Far-Red (SD+EODFR) conditions or low light irradiation. In some embodiments, the plants may have increased SD+EODFR tolerance and increased low light tolerance. The methods can include transforming a plant cell with a nucleic acid encoding an SD+EODFR and/or low light-tolerance polypeptide, wherein expression of the polypeptide results in increased SD+EODFR and/or low light tolerance. Plant cells produced using such methods can be grown to produce plants having an increased SD+EODFR and/or low light tolerance. Such plants can also be used to produce crops, plant products, biomass, and/or nitrogen fixating plants in shady or low light areas, such as under the canopy of another crop. For example, the methods and materials provided herein can be used to produce a legume (a member of Fabaceae, e.g., peas, beans, lupins, lentils, chick peas, vethes, soybeans, clovers, alfalfas, and peanuts) having an increased SD+EODFR and/or low light tolerance and which can be grown under the canopy of a taller crop (e.g., corn, switchgrass, sorghum, sugar cane, or miscanthus). In other embodiments, the taller plant is a nitrogen fixating plant (e.g., a member of Fabaceae, such as tamarind, mimosa, acacia, and carob) and the SD+EODFR and/or low light tolerant plant is a shorter plant, such as corn, switchgrass, sorghum, sugar cane, or miscanthus.

I. DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases the level of an expression product (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of tolerance to a stimulus (e.g., low light conditions or SD+EODFR conditions) refers to the change in the level of tolerance of the indicated stimulus that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. POLYPEPTIDES

Polypeptides described herein include SD+EODFR and/or low light tolerance polypeptides. SD+EODFR and/or low light tolerance polypeptides can be effective to increase SD+EODFR and/or low light tolerance when expressed in a plant or plant cell. Such polypeptides typically contain at least one domain indicative of SD+EODFR and/or low light tolerance polypeptides, as described in more detail herein. SD+EODFR and/or low light tolerance polypeptides typically have an HMM bit score that is greater than 20 for an HMM model based on one of the alignments set forth in FIGS. 1-24, as described in more detail herein. In some embodiments, SD+EODFR and/or low light tolerance polypeptides have greater than 40% identity to SEQ ID NO:3, SEQ ID NO:70, SEQ ID NO:129, SEQ ID NO:317, SEQ ID NO:337, SEQ ID NO:456, SEQ ID NO:538, SEQ ID NO:570, SEQ ID NO:606, SEQ ID NO:634, SEQ ID NO:644, SEQ ID NO:850, SEQ ID NO:907, SEQ ID NO:953, SEQ ID NO:1024, SEQ ID NO:1047, SEQ ID NO:1151, SEQ ID NO:1277, SEQ ID NO:1347, SEQ ID NO:1457, SEQ ID NO:1497, SEQ ID NO:1540, SEQ ID NO:1587, SEQ ID NO:1630, or SEQ ID NO:1635 as described in more detail herein.

Polypeptides described herein include red light specific response pathway polypeptides. Red light specific response pathway polypeptides can be effective to decrease hypocotyl length when over-expressed in a plant or plant cell. Such polypeptides typically contain at least one domain indicative of red light specific response pathway polypeptides, as described in more detail herein. Red light specific response pathway polypeptides typically have an HMM bit score that is greater than for an HMM model based on one of the alignments set forth in FIGS. 6, 11, and 24, as described in more detail herein. In some embodiments, red light specific response pathway polypeptides have greater than 40% identity to SEQ ID NO:456, SEQ ID NO:953, or SEQ ID NO:1540 as described in more detail herein.

A. Domains Indicative of SD+EODFR and/or Low Light Tolerance Polypeptides

A low light tolerance polypeptide can contain a cyclin dependent kinase inhibitor (CDI) domain. Cell cycle progression is negatively controlled by cyclin-dependent kinases inhibitors (CDIs). CDIs are involved in cell cycle arrest at the G1 phase. The motif is also present in SEQ ID NO:70, which sets forth the amino acid sequence of an *Arabidopsis* clone, identified herein as At2g32710 (SEQ ID NO:69), that is predicted to encode a cyclin-dependent kinase inhibitor 4 (KIP4) polypeptide.

A low light tolerance polypeptide can contain an AUX/IAA domain, which is predicted to be characteristic of an Aux/IAA transcriptional repressor. AUX/IAA proteins act as repressors of auxin-induced gene expression, possibly through modulating the activity of DNA-binding auxin response factors (ARFs). SEQ ID NO:129 sets forth the amino acid sequence of an *Arabidopsis* clone, identified herein as At2g46990 (SEQ ID NO:127), that is predicted to encode an auxin-induced IAA21 polypeptide. An SD+EODFR tolerance and low light tolerance polypeptide can also contain an AUX/IAA domain. SEQ ID NO:1347 sets forth the amino acid sequence of an *Arabidopsis* clone, identified herein as At1g32280 (SEQ ID NO:1345), that is predicted to encode an auxin-responsive IAA29 polypeptide containing an AUX/IAA domain.

A low light tolerance polypeptide can contain a homeobox domain. Homeobox domains bind DNA through a helix-turn-helix (HTH) structure. The HTH motif is characterised by two alpha-helices, which make intimate contacts with the DNA and are joined by a short turn. The second helix binds to DNA via a number of hydrogen bonds and hydrophobic interactions, which occur between specific side chains and the exposed bases and thymine methyl groups within the major groove of the DNA. The first helix helps to stabilise the structure. SEQ ID NO:317 sets forth the amino acid sequence of an *Arabidopsis* clone, identified herein as At4g03250 (SEQ ID NO:315), that is predicted to encode a polypeptide containing a homeobox domain.

A low light tolerance polypeptide can contain a C3HC4 type zinc-finger (zf_C3HC4) domain. The C3HC4 type zinc-finger (RING finger) is a cysteine-rich domain of 40 to 60 residues that coordinates two zinc ions, and has the consensus sequence: C-X2-C-X(9-39)-C-X(1-3)-H-X(2-3)-C-X2-C-X(4-48)-C-X2-C where X is any amino acid. Many proteins containing a RING finger play a role in the ubiquitination pathway. SEQ ID NO:337 sets forth the amino acid sequence of an *Arabidopsis* clone, identified herein as At2g04240 (SEQ ID NO:335), that is predicted to encode a polypeptide containing zf_C3HC4 domain.

A low light tolerance polypeptide can contain a B-box zinc finger (zf-B_box) domain and a CCT motif A B-box zinc finger domain is about 40 amino acids in length. One or two copies of this domain are generally associated with a ring finger and a coiled coil motif B-box zinc finger domains are found in transcription factors, ribonucleoproteins and protooncoproteins, but no function is clearly assigned. The CCT (CONSTANS, CO-like, and TOC1) motif is a highly conserved basic domain of about 43 amino acids, and is found near the C-terminus of plant proteins often involved in light signal transduction. The CCT motif is found in association with other domains, such as B-box zinc finger domains, GATA-type zinc finger domains, ZIM motifs, or response regulatory domains. The CCT motif contains a putative nuclear localization signal within the second half of the CCT motif, has been shown to be involved in nuclear localization, and likely has a role in protein-protein interaction. SEQ ID NO:456 sets forth the amino acid sequence of an *Arabidopsis* clone, identified herein as At5g14370

(SEQ ID NO:454), that is predicted to encode a polypeptide containing a B-box zinc finger domain and a CCT motif.

An SD+EODFR tolerance polypeptide can contain a DNA photolyase domain and a FAD_binding_7 domain (FAD binding domain of DNA photolyase). DNA photolyases are enzymes that repair mismatched pyrimidine dimers in DNA that are induced by exposure to ultra-violet light. Proteins containing a FAD_binding_7 domain include *Arabidopsis* cryptochromes 1 (CRY1) and 2 (CRY2), which are blue light photoreceptors that mediate blue light-induced gene expression. SEQ ID NO:538 sets forth the amino acid sequence of an *Arabidopsis* clone, identified herein as At1g04400 (SEQ ID NO:537), that is predicted to encode a cryptochrome 2 apoprotein polypeptide containing a FAD_binding_7 domain and a DNA photolyase domain. A low light-tolerance polypeptide can also FAD_binding_7 domain and a DNA photolyase domain. SEQ ID NO:1497 sets forth the amino acid sequence of an *Arabidopsis* clone, identified herein as At4g08920 (SEQ ID NO:1496), that is predicted to encode a cryptochrome 1 (CRY1), flavin-type blue-light photoreceptor apoprotein polypeptide containing a FAD_binding_7 domain and a DNA photolyase domain.

An SD+EODFR tolerance polypeptide can contain a zf_Dof domain, which is predicted to be characteristic of a Dof domain zinc finger polypeptide. SEQ ID NO:606 sets forth the amino acid sequence of an *Arabidopsis* clone, identified herein as At3g45610 (SEQ ID NO:605), that is predicted to encode a polypeptide containing a zf_Dof domain.

A low light tolerance polypeptide can contain an AP2 domain, which is predicted to be characteristic of an ERF/AP2 transcription factor. AP2 domains are typically about 60 amino acid residues in length. SEQ ID NO:645 sets forth the amino acid sequence of an *Arabidopsis* clone, identified herein as At4g25480 (SEQ ID NO:642), that is predicted to encode a DREB subfamily A-1 polypeptide of the ERF/AP2 transcription factor family containing an AP2 domain.

A low light tolerance polypeptide can contain a VQ motif. VQ motifs are short conserved motifs of FXhVQChTG, where X is any amino acid and h is a hydrophobic amino acid, that is found in a variety of plant proteins. SEQ ID NO:850 sets forth the amino acid sequence of an *Arabidopsis* clone, identified herein as At2g33780 (SEQ ID NO:848), that is predicted to encode a polypeptide containing a VQ motif.

A low light tolerance polypeptide can contain a zf_C2H2 domain, which is predicted to be characteristic of a C2H2-type zinc finger. C2H2 zinc fingers are composed of two short beta strands followed by an alpha helix. The amino terminal part of the helix binds the major groove of DNA. The two conserved cysteines and histidines of a C2H2 zinc finger domain coordinate a zinc ion. SEQ ID NO:907 sets forth the amino acid sequence of an *Arabidopsis* clone, identified herein as At4g17810 (SEQ ID NO:905), that is predicted to encode a polypeptide containing a zf_C2H2 domain.

A low light tolerance polypeptide can contain a TCP domain, which is predicted to be characteristic of a TCP family transcription factor. The TCP family of transcription factors is named after its first characterized members, TB1, CYC and PCF1 and PCF2. TCP domains are predicted to form non-canonical basic-Helix-Loop-Helix (bHLP) structures. The TCP domains found in two rice DNA-binding proteins, PCF1 and PCF2, have been shown to be involved in DNA-binding and dimerization. SEQ ID NO:1151 sets forth the amino acid sequence of an *Arabidopsis* clone, identified herein as At1g58100 (SEQ ID NO:1150), that is predicted to encode a polypeptide containing a TCP domain.

A low light tolerance polypeptide can contain an F-box domain. F-box domains have a role in mediating protein-protein interactions in a variety of contexts, such as polyubiquitination, transcription elongation, centromere binding and translational repression. Two motifs that are commonly found associated with F-box domains are leucine rich repeats and WD repeats. SEQ ID NO:1277 sets forth the amino acid sequence of an *Arabidopsis* clone, identified herein as At5g46170 (SEQ ID NO:1276), that is predicted to encode a polypeptide containing an F-box domain.

A low light tolerance polypeptide can contain a zf_CCCH domain, which is predicted to be characteristic of a C-x8-C-x5-C-x3-H type zinc finger polypeptide. The zf-CCCH domain is often found associated with proteins that interact with the 3' untranslated region of various mRNAs. SEQ ID NO:1457 sets forth the amino acid sequence of an *Arabidopsis* clone, identified herein as At3g02830 (SEQ ID NO:1456), that is predicted to encode a polypeptide containing a zf_CCCH domain.

An SD+EODFR tolerance and low light tolerance polypeptide can contain a POX domain and a homeobox domain. POX domains are often found in plant proteins with a homeobox domain, indicating that such proteins are likely transcription factors. SEQ ID NO:1540 sets forth the amino acid sequence of an *Arabidopsis* clone, identified herein as At2g35940 (SEQ ID NO:1537), that is predicted to encode a BEL1-like homeodomain 1 polypeptide containing a POX domain and a homeobox domain.

A low light tolerance polypeptide can contain an HSF-type DNA-binding domain, which is predicted to be characteristic of heat shock factor transcription activator. Heat shock factor transcription activators are often found associated with heat shock protein promoters during heat shock. SEQ ID NO:1587 sets forth the amino acid sequence of an *Arabidopsis* clone, identified herein as At4g11660 (SEQ ID NO:1586), that is predicted to encode a polypeptide containing an HSF-type DNA-binding domain.

A low light tolerance polypeptide can contain a sterile alpha motif (SAM_1) domain and a DNA repair metallo-beta-lactamase (DRMBL) domain, which is predicted to be characteristic of a DNA repair metallo-beta-lactamase. SEQ ID NO:1635 sets forth the amino acid sequence of an *Arabidopsis* clone, identified herein as Ceres At2g45700 (SEQ ID NO:1634), that is predicted to encode a polypeptide containing a SAM domain and a DRMBL domain.

B. Domains Indicative of Red Light Specific Response Pathway Polypeptides

A red light specific response pathway polypeptide can contain a B-box zinc finger (zf-B_box) domain and a CCT motif A B-box zinc finger domain is about 40 amino acids in length. One or two copies of this domain are generally associated with a ring finger and a coiled coil motif B-box zinc finger domains are found in transcription factors, ribonucleoproteins and protooncoproteins, but no function is clearly assigned. The CCT (CONSTANS, CO-like, and TOC1) motif is a highly conserved basic domain of about 43 amino acids, and is found near the C-terminus of plant proteins often involved in light signal transduction. The CCT motif is found in association with other domains, such as B-box zinc finger domains, GATA-type zinc finger domains, ZIM motifs, or response regulatory domains. The CCT motif contains a putative nuclear localization signal within the second half of the CCT motif, has been shown to be involved in nuclear localization, and likely has a role in protein-protein interaction. SEQ ID NO:456 sets forth the amino acid sequence of an *Arabidopsis* clone, identified herein as At5g14370 (SEQ ID NO:454), that is predicted to encode a polypeptide containing a B-box zinc finger domain and a CCT motif.

A red light specific response pathway polypeptide can contain a POX domain and a homeobox domain. POX domains are often found in plant proteins with a homeobox domain, indicating that such proteins are likely transcription factors. SEQ ID NO:1540 sets forth the amino acid sequence of an *Arabidopsis* clone, identified herein as At2g35940 (SEQ ID NO:1537), that is predicted to encode a BELL-like homeodomain 1 polypeptide containing a POX domain and a homeobox domain.

C. Functional Homologs Identified by Reciprocal BLAST

In some embodiments, one or more functional homologs of a reference SD+EODFR and/or low light tolerance polypeptide defined by one or more of the pfam descriptions indicated above are suitable for use as SD+EODFR and/or low light tolerance polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for an SD+EODFR and/or low light tolerance polypeptide, or by combining domains from the coding sequences for different naturally-occurring SD+EODFR and/or low light tolerance polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of SD+EODFR and/or low light tolerance polypeptides. Sequence analysis can involve BLAST, Reciprocal BLAST, or PSI-BLAST analysis of nonredundant databases using an SD+EODFR and/or low light tolerance polypeptide amino acid sequence as the reference sequence. Amino acid sequence is, in some instances, deduced from the nucleotide sequence. Those polypeptides in the database that have greater than 40% sequence identity are candidates for further evaluation for suitability as an SD+EODFR and/or low light tolerance polypeptide Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in SD+EODFR and/or low light tolerance polypeptides, e.g., conserved functional domains.

Conserved regions can be identified by locating a region within the primary amino acid sequence of an SD+EODFR and/or low light tolerance polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Amino acid sequences of functional homologs of the polypeptide set forth in SEQ ID NO:3 are provided in FIG. 1. Such functional homologs include Ceres CLONE ID no. 1844057 (SEQ ID NO:7), Ceres ANNOT ID no. 1469148 (SEQ ID NO:22), Public GI ID no. 18390998 (SEQ ID NO:25), Ceres CLONE ID no. 1065656 (SEQ ID NO:32), Ceres CLONE ID no. 1652677 (SEQ ID NO:36), Public GI ID no. 92874556 (SEQ ID NO:49), Ceres CLONE ID no. 1329161 (SEQ ID NO:53), Ceres CLONE ID no. 1030378 (SEQ ID NO:55), Ceres CLONE ID no. 1413787 (SEQ ID NO:57), and Public GI ID no. 125543598 (SEQ ID NO:60). Other functional homologs of SEQ ID NO:3 include Ceres CLONE ID no. 1793691 (SEQ ID NO:5), Ceres CLONE ID no. 1933784 (SEQ ID NO:9), Ceres CLONE ID no. 100030408 (SEQ ID NO:10), Ceres CLONE ID no. 1837059 (SEQ ID NO:12), Ceres CLONE ID no. 1793801 (SEQ ID NO:14), Ceres CLONE ID no. 1855480 (SEQ ID NO:16), Ceres CLONE ID no. 1915644 (SEQ ID NO:18), Ceres CLONE ID no. 1898104 (SEQ ID NO:20), Ceres ANNOT ID no. 1464241 (SEQ ID NO:24), Public GI ID no. 18697627 (SEQ ID NO:26), Ceres CLONE ID no. 9391 (SEQ ID NO:28), Ceres CLONE ID no. 111154 (SEQ ID NO:30), Ceres CLONE ID no. 973975 (SEQ ID NO:34), Ceres CLONE ID no. 676695 (SEQ ID NO:38), Ceres CLONE ID no. 680331 (SEQ ID NO:40), Ceres CLONE ID no. 654515 (SEQ ID NO:42), Ceres CLONE ID no. 626154 (SEQ ID NO:44), Ceres CLONE ID no. 710603 (SEQ ID NO:46), Ceres CLONE ID no. 648076 (SEQ ID NO:48), Ceres CLONE ID no. 749439 (SEQ ID NO:51), Ceres CLONE ID no. 295936 (SEQ ID NO:59), Public GI ID no. 125525139 (SEQ ID NO:61), Public GI ID no. 115452643 (SEQ ID NO:62), Public GI ID no. 24059889 (SEQ ID NO:63), Ceres ANNOT ID no. 6012747 (SEQ ID NO:65), Ceres ANNOT ID no. 6027628 (SEQ ID NO:67), and sequences identified as functional homologs of the sequences of FIG. 1, as set forth in the sequence listing. In some cases, a functional homolog of SEQ ID NO:3 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3.

Amino acid sequences of functional homologs of the polypeptide set forth in SEQ ID NO:70 are provided in FIG. 2. Such functional homologs include Ceres CLONE ID no. 1975934 (SEQ ID NO:72), Ceres ANNOT ID no. 1529913 (SEQ ID NO:80), Ceres CLONE ID no. 977794 (SEQ ID NO:93), Public GI ID no. 42362378 (SEQ ID NO:96), Public GI ID no. 23899378 (SEQ ID NO:99), Public GI ID no. 15963346 (SEQ ID NO:101), Public GI ID no. 15963344+B816 (SEQ ID NO:102), Public GI ID no. 92429657 (SEQ ID NO:103), Ceres CLONE ID no. 746644 (SEQ ID NO:105), Ceres CLONE ID no. 623089 (SEQ ID NO:109), Ceres CLONE ID no. 1913678 (SEQ ID NO:115), and Public GI ID no. 115450609 (SEQ ID NO:119). Other functional homologs of SEQ ID NO:70 include Ceres CLONE ID no. 1835084 (SEQ ID NO:74), Ceres CLONE ID no. 1846153 (SEQ ID NO:76), Ceres CLONE ID no. 1930884 (SEQ ID NO:78), Ceres ANNOT ID no. 1493858 (SEQ ID NO:82), Ceres ANNOT ID no. 1498646 (SEQ ID NO:84), Ceres ANNOT ID no. 1440974 (SEQ ID NO:86), Ceres CLONE ID no. 1189183 (SEQ ID NO:88), Public GI ID no. 26450253 (SEQ ID NO:89), Public GI ID no. 15239719 (SEQ ID NO:90), Public GI ID no. 15230194 (SEQ ID NO:91), Ceres CLONE ID no. 630905 (SEQ ID NO:95), Public GI ID no. 42362389 (SEQ ID NO:97), Public GI ID no. 70906129 (SEQ ID NO:98), Public GI ID no. 23899381 (SEQ ID NO:100), Ceres CLONE ID no. 298166 (SEQ ID NO:107), Ceres CLONE ID no. 1448390 (SEQ ID NO:111), Ceres CLONE ID no. 1734216 (SEQ ID NO:113), Public GI ID no. 125542322 (SEQ ID NO:116), Public GI ID no. 125532331 (SEQ ID NO:117), Public GI ID no. 125541233 (SEQ ID NO:118), Public GI ID no. 125584844 (SEQ ID NO:120), Public GI ID no. 115482472 (SEQ ID NO:121), Public GI ID no. 125575112 (SEQ ID NO:122), Ceres ANNOT ID no. 6003994 (SEQ ID NO:124), Ceres ANNOT ID no. 6068427 (SEQ ID NO:126), and sequences identified as functional homologs of the sequences of FIG. 2, as set forth in the sequence listing. In some cases, a functional homolog of SEQ ID NO:70 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:70.

Amino acid sequences of functional homologs of the polypeptide set forth in SEQ ID NO:129 are provided in FIG. 3. Such functional homologs include Public GI ID no. 34550779 (SEQ ID NO:133), Ceres CLONE ID no. 1932235 (SEQ ID NO:137), Ceres CLONE ID no. 981738 (SEQ ID NO:201), Ceres CLONE ID no. 565974 (SEQ ID NO:209), Public GI ID no. 1352058 (SEQ ID NO:231), Public GI ID no. 11131101 (SEQ ID NO:234), Public GI ID no. 4887018 (SEQ ID NO:236), Public GI ID no. 4887018 (SEQ ID NO:236), Ceres CLONE ID no. 644455 (SEQ ID NO:247), Ceres CLONE ID no. 1731500 (SEQ ID NO:270), Public GI ID no. 20269063 (SEQ ID NO:300), Public GI ID no. 50404477 (SEQ ID NO:302), and Public GI ID no. 62125392 (SEQ ID NO:303). Other functional homologs of SEQ ID NO:129 include Public GI ID no. 32396293 (SEQ ID NO:130), Public GI ID no. 32396299 (SEQ ID NO:131), Public GI ID no. 32396295 (SEQ ID NO:132), Ceres CLONE ID no. 1855369 (SEQ ID NO:135), Ceres CLONE ID no. 1948456 (SEQ ID NO:139), Ceres CLONE ID no. 1920182 (SEQ ID NO:141), Ceres CLONE ID no. 1835797 (SEQ ID NO:143), Ceres CLONE ID no. 1794204 (SEQ ID NO:145), Ceres CLONE ID no. 1853542 (SEQ ID NO:147), Ceres CLONE ID no. 1838776 (SEQ ID NO:149), Ceres CLONE ID no. 1854675 (SEQ ID NO:151), Ceres CLONE ID no. 1833078 (SEQ ID NO:153), Ceres CLONE ID no. 1850667 (SEQ ID NO:155), Ceres CLONE ID no. 1918745 (SEQ ID NO:157), Ceres CLONE ID no. 1929487 (SEQ ID NO:159), Ceres ANNOT ID no. 1497918 (SEQ ID NO:161), Ceres ANNOT ID no. 1459563 (SEQ ID NO:163), Ceres ANNOT ID no. 1452610 (SEQ ID NO:165), Ceres ANNOT ID no. 1496539 (SEQ ID NO:167), Ceres ANNOT ID no. 1498819 (SEQ ID NO:169), Ceres ANNOT ID no. 1446583 (SEQ ID NO:171), Ceres ANNOT ID no. 1535123 (SEQ ID NO:173), Ceres ANNOT ID no. 1463397 (SEQ ID NO:175), Ceres ANNOT ID no. 1499563 (SEQ ID NO:177), Ceres ANNOT ID no. 1495753 (SEQ ID NO:179), Ceres ANNOT ID no. 1488767 (SEQ ID NO:181), Ceres ANNOT ID no. 1522920 (SEQ ID NO:185), Ceres ANNOT ID no. 1469532 (SEQ ID NO:187), Public GI ID no. 15219692 (SEQ ID NO:188), Public GI ID no. 18420964 (SEQ ID NO:189), Ceres CLONE ID no. 1342080 (SEQ ID NO:191), Ceres CLONE ID no. 123105 (SEQ ID NO:193), Ceres CLONE ID no. 32727 (SEQ ID NO:195), Ceres CLONE ID no. 41161 (SEQ ID NO:197), Ceres CLONE ID no. 37274 (SEQ ID NO:199), Ceres CLONE ID no. 538020 (SEQ ID NO:203), Ceres CLONE ID no. 476244 (SEQ ID NO:205), Ceres CLONE ID no. 1623662 (SEQ ID NO:207), Ceres CLONE ID no. 626817 (SEQ ID NO:211), Ceres CLONE ID no. 537469 (SEQ ID NO:213), Ceres CLONE ID no. 582463 (SEQ ID NO:215), Ceres CLONE ID no. 1069818 (SEQ ID NO:217), Ceres CLONE ID no. 511737 (SEQ ID NO:219), Ceres CLONE ID no. 565422 (SEQ ID NO:221), Ceres CLONE ID no. 514595 (SEQ ID NO:223), Ceres CLONE ID no. 566396 (SEQ ID NO:225), Ceres CLONE ID no. 612705 (SEQ ID NO:227), Ceres CLONE ID no. 564134 (SEQ ID NO:229), Public GI ID no. 92872146 (SEQ ID NO:230), Public GI ID no. 11131103 (SEQ ID NO:232), Public GI ID no. 416641 (SEQ ID NO:233), Public GI ID no. 11131105 (SEQ ID NO:235), Public GI ID no. 4887016 (SEQ ID NO:237), Public GI ID no. 4887022 (SEQ ID NO:238), Public GI ID no. 81074526 (SEQ ID NO:239), Ceres CLONE ID no. 742023 (SEQ ID NO:241), Ceres CLONE ID no. 576268 (SEQ ID NO:243), Ceres CLONE ID no. 615386 (SEQ ID NO:245), Ceres CLONE ID no. 756966 (SEQ ID NO:249), Ceres CLONE ID no. 1052710 (SEQ ID NO:251), Ceres CLONE ID no. 697018 (SEQ ID NO:253), Ceres CLONE ID no. 618577 (SEQ ID NO:255), Ceres CLONE ID no. 935194 (SEQ ID NO:257), Ceres CLONE ID no. 1557429 (SEQ ID NO:259), Ceres CLONE ID no. 305337 (SEQ ID NO:261), Ceres CLONE ID no. 100872943 (SEQ ID NO:262), Ceres CLONE ID no. 305454 (SEQ ID NO:264), Ceres CLONE ID no. 1534670 (SEQ ID NO:266), Ceres CLONE ID no. 207963 (SEQ ID NO:268), Public GI ID no. 20257219 (SEQ ID NO:271), Ceres CLONE ID no. 1876818 (SEQ ID NO:273), Ceres CLONE ID no. 1817533 (SEQ ID NO:275), Ceres CLONE ID no. 1958631 (SEQ ID NO:277), Ceres CLONE ID no. 1963215 (SEQ ID NO:279), Ceres CLONE ID no. 1770022 (SEQ ID NO:281), Ceres CLONE ID no. 1796223 (SEQ ID NO:283), Ceres CLONE ID no. 2016695 (SEQ ID NO:285), Ceres CLONE ID no. 1757085 (SEQ ID NO:287), Ceres CLONE ID no. 1769256 (SEQ ID NO:289), Ceres CLONE ID no. 1994871 (SEQ ID NO:291), Public GI ID no. 17154533 (SEQ ID NO:292), Public GI ID no. 125557426 (SEQ ID NO:293), Public GI ID no. 125524736 (SEQ ID NO:294), Public GI ID no. 125527656 (SEQ ID NO:295), Public GI ID no. 125599342 (SEQ ID NO:296), Public GI ID no. 125569626 (SEQ ID NO:297), Public GI ID no. 115465401 (SEQ ID NO:298), Public GI ID no. 40539038 (SEQ ID NO:299), Public GI ID no. 20269059 (SEQ ID NO:301), Public GI ID no. 110826446 (SEQ ID NO:304), Ceres ANNOT ID no. 6029073 (SEQ ID NO:306), Ceres ANNOT ID no. 6011329 (SEQ ID NO:308), Ceres ANNOT ID no. 6034498 (SEQ ID NO:310), Ceres ANNOT ID no. 6095057 (SEQ ID NO:312), Ceres ANNOT ID no. 6095058 (SEQ ID NO:314), and sequences identified as functional homologs of the sequences of FIG. 3, as set forth in the sequence listing. In some cases, a functional homolog of SEQ ID NO:129 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:129.

Amino acid sequences of functional homologs of the polypeptide set forth in SEQ ID NO:317 are provided in FIG. 4. Such functional homologs include Ceres CLONE ID no. 1842125 (SEQ ID NO:319), Ceres ANNOT ID no. 1461360 (SEQ ID NO:321), Ceres CLONE ID no. 480906 (SEQ ID NO:327), Public GI ID no. 92889352 (SEQ ID NO:330), and Public GI ID no. 56201850 (SEQ ID NO:330). Other functional homologs of SEQ ID NO:317 include Ceres ANNOT ID no. 1440334 (SEQ ID NO:323), Ceres ANNOT ID no. 1493205 (SEQ ID NO:325), Ceres CLONE ID no. 482270 (SEQ ID NO:329), Public GI ID no. 125571531 (SEQ ID NO:332), Ceres ANNOT ID no. 6042411 (SEQ ID NO:334), and sequences identified as functional homologs of the sequences of FIG. 4, as set forth in the sequence listing. In some cases, a functional homolog of SEQ ID NO:317 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:317.

Amino acid sequences of functional homologs of the polypeptide set forth in SEQ ID NO:337 are provided in FIG. 5. Such functional homologs include Ceres CLONE ID no. 952050 (SEQ ID NO:339), Public GI ID no. 115477050 (SEQ ID NO:349), Public GI ID no. 87162911 (SEQ ID NO:355), Ceres CLONE ID no. 1790901 (SEQ ID NO:357), Ceres CLONE ID no. 1460088 (SEQ ID NO:370), Ceres CLONE ID no. 1734065 (SEQ ID NO:393), Ceres CLONE ID no. 473509 (SEQ ID NO:395), Ceres CLONE ID no. 849918 (SEQ ID NO:401), Ceres CLONE ID no. 633470 (SEQ ID NO:409), Ceres CLONE ID no. 1808334 (SEQ ID NO:417), and Ceres ANNOT ID no. 1525600 (SEQ ID NO:437). Other functional homologs of SEQ ID NO:337 include Ceres CLONE ID no. 1265097 (SEQ ID NO:341), Ceres CLONE ID no. 942980 (SEQ ID NO:343), Public GI ID no. 37901055 (SEQ ID NO:344), Ceres CLONE ID no. 1609912 (SEQ ID NO:346), Public GI ID no. 76446335 (SEQ ID NO:347), Public GI ID no. 125560204 (SEQ ID NO:348), Public GI ID no. 125303087 (SEQ ID NO:350), Public GI ID no. 115460088 (SEQ ID NO:351), Public GI ID no. 125591385 (SEQ ID NO:352), Public GI ID no. 115447931 (SEQ ID NO:353), Public GI ID no. 92893514 (SEQ ID NO:354), Ceres CLONE ID no. 2019320 (SEQ ID NO:359), Ceres CLONE ID no. 1890013 (SEQ ID NO:361), Public GI ID no. 20340241 (SEQ ID NO:362), Ceres CLONE ID no. 25801 (SEQ ID NO:364), Public GI ID no. 9743343 (SEQ ID NO:365), Public GI ID no. 15238072 (SEQ ID NO:366), Public GI ID no. 15222553 (SEQ ID NO:367), Public GI ID no. 21554155 (SEQ ID NO:368), Ceres CLONE ID no. 374439 (SEQ ID NO:372), Ceres CLONE ID no. 1465572 (SEQ ID NO:374), Ceres CLONE ID no. 1565524 (SEQ ID NO:376), Ceres CLONE ID no. 322302 (SEQ ID NO:378), Ceres CLONE ID no. 101136485 (SEQ ID NO:379), Ceres CLONE ID no. 1376133 (SEQ ID NO:381), Ceres CLONE ID no. 1374381 (SEQ ID NO:383), Ceres CLONE ID no. 1566473 (SEQ ID NO:385), Ceres CLONE ID no. 318088 (SEQ ID NO:387), Ceres CLONE ID no. 1452604 (SEQ ID NO:389), Ceres CLONE ID no. 337906 (SEQ ID NO:391), Ceres CLONE ID no. 1662513 (SEQ ID NO:397), Ceres CLONE ID no. 1662527 (SEQ ID NO:399), Ceres CLONE ID no. 571184 (SEQ ID NO:403), Ceres CLONE ID no. 665689 (SEQ ID NO:405), Ceres CLONE ID no. 1365853 (SEQ ID NO:407), Ceres CLONE ID no. 1052457 (SEQ ID NO:411), Ceres CLONE ID no. 579918 (SEQ ID NO:413), Ceres CLONE ID no. 863299 (SEQ ID NO:415), Ceres CLONE ID no. 1855611 (SEQ ID NO:419), Ceres CLONE ID no. 1845975 (SEQ ID NO:421), Ceres CLONE ID no. 1808298 (SEQ ID NO:423), Ceres CLONE ID no. 1841236 (SEQ ID NO:425), Ceres CLONE ID no. 1808269 (SEQ ID NO:427), Ceres CLONE ID no. 1850628 (SEQ ID NO:429), Ceres CLONE ID no. 1846911 (SEQ ID NO:431), Ceres CLONE ID no. 1916014 (SEQ ID NO:433), Ceres CLONE ID no. 1842594 (SEQ ID NO:435), Ceres ANNOT ID no. 1472192 (SEQ ID NO:439), Ceres ANNOT ID no. 1447489 (SEQ ID NO:441), Ceres ANNOT ID no. 1513000 (SEQ ID NO:443), Ceres ANNOT ID no. 1438658 (SEQ ID NO:445), Ceres ANNOT ID no. 1497255 (SEQ ID NO:447), Ceres ANNOT ID no. 6092104 (SEQ ID NO:449), Ceres ANNOT ID no. 6041700 (SEQ ID NO:451), Ceres ANNOT ID no. 6007297 (SEQ ID NO:453), and sequences identified as functional homologs of the sequences of FIG. 5, as set forth in the sequence listing. In some cases, a functional homolog of SEQ ID NO:337 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:337.

Amino acid sequences of functional homologs of the polypeptide set forth in SEQ ID NO:456 are provided in FIG. 6. Such functional homologs include Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 21655154 (SEQ ID NO:532), Public GI ID no. 90657642 (SEQ ID NO:536), and Ceres CLONE ID no. 1569555 (SEQ ID NO:1842). Other homologs of SEQ ID NO:456 include Public GI ID no. 66841018 (SEQ ID NO:458), Public GI ID no. 66841020 (SEQ ID NO:459), Public GI ID no. 108859343 (SEQ ID NO:460), Ceres CLONE ID no. 1937613 (SEQ ID NO:462), Ceres CLONE ID no. 1834027 (SEQ ID NO:464), Ceres ANNOT ID no. 1477832 (SEQ ID NO:468), Ceres ANNOT ID no. 1482536 (SEQ ID NO:470), Ceres ANNOT ID no. 1478227 (SEQ ID NO:472), Ceres CLONE ID no. 19906 (SEQ ID NO:478), Public GI ID no. 2895184 (SEQ ID NO:479), Public GI ID no. 2895188 (SEQ ID NO:480), Public GI ID no. 11037313 (SEQ ID NO:482), Public GI ID no. 22854908 (SEQ ID NO:483), Public GI ID no. 40787165 (SEQ ID NO:484), Public GI ID no. 116010475 (SEQ ID NO:486), Public GI ID no. 3341723 (SEQ ID NO:487), Public GI ID no. 4091806 (SEQ ID NO:489), Ceres CLONE ID no. 523203 (SEQ ID NO:491), Ceres CLONE ID no. 463157 (SEQ ID NO:493), Public GI ID no. 61611678 (SEQ ID NO:495), Public GI ID no. 45544887 (SEQ ID NO:497), Public GI ID no. 36789793 (SEQ ID NO:481), Ceres CLONE ID no. 907473 (SEQ ID NO:501), Ceres CLONE ID no. 1674443 (SEQ ID NO:503), Ceres CLONE ID no. 1559496 (SEQ ID NO:505), Ceres CLONE ID no. 530984 (SEQ ID NO:507), Public GI ID no. 61611682 (SEQ ID NO:509), Public GI ID no.

36789785 (SEQ ID NO:512), Ceres CLONE ID no. 702632 (SEQ ID NO:514), Public GI ID no. 61657299 (SEQ ID NO:515), Public GI ID no. 10946337 (SEQ ID NO:516), Ceres CLONE ID no. 1996408 (SEQ ID NO:518), Ceres CLONE ID no. 1725313 (SEQ ID NO:520), Public GI ID no. 78058606 (SEQ ID NO:521), Public GI ID no. 125538317 (SEQ ID NO:522), Public GI ID no. 125556324 (SEQ ID NO:523), Public GI ID no. 125548890 (SEQ ID NO:524), Public GI ID no. 93211100 (SEQ ID NO:525), Public GI ID no. 115444217 (SEQ ID NO:526), Public GI ID no. 115467558 (SEQ ID NO:527), Public GI ID no. 11094209 (SEQ ID NO:528), Public GI ID no. 125596830 (SEQ ID NO:529), Public GI ID no. 115469296 (SEQ ID NO:530), Public GI ID no. 115447239 (SEQ ID NO:531), Public GI ID no. 21667485 (SEQ ID NO:533), Public GI ID no. 21667475 (SEQ ID NO:534), Public GI ID no. 21655158 (SEQ ID NO:535), and sequences identified as functional homologs of the sequences of FIG. 6, as set forth in the sequence listing. In some cases, a functional homolog of SEQ ID NO:456 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:456.

Amino acid sequences of functional homologs of the polypeptide set forth in SEQ ID NO:634 are provided in FIG. 7. Such functional homologs include Public GI ID no. 98961985 (SEQ ID NO:637). Other functional homologs of SEQ ID NO:634 include Ceres CLONE ID no. 1916112 (SEQ ID NO:636), Public GI ID no. 9369405 (SEQ ID NO:638), Public GI ID no. 9369406 (SEQ ID NO:639), Ceres CLONE ID no. 1238706 (SEQ ID NO:641), and sequences identified as functional homologs of the sequences of FIG. 7, as set forth in the sequence listing. In some cases, a functional homolog of SEQ ID NO:634 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:634.

Amino acid sequences of functional homologs of the polypeptide set forth in SEQ ID NO:644 are provided in FIG. 8. Such functional homologs include SEQ ID NO:645, Ceres CLONE ID no. 1849479 (SEQ ID NO:767), Public GI ID no. 89275008 (SEQ ID NO:796), Public GI ID no. 120400525 (SEQ ID NO:797), Public GI ID no. 98980426 (SEQ ID NO:804), Public GI ID no. 71983373 (SEQ ID NO:808), Public GI ID no. 41351817 (SEQ ID NO:809), Public GI ID no. 76446191 (SEQ ID NO:811), Public GI ID no. 5616086 (SEQ ID NO:813), Ceres CLONE ID no. 1052602 (SEQ ID NO:826), Public GI ID no. 72068957 (SEQ ID NO:830), Public GI ID no. 71534113 (SEQ ID NO:831), Public GI ID no. 37147896 (SEQ ID NO:832), Public GI ID no. 92918850 (SEQ ID NO:834), Public GI ID no. 40647095 (SEQ ID NO:835), Ceres ANNOT ID no. 1527711 (SEQ ID NO:837), Public GI ID no. 71041116 (SEQ ID NO:838), Public GI ID no. 12003384 (SEQ ID NO:839), Public GI ID no. 18535580 (SEQ ID NO:840), and Public GI ID no. 115353971 (SEQ ID NO:1843). Other functional homologs of SEQ ID NO:644 include Ceres CLONE ID no. 991178 (SEQ ID NO:647), Ceres CLONE ID no. 1626038 (SEQ ID NO:649), Ceres CLONE ID no. 341615 (SEQ ID NO:651), Ceres CLONE ID no. 1832518 (SEQ ID NO:653), Ceres CLONE ID no. 1832588 (SEQ ID NO:655), Ceres CLONE ID no. 1936806 (SEQ ID NO:657), Ceres CLONE ID no. 973892 (SEQ ID NO:659), Ceres CLONE ID no. 565251 (SEQ ID NO:661), Ceres CLONE ID no. 681088 (SEQ ID NO:663), Ceres CLONE ID no. 707775 (SEQ ID NO:665), Ceres CLONE ID no. 453357 (SEQ ID NO:667), Ceres CLONE ID no. 1916958 (SEQ ID NO:669), Ceres CLONE ID no. 1940632 (SEQ ID NO:671), Ceres CLONE ID no. 476784 (SEQ ID NO:673), Ceres CLONE ID no. 1869284 (SEQ ID NO:675), Public GI ID no. 125540662 (SEQ ID NO:676), Ceres CLONE ID no. 1648272 (SEQ ID NO:678), Ceres CLONE ID no. 1987804 (SEQ ID NO:680), Ceres CLONE ID no. 1675695 (SEQ ID NO:682), Ceres CLONE ID no. 1169111 (SEQ ID NO:684), Ceres CLONE ID no. 572121 (SEQ ID NO:686), Ceres CLONE ID no. 1674836 (SEQ ID NO:688), Ceres ANNOT ID no. 1486207 (SEQ ID NO:690), Ceres CLONE ID no. 2023610 (SEQ ID NO:692), Ceres ANNOT ID no. 1496976 (SEQ ID NO:694), Public GI ID no. 116310031 (SEQ ID NO:695), Ceres CLONE ID no. 1626363 (SEQ ID NO:697), Ceres ANNOT ID no. 1483747 (SEQ ID NO:699), Ceres ANNOT ID no. 1471330 (SEQ ID NO:701), Ceres CLONE ID no. 101144964 (SEQ ID NO:702), Ceres ANNOT ID no. 1439439 (SEQ ID NO:704), Ceres CLONE ID no. 1446565 (SEQ ID NO:706), Ceres CLONE ID no. 1951962 (SEQ ID NO:708), Ceres CLONE ID no. 100960656 (SEQ ID NO:709), Ceres CLONE ID no. 285154 (SEQ ID NO:711), Public GI ID no. 61968916 (SEQ ID NO:712), Public GI ID no. 118026854 (SEQ ID NO:713), Public GI ID no. 63098612 (SEQ ID NO:714), Ceres ANNOT ID no. 1522310 (SEQ ID NO:716), Ceres CLONE ID no. 1854375 (SEQ ID NO:718), Ceres CLONE ID no. 709819 (SEQ ID NO:720), Public GI ID no. 115447695 (SEQ ID NO:721), Ceres CLONE ID no. 1726356 (SEQ ID NO:723), Ceres CLONE ID no. 1762419 (SEQ ID NO:725), Public GI ID no. 63098606 (SEQ ID NO:726), Ceres CLONE ID no. 1766572 (SEQ ID NO:728), Ceres CLONE ID no. 281871 (SEQ ID NO:730), Ceres CLONE ID no. 1560970 (SEQ ID NO:732), Ceres CLONE ID no. 1760747 (SEQ ID NO:734), Ceres ANNOT ID no. 1438772 (SEQ ID NO:736), Ceres ANNOT ID no. 1447378 (SEQ ID NO:738), Ceres ANNOT ID no. 1453360 (SEQ ID NO:740), Public GI ID no. 33637698 (SEQ ID NO:741), Public GI ID no. 118026860 (SEQ ID NO:742), Public GI ID no. 60116232 (SEQ ID NO:743), Public GI ID no. 115477639 (SEQ ID NO:744), Public GI ID no. 126567023 (SEQ ID NO:745), Ceres CLONE ID no. 988971 (SEQ ID NO:747), Ceres CLONE ID no. 1464521 (SEQ ID NO:749), Public GI ID no. 63098610 (SEQ ID NO:750), Public GI ID no. 126566972 (SEQ ID NO:751), Ceres CLONE ID no. 1556129 (SEQ ID NO:753), Ceres CLONE ID no. 1761385 (SEQ ID NO:755), Ceres ANNOT ID no. 1488325 (SEQ ID NO:757), Ceres ANNOT ID no. 1460483 (SEQ ID NO:759), Ceres CLONE ID no. 1837825 (SEQ ID NO:761), Public GI ID no. 27228310 (SEQ ID NO:762), Public GI ID no. 117653881 (SEQ ID NO:763), Public GI ID no. 115480233 (SEQ ID NO:764), Public GI ID no. 37694048 (SEQ ID NO:765), Ceres CLONE ID no. 1934653 (SEQ ID NO:769), Ceres CLONE ID no. 1608106 (SEQ ID NO:771), Ceres CLONE ID no. 1604576 (SEQ ID NO:773), Public GI ID no. 55824656 (SEQ ID NO:774), Ceres CLONE ID no. 1620272 (SEQ ID NO:776), Ceres CLONE ID no. 1853170 (SEQ ID NO:778), Public GI ID no. 79013962 (SEQ ID NO:779), Public GI ID no. 98975385 (SEQ ID NO:780), Ceres ANNOT ID no. 1438775 (SEQ ID NO:782), Public GI ID no. 23495460 (SEQ ID NO:783), Public GI ID no. 98975377 (SEQ ID NO:784), Ceres ANNOT ID no. 1438776 (SEQ ID NO:786), Ceres CLONE ID no. 1853601 (SEQ ID NO:788), Ceres CLONE ID no. 1609048 (SEQ ID NO:790), Ceres CLONE ID no. 322305 (SEQ ID NO:792), Ceres CLONE ID no. 1823713 (SEQ ID NO:794), Public GI ID no. 3660548 (SEQ ID NO:795), Public GI ID no.

56154991 (SEQ ID NO:798), Public GI ID no. 2980802 (SEQ ID NO:799), Public GI ID no. 7269398 (SEQ ID NO:800), Public GI ID no. 18416557 (SEQ ID NO:801), Public GI ID no. 56154992 (SEQ ID NO:802), Public GI ID no. 4091984 (SEQ ID NO:803), Public GI ID no. 1899058 (SEQ ID NO:805), Public GI ID no. 56154990 (SEQ ID NO:806), Public GI ID no. 18416562 (SEQ ID NO:807), Public GI ID no. 38683266 (SEQ ID NO:810), Public GI ID no. 39983638 (SEQ ID NO:812), Public GI ID no. 38426954 (SEQ ID NO:814), Public GI ID no. 38426948 (SEQ ID NO:815), Public GI ID no. 38146944 (SEQ ID NO:816), Public GI ID no. 38426952 (SEQ ID NO:817), Public GI ID no. 20303011 (SEQ ID NO:818), Public GI ID no. 66269982 (SEQ ID NO:819), Public GI ID no. 89212816 (SEQ ID NO:820), Public GI ID no. 20303015 (SEQ ID NO:821), Public GI ID no. 38426950 (SEQ ID NO:822), Public GI ID no. 15242244 (SEQ ID NO:823), Public GI ID no. 116831599 (SEQ ID NO:824), Public GI ID no. 66269671 (SEQ ID NO:827), Ceres ANNOT ID no. 1468919 (SEQ ID NO:829), Public GI ID no. 57903606 (SEQ ID NO:833), Public GI ID no. 45826358 (SEQ ID NO:841), Ceres ANNOT ID no. 6085912 (SEQ ID NO:843), Ceres ANNOT ID no. 6026171 (SEQ ID NO:845), Ceres ANNOT ID no. 6031706 (SEQ ID NO:847), and sequences listing identified as functional homologs of the sequences of FIG. 8, as set forth in the sequence. In some cases, a functional homolog of SEQ ID NO:644 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:644.

Amino acid sequences of functional homologs of the polypeptide set forth in SEQ ID NO:850 are provided in FIG. 9. Such functional homologs include Ceres CLONE ID no. 1833093 (SEQ ID NO:853), Ceres ANNOT ID no. 1502190 (SEQ ID NO:857), Ceres CLONE ID no. 565641 (SEQ ID NO:876), Public GI ID no. 87240507 (SEQ ID NO:877), Ceres CLONE ID no. 1325382 (SEQ ID NO:881), Ceres CLONE ID no. 1558265 (SEQ ID NO:885), Ceres CLONE ID no. 1823669 (SEQ ID NO:895), and Public GI ID no. 115464921 (SEQ ID NO:898). Other functional homologs of SEQ ID NO:850 include Ceres CLONE ID no. 100040598 (SEQ ID NO:851), Ceres CLONE ID no. 1847967 (SEQ ID NO:855), Ceres ANNOT ID no. 1449186 (SEQ ID NO:859), Ceres ANNOT ID no. 1466723 (SEQ ID NO:861), Public GI ID no. 21805688 (SEQ ID NO:862), Public GI ID no. 9795609 (SEQ ID NO:863), Public GI ID no. 13877535 (SEQ ID NO:864), Public GI ID no. 15232547 (SEQ ID NO:865), Public GI ID no. 15238851 (SEQ ID NO:866), Ceres CLONE ID no. 123863 (SEQ ID NO:868), Ceres CLONE ID no. 652496 (SEQ ID NO:870), Ceres CLONE ID no. 1656707 (SEQ ID NO:872), Ceres CLONE ID no. 1660346 (SEQ ID NO:874), Ceres CLONE ID no. 678878 (SEQ ID NO:879), Ceres CLONE ID no. 340102 (SEQ ID NO:883), Ceres CLONE ID no. 330491 (SEQ ID NO:887), Ceres CLONE ID no. 992304 (SEQ ID NO:889), Ceres CLONE ID no. 1509925 (SEQ ID NO:891), Ceres CLONE ID no. 1543852 (SEQ ID NO:893), Ceres CLONE ID no. 1785736 (SEQ ID NO:897), Ceres ANNOT ID no. 6079909 (SEQ ID NO:900), Ceres ANNOT ID no. 6040353 (SEQ ID NO:902), Ceres ANNOT ID no. 6100173 (SEQ ID NO:904), and sequences listing identified as functional homologs of the sequences of FIG. 9, as set forth in the sequence. In some cases, a functional homolog of SEQ ID NO:850 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:850.

Amino acid sequences of functional homologs of the polypeptide set forth in SEQ ID NO:907 are provided in FIG. 10. Such functional homologs include Ceres CLONE ID no. 1940797 (SEQ ID NO:909), Ceres ANNOT ID no. 1538900 (SEQ ID NO:911), Ceres CLONE ID no. 1126868 (SEQ ID NO:922), Public GI ID no. 89257684 (SEQ ID NO:923), Public GI ID no. 124360460 (SEQ ID NO:929), Public GI ID no. 62865694 (SEQ ID NO:931), Public GI ID no. 62865692 (SEQ ID NO:932), Ceres CLONE ID no. 260368 (SEQ ID NO:936), Ceres CLONE ID no. 1873510 (SEQ ID NO:947), Public GI ID no. 125541662 (SEQ ID NO:948), Public GI ID no. 48716268 (SEQ ID NO:950), and Public GI ID no. 62865696 (SEQ ID NO:1844). Other functional homologs of SEQ ID NO:907 include Ceres ANNOT ID no. 1529131 (SEQ ID NO:913), Ceres ANNOT ID no. 1454060 (SEQ ID NO:915), Ceres ANNOT ID no. 1442787 (SEQ ID NO:917), Ceres ANNOT ID no. 1452648 (SEQ ID NO:919), Public GI ID no. 2245140 (SEQ ID NO:920), Public GI ID no. 89274212 (SEQ ID NO:924), Ceres CLONE ID no. 1104523 (SEQ ID NO:926), Ceres CLONE ID no. 654265 (SEQ ID NO:928), Public GI ID no. 42627704 (SEQ ID NO:930), Ceres CLONE ID no. 887222 (SEQ ID NO:934), Public GI ID no. 62865690 (SEQ ID NO:937), Public GI ID no. 64175600 (SEQ ID NO:938), Public GI ID no. 64175634 (SEQ ID NO:939), Public GI ID no. 64175606 (SEQ ID NO:940), Public GI ID no. 64175648 (SEQ ID NO:941), Ceres CLONE ID no. 312184 (SEQ ID NO:943), Ceres CLONE ID no. 380740 (SEQ ID NO:945), Public GI ID no. 125531536 (SEQ ID NO:949), and sequences identified as functional homologs of the sequences of FIG. 10, as set forth in the sequence listing. In some cases, a functional homolog of SEQ ID NO:907 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:907.

Amino acid sequences of functional homologs of the polypeptide set forth in SEQ ID NO:953 are provided in FIG. 11. Such functional homologs include Ceres CLONE ID no. 1798705 (SEQ ID NO:955), Ceres ANNOT ID no. 1458907 (SEQ ID NO:963), Ceres CLONE ID no. 1090409 (SEQ ID NO:971), Ceres CLONE ID no. 479817 (SEQ ID NO:977), Ceres CLONE ID no. 1041793 (SEQ ID NO:979), Ceres CLONE ID no. 684633 (SEQ ID NO:985), Ceres CLONE ID no. 371815 (SEQ ID NO:991), Ceres CLONE ID no. 1686460 (SEQ ID NO:993), Ceres CLONE ID no. 1448595 (SEQ ID NO:995), Ceres CLONE ID no. 1734477 (SEQ ID NO:999), Ceres CLONE ID no. 1605693 (SEQ ID NO:1005), Ceres CLONE ID no. 1757400 (SEQ ID NO:1009), and Public GI ID no. 115434334 (SEQ ID NO:1015). Other functional homologs of SEQ ID NO:953 include Ceres CLONE ID no. 1793754 (SEQ ID NO:957), Ceres CLONE ID no. 1938045 (SEQ ID NO:959), Ceres CLONE ID no. 1850004 (SEQ ID NO:961), Ceres ANNOT ID no. 1489548 (SEQ ID NO:965), Public GI ID no. 22329538 (SEQ ID NO:966), Public GI ID no. 18404714 (SEQ ID NO:967), Ceres CLONE ID no. 1110032 (SEQ ID NO:969), Ceres CLONE ID no. 1095353 (SEQ ID NO:973), Ceres CLONE ID no. 872121 (SEQ ID NO:975), Ceres CLONE ID no. 562208 (SEQ ID NO:981), Ceres CLONE ID no. 1042364 (SEQ ID NO:983), Ceres CLONE ID no. 1031873 (SEQ ID NO:987), Ceres CLONE ID no. 1377698 (SEQ ID NO:989), Ceres CLONE ID no. 1742945 (SEQ ID NO:997), Ceres CLONE ID no. 1742053 (SEQ ID NO:1001), Ceres CLONE ID no. 1728365 (SEQ ID NO:1003), Ceres CLONE ID no. 1609807 (SEQ ID NO:1007), Ceres CLONE ID no. 1778566 (SEQ ID NO:1011), Ceres CLONE ID no. 2020580 (SEQ ID NO:1013), Public GI ID no. 125524285 (SEQ ID NO:1014), Public GI ID no. 125568898 (SEQ ID NO:1016), Ceres ANNOT ID no. 6055303 (SEQ ID NO:1018), and sequences identified as functional homologs of the sequences of FIG. 11, as set forth in the sequence listing. In some cases, a functional homolog of SEQ ID NO:953 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:953.

Amino acid sequences of functional homologs of the polypeptide set forth in SEQ ID NO:1024 are provided in FIG. 12. Such functional homologs include Ceres ANNOT ID no. 1452905 (SEQ ID NO:1029), Ceres CLONE ID no. 956176 (SEQ ID NO:1039), Public GI ID no. 92870366 (SEQ ID NO:1040), Ceres CLONE ID no. 294166 (SEQ ID NO:1042), and Public GI ID no. 125543067 (SEQ ID NO:1043). Other functional homologs of SEQ ID NO:1024 include SEQ ID NO:1025, Ceres ANNOT ID no. 1442522 (SEQ ID NO:1027), Public GI ID no. 8778818 (SEQ ID NO:1030), Ceres CLONE ID no. 108095 (SEQ ID NO:1032), Public GI ID no. 18394821 (SEQ ID NO:1033), Ceres CLONE ID no. 6332 (SEQ ID NO:1035), Ceres CLONE ID no. 1069047 (SEQ ID NO:1037), Public GI ID no. 115480956 (SEQ ID NO:1044), and sequences identified as functional homologs of the sequences of FIG. 12, as set forth in the sequence listing. In some cases, a functional homolog of SEQ ID NO:1024 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1024.

Amino acid sequences of functional homologs of the polypeptide set forth in SEQ ID NO:1047 are provided in FIG. 13. Such functional homologs include Ceres CLONE ID no. 1837694 (SEQ ID NO:1053), Ceres ANNOT ID no. 1483367 (SEQ ID NO:1057), Ceres CLONE ID no. 1077781 (SEQ ID NO:1083), Ceres CLONE ID no. 471026 (SEQ ID NO:1085), Public GI ID no. 92888885 (SEQ ID NO:1099), Public GI ID no. 45544873 (SEQ ID NO:1100), Public GI ID no. 45758663 (SEQ ID NO:1101), Ceres CLONE ID no. 772927 (SEQ ID NO:1105), Ceres CLONE ID no. 895080 (SEQ ID NO:1111), Ceres CLONE ID no. 1806128 (SEQ ID NO:1131), Public GI ID no. 115458192 (SEQ ID NO:1134), and Public GI ID no. 82470795 (SEQ ID NO:1139). Other functional homologs of SEQ ID NO:1047 include Ceres CLONE ID no. 1837746 (SEQ ID NO:1049), Ceres CLONE ID no. 1834764 (SEQ ID NO:1051), Ceres CLONE ID no. 1853547 (SEQ ID NO:1055), Ceres ANNOT ID no. 1474088 (SEQ ID NO:1059), Ceres ANNOT ID no. 1536919 (SEQ ID NO:1061), Ceres ANNOT ID no. 1467033 (SEQ ID NO:1063), Ceres ANNOT ID no. 1485401 (SEQ ID NO:1065), Ceres ANNOT ID no. 1486505 (SEQ ID NO:1067), Public GI ID no. 17065054 (SEQ ID NO:1068), Public GI ID no. 30694690 (SEQ ID NO:1069), Ceres CLONE ID no. 12997 (SEQ ID NO:1071), Public GI ID no. 30694694 (SEQ ID NO:1072), Public GI ID no. 42572167 (SEQ ID NO:1073), Public GI ID no. 110739742 (SEQ ID NO:1074), Public GI ID no. 18412263 (SEQ ID NO:1075), Ceres CLONE ID no. 36412 (SEQ ID NO:1077), Public GI ID no. 18399792 (SEQ ID NO:1078), Ceres CLONE ID no. 924 (SEQ ID NO:1080), Public GI ID no. 15238000 (SEQ ID NO:1081), Ceres CLONE ID no. 1626330 (SEQ ID NO:1087), Ceres CLONE ID no. 1650419 (SEQ ID NO:1089), Ceres CLONE ID no. 1641329 (SEQ ID NO:1091), Ceres CLONE ID no. 1620406 (SEQ ID NO:1093), Ceres CLONE ID no. 546832 (SEQ ID NO:1095), Ceres CLONE ID no. 1243138 (SEQ ID NO:1097), Public GI ID no. 92887260 (SEQ ID NO:1098), Ceres CLONE ID no. 885628 (SEQ ID NO:1103), Ceres CLONE ID no. 1376391 (SEQ ID NO:1107), Ceres CLONE ID no. 465893 (SEQ ID NO:1109), Ceres CLONE ID no. 218243 (SEQ ID NO:1113), Ceres CLONE ID no. 1558456 (SEQ ID NO:1115), Ceres CLONE ID no. 343008 (SEQ ID NO:1117), Ceres CLONE ID no. 218463 (SEQ ID NO:1119), Ceres CLONE ID no. 1565409 (SEQ ID NO:1121), Ceres CLONE ID no. 1060968 (SEQ ID NO:1123), Ceres CLONE ID no. 236111 (SEQ ID NO:1125), Ceres CLONE ID no. 285598 (SEQ ID NO:1127), Ceres CLONE ID no. 225881 (SEQ ID NO:1129), Ceres CLONE ID no. 1811383 (SEQ ID NO:1133), Public GI ID no. 49388268 (SEQ ID NO:1135), Public GI ID no. 125590268 (SEQ ID NO:1136), Public GI ID no. 115444009 (SEQ ID NO:1137), Public GI ID no. 115447993 (SEQ ID NO:1138), Ceres ANNOT ID no. 6033842 (SEQ ID NO:1141), Ceres ANNOT ID no. 6029952 (SEQ ID NO:1143), Ceres ANNOT ID no. 6035837 (SEQ ID NO:1145), Ceres ANNOT ID no. 6035830 (SEQ ID NO:1147), Ceres ANNOT ID no. 6029981 (SEQ ID NO:1149), and sequences identified as functional homologs of the sequences of FIG. 13, as set forth in the sequence listing. In some cases, a functional homolog of SEQ ID NO:1047 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1047.

Amino acid sequences of functional homologs of the polypeptide set forth in SEQ ID NO:1151 are provided in FIG. 14. Such functional homologs include Ceres CLONE ID no. 1851526 (SEQ ID NO:1155), Ceres ANNOT ID no. 1486769 (SEQ ID NO:1172), Public GI ID no. 83032232 (SEQ ID NO:1209), Ceres CLONE ID no. 1620420 (SEQ ID NO:1211), Public GI ID no. 92892428 (SEQ ID NO:1215), Ceres CLONE ID no. 884742 (SEQ ID NO:1223), Ceres CLONE ID no. 1821559 (SEQ ID NO:1246), Public GI ID no. 51535021 (SEQ ID NO:1258), Public GI ID no. 113205304 (SEQ ID NO:1263), and Public GI ID no. 37719051 (SEQ ID NO:1264). Other functional homologs of SEQ ID NO:1151 include Ceres CLONE ID no. 1918070 (SEQ ID NO:1153), Ceres CLONE ID no. 1948426 (SEQ ID NO:1157), Ceres CLONE ID no. 1937875 (SEQ ID NO:1159), Ceres CLONE ID no. 100056542 (SEQ ID NO:1160), Public GI ID no. 5731257 (SEQ ID NO:1161), Ceres CLONE ID no. 100058043 (SEQ ID NO:1162), Ceres CLONE ID no. 1838288 (SEQ ID NO:1164), Ceres CLONE ID no. 1793597 (SEQ ID NO:1166), Ceres ANNOT ID no. 1543031 (SEQ ID NO:1168), Ceres ANNOT ID no. 1489643 (SEQ ID NO:1170), Ceres ANNOT ID no. 1479721 (SEQ ID NO:1174), Ceres ANNOT ID no. 1449170 (SEQ ID NO:1176), Ceres ANNOT ID no. 1493696 (SEQ ID NO:1178), Ceres ANNOT ID no. 1543534 (SEQ ID NO:1180), Ceres ANNOT ID no. 1440815 (SEQ ID NO:1182), Ceres ANNOT ID no. 1490137 (SEQ ID NO:1184), Ceres ANNOT ID no. 1451054 (SEQ ID NO:1186), Ceres ANNOT ID no. 1456669 (SEQ ID NO:1188), Ceres ANNOT ID no. 1509865 (SEQ ID NO:1190), Ceres ANNOT ID no. 1447910 (SEQ ID NO:1192), Ceres ANNOT ID no. 1471068 (SEQ ID NO:1194), Ceres ANNOT ID no. 1504118 (SEQ ID NO:1196), Ceres CLONE ID no. 1343621 (SEQ ID NO:1198), Public GI ID no. 15218305 (SEQ ID NO:1199), Public GI ID no. 15219640 (SEQ ID NO:1200), Public GI ID no. 18409345 (SEQ ID NO:1201), Public GI ID no. 6522545 (SEQ ID NO:1202), Public GI ID no. 15237274 (SEQ ID NO:1203), Public GI ID no. 26452377 (SEQ ID NO:1204), Ceres CLONE ID no. 33629 (SEQ ID NO:1206), Ceres CLONE ID no. 1064407 (SEQ ID NO:1208), Ceres CLONE ID no. 1656310 (SEQ ID NO:1213), Public GI ID no. 92885257 (SEQ ID NO:1214), Public GI ID no. 92868571 (SEQ ID NO:1216), Public GI ID no. 53689778 (SEQ ID NO:1217), Ceres CLONE ID no. 835598 (SEQ ID NO:1219), Ceres CLONE ID no. 575649 (SEQ ID NO:1221), Ceres CLONE ID no. 376567 (SEQ ID NO:1225), Ceres CLONE ID no. 1284191 (SEQ ID NO:1227), Ceres CLONE ID no. 367175 (SEQ ID NO:1229), Ceres CLONE ID no. 100748296 (SEQ ID NO:1230), Ceres CLONE ID no. 1597176 (SEQ ID NO:1232), Ceres CLONE ID no. 375636 (SEQ ID NO:1234), Ceres CLONE ID no. 288123 (SEQ ID NO:1236), Ceres CLONE ID no. 303582 (SEQ ID NO:1238), Ceres CLONE ID no. 1604759 (SEQ ID NO:1240), Ceres CLONE ID no. 1955192 (SEQ ID NO:1242), Ceres CLONE ID no. 2008687 (SEQ ID NO:1244), Ceres CLONE ID no. 1995843 (SEQ ID NO:1248), Ceres CLONE ID no. 2008591 (SEQ ID NO:1250), Ceres CLONE ID no. 2046826 (SEQ ID NO:1252), Ceres CLONE ID no. 1985573 (SEQ ID NO:1254), Public GI ID no. 125541129 (SEQ ID NO:1255), Public GI ID no. 125528922 (SEQ ID NO:1256), Public GI ID no. 115487590 (SEQ ID NO:1257), Public GI ID no. 115448671 (SEQ ID NO:1259), Public GI ID no. 125596564 (SEQ ID NO:1260), Public GI ID no. 125573161 (SEQ ID NO:1261), Public GI ID no. 48716463 (SEQ ID NO:1262), Ceres ANNOT ID no. 6054246 (SEQ ID NO:1266), Ceres ANNOT ID no. 6086570 (SEQ ID NO:1268), Ceres ANNOT ID no. 6024957 (SEQ ID NO:1270), Ceres ANNOT ID no. 6016867 (SEQ ID NO:1272), Ceres ANNOT ID no. 6091369 (SEQ ID NO:1274), and sequences identified as functional homologs of the sequences of FIG. 14, as set forth in the sequence listing. In some cases, a functional homolog of SEQ ID NO:1151 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1151.

Amino acid sequences of functional homologs of the polypeptide set forth in SEQ ID NO:1277 are provided in FIG. 15. Such functional homologs include Ceres CLONE ID no. 1926352 (SEQ ID NO:1279), Ceres ANNOT ID no. 1448905 (SEQ ID NO:1285), Public GI ID no. 15236865 (SEQ ID NO:1294), Ceres CLONE ID no. 934771 (SEQ ID NO:1301), Ceres CLONE ID no. 338386 (SEQ ID NO:1303), Ceres CLONE ID no. 1780691 (SEQ ID NO:1317), and Public GI ID no. 115464819 (SEQ ID NO:1326). Other functional homologs of SEQ ID NO:1277 include Ceres CLONE ID no. 1848576 (SEQ ID NO:1281), Ceres CLONE ID no. 1981528 (SEQ ID NO:1283), Ceres ANNOT ID no. 1465978 (SEQ ID NO:1287), Ceres ANNOT ID no. 1504997 (SEQ ID NO:1289), Ceres ANNOT ID no. 1451909 (SEQ ID NO:1291), Ceres ANNOT ID no. 1461635 (SEQ ID NO:1293), Public GI ID no. 18397400 (SEQ ID NO:1295), Ceres CLONE ID no. 16226 (SEQ ID NO:1297), Public GI ID no. 18411823 (SEQ ID NO:1298), Public GI ID no. 15219845 (SEQ ID NO:1299), Ceres CLONE ID no. 1276710 (SEQ ID NO:1305), Ceres CLONE ID no. 1479310 (SEQ ID NO:1307), Ceres CLONE ID no. 376230 (SEQ ID NO:1309), Ceres CLONE ID no. 1290713 (SEQ ID NO:1311), Ceres CLONE ID no. 321681 (SEQ ID NO:1313), Ceres CLONE ID no. 1869072 (SEQ ID NO:1315), Ceres CLONE ID no. 1818502 (SEQ ID NO:1319), Ceres CLONE ID no. 1750477 (SEQ ID NO:1321), Public GI ID no. 125552947 (SEQ ID NO:1322), Public GI ID no. 125527862 (SEQ ID NO:1323), Public GI ID no. 125543660 (SEQ ID NO:1324), Public GI ID no. 125528123 (SEQ ID NO:1325), Public GI ID no. 115440195 (SEQ ID NO:1327), Public GI ID no. 115452717 (SEQ ID NO:1328), Public GI ID no. 115440629 (SEQ ID NO:1329), Public GI ID no. 115464599 (SEQ ID NO:1330), Public GI ID no. 20161462 (SEQ ID NO:1331), Public GI ID no. 125586076 (SEQ ID NO:1332), Ceres CLONE ID no. 1823216 (SEQ ID NO:1334), Ceres ANNOT ID no. 6040230 (SEQ ID NO:1336), Ceres ANNOT ID no. 6015489 (SEQ ID NO:1338), Ceres ANNOT ID no. 6042890 (SEQ ID NO:1340), Ceres ANNOT ID no. 6040033 (SEQ ID NO:1342), Ceres ANNOT ID no. 6018414 (SEQ ID NO:1344), and sequences identified as functional homologs of the sequences of FIG. 15, as set forth in the sequence listing. In some cases, a functional homolog of SEQ ID NO:1277 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1277.

Amino acid sequences of functional homologs of the polypeptide set forth in SEQ ID NO:1347 are provided in FIG. 16. Such functional homologs include Ceres CLONE ID no. 285028 (SEQ ID NO:1419), Ceres CLONE ID no. 100969565 (SEQ ID NO:1422), Public GI ID no. 1352057 (SEQ ID NO:1427), Ceres ANNOT ID no. 1453784 (SEQ ID NO:1429), Public GI ID no. 452777 (SEQ ID NO:1430), and Public GI ID no. 92873297 (SEQ ID NO:1431). Other functional homologs of SEQ ID NO:1347 include Ceres ANNOT ID no. 1452612 (SEQ ID NO:1349), Ceres CLONE ID no. 520455 (SEQ ID NO:1351), Public GI ID no. 75271810 (SEQ ID NO:1352), Public GI ID no. 115489446 (SEQ ID NO:1353), Ceres CLONE ID no. 499878 (SEQ ID NO:1355), Ceres ANNOT ID no. 1491840 (SEQ ID NO:1357), Public GI ID no. 125587204 (SEQ ID NO:1358), Ceres CLONE ID no. 320997 (SEQ ID NO:1360), Ceres ANNOT ID no. 1455585 (SEQ ID NO:1362), Ceres ANNOT ID no. 1499460 (SEQ ID NO:1364), Ceres CLONE ID no. 334484 (SEQ ID NO:1366), Ceres CLONE ID no. 100819481 (SEQ ID NO:1367), Public GI ID no. 115462401 (SEQ ID NO:1368), Ceres CLONE ID no. 1448136 (SEQ ID NO:1370), Ceres CLONE ID no. 277751 (SEQ ID NO:1372), Ceres ANNOT ID no. 1491839 (SEQ ID NO:1374), Ceres CLONE ID no. 100913241 (SEQ ID NO:1375), Ceres CLONE ID no. 1053224 (SEQ ID NO:1377), Ceres CLONE ID no. 425766 (SEQ ID NO:1379), Ceres CLONE ID no. 485480 (SEQ ID NO:1381), Ceres CLONE ID no. 474845 (SEQ ID NO:1383), Ceres CLONE ID no. 354561 (SEQ ID NO:1385), Ceres CLONE ID no. 540858 (SEQ ID NO:1387), Ceres CLONE ID no. 2032994 (SEQ ID NO:1389), Ceres CLONE ID no. 2015315 (SEQ ID NO:1391), Ceres CLONE ID no. 2016149 (SEQ ID NO:1393), Ceres CLONE ID no. 1922843 (SEQ ID NO:1395), Ceres CLONE ID no. 2000263 (SEQ ID NO:1397), Ceres CLONE ID no. 1943510 (SEQ ID NO:1399), Ceres CLONE ID no. 1835498 (SEQ ID NO:1401), Ceres CLONE ID no. 101116694 (SEQ ID NO:1402), Ceres CLONE ID no. 1930596 (SEQ ID NO:1404), Ceres CLONE ID no. 846036 (SEQ ID NO:1406), Ceres CLONE ID no. 941614 (SEQ ID NO:1408), Ceres CLONE ID no. 238788 (SEQ ID NO:1410), Public GI ID no. 125554220 (SEQ ID NO:1411), Public GI ID no. 125559895 (SEQ ID NO:1412), Public GI ID no. 75252070 (SEQ ID NO:1413), Public GI ID no. 115466632 (SEQ ID NO:1414), Public GI ID no. 125541525 (SEQ ID NO:1415), Ceres CLONE ID no. 1805110 (SEQ ID NO:1417), Ceres CLONE ID no. 1725309 (SEQ ID NO:1421), Ceres CLONE ID no. 100861679 (SEQ ID NO:1423), Public GI ID no. 75226278 (SEQ ID NO:1424), Public GI ID no. 125525030 (SEQ ID NO:1425), Public GI ID no. 115435474 (SEQ ID NO:1426), Ceres CLONE ID no. 1728516 (SEQ ID NO:1433), Public GI ID no. 115467910 (SEQ ID NO:1434), Public GI ID no. 15239950 (SEQ ID NO:1435), Public GI ID no. 4887012 (SEQ ID NO:1436), Ceres ANNOT ID no. 1478544 (SEQ ID NO:1438), Public GI ID no. 90811713 (SEQ ID NO:1439), Public GI ID no. 25989504 (SEQ ID NO:1440), Ceres CLONE ID no. 1113354 (SEQ ID NO:1442), Ceres CLONE ID no. 1113630 (SEQ ID NO:1444), Ceres ANNOT ID no. 6072030 (SEQ ID NO:1446), Ceres ANNOT ID no. 6025654 (SEQ ID NO:1448), Ceres ANNOT ID no. 6091150 (SEQ ID NO:1450), Ceres ANNOT ID no. 6100390 (SEQ ID NO:1452), and sequences identified as functional homologs of the sequences of FIG. 16, as set forth in the sequence listing. In some cases, a functional homolog of SEQ ID NO:1347 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1347.

Amino acid sequences of functional homologs of the polypeptide set forth in SEQ ID NO:1457 are provided in FIG. 17. Such functional homologs include Ceres CLONE ID no. 1924904 (SEQ ID NO:1460), Ceres ANNOT ID no. 1543346 (SEQ ID NO:1462), Public GI ID no. 18396338 (SEQ ID NO:1467), Ceres CLONE ID no. 833872 (SEQ ID NO:1471), Ceres CLONE ID no. 1579587 (SEQ ID NO:1475), Ceres CLONE ID no. 1786411 (SEQ ID NO:1477), and Public GI ID no. 108864370 (SEQ ID NO:1480). Other functional homologs of SEQ ID NO:1457 include SEQ ID NO:1458, Ceres ANNOT ID no. 1532932 (SEQ ID NO:1464), Ceres ANNOT ID no. 1489955 (SEQ ID NO:1466), Public GI ID no. 4928917 (SEQ ID NO:1468), Public GI ID no. 6728979 (SEQ ID NO:1469), Ceres CLONE ID no. 285780 (SEQ ID NO:1473), Public GI ID no. 125528863 (SEQ ID NO:1478), Public GI ID no. 125536365 (SEQ ID NO:1479), Public GI ID no. 108864369 (SEQ ID NO:1481), Public GI ID no. 115488274 (SEQ ID NO:1482), Public GI ID no. 125577099 (SEQ ID NO:1483), Public GI ID no. 125573110 (SEQ ID NO:1484), Public GI ID no. 124359159 (SEQ ID NO:1485), Public GI ID no. 62901479 (SEQ ID NO:1486), Ceres ANNOT ID no. 6016783 (SEQ ID NO:1488), Ceres ANNOT ID no. 6020759 (SEQ ID NO:1490), Ceres ANNOT ID no. 6028676 (SEQ ID NO:1492), Ceres ANNOT ID no. 6028677 (SEQ ID NO:1494), and sequences identified as functional homologs of the sequences of FIG. 17, as set forth in the sequence listing. In some cases, a functional homolog of SEQ ID NO:1457 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1457.

Amino acid sequences of functional homologs of the polypeptide set forth in SEQ ID NO:1497 are provided in FIG. 18. Such functional homologs include Ceres ANNOT ID no. 1443463 (SEQ ID NO:1499), Public GI ID no. 13605525 (SEQ ID NO:1502), Public GI ID no. 94965681 (SEQ ID NO:1506), and Public GI ID no. 28201254 (SEQ ID NO:1512). Other functional homologs of SEQ ID NO:1497 include Ceres ANNOT ID no. 1504954 (SEQ ID NO:1501), Public GI ID no. 2499553 (SEQ ID NO:1503), Public GI ID no. 738308 (SEQ ID NO:1504), Public GI ID no. 4325368 (SEQ ID NO:1505), Ceres CLONE ID no. 919923 (SEQ ID NO:1508), Ceres CLONE ID no. 1659764 (SEQ ID NO:1510), Public GI ID no. 125539984 (SEQ ID NO:1511), Public GI ID no. 21740729 (SEQ ID NO:1513), Public GI ID no. 115458700 (SEQ ID NO:1514), Public GI ID no. 125590574 (SEQ ID NO:1515), Public GI ID no. 16444957 (SEQ ID NO:1516), Ceres CLONE ID no. 1784494 (SEQ ID NO:1518), Public GI ID no. 77963980 (SEQ ID NO:1519), Public GI ID no. 124361190 (SEQ ID NO:1520), Public GI ID no. 37725007 (SEQ ID NO:1521), Public GI ID no. 45935258 (SEQ ID NO:1522), Public GI ID no. 15559008 (SEQ ID NO:1523), Public GI ID no. 38037416 (SEQ ID NO:1524), Public GI ID no. 77963974 (SEQ ID NO:1525), Ceres ANNOT ID no. 6112581 (SEQ ID NO:1527), Public GI ID no. 56553448 (SEQ ID NO:1528), Public GI ID no. 23506659 (SEQ ID NO:1529), Ceres ANNOT ID no. 6118060 (SEQ ID NO:1531), Public GI ID no. 46446306 (SEQ ID NO:1532), Public GI ID no. 114321405 (SEQ ID NO:1533), Public GI ID no. 83858274 (SEQ ID NO:1534), Public GI ID no. 154250969 (SEQ ID NO:1535), Public GI ID no. 83594235 (SEQ ID NO:1536), and sequences identified as functional homologs of the sequences of FIG. 18, as set forth in the sequence listing. In some cases, a functional homolog of SEQ ID NO:1497 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1497.

Amino acid sequences of functional homologs of the polypeptide set forth in SEQ ID NO:1587 are provided in FIG. 19. Such functional homologs include Ceres CLONE ID no. 1839577 (SEQ ID NO:1589), Ceres ANNOT ID no. 1491567 (SEQ ID NO:1591), Ceres CLONE ID no. 574505 (SEQ ID NO:1596), Public GI ID no. 56117815 (SEQ ID NO:1597), Public GI ID no. 92874021 (SEQ ID NO:1603), Public GI ID no. 123684 (SEQ ID NO:1605), Public GI ID no. 5821136 (SEQ ID NO:1606), Ceres CLONE ID no. 283366 (SEQ ID NO:1609), Public GI ID no. 16118447 (SEQ ID NO:1612), and Public GI ID no. 125562434 (SEQ ID NO:1614). Other functional homologs of SEQ ID NO:1587 include Ceres ANNOT ID no. 1438739 (SEQ ID NO:1593), Public GI ID no. 89274218 (SEQ ID NO:1594), Public GI ID no. 115521211 (SEQ ID NO:1598), Public GI ID no. 115521213 (SEQ ID NO:1599), Public GI ID no. 115521217 (SEQ ID NO:1600), Public GI ID no. 115521209 (SEQ ID NO:1601), Public GI ID no. 115521215 (SEQ ID NO:1602), Public GI ID no. 11386827 (SEQ ID NO:1604), Public GI ID no. 25052685 (SEQ ID NO:1607), Ceres CLONE ID no. 1440437 (SEQ ID NO:1611), Public GI ID no. 125564440 (SEQ ID NO:1613), Public GI ID no. 116309817 (SEQ ID NO:1615), Public GI ID no. 125549382 (SEQ ID NO:1616), Public GI ID no. 52077317 (SEQ ID NO:1617), Public GI ID no. 115477655 (SEQ ID NO:1618), Public GI ID no. 42408097 (SEQ ID NO:1619), Public GI ID no. 115459982 (SEQ ID NO:1620), Public GI ID no. 33591096 (SEQ ID NO:1621), Ceres CLONE ID no. 484753 (SEQ ID NO:1623), Ceres ANNOT ID no. 6035291 (SEQ ID NO:1625), and sequences identified as functional homologs of the sequences of FIG. 19, as set forth in the sequence listing. In some cases, a functional homolog of SEQ ID NO:1587 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1587.

Amino acid sequences of functional homologs of the polypeptide set forth in SEQ ID NO:1635 are provided in FIG. 20. Such functional homologs include Ceres ANNOT ID no. 1508307 (SEQ ID NO:1637), Public GI ID no. 1495267 (SEQ ID NO:1642), Public GI ID no. 87241310 (SEQ ID NO:1644), Ceres CLONE ID no. 938390 (SEQ ID NO:1646), Ceres CLONE ID no. 272338 (SEQ ID NO:1648), Ceres CLONE ID no. 1993510 (SEQ ID NO:1650), Public GI ID no. 125563862 (SEQ ID NO:1651), and Public GI ID no. 125605833 (SEQ ID NO:1653). Other functional homologs of SEQ ID NO:1635 include Public GI ID no. 6899919 (SEQ ID NO:1632), Ceres ANNOT ID no. 1455110 (SEQ ID NO:1639), Ceres ANNOT ID no. 1525218 (SEQ ID NO:1641), Public GI ID no. 15231597 (SEQ ID NO:1643), Public GI ID no. 125548147 (SEQ ID NO:1652), Public GI ID no. 51091343 (SEQ ID NO:1654), Public GI ID no. 115479355 (SEQ ID NO:1655), Ceres ANNOT ID no. 6042086 (SEQ ID NO:1657), Ceres ANNOT ID no. 6029903 (SEQ ID NO:1659), and sequences identified as functional homologs of the sequences of FIG. 20, as set forth in the sequence listing. In some cases, a functional homolog of SEQ ID NO:1635 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1635.

Amino acid sequences of functional homologs of the polypeptide set forth in SEQ ID NO:1540 are provided in FIG. 21. Such functional homologs include Ceres CLONE ID no. 1943265 (SEQ ID NO:1543), Ceres ANNOT ID no. 1454522 (SEQ ID NO:1547), Public GI ID no. 31323447 (SEQ ID NO:1556), Ceres CLONE ID no. 1583941 (SEQ ID NO:1561), Ceres CLONE ID no. 1792942 (SEQ ID NO:1563), Public GI ID no. 77548772 (SEQ ID NO:1565), and Public GI ID no. 84453182 (SEQ ID NO:1567). Other functional homologs of SEQ ID NO:1540 include Public GI ID no. 31746344 (SEQ ID NO:1541), Ceres CLONE ID no. 1926640 (SEQ ID NO:1545), Ceres ANNOT ID no. 1475125 (SEQ ID NO:1549), Ceres ANNOT ID no. 1439653 (SEQ ID NO:1551), Ceres ANNOT ID no. 1461995 (SEQ ID NO:1553), Public GI ID no. 13877517 (SEQ ID NO:1554), Public GI ID no. 7239157 (SEQ ID NO:1555), Public GI ID no. 22652125 (SEQ ID NO:1557), Public GI ID no. 22652115 (SEQ ID NO:1558), Public GI ID no. 22652117 (SEQ ID NO:1559), Public GI ID no. 125535858 (SEQ ID NO:1564), Public GI ID no. 125578581 (SEQ ID NO:1566), Public GI ID no. 13752407 (SEQ ID NO:1568), Ceres ANNOT ID no. 6098817 (SEQ ID NO:1570), Ceres ANNOT ID no. 6039430 (SEQ ID NO:1572), Ceres ANNOT ID no. 6068141 (SEQ ID NO:1574), Ceres ANNOT ID no. 6033916 (SEQ ID NO:1576), Ceres ANNOT ID no. 6034399 (SEQ ID NO:1578), Ceres ANNOT ID no. 6068617 (SEQ ID NO:1580), Ceres ANNOT ID no. 6026318 (SEQ ID NO:1582), Ceres ANNOT ID no. 6107650 (SEQ ID NO:1584), and sequences identified as functional homologs of the sequences of FIG. 21, as set forth in the sequence listing. In some cases, a functional homolog of SEQ ID NO:1540 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1540.

Amino acid sequences of functional homologs of the polypeptide set forth in SEQ ID NO:538 are provided in FIG. 22. Such functional homologs include Public GI ID no. 5731739 (SEQ ID NO:539), Ceres ANNOT ID no. 1538045 (SEQ ID NO:541), Public GI ID no. 29467479 (SEQ ID NO:542), Public GI ID no. 133921974 (SEQ ID NO:543), Public GI ID no. 113197027 (SEQ ID NO:544), Public GI ID no. 92879277 (SEQ ID NO:545), Public GI ID no. 45935260 (SEQ ID NO:546), Public GI ID no. 8101444 (SEQ ID NO:547), Public GI ID no. 78217443 (SEQ ID NO:548), and Public GI ID no. 28372347 (SEQ ID NO:549). Other functional homologs of SEQ ID NO:538 include Public GI ID no. 16416405 (SEQ ID NO:550), Ceres ANNOT ID no. 1484634 (SEQ ID NO:552), Ceres ANNOT ID no. 1451869 (SEQ ID NO:554), Public GI ID no. 25407462 (SEQ ID NO:555), Public GI ID no. 29467481 (SEQ ID NO:556), Public GI ID no. 29467477 (SEQ ID NO:557), Public GI ID no. 45935264 (SEQ ID NO:558), Public GI ID no. 5524201 (SEQ ID NO:559), Public GI ID no. 78217441 (SEQ ID NO:560), Public GI ID no. 3551221 (SEQ ID NO:561), Public GI ID no. 3551219 (SEQ ID NO:562), Public GI ID no. 23954324 (SEQ ID NO:563), Public GI ID no. 125582937 (SEQ ID NO:564), Public GI ID no. 83764373 (SEQ ID NO:565), Ceres ANNOT ID no. 6045327 (SEQ ID NO:567), and sequences identified as functional homologs of the sequences of FIG. 22, as set forth in the sequence listing. In some cases, a functional homolog of SEQ ID NO:538 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:538.

Amino acid sequences of functional homologs of the polypeptide set forth in SEQ ID NO:606 are provided in FIG. 23. Such functional homologs include Public GI ID no. 92873064 (SEQ ID NO:607), Public GI ID no. 37051125 (SEQ ID NO:608), and Public GI ID no. 112363376 (SEQ ID NO:609). Other functional homologs of SEQ ID NO:606 include Ceres CLONE ID no. 1938524 (SEQ ID NO:611), Ceres ANNOT ID no. 1473601 (SEQ ID NO:613), Ceres ANNOT ID no. 1468397 (SEQ ID NO:615), Public GI ID no. 21554185 (SEQ ID NO:616), Public GI ID no. 18424330 (SEQ ID NO:617), Public GI ID no. 8885571 (SEQ ID NO:618), Ceres CLONE ID no. 20852 (SEQ ID NO:620), Public GI ID no. 21553763 (SEQ ID NO:621), Public GI ID no. 18401763 (SEQ ID NO:622), Ceres CLONE ID no. 16423 (SEQ ID NO:624), Public GI ID no. 112363380 (SEQ ID NO:625), Public GI ID no. 6092016 (SEQ ID NO:626), Ceres CLONE ID no. 770468 (SEQ ID NO:628), Public GI ID no. 113205234 (SEQ ID NO:629), Ceres ANNOT ID no. 6094775 (SEQ ID NO:631), and sequences identified as functional homologs of the sequences of FIG. 23, as set forth in the sequence listing. In some cases, a functional homolog of SEQ ID NO:606 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:606.

Amino acid sequences of functional homologs of the polypeptide set forth in SEQ ID NO:570 are provided in FIG. 24. Such functional homologs include Ceres CLONE ID no. 1919714 (SEQ ID NO:572), Ceres ANNOT ID no. 1443290 (SEQ ID NO:574), Ceres CLONE ID no. 1042157 (SEQ ID NO:576), Ceres CLONE ID no. 1384304 (SEQ ID NO:578), and Public GI ID no. 115464375 (SEQ ID NO:579). Other functional homologs of SEQ ID NO:570 include Ceres CLONE ID no. 100028078 (SEQ ID NO:580), Ceres ANNOT ID no. 1452096 (SEQ ID NO:582), Ceres ANNOT ID no. 1503869 (SEQ ID NO:584), Ceres ANNOT ID no. 1525651 (SEQ ID NO:586), Ceres CLONE ID no. 1645639 (SEQ ID NO:588), Ceres CLONE ID no. 603237 (SEQ ID NO:590), Ceres CLONE ID no. 340925 (SEQ ID NO:592), Ceres CLONE ID no. 293238 (SEQ ID NO:594), Ceres CLONE ID no. 483742 (SEQ ID NO:596), Ceres CLONE ID no. 1460255 (SEQ ID NO:598), Ceres CLONE ID no. 1400107 (SEQ ID NO:600), Public GI ID no. 115440865 (SEQ ID NO:601), Ceres ANNOT ID no. 6016008 (SEQ ID NO:603), and sequences identified as functional homologs of the sequences of FIG. 24, as set forth in the sequence listing. In some cases, a functional homolog of SEQ ID NO:570 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:570.

The identification of conserved regions in an SD+EODFR and/or low light tolerance polypeptide facilitates production of variants of SD+EODFR and/or low light tolerance polypeptides. Variants of SD+EODFR and/or low light tolerance polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIGS. 1-24. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

D. Functional Homologs Identified by HMMER

In some embodiments, useful SD+EODFR and/or low light tolerance polypeptides include those that fit a Hidden Markov Model based on the polypeptides set forth in any one of FIGS. 1-24. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, -consistency REPS of 2; -ir, -iterative-refinement REPS of 100; -pre, -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate SD+EODFR and/or low light tolerance polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The SD+EODFR and/or low light tolerance polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of an SD+EODFR and/or low light tolerance polypeptide discussed below is about 50%, 60%, 70%, 80%, 90%, or 95% of the HMM bit score of a functional homolog provided in the Sequence Listing. In some embodiments, an SD+EODFR and/or low light tolerance polypeptide discussed below fits the indicated HMM with an HMM bit score greater than 20, and has a domain indicative of an SD+EODFR and/or low light tolerance polypeptide. In some embodiments, an SD+EODFR and/or low light tolerance polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-24.

Polypeptides are shown in the sequence listing that have HMM bit scores greater than 170 when fitted to an HMM generated from the amino acid sequences set forth in FIG. 1. Such polypeptides include At4g37295 (SEQ ID NO:3), Ceres CLONE ID no. 1844057 (SEQ ID NO:7), Ceres ANNOT ID no. 1469148 (SEQ ID NO:22), Public GI ID no. 18390998 (SEQ ID NO:25), Ceres CLONE ID no. 1065656 (SEQ ID NO:32), Ceres CLONE ID no. 1652677 (SEQ ID NO:36), Public GI ID no. 92874556 (SEQ ID NO:49), Ceres CLONE ID no. 1329161 (SEQ ID NO:53), Ceres CLONE ID no. 1030378 (SEQ ID NO:55), Ceres CLONE ID no. 1413787 (SEQ ID NO:57), Public GI ID no. 125543598 (SEQ ID NO:60), Ceres CLONE ID no. 1793691 (SEQ ID NO:5), Ceres CLONE ID no. 1933784 (SEQ ID NO:9), Ceres CLONE ID no. 100030408 (SEQ ID NO:10), Ceres CLONE ID no. 1837059 (SEQ ID NO:12), Ceres CLONE ID no. 1793801 (SEQ ID NO:14), Ceres CLONE ID no. 1855480 (SEQ ID NO:16), Ceres CLONE ID no. 1915644 (SEQ ID NO:18), Ceres CLONE ID no. 1898104 (SEQ ID NO:20), Ceres ANNOT ID no. 1464241 (SEQ ID NO:24), Public GI ID no. 18697627 (SEQ ID NO:26), Ceres CLONE ID no. 9391 (SEQ ID NO:28), Ceres CLONE ID no. 111154 (SEQ ID NO:30), Ceres CLONE ID no. 973975 (SEQ ID NO:34), Ceres CLONE ID no. 676695 (SEQ ID NO:38), Ceres CLONE ID no. 680331 (SEQ ID NO:40), Ceres CLONE ID no. 654515 (SEQ ID NO:42), Ceres CLONE ID no. 626154 (SEQ ID NO:44), Ceres CLONE ID no. 710603 (SEQ ID NO:46), Ceres CLONE ID no. 648076 (SEQ ID NO:48), Ceres CLONE ID no. 749439 (SEQ ID NO:51), Ceres CLONE ID no. 295936 (SEQ ID NO:59), Public GI ID no. 125525139 (SEQ ID NO:61), Public GI ID no. 115452643 (SEQ ID NO:62), Public GI ID no. 24059889 (SEQ ID NO:63), Ceres ANNOT ID no. 6012747 (SEQ ID NO:65), Ceres ANNOT ID no. 6027628 (SEQ ID NO:67), and sequences identified as functional homologs of the sequences of FIG. 1, as set forth in the sequence listing.

Polypeptides are shown in the sequence listing that have HMM bit scores greater than 80 when fitted to an HMM generated from the amino acid sequences set forth in FIG. 2. Such polypeptides include At2g32710 (SEQ ID NO:70), Ceres CLONE ID no. 1975934 (SEQ ID NO:72), Ceres ANNOT ID no. 1529913 (SEQ ID NO:80), Ceres CLONE ID no. 977794 (SEQ ID NO:93), Public GI ID no. 42362378 (SEQ ID NO:96), Public GI ID no. 23899378 (SEQ ID NO:99), Public GI ID no. 15963346 (SEQ ID NO:101), Public GI ID no. 15963344+B816 (SEQ ID NO:102), Public GI ID no. 92429657 (SEQ ID NO:103), Ceres CLONE ID no. 746644 (SEQ ID NO:105), Ceres CLONE ID no. 623089 (SEQ ID NO:109), Ceres CLONE ID no. 1913678 (SEQ ID NO:115), Public GI ID no. 115450609 (SEQ ID NO:119), Ceres CLONE ID no. 1835084 (SEQ ID NO:74), Ceres CLONE ID no. 1846153 (SEQ ID NO:76), Ceres CLONE ID no. 1930884 (SEQ ID NO:78), Ceres ANNOT ID no. 1493858 (SEQ ID NO:82), Ceres ANNOT ID no. 1498646 (SEQ ID NO:84), Ceres ANNOT ID no. 1440974 (SEQ ID NO:86), Ceres CLONE ID no. 1189183 (SEQ ID NO:88), Public GI ID no. 26450253 (SEQ ID NO:89), Public GI ID no. 15239719 (SEQ ID NO:90), Public GI ID no. 15230194 (SEQ ID NO:91), Ceres CLONE ID no. 630905 (SEQ ID NO:95), Public GI ID no. 42362389 (SEQ ID NO:97), Public GI ID no. 70906129 (SEQ ID NO:98), Public GI ID no. 23899381 (SEQ ID NO:100), Ceres CLONE ID no. 298166 (SEQ ID NO:107), Ceres CLONE ID no. 1448390 (SEQ ID NO:111), Ceres CLONE ID no. 1734216 (SEQ ID NO:113), Public GI ID no. 125542322 (SEQ ID NO:116), Public GI ID no. 125532331 (SEQ ID NO:117), Public GI ID no. 125541233 (SEQ ID NO:118), Public GI ID no. 125584844 (SEQ ID NO:120), Public GI ID no. 115482472 (SEQ ID NO:121), Public GI ID no. 125575112 (SEQ ID NO:122), Ceres ANNOT ID no. 6003994 (SEQ ID NO:124), Ceres ANNOT ID no. 6068427 (SEQ ID NO:126), and sequences identified as functional homologs of the sequences of FIG. 2, as set forth in the sequence listing.

Polypeptides are shown in the sequence listing that have HMM bit scores greater than 80 when fitted to an HMM generated from the amino acid sequences set forth in FIG. 3. Such polypeptides include Public GI ID no. 34550779 (SEQ ID NO:133), Ceres CLONE ID no. 1932235 (SEQ ID NO:137), Ceres CLONE ID no. 981738 (SEQ ID NO:201), Ceres CLONE ID no. 565974 (SEQ ID NO:209), Public GI ID no. 1352058 (SEQ ID NO:231), Public GI ID no. 11131101 (SEQ ID NO:234), Public GI ID no. 4887018 (SEQ ID NO:236), Public GI ID no. 4887018 (SEQ ID NO:236), Ceres CLONE ID no. 644455 (SEQ ID NO:247), Ceres CLONE ID no. 1731500 (SEQ ID NO:270), Public GI ID no. 20269063 (SEQ ID NO:300), Public GI ID no. 50404477 (SEQ ID NO:302), Public GI ID no. 62125392 (SEQ ID NO:303), Public GI ID no. 32396293 (SEQ ID NO:130), Public GI ID no. 32396299 (SEQ ID NO:131), Public GI ID no. 32396295 (SEQ ID NO:132), Ceres CLONE ID no. 1855369 (SEQ ID NO:135), Ceres CLONE ID no. 1948456 (SEQ ID NO:139), Ceres CLONE ID no. 1920182 (SEQ ID NO:141), Ceres CLONE ID no. 1835797 (SEQ ID NO:143), Ceres CLONE ID no. 1794204 (SEQ ID NO:145), Ceres CLONE ID no. 1853542 (SEQ ID NO:147), Ceres CLONE ID no. 1838776 (SEQ ID NO:149), Ceres CLONE ID no. 1854675 (SEQ ID NO:151), Ceres CLONE ID no. 1833078 (SEQ ID NO:153), Ceres CLONE ID no. 1850667 (SEQ ID NO:155), Ceres CLONE ID no. 1918745 (SEQ ID NO:157), Ceres CLONE ID no. 1929487 (SEQ ID NO:159), Ceres ANNOT ID no. 1497918 (SEQ ID NO:161), Ceres ANNOT ID no. 1459563 (SEQ ID NO:163), Ceres ANNOT ID no. 1452610 (SEQ ID NO:165), Ceres ANNOT ID no. 1496539 (SEQ ID NO:167), Ceres ANNOT ID no. 1498819 (SEQ ID NO:169), Ceres ANNOT ID no. 1446583 (SEQ ID NO:171), Ceres ANNOT ID no. 1535123 (SEQ ID NO:173), Ceres ANNOT ID no. 1463397 (SEQ ID NO:175), Ceres ANNOT ID no. 1499563 (SEQ ID NO:177), Ceres ANNOT ID no. 1495753 (SEQ ID NO:179), Ceres ANNOT ID no. 1488767 (SEQ ID NO:181), Ceres ANNOT ID no. 1522920 (SEQ ID NO:185), Ceres ANNOT ID no. 1469532 (SEQ ID NO:187), Public GI ID no. 15219692 (SEQ ID NO:188), Public GI ID no. 18420964 (SEQ ID NO:189), Ceres CLONE ID no. 1342080 (SEQ ID NO:191), Ceres CLONE ID no. 123105 (SEQ ID NO:193), Ceres CLONE ID no. 32727 (SEQ ID NO:195), Ceres CLONE ID no. 41161 (SEQ ID NO:197), Ceres CLONE ID no. 37274 (SEQ ID NO:199), Ceres CLONE ID no. 538020 (SEQ ID NO:203), Ceres CLONE ID no. 476244 (SEQ ID NO:205), Ceres CLONE ID no. 1623662 (SEQ ID NO:207), Ceres CLONE ID no. 626817 (SEQ ID NO:211), Ceres CLONE ID no. 537469 (SEQ ID NO:213), Ceres CLONE ID no. 582463 (SEQ ID NO:215), Ceres CLONE ID no. 1069818 (SEQ ID NO:217), Ceres CLONE ID no. 511737 (SEQ ID NO:219), Ceres CLONE ID no. 565422 (SEQ ID NO:221), Ceres CLONE ID no. 514595 (SEQ ID NO:223), Ceres CLONE ID no. 566396 (SEQ ID NO:225), Ceres CLONE ID no. 612705 (SEQ ID NO:227), Ceres CLONE ID no. 564134 (SEQ ID NO:229), Public GI ID no. 92872146 (SEQ ID NO:230), Public GI ID no. 11131103 (SEQ ID NO:232), Public GI ID no. 416641 (SEQ ID NO:233), Public GI ID no. 11131105 (SEQ ID NO:235), Public GI ID no. 4887016 (SEQ ID NO:237), Public GI ID no. 4887022 (SEQ ID NO:238), Public GI ID no. 81074526 (SEQ ID NO:239), Ceres CLONE ID no. 742023 (SEQ ID NO:241), Ceres CLONE ID no. 576268 (SEQ ID NO:243), Ceres CLONE ID no. 615386 (SEQ ID NO:245), Ceres CLONE ID no. 756966 (SEQ ID NO:249), Ceres CLONE ID no. 1052710 (SEQ ID NO:251), Ceres CLONE ID no. 697018 (SEQ ID NO:253), Ceres CLONE ID no. 618577 (SEQ ID NO:255), Ceres CLONE ID no. 935194 (SEQ ID NO:257), Ceres CLONE ID no. 1557429 (SEQ ID NO:259), Ceres CLONE ID no. 305337 (SEQ ID NO:261), Ceres CLONE ID no. 100872943 (SEQ ID NO:262), Ceres CLONE ID no. 305454 (SEQ ID NO:264), Ceres CLONE ID no. 1534670 (SEQ ID NO:266), Ceres CLONE ID no. 207963 (SEQ ID NO:268), Public GI ID no. 20257219 (SEQ ID NO:271), Ceres CLONE ID no. 1876818 (SEQ ID NO:273), Ceres CLONE ID no. 1817533 (SEQ ID NO:275), Ceres CLONE ID no. 1958631 (SEQ ID NO:277), Ceres CLONE ID no. 1963215 (SEQ ID NO:279), Ceres CLONE ID no. 1770022 (SEQ ID NO:281), Ceres CLONE ID no. 1796223 (SEQ ID NO:283), Ceres CLONE ID no. 2016695 (SEQ ID NO:285), Ceres CLONE ID no. 1757085 (SEQ ID NO:287), Ceres CLONE ID no. 1769256 (SEQ ID NO:289), Ceres CLONE ID no. 1994871 (SEQ ID NO:291), Public GI ID no. 17154533 (SEQ ID NO:292), Public GI ID no. 125557426 (SEQ ID NO:293), Public GI ID no. 125524736 (SEQ ID NO:294), Public GI ID no. 125527656 (SEQ ID NO:295), Public GI ID no. 125599342 (SEQ ID NO:296), Public GI ID no. 125569626 (SEQ ID NO:297), Public GI ID no. 115465401 (SEQ ID NO:298), Public GI ID no. 40539038 (SEQ ID NO:299), Public GI ID no. 20269059 (SEQ ID NO:301), Public GI ID no. 110826446 (SEQ ID NO:304), Ceres ANNOT ID no. 6029073 (SEQ ID NO:306), Ceres ANNOT ID no. 6011329 (SEQ ID NO:308), Ceres ANNOT ID no. 6034498 (SEQ ID NO:310), Ceres ANNOT ID no. 6095057 (SEQ ID NO:312), Ceres ANNOT ID no. 6095058 (SEQ ID NO:314), and sequences identified as functional homologs of the sequences of FIG. 3, as set forth in the sequence listing.

Polypeptides are shown in the sequence listing that have HMM bit scores greater than 200 when fitted to an HMM generated from the amino acid sequences set forth in FIG. 4. Such polypeptides include At4g03250 (Ceres Seedline ME10007; SEQ ID NO:317), Ceres CLONE ID no. 1842125 (SEQ ID NO:319), Ceres ANNOT ID no. 1461360 (SEQ ID NO:321), Ceres CLONE ID no. 480906 (SEQ ID NO:327), Public GI ID no. 92889352 (SEQ ID NO:330), Public GI ID no. 56201850 (SEQ ID NO:330), Ceres ANNOT ID no. 1440334 (SEQ ID NO:323), Ceres ANNOT ID no. 1493205 (SEQ ID NO:325), Ceres CLONE ID no. 482270 (SEQ ID NO:329), Public GI ID no. 125571531 (SEQ ID NO:332), Ceres ANNOT ID no. 6042411 (SEQ ID NO:334), and sequences identified as functional homologs of the sequences of FIG. 4, as set forth in the sequence listing.

Polypeptides are shown in the sequence listing that have HMM bit scores greater than 80 when fitted to an HMM generated from the amino acid sequences set forth in FIG. 5. Such polypeptides include At2g04240 (SEQ ID NO:337), Ceres CLONE ID no. 952050 (SEQ ID NO:339), Public GI ID no. 115477050 (SEQ ID NO:349), Public GI ID no. 87162911 (SEQ ID NO:355), Ceres CLONE ID no. 1790901 (SEQ ID NO:357), Ceres CLONE ID no. 1460088 (SEQ ID NO:370), Ceres CLONE ID no. 1734065 (SEQ ID NO:393), Ceres CLONE ID no. 473509 (SEQ ID NO:395), Ceres CLONE ID no. 849918 (SEQ ID NO:401), Ceres CLONE ID no. 633470 (SEQ ID NO:409), Ceres CLONE ID no. 1808334 (SEQ ID NO:417), Ceres ANNOT ID no. 1525600 (SEQ ID NO:437), Ceres CLONE ID no. 1265097 (SEQ ID NO:341), Ceres CLONE ID no. 942980 (SEQ ID NO:343), Public GI ID no. 37901055 (SEQ ID NO:344), Ceres CLONE ID no. 1609912 (SEQ ID NO:346), Public GI ID no. 76446335 (SEQ ID NO:347), Public GI ID no. 125560204 (SEQ ID NO:348), Public GI ID no. 125303087 (SEQ ID NO:350), Public GI ID no. 115460088 (SEQ ID NO:351), Public GI ID no. 125591385 (SEQ ID NO:352), Public GI ID no. 115447931 (SEQ ID NO:353), Public GI ID no. 92893514 (SEQ ID NO:354), Ceres CLONE ID no. 2019320 (SEQ ID NO:359), Ceres CLONE ID no. 1890013 (SEQ ID NO:361), Public GI ID no. 20340241 (SEQ ID NO:362), Ceres CLONE ID no. 25801 (SEQ ID NO:364), Public GI ID no. 9743343 (SEQ ID NO:365), Public GI ID no. 15238072 (SEQ ID NO:366), Public GI ID no. 15222553 (SEQ ID NO:367), Public GI ID no. 21554155 (SEQ ID NO:368), Ceres CLONE ID no. 374439 (SEQ ID NO:372), Ceres CLONE ID no. 1465572 (SEQ ID NO:374), Ceres CLONE ID no. 1565524 (SEQ ID NO:376), Ceres CLONE ID no. 322302 (SEQ ID NO:378), Ceres CLONE ID no. 101136485 (SEQ ID NO:379), Ceres CLONE ID no. 1376133 (SEQ ID NO:381), Ceres CLONE ID no. 1374381 (SEQ ID NO:383), Ceres CLONE ID no. 1566473 (SEQ ID NO:385), Ceres CLONE ID no. 318088 (SEQ ID NO:387), Ceres CLONE ID no. 1452604 (SEQ ID NO:389), Ceres CLONE ID no. 337906 (SEQ ID NO:391), Ceres CLONE ID no. 1662513 (SEQ ID NO:397), Ceres CLONE ID no. 1662527 (SEQ ID NO:399), Ceres CLONE ID no. 571184 (SEQ ID NO:403), Ceres CLONE ID no. 665689 (SEQ ID NO:405), Ceres CLONE ID no. 1365853 (SEQ ID NO:407), Ceres CLONE ID no. 1052457 (SEQ ID NO:411), Ceres CLONE ID no. 579918 (SEQ ID NO:413), Ceres CLONE ID no. 863299 (SEQ ID NO:415), Ceres CLONE ID no. 1855611 (SEQ ID NO:419), Ceres CLONE ID no. 1845975 (SEQ ID NO:421), Ceres CLONE ID no. 1808298 (SEQ ID NO:423), Ceres CLONE ID no. 1841236 (SEQ ID NO:425), Ceres CLONE ID no. 1808269 (SEQ ID NO:427), Ceres CLONE ID no. 1850628 (SEQ ID NO:429), Ceres CLONE ID no. 1846911 (SEQ ID NO:431), Ceres CLONE ID no. 1916014 (SEQ ID NO:433), Ceres CLONE ID no. 1842594 (SEQ ID NO:435), Ceres ANNOT ID no. 1472192 (SEQ ID NO:439), Ceres ANNOT ID no. 1447489 (SEQ ID NO:441), Ceres ANNOT ID no. 1513000 (SEQ ID NO:443), Ceres ANNOT ID no. 1438658 (SEQ ID NO:445), Ceres ANNOT ID no. 1497255 (SEQ ID NO:447), Ceres ANNOT ID no. 6092104 (SEQ ID NO:449), Ceres ANNOT ID no. 6041700 (SEQ ID NO:451), Ceres ANNOT ID no. 6007297 (SEQ ID NO:453), and sequences identified as functional homologs of the sequences of FIG. 5, as set forth in the sequence listing.

Polypeptides are shown in the sequence listing that have HMM bit scores greater than 60 when fitted to an HMM generated from the amino acid sequences set forth in FIG. 6. Such polypeptides include At5g14370 (SEQ ID NO:456), Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 90657642 (SEQ ID NO:536), Ceres CLONE ID no. 1569555 (SEQ ID NO:1842) Public GI ID no. 66841018 (SEQ ID NO:458), Public GI ID no. 66841020 (SEQ ID NO:459), Public GI ID no. 108859343 (SEQ ID NO:460), Ceres CLONE ID no. 1937613 (SEQ ID NO:462), Ceres CLONE ID no. 1834027 (SEQ ID NO:464), Ceres ANNOT ID no. 1477832 (SEQ ID NO:468), Ceres ANNOT ID no. 1482536 (SEQ ID NO:470), Ceres ANNOT ID no. 1478227 (SEQ ID NO:472), Ceres CLONE ID no. 19906 (SEQ ID NO:478), Public GI ID no. 2895184 (SEQ ID NO:479), Public GI ID no. 2895188 (SEQ ID NO:480), Public GI ID no. 11037313 (SEQ ID NO:482), Public GI ID no. 22854908 (SEQ ID NO:483), Public GI ID no. 40787165 (SEQ ID NO:484), Public GI ID no. 116010475 (SEQ ID NO:486), Public GI ID no. 3341723 (SEQ ID NO:487), Public GI ID no. 4091806 (SEQ ID NO:489), Ceres CLONE ID no. 523203 (SEQ ID NO:491), Ceres CLONE ID no.

463157 (SEQ ID NO:493), Public GI ID no. 61611678 (SEQ ID NO:495), Public GI ID no. 45544887 (SEQ ID NO:497), Public GI ID no. 36789793 (SEQ ID NO:481), Ceres CLONE ID no. 907473 (SEQ ID NO:501), Ceres CLONE ID no. 1674443 (SEQ ID NO:503), Ceres CLONE ID no. 1559496 (SEQ ID NO:505), Ceres CLONE ID no. 530984 (SEQ ID NO:507), Public GI ID no. 61611682 (SEQ ID NO:509), Public GI ID no. 36789785 (SEQ ID NO:512), Ceres CLONE ID no. 702632 (SEQ ID NO:514), Public GI ID no. 61657299 (SEQ ID NO:515), Public GI ID no. 10946337 (SEQ ID NO:516), Ceres CLONE ID no. 1996408 (SEQ ID NO:518), Ceres CLONE ID no. 1725313 (SEQ ID NO:520), Public GI ID no. 78058606 (SEQ ID NO:521), Public GI ID no. 125538317 (SEQ ID NO:522), Public GI ID no. 125556324 (SEQ ID NO:523), Public GI ID no. 125548890 (SEQ ID NO:524), Public GI ID no. 93211100 (SEQ ID NO:525), Public GI ID no. 115444217 (SEQ ID NO:526), Public GI ID no. 115467558 (SEQ ID NO:527), Public GI ID no. 11094209 (SEQ ID NO:528), Public GI ID no. 125596830 (SEQ ID NO:529), Public GI ID no. 115469296 (SEQ ID NO:530), Public GI ID no. 115447239 (SEQ ID NO:531), Public GI ID no. 21655154 (SEQ ID NO:532), Public GI ID no. 21667485 (SEQ ID NO:533), Public GI ID no. 21667475 (SEQ ID NO:534), Public GI ID no. 21655158 (SEQ ID NO:535), and sequences identified as functional homologs of the sequences of FIG. 6, as set forth in the sequence listing.

Polypeptides are shown in the sequence listing that have HMM bit scores greater than 20 when fitted to an HMM generated from the amino acid sequences set forth in FIG. 7. Such polypeptides include At1g70270 (SEQ ID NO:634), Public GI ID no. 98961985 (SEQ ID NO:637), Ceres CLONE ID no. 1916112 (SEQ ID NO:636), Public GI ID no. 9369405 (SEQ ID NO:638), Public GI ID no. 9369406 (SEQ ID NO:639), Ceres CLONE ID no. 1238706 (SEQ ID NO:641), and sequences identified as functional homologs of the sequences of FIG. 7, as set forth in the sequence listing.

Polypeptides are shown in the sequence listing that have HMM bit scores greater than 80 when fitted to an HMM generated from the amino acid sequences set forth in FIG. 8. Such polypeptides include At4g25480 (SEQ ID NO:644), SEQ ID NO:645, Ceres CLONE ID no. 1849479 (SEQ ID NO:767), Public GI ID no. 89275008 (SEQ ID NO:796), Public GI ID no. 120400525 (SEQ ID NO:797), Public GI ID no. 98980426 (SEQ ID NO:804), Public GI ID no. 71983373 (SEQ ID NO:808), Public GI ID no. 41351817 (SEQ ID NO:809), Public GI ID no. 76446191 (SEQ ID NO:811), Public GI ID no. 5616086 (SEQ ID NO:813), Ceres CLONE ID no. 1052602 (SEQ ID NO:826), Public GI ID no. 72068957 (SEQ ID NO:830), Public GI ID no. 71534113 (SEQ ID NO:831), Public GI ID no. 37147896 (SEQ ID NO:832), Public GI ID no. 92918850 (SEQ ID NO:834), Public GI ID no. 40647095 (SEQ ID NO:835), Ceres ANNOT ID no. 1527711 (SEQ ID NO:837), Public GI ID no. 71041116 (SEQ ID NO:838), Public GI ID no. 12003384 (SEQ ID NO:839), Public GI ID no. 18535580 (SEQ ID NO:840), Ceres CLONE ID no. 991178 (SEQ ID NO:647), Ceres CLONE ID no. 1626038 (SEQ ID NO:649), Ceres CLONE ID no. 341615 (SEQ ID NO:651), Ceres CLONE ID no. 1832518 (SEQ ID NO:653), Ceres CLONE ID no. 1832588 (SEQ ID NO:655), Ceres CLONE ID no. 1936806 (SEQ ID NO:657), Ceres CLONE ID no. 973892 (SEQ ID NO:659), Ceres CLONE ID no. 565251 (SEQ ID NO:661), Ceres CLONE ID no. 681088 (SEQ ID NO:663), Ceres CLONE ID no. 707775 (SEQ ID NO:665), Ceres CLONE ID no. 453357 (SEQ ID NO:667), Ceres CLONE ID no. 1916958 (SEQ ID NO:669), Ceres CLONE ID no. 1940632 (SEQ ID NO:671), Ceres CLONE ID no. 476784 (SEQ ID NO:673), Ceres CLONE ID no. 1869284 (SEQ ID NO:675), Public GI ID no. 125540662 (SEQ ID NO:676), Ceres CLONE ID no. 1648272 (SEQ ID NO:678), Ceres CLONE ID no. 1987804 (SEQ ID NO:680), Ceres CLONE ID no. 1675695 (SEQ ID NO:682), Ceres CLONE ID no. 1169111 (SEQ ID NO:684), Ceres CLONE ID no. 572121 (SEQ ID NO:686), Ceres CLONE ID no. 1674836 (SEQ ID NO:688), Ceres ANNOT ID no. 1486207 (SEQ ID NO:690), Ceres CLONE ID no. 2023610 (SEQ ID NO:692), Ceres ANNOT ID no. 1496976 (SEQ ID NO:694), Public GI ID no. 116310031 (SEQ ID NO:695), Ceres CLONE ID no. 1626363 (SEQ ID NO:697), Ceres ANNOT ID no. 1483747 (SEQ ID NO:699), Ceres ANNOT ID no. 1471330 (SEQ ID NO:701), Ceres CLONE ID no. 101144964 (SEQ ID NO:702), Ceres ANNOT ID no. 1439439 (SEQ ID NO:704), Ceres CLONE ID no. 1446565 (SEQ ID NO:706), Ceres CLONE ID no. 1951962 (SEQ ID NO:708), Ceres CLONE ID no. 100960656 (SEQ ID NO:709), Ceres CLONE ID no. 285154 (SEQ ID NO:711), Public GI ID no. 61968916 (SEQ ID NO:712), Public GI ID no. 118026854 (SEQ ID NO:713), Public GI ID no. 63098612 (SEQ ID NO:714), Ceres ANNOT ID no. 1522310 (SEQ ID NO:716), Ceres CLONE ID no. 1854375 (SEQ ID NO:718), Ceres CLONE ID no. 709819 (SEQ ID NO:720), Public GI ID no. 115447695 (SEQ ID NO:721), Ceres CLONE ID no. 1726356 (SEQ ID NO:723), Ceres CLONE ID no. 1762419 (SEQ ID NO:725), Public GI ID no. 63098606 (SEQ ID NO:726), Ceres CLONE ID no. 1766572 (SEQ ID NO:728), Ceres CLONE ID no. 281871 (SEQ ID NO:730), Ceres CLONE ID no. 1560970 (SEQ ID NO:732), Ceres CLONE ID no. 1760747 (SEQ ID NO:734), Ceres ANNOT ID no. 1438772 (SEQ ID NO:736), Ceres ANNOT ID no. 1447378 (SEQ ID NO:738), Ceres ANNOT ID no. 1453360 (SEQ ID NO:740), Public GI ID no. 33637698 (SEQ ID NO:741), Public GI ID no. 118026860 (SEQ ID NO:742), Public GI ID no. 60116232 (SEQ ID NO:743), Public GI ID no. 115477639 (SEQ ID NO:744), Public GI ID no. 126567023 (SEQ ID NO:745), Ceres CLONE ID no. 988971 (SEQ ID NO:747), Ceres CLONE ID no. 1464521 (SEQ ID NO:749), Public GI ID no. 63098610 (SEQ ID NO:750), Public GI ID no. 126566972 (SEQ ID NO:751), Ceres CLONE ID no. 1556129 (SEQ ID NO:753), Ceres CLONE ID no. 1761385 (SEQ ID NO:755), Ceres ANNOT ID no. 1488325 (SEQ ID NO:757), Ceres ANNOT ID no. 1460483 (SEQ ID NO:759), Ceres CLONE ID no. 1837825 (SEQ ID NO:761), Public GI ID no. 27228310 (SEQ ID NO:762), Public GI ID no. 117653881 (SEQ ID NO:763), Public GI ID no. 115480233 (SEQ ID NO:764), Public GI ID no. 37694048 (SEQ ID NO:765), Ceres CLONE ID no. 1934653 (SEQ ID NO:769), Ceres CLONE ID no. 1608106 (SEQ ID NO:771), Ceres CLONE ID no. 1604576 (SEQ ID NO:773), Public GI ID no. 55824656 (SEQ ID NO:774), Ceres CLONE ID no. 1620272 (SEQ ID NO:776), Ceres CLONE ID no. 1853170 (SEQ ID NO:778), Public GI ID no. 79013962 (SEQ ID NO:779), Public GI ID no. 98975385 (SEQ ID NO:780), Ceres ANNOT ID no. 1438775 (SEQ ID NO:782), Public GI ID no. 23495460 (SEQ ID NO:783), Public GI ID no. 98975377 (SEQ ID NO:784), Ceres ANNOT ID no. 1438776 (SEQ ID NO:786), Ceres CLONE ID no. 1853601 (SEQ ID NO:788), Ceres CLONE ID no. 1609048 (SEQ ID NO:790), Ceres CLONE ID no. 322305 (SEQ ID NO:792), Ceres CLONE ID no. 1823713 (SEQ ID NO:794), Public GI ID no. 3660548 (SEQ ID NO:795), Public GI ID no. 56154991 (SEQ ID NO:798), Public GI ID no. 2980802 (SEQ ID NO:799), Public GI ID no. 7269398 (SEQ ID NO:800), Public GI ID no. 18416557 (SEQ ID NO:801), Public GI ID no. 56154992 (SEQ ID NO:802), Public GI ID no. 4091984 (SEQ ID NO:803), Public GI ID no. 1899058 (SEQ ID NO:805), Public GI ID no. 56154990 (SEQ ID NO:806), Public GI ID no. 18416562 (SEQ ID NO:807), Public GI ID no. 38683266 (SEQ ID NO:810), Public GI ID no. 39983638 (SEQ ID NO:812), Public GI ID no. 38426954 (SEQ ID NO:814), Public GI ID no. 38426948 (SEQ ID NO:815), Public GI ID no. 38146944 (SEQ ID NO:816), Public GI ID no. 38426952 (SEQ ID NO:817), Public GI ID no. 20303011 (SEQ ID NO:818), Public GI ID no. 66269982 (SEQ ID NO:819), Public GI ID no. 89212816 (SEQ ID NO:820), Public GI ID no. 20303015 (SEQ ID NO:821), Public GI ID no. 38426950 (SEQ ID NO:822), Public GI ID no. 15242244 (SEQ ID NO:823), Public GI ID no. 116831599 (SEQ ID NO:824), Public GI ID no. 66269671 (SEQ ID NO:827), Ceres ANNOT ID no. 1468919 (SEQ ID NO:829), Public GI ID no. 57903606 (SEQ ID NO:833), Public GI ID no. 45826358 (SEQ ID NO:841), Ceres ANNOT ID no. 6085912 (SEQ ID NO:843), Ceres ANNOT ID no. 6026171 (SEQ ID NO:845), Ceres ANNOT ID no. 6031706 (SEQ ID NO:847), Public GI ID no. 115353971 (SEQ ID NO:1843), and sequences identified as functional homologs of the sequences of FIG. 8, as set forth in the sequence listing.

Polypeptides are shown in the sequence listing that have HMM bit scores greater than 170 when fitted to an HMM generated from the amino acid sequences set forth in FIG. 9. Such polypeptides include A2g33780 (SEQ ID NO:850), Ceres CLONE ID no. 1833093 (SEQ ID NO:853), Ceres ANNOT ID no. 1502190 (SEQ ID NO:857), Ceres CLONE ID no. 565641 (SEQ ID NO:876), Public GI ID no. 87240507 (SEQ ID NO:877), Ceres CLONE ID no. 1325382 (SEQ ID NO:881), Ceres CLONE ID no. 1558265 (SEQ ID NO:885), Ceres CLONE ID no. 1823669 (SEQ ID NO:895), Public GI ID no. 115464921 (SEQ ID NO:898), Ceres CLONE ID no. 100040598 (SEQ ID NO:851), Ceres CLONE ID no. 1847967 (SEQ ID NO:855), Ceres ANNOT ID no. 1449186 (SEQ ID NO:859), Ceres ANNOT ID no. 1466723 (SEQ ID NO:861), Public GI ID no. 21805688 (SEQ ID NO:862), Public GI ID no. 9795609 (SEQ ID NO:863), Public GI ID no. 13877535 (SEQ ID NO:864), Public GI ID no. 15232547 (SEQ ID NO:865), Public GI ID no. 15238851 (SEQ ID NO:866), Ceres CLONE ID no. 123863 (SEQ ID NO:868), Ceres CLONE ID no. 652496 (SEQ ID NO:870), Ceres CLONE ID no. 1656707 (SEQ ID NO:872), Ceres CLONE ID no. 1660346 (SEQ ID NO:874), Ceres CLONE ID no. 678878 (SEQ ID NO:879), Ceres CLONE ID no. 340102 (SEQ ID NO:883), Ceres CLONE ID no. 330491 (SEQ ID NO:887), Ceres CLONE ID no. 992304 (SEQ ID NO:889), Ceres CLONE ID no. 1509925 (SEQ ID NO:891), Ceres CLONE ID no. 1543852 (SEQ ID NO:893), Ceres CLONE ID no. 1785736 (SEQ ID NO:897), Ceres ANNOT ID no. 6079909 (SEQ ID NO:900), Ceres ANNOT ID no. 6040353 (SEQ ID NO:902), Ceres ANNOT ID no. 6100173 (SEQ ID NO:904), and sequences identified as functional homologs of the sequences of FIG. 9, as set forth in the sequence listing.

Polypeptides are shown in the sequence listing that have HMM bit scores greater than 80 when fitted to an HMM generated from the amino acid sequences set forth in FIG. 10. Such polypeptides include At4g17810 (SEQ ID NO:907), Ceres CLONE ID no. 1940797 (SEQ ID NO:909), Ceres ANNOT ID no. 1538900 (SEQ ID NO:911), Ceres CLONE ID no. 1126868 (SEQ ID NO:922), Public GI ID no. 89257684 (SEQ ID NO:923), Public GI ID no. 124360460 (SEQ ID NO:929), Public GI ID no. 62865694 (SEQ ID NO:931), Public GI ID no. 62865692 (SEQ ID NO:932), Ceres CLONE ID no. 260368 (SEQ ID NO:936), Ceres CLONE ID no. 1873510 (SEQ ID NO:947), Public GI ID no. 125541662 (SEQ ID NO:948), Public GI ID no. 48716268 (SEQ ID NO:950), Ceres ANNOT ID no. 1529131 (SEQ ID NO:913), Ceres ANNOT ID no. 1454060 (SEQ ID NO:915), Ceres ANNOT ID no. 1442787 (SEQ ID NO:917), Ceres ANNOT ID no. 1452648 (SEQ ID NO:919), Public GI ID no. 2245140 (SEQ ID NO:920), Public GI ID no. 89274212 (SEQ ID NO:924), Ceres CLONE ID no. 1104523 (SEQ ID NO:926), Ceres CLONE ID no. 654265 (SEQ ID NO:928), Public GI ID no. 42627704 (SEQ ID NO:930), Ceres CLONE ID no. 887222 (SEQ ID NO:934), Public GI ID no. 62865690 (SEQ ID NO:937), Public GI ID no. 64175600 (SEQ ID NO:938), Public GI ID no. 64175634 (SEQ ID NO:939), Public GI ID no. 64175606 (SEQ ID NO:940), Public GI ID no. 64175648 (SEQ ID NO:941), Ceres CLONE ID no. 312184 (SEQ ID NO:943), Ceres CLONE ID no. 380740 (SEQ ID NO:945), Public GI ID no. 125531536 (SEQ ID NO:949), Public GI ID no. 62865696 (SEQ ID NO:1844), and sequences identified as functional homologs of the sequences of FIG. 10, as set forth in the sequence listing.

Polypeptides are shown in the sequence listing that have HMM bit scores greater than 60 when fitted to an HMM generated from the amino acid sequences set forth in FIG. 11. Such polypeptides include At1g13360 (SEQ ID NO:951), Ceres CLONE ID no. 1798705 (SEQ ID NO:955), Ceres ANNOT ID no. 1458907 (SEQ ID NO:963), Ceres CLONE ID no. 1090409 (SEQ ID NO:971), Ceres CLONE ID no. 479817 (SEQ ID NO:977), Ceres CLONE ID no. 1041793 (SEQ ID NO:979), Ceres CLONE ID no. 684633 (SEQ ID NO:985), Ceres CLONE ID no. 371815 (SEQ ID NO:991), Ceres CLONE ID no. 1686460 (SEQ ID NO:993), Ceres CLONE ID no. 1448595 (SEQ ID NO:995), Ceres CLONE ID no. 1734477 (SEQ ID NO:999), Ceres CLONE ID no. 1605693 (SEQ ID NO:1005), Ceres CLONE ID no. 1757400 (SEQ ID NO:1009), Public GI ID no. 115434334 (SEQ ID NO:1015), Ceres CLONE ID no. 1793754 (SEQ ID NO:957), Ceres CLONE ID no. 1938045 (SEQ ID NO:959), Ceres CLONE ID no. 1850004 (SEQ ID NO:961), Ceres ANNOT ID no. 1489548 (SEQ ID NO:965), Public GI ID no. 22329538 (SEQ ID NO:966), Public GI ID no. 18404714 (SEQ ID NO:967), Ceres CLONE ID no. 1110032 (SEQ ID NO:969), Ceres CLONE ID no. 1095353 (SEQ ID NO:973), Ceres CLONE ID no. 872121 (SEQ ID NO:975), Ceres CLONE ID no. 562208 (SEQ ID NO:981), Ceres CLONE ID no. 1042364 (SEQ ID NO:983), Ceres CLONE ID no. 1031873 (SEQ ID NO:987), Ceres CLONE ID no. 1377698 (SEQ ID NO:989), Ceres CLONE ID no. 1742945 (SEQ ID NO:997), Ceres CLONE ID no. 1742053 (SEQ ID NO:1001), Ceres CLONE ID no. 1728365 (SEQ ID NO:1003), Ceres CLONE ID no. 1609807 (SEQ ID NO:1007), Ceres CLONE ID no. 1778566 (SEQ ID NO:1011), Ceres CLONE ID no. 2020580 (SEQ ID NO:1013), Public GI ID no. 125524285 (SEQ ID NO:1014), Public GI ID no. 125568898 (SEQ ID NO:1016), Ceres ANNOT ID no. 6055303 (SEQ ID NO:1018), and sequences identified as functional homologs of the sequences of FIG. 11, as set forth in the sequence listing.

Polypeptides are shown in the sequence listing that have HMM bit scores greater than 140 when fitted to an HMM generated from the amino acid sequences set forth in FIG. 12. Such polypeptides include At1g75860 (SEQ ID NO:1024), Ceres ANNOT ID no. 1452905 (SEQ ID NO:1029), Ceres CLONE ID no. 956176 (SEQ ID NO:1039), Public GI ID no. 92870366 (SEQ ID NO:1040), Ceres CLONE ID no. 294166 (SEQ ID NO:1042), Public GI ID no. 125543067 (SEQ ID NO:1043), SEQ ID NO:1025, Ceres ANNOT ID no. 1442522 (SEQ ID NO:1027), Public GI ID no. 8778818 (SEQ ID NO:1030), Ceres CLONE ID no. 108095 (SEQ ID NO:1032), Public GI ID no. 18394821 (SEQ ID NO:1033), Ceres CLONE ID no. 6332 (SEQ ID NO:1035), Ceres CLONE ID no. 1069047 (SEQ ID NO:1037), Public GI ID no. 115480956 (SEQ ID NO:1044), and sequences identified as functional homologs of the sequences of FIG. 12, as set forth in the sequence listing.

Polypeptides are shown in the sequence listing that have HMM bit scores greater than 80 when fitted to an HMM generated from the amino acid sequences set forth in FIG. 13. Such polypeptides include At4g19700 (SEQ ID NO:1047), Ceres CLONE ID no. 1837694 (SEQ ID NO:1053), Ceres ANNOT ID no. 1483367 (SEQ ID NO:1057), Ceres CLONE ID no. 1077781 (SEQ ID NO:1083), Ceres CLONE ID no. 471026 (SEQ ID NO:1085), Public GI ID no. 92888885 (SEQ ID NO:1099), Public GI ID no. 45544873 (SEQ ID NO:1100), Public GI ID no. 45758663 (SEQ ID NO:1101), Ceres CLONE ID no. 772927 (SEQ ID NO:1105), Ceres CLONE ID no. 895080 (SEQ ID NO:1111), Ceres CLONE ID no. 1806128 (SEQ ID NO:1131), Public GI ID no. 115458192 (SEQ ID NO:1134), Public GI ID no. 82470795 (SEQ ID NO:1139), Ceres CLONE ID no. 1837746 (SEQ ID NO:1049), Ceres CLONE ID no. 1834764 (SEQ ID NO:1051), Ceres CLONE ID no. 1853547 (SEQ ID NO:1055), Ceres ANNOT ID no. 1474088 (SEQ ID NO:1059), Ceres ANNOT ID no. 1536919 (SEQ ID NO:1061), Ceres ANNOT ID no. 1467033 (SEQ ID NO:1063), Ceres ANNOT ID no. 1485401 (SEQ ID NO:1065), Ceres ANNOT ID no. 1486505 (SEQ ID NO:1067), Public GI ID no. 17065054 (SEQ ID NO:1068), Public GI ID no. 30694690 (SEQ ID NO:1069), Ceres CLONE ID no. 12997 (SEQ ID NO:1071), Public GI ID no. 30694694 (SEQ ID NO:1072), Public GI ID no. 42572167 (SEQ ID NO:1073), Public GI ID no. 110739742 (SEQ ID NO:1074), Public GI ID no. 18412263 (SEQ ID NO:1075), Ceres CLONE ID no. 36412 (SEQ ID NO:1077), Public GI ID no. 18399792 (SEQ ID NO:1078), Ceres CLONE ID no. 924 (SEQ ID NO:1080), Public GI ID no. 15238000 (SEQ ID NO:1081), Ceres CLONE ID no. 1626330 (SEQ ID NO:1087), Ceres CLONE ID no. 1650419 (SEQ ID NO:1089), Ceres CLONE ID no. 1641329 (SEQ ID NO:1091), Ceres CLONE ID no. 1620406 (SEQ ID NO:1093), Ceres CLONE ID no. 546832 (SEQ ID NO:1095), Ceres CLONE ID no. 1243138 (SEQ ID NO:1097), Public GI ID no. 92887260 (SEQ ID NO:1098), Ceres CLONE ID no. 885628 (SEQ ID NO:1103), Ceres CLONE ID no. 1376391 (SEQ ID NO:1107), Ceres CLONE ID no. 465893 (SEQ ID NO:1109), Ceres CLONE ID no. 218243 (SEQ ID NO:1113), Ceres CLONE ID no. 1558456 (SEQ ID NO:1115), Ceres CLONE ID no. 343008 (SEQ ID NO:1117), Ceres CLONE ID no. 218463 (SEQ ID NO:1119), Ceres CLONE ID no. 1565409 (SEQ ID NO:1121), Ceres CLONE ID no. 1060968 (SEQ ID NO:1123), Ceres CLONE ID no. 236111 (SEQ ID NO:1125), Ceres CLONE ID no. 285598 (SEQ ID NO:1127), Ceres CLONE ID no. 225881 (SEQ ID NO:1129), Ceres CLONE ID no. 1811383 (SEQ ID NO:1133), Public GI ID no. 49388268 (SEQ ID NO:1135), Public GI ID no. 125590268 (SEQ ID NO:1136), Public GI ID no. 115444009 (SEQ ID NO:1137), Public GI ID no. 115447993 (SEQ ID NO:1138), Ceres ANNOT ID no. 6033842 (SEQ ID NO:1141), Ceres ANNOT ID no. 6029952 (SEQ ID NO:1143), Ceres ANNOT ID no. 6035837 (SEQ ID NO:1145), Ceres ANNOT ID no. 6035830 (SEQ ID NO:1147), Ceres ANNOT ID no. 6029981 (SEQ ID NO:1149), and sequences identified as functional homologs of the sequences of FIG. 13, as set forth in the sequence listing.

Polypeptides are shown in the sequence listing that have HMM bit scores greater than 80 when fitted to an HMM generated from the amino acid sequences set forth in FIG. 14. Such polypeptides include At1g58100 (SEQ ID NO:1151), Ceres CLONE ID no. 1851526 (SEQ ID NO:1155), Ceres ANNOT ID no. 1486769 (SEQ ID NO:1172), Public GI ID no. 83032232 (SEQ ID NO:1209), Ceres CLONE ID no. 1620420 (SEQ ID NO:1211), Public GI ID no. 92892428 (SEQ ID NO:1215), Ceres CLONE ID no. 884742 (SEQ ID NO:1223), Ceres CLONE ID no. 1821559 (SEQ ID NO:1246), Public GI ID no. 51535021 (SEQ ID NO:1258), Public GI ID no. 113205304 (SEQ ID NO:1263), Public GI ID no. 37719051 (SEQ ID NO:1264), Ceres CLONE ID no. 1918070 (SEQ ID NO:1153), Ceres CLONE ID no. 1948426 (SEQ ID NO:1157), Ceres CLONE ID no. 1937875 (SEQ ID NO:1159), Ceres CLONE ID no. 100056542 (SEQ ID NO:1160), Public GI ID no. 5731257 (SEQ ID NO:1161), Ceres CLONE ID no. 100058043 (SEQ ID NO:1162), Ceres CLONE ID no. 1838288 (SEQ ID NO:1164), Ceres CLONE ID no. 1793597 (SEQ ID NO:1166), Ceres ANNOT ID no. 1543031 (SEQ ID NO:1168), Ceres ANNOT ID no. 1489643 (SEQ ID NO:1170), Ceres ANNOT ID no. 1479721 (SEQ ID NO:1174), Ceres ANNOT ID no. 1449170 (SEQ ID NO:1176), Ceres ANNOT ID no. 1493696 (SEQ ID NO:1178), Ceres ANNOT ID no. 1543534 (SEQ ID NO:1180), Ceres ANNOT ID no. 1440815 (SEQ ID NO:1182), Ceres ANNOT ID no. 1490137 (SEQ ID NO:1184), Ceres ANNOT ID no. 1451054 (SEQ ID NO:1186), Ceres ANNOT ID no. 1456669 (SEQ ID NO:1188), Ceres ANNOT ID no. 1509865 (SEQ ID NO:1190), Ceres ANNOT ID no. 1447910 (SEQ ID NO:1192), Ceres ANNOT ID no. 1471068 (SEQ ID NO:1194), Ceres ANNOT ID no. 1504118 (SEQ ID NO:1196), Ceres CLONE ID no. 1343621 (SEQ ID NO:1198), Public GI ID no. 15218305 (SEQ ID NO:1199), Public GI ID no. 15219640 (SEQ ID NO:1200), Public GI ID no. 18409345 (SEQ ID NO:1201), Public GI ID no. 6522545 (SEQ ID NO:1202), Public GI ID no. 15237274 (SEQ ID NO:1203), Public GI ID no. 26452377 (SEQ ID NO:1204), Ceres CLONE ID no. 33629 (SEQ ID NO:1206), Ceres CLONE ID no. 1064407 (SEQ ID NO:1208), Ceres CLONE ID no. 1656310 (SEQ ID NO:1213), Public GI ID no. 92885257 (SEQ ID NO:1214), Public GI ID no. 92868571 (SEQ ID NO:1216), Public GI ID no. 53689778 (SEQ ID NO:1217), Ceres CLONE ID no. 835598 (SEQ ID NO:1219), Ceres CLONE ID no. 575649 (SEQ ID NO:1221), Ceres CLONE ID no. 376567 (SEQ ID NO:1225), Ceres CLONE ID no. 1284191 (SEQ ID NO:1227), Ceres CLONE ID no. 367175 (SEQ ID NO:1229), Ceres CLONE ID no. 100748296 (SEQ ID NO:1230), Ceres CLONE ID no. 1597176 (SEQ ID NO:1232), Ceres CLONE ID no. 375636 (SEQ ID NO:1234), Ceres CLONE ID no. 288123 (SEQ ID NO:1236), Ceres CLONE ID no. 303582 (SEQ ID NO:1238), Ceres CLONE ID no. 1604759 (SEQ ID NO:1240), Ceres CLONE ID no. 1955192 (SEQ ID NO:1242), Ceres CLONE ID no. 2008687 (SEQ ID NO:1244), Ceres CLONE ID no. 1995843 (SEQ ID NO:1248), Ceres CLONE ID no. 2008591 (SEQ ID NO:1250), Ceres CLONE ID no. 2046826 (SEQ ID NO:1252), Ceres CLONE ID no. 1985573 (SEQ ID NO:1254), Public GI ID no. 125541129 (SEQ ID NO:1255), Public GI ID no. 125528922 (SEQ ID NO:1256), Public GI ID no. 115487590 (SEQ ID NO:1257), Public GI ID no. 115448671 (SEQ ID NO:1259), Public GI ID no. 125596564 (SEQ ID NO:1260), Public GI ID no. 125573161 (SEQ ID NO:1261), Public GI ID no. 48716463 (SEQ ID NO:1262), Ceres ANNOT ID no. 6054246 (SEQ ID NO:1266), Ceres ANNOT ID no. 6086570 (SEQ ID NO:1268), Ceres ANNOT ID no. 6024957 (SEQ ID NO:1270), Ceres ANNOT ID no. 6016867 (SEQ ID NO:1272), Ceres ANNOT ID no. 6091369 (SEQ ID NO:1274), and sequences identified as functional homologs of the sequences of FIG. 14, as set forth in the sequence listing.

Polypeptides are shown in the sequence listing that have HMM bit scores greater than 180 when fitted to an HMM generated from the amino acid sequences set forth in FIG. 15. Such polypeptides include At5g46170 (SEQ ID NO:1277), Ceres CLONE ID no. 1926352 (SEQ ID NO:1279), Ceres ANNOT ID no. 1448905 (SEQ ID NO:1285), Public GI ID no. 15236865 (SEQ ID NO:1294), Ceres CLONE ID no. 934771 (SEQ ID NO:1301), Ceres CLONE ID no. 338386 (SEQ ID NO:1303), Ceres CLONE ID no. 1780691 (SEQ ID NO:1317), Public GI ID no. 115464819 (SEQ ID NO:1326), Ceres CLONE ID no. 1848576 (SEQ ID NO:1281), Ceres CLONE ID no. 1981528 (SEQ ID NO:1283), Ceres ANNOT ID no. 1465978 (SEQ ID NO:1287), Ceres ANNOT ID no. 1504997 (SEQ ID NO:1289), Ceres ANNOT ID no. 1451909 (SEQ ID NO:1291), Ceres ANNOT ID no. 1461635 (SEQ ID NO:1293), Public GI ID no. 18397400 (SEQ ID NO:1295), Ceres CLONE ID no. 16226 (SEQ ID NO:1297), Public GI ID no. 18411823 (SEQ ID NO:1298), Public GI ID no. 15219845 (SEQ ID NO:1299), Ceres CLONE ID no. 1276710 (SEQ ID NO:1305), Ceres CLONE ID no. 1479310 (SEQ ID NO:1307), Ceres CLONE ID no. 376230 (SEQ ID NO:1309), Ceres CLONE ID no. 1290713 (SEQ ID NO:1311), Ceres CLONE ID no. 321681 (SEQ ID NO:1313), Ceres CLONE ID no. 1869072 (SEQ ID NO:1315), Ceres CLONE ID no. 1818502 (SEQ ID NO:1319), Ceres CLONE ID no. 1750477 (SEQ ID NO:1321), Public GI ID no. 125552947 (SEQ ID NO:1322), Public GI ID no. 125527862 (SEQ ID NO:1323), Public GI ID no. 125543660 (SEQ ID NO:1324), Public GI ID no. 125528123 (SEQ ID NO:1325), Public GI ID no. 115440195 (SEQ ID NO:1327), Public GI ID no. 115452717 (SEQ ID NO:1328), Public GI ID no. 115440629 (SEQ ID NO:1329), Public GI ID no. 115464599 (SEQ ID NO:1330), Public GI ID no. 20161462 (SEQ ID NO:1331), Public GI ID no. 125586076 (SEQ ID NO:1332), Ceres CLONE ID no. 1823216 (SEQ ID NO:1334), Ceres ANNOT ID no. 6040230 (SEQ ID NO:1336), Ceres ANNOT ID no. 6015489 (SEQ ID NO:1338), Ceres ANNOT ID no. 6042890 (SEQ ID NO:1340), Ceres ANNOT ID no. 6040033 (SEQ ID NO:1342), Ceres ANNOT ID no. 6018414 (SEQ ID NO:1344), and sequences identified as functional homologs of the sequences of FIG. 15, as set forth in the sequence listing.

Polypeptides are shown in the sequence listing that have HMM bit scores greater than 60 when fitted to an HMM generated from the amino acid sequences set forth in FIG. 16. Such polypeptides include At4g32280 (SEQ ID NO:1347), Ceres CLONE ID no. 285028 (SEQ ID NO:1419), Ceres CLONE ID no. 100969565 (SEQ ID NO:1422), Public GI ID no. 1352057 (SEQ ID NO:1427), Ceres ANNOT ID no. 1453784 (SEQ ID NO:1429), Public GI ID no. 452777 (SEQ ID NO:1430), Public GI ID no. 92873297 (SEQ ID NO:1431), Ceres ANNOT ID no. 1452612 (SEQ ID NO:1349), Ceres CLONE ID no. 520455 (SEQ ID NO:1351), Public GI ID no. 75271810 (SEQ ID NO:1352), Public GI ID no. 115489446 (SEQ ID NO:1353), Ceres CLONE ID no. 499878 (SEQ ID NO:1355), Ceres ANNOT ID no. 1491840 (SEQ ID NO:1357), Public GI ID no. 125587204 (SEQ ID NO:1358), Ceres CLONE ID no. 320997 (SEQ ID NO:1360), Ceres ANNOT ID no. 1455585 (SEQ ID NO:1362), Ceres ANNOT ID no. 1499460 (SEQ ID NO:1364), Ceres CLONE ID no. 334484 (SEQ ID NO:1366), Ceres CLONE ID no. 100819481 (SEQ ID NO:1367), Public GI ID no. 115462401 (SEQ ID NO:1368), Ceres CLONE ID no. 1448136 (SEQ ID NO:1370), Ceres CLONE ID no. 277751 (SEQ ID NO:1372), Ceres ANNOT ID no. 1491839 (SEQ ID NO:1374), Ceres CLONE ID no. 100913241 (SEQ ID NO:1375), Ceres CLONE ID no. 1053224 (SEQ ID NO:1377), Ceres CLONE ID no. 425766 (SEQ ID NO:1379), Ceres CLONE ID no. 485480 (SEQ ID NO:1381), Ceres CLONE ID no. 474845 (SEQ ID NO:1383), Ceres CLONE ID no. 354561 (SEQ ID NO:1385), Ceres CLONE ID no. 540858 (SEQ ID NO:1387), Ceres CLONE ID no. 2032994 (SEQ ID NO:1389), Ceres CLONE ID no. 2015315 (SEQ ID NO:1391), Ceres CLONE ID no. 2016149 (SEQ ID NO:1393), Ceres CLONE ID no. 1922843 (SEQ ID NO:1395), Ceres CLONE ID no. 2000263 (SEQ ID NO:1397), Ceres CLONE ID no. 1943510 (SEQ ID NO:1399), Ceres CLONE ID no. 1835498 (SEQ ID NO:1401), Ceres CLONE ID no. 101116694 (SEQ ID NO:1402), Ceres CLONE ID no. 1930596 (SEQ ID NO:1404), Ceres CLONE ID no. 846036 (SEQ ID NO:1406), Ceres CLONE ID no. 941614 (SEQ ID NO:1408), Ceres CLONE ID no. 238788 (SEQ ID NO:1410), Public GI ID no. 125554220 (SEQ ID NO:1411), Public GI ID no. 125559895 (SEQ ID NO:1412), Public GI ID no. 75252070 (SEQ ID NO:1413), Public GI ID no. 115466632 (SEQ ID NO:1414), Public GI ID no. 125541525 (SEQ ID NO:1415), Ceres CLONE ID no. 1805110 (SEQ ID NO:1417), Ceres CLONE ID no. 1725309 (SEQ ID NO:1421), Ceres CLONE ID no. 100861679 (SEQ ID NO:1423), Public GI ID no. 75226278 (SEQ ID NO:1424), Public GI ID no. 125525030 (SEQ ID NO:1425), Public GI ID no. 115435474 (SEQ ID NO:1426), Ceres CLONE ID no. 1728516 (SEQ ID NO:1433), Public GI ID no. 115467910 (SEQ ID NO:1434), Public GI ID no. 15239950 (SEQ ID NO:1435), Public GI ID no. 4887012 (SEQ ID NO:1436), Ceres ANNOT ID no. 1478544 (SEQ ID NO:1438), Public GI ID no. 90811713 (SEQ ID NO:1439), Public GI ID no. 25989504 (SEQ ID NO:1440), Ceres CLONE ID no. 1113354 (SEQ ID NO:1442), Ceres CLONE ID no. 1113630 (SEQ ID NO:1444), Ceres ANNOT ID no. 6072030 (SEQ ID NO:1446), Ceres ANNOT ID no. 6025654 (SEQ ID NO:1448), Ceres ANNOT ID no. 6091150 (SEQ ID NO:1450), Ceres ANNOT ID no. 6100390 (SEQ ID NO:1452), and sequences identified as functional homologs of the sequences of FIG. 16, as set forth in the sequence listing.

Polypeptides are shown in the sequence listing that have HMM bit scores greater than 270 when fitted to an HMM generated from the amino acid sequences set forth in FIG. 17. Such polypeptides include At3g02830 (SEQ ID NO:1457), Ceres CLONE ID no. 1924904 (SEQ ID NO:1460), Ceres ANNOT ID no. 1543346 (SEQ ID NO:1462), Public GI ID no. 18396338 (SEQ ID NO:1467), Ceres CLONE ID no. 833872 (SEQ ID NO:1471), Ceres CLONE ID no. 1579587 (SEQ ID NO:1475), Ceres CLONE ID no. 1786411 (SEQ ID NO:1477), Public GI ID no. 108864370 (SEQ ID NO:1480), SEQ ID NO:1458, Ceres ANNOT ID no. 1532932 (SEQ ID NO:1464), Ceres ANNOT ID no. 1489955 (SEQ ID NO:1466), Public GI ID no. 4928917 (SEQ ID NO:1468), Public GI ID no. 6728979 (SEQ ID NO:1469), Ceres CLONE ID no. 285780 (SEQ ID NO:1473), Public GI ID no. 125528863 (SEQ ID NO:1478), Public GI ID no. 125536365 (SEQ ID NO:1479), Public GI ID no. 108864369 (SEQ ID NO:1481), Public GI ID no. 115488274 (SEQ ID NO:1482), Public GI ID no. 125577099 (SEQ ID NO:1483), Public GI ID no. 125573110 (SEQ ID NO:1484), Public GI ID no. 124359159 (SEQ ID NO:1485), Public GI ID no. 62901479 (SEQ ID NO:1486), Ceres ANNOT ID no. 6016783 (SEQ ID NO:1488), Ceres ANNOT ID no. 6020759 (SEQ ID NO:1490), Ceres ANNOT ID no. 6028676 (SEQ ID NO:1492), Ceres ANNOT ID no. 6028677 (SEQ ID NO:1494), and sequences identified as functional homologs of the sequences of FIG. 17, as set forth in the sequence listing.

Polypeptides are shown in the sequence listing that have HMM bit scores greater than 70 when fitted to an HMM generated from the amino acid sequences set forth in FIG. 18. Such polypeptides include At4g08920 (SEQ ID NO:1497), Ceres ANNOT ID no. 1443463 (SEQ ID NO:1499), Public GI ID no. 13605525 (SEQ ID NO:1502), Public GI ID no. 94965681 (SEQ ID NO:1506), Public GI ID no. 28201254 (SEQ ID NO:1512), Ceres ANNOT ID no. 1504954 (SEQ ID NO:1501), Public GI ID no. 2499553 (SEQ ID NO:1503), Public GI ID no. 738308 (SEQ ID NO:1504), Public GI ID no. 4325368 (SEQ ID NO:1505), Ceres CLONE ID no. 919923 (SEQ ID NO:1508), Ceres CLONE ID no. 1659764 (SEQ ID NO:1510), Public GI ID no. 125539984 (SEQ ID NO:1511), Public GI ID no. 21740729 (SEQ ID NO:1513), Public GI ID no. 115458700 (SEQ ID NO:1514), Public GI ID no. 125590574 (SEQ ID NO:1515), Public GI ID no. 16444957 (SEQ ID NO:1516), Ceres CLONE ID no. 1784494 (SEQ ID NO:1518), Public GI ID no. 77963980 (SEQ ID NO:1519), Public GI ID 110.124361190 (SEQ ID NO:1520), Public GI ID no. 37725007 (SEQ ID NO:1521), Public GI ID no. 45935258 (SEQ ID NO:1522), Public GI ID no. 15559008 (SEQ ID NO:1523), Public GI ID no. 38037416 (SEQ ID NO:1524), Public GI ID no. 77963974 (SEQ ID NO:1525), Ceres ANNOT ID no. 6112581 (SEQ ID NO:1527), Public GI ID no. 56553448 (SEQ ID NO:1528), Public GI ID no. 23506659 (SEQ ID NO:1529), Ceres ANNOT ID no. 6118060 (SEQ ID NO:1531), Public GI ID no. 46446306 (SEQ ID NO:1532), Public GI ID no. 114321405 (SEQ ID NO:1533), Public GI ID no. 83858274 (SEQ ID NO:1534), Public GI ID no. 154250969 (SEQ ID NO:1535), Public GI ID no. 83594235 (SEQ ID NO:1536), and sequences identified as functional homologs of the sequences of FIG. 18, as set forth in the sequence listing.

Polypeptides are shown in the sequence listing that have HMM bit scores greater than 130 when fitted to an HMM generated from the amino acid sequences set forth in FIG. 19. Such polypeptides include At4g11660 (SEQ ID NO:1587), Ceres CLONE ID no. 1839577 (SEQ ID NO:1589), Ceres ANNOT ID no. 1491567 (SEQ ID NO:1591), Ceres CLONE ID no. 574505 (SEQ ID NO:1596), Public GI ID no. 56117815 (SEQ ID NO:1597), Public GI ID no. 92874021 (SEQ ID NO:1603), Public GI ID no. 123684 (SEQ ID NO:1605), Public GI ID no. 5821136 (SEQ ID NO:1606), Ceres CLONE ID no. 283366 (SEQ ID NO:1609), Public GI ID no. 16118447 (SEQ ID NO:1612), Public GI ID no. 125562434 (SEQ ID NO:1614), Ceres ANNOT ID no. 1438739 (SEQ ID NO:1593), Public GI ID no. 89274218 (SEQ ID NO:1594), Public GI ID no. 115521211 (SEQ ID NO:1598), Public GI ID no. 115521213 (SEQ ID NO:1599), Public GI ID no. 115521217 (SEQ ID NO:1600), Public GI ID no. 115521209 (SEQ ID NO:1601), Public GI ID no. 115521215 (SEQ ID NO:1602), Public GI ID no. 11386827 (SEQ ID NO:1604), Public GI ID no. 25052685 (SEQ ID NO:1607), Ceres CLONE ID no. 1440437 (SEQ ID NO:1611), Public GI ID no. 125564440 (SEQ ID NO:1613), Public GI ID no. 116309817 (SEQ ID NO:1615), Public GI ID no. 125549382 (SEQ ID NO:1616), Public GI ID no. 52077317 (SEQ ID NO:1617), Public GI ID no. 115477655 (SEQ ID NO:1618), Public GI ID no. 42408097 (SEQ ID NO:1619), Public GI ID no. 115459982 (SEQ ID NO:1620), Public GI ID no. 33591096 (SEQ ID NO:1621), Ceres CLONE ID no. 484753 (SEQ ID NO:1623), Ceres ANNOT ID no. 6035291 (SEQ ID NO:1625), and sequences identified as functional homologs of the sequences of FIG. 19, as set forth in the sequence listing.

Polypeptides are shown in the sequence listing that have HMM bit scores greater than 570 when fitted to an HMM generated from the amino acid sequences set forth in FIG. 20. Such polypeptides include At2g45700 (SEQ ID NO:1635), Ceres ANNOT ID no. 1508307 (SEQ ID NO:1637), Public GI ID no. 1495267 (SEQ ID NO:1642), Public GI ID no. 87241310 (SEQ ID NO:1644), Ceres CLONE ID no. 938390 (SEQ ID NO:1646), Ceres CLONE ID no. 272338 (SEQ ID NO:1648), Ceres CLONE ID no. 1993510 (SEQ ID NO:1650), Public GI ID no. 125563862 (SEQ ID NO:1651), Public GI ID no. 125605833 (SEQ ID NO:1653), Public GI ID no. 6899919 (SEQ ID NO:1632), Ceres ANNOT ID no. 1455110 (SEQ ID NO:1639), Ceres ANNOT ID no. 1525218 (SEQ ID NO:1641), Public GI ID no. 15231597 (SEQ ID NO:1643), Public GI ID no. 125548147 (SEQ ID NO:1652), Public GI ID no. 51091343 (SEQ ID NO:1654), Public GI ID no. 115479355 (SEQ ID NO:1655), Ceres ANNOT ID no. 6042086 (SEQ ID NO:1657), Ceres ANNOT ID no. 6029903 (SEQ ID NO:1659), and sequences identified as functional homologs of the sequences of FIG. 20, as set forth in the sequence listing.

Polypeptides are shown in the sequence listing that have HMM bit scores greater than 150 when fitted to an HMM generated from the amino acid sequences set forth in FIG. 21. Such polypeptides include At2g35940 (SEQ ID NO:1540), Ceres CLONE ID no. 1943265 (SEQ ID NO:1543), Ceres ANNOT ID no. 1454522 (SEQ ID NO:1547), Public GI ID no. 31323447 (SEQ ID NO:1556), Ceres CLONE ID no. 1583941 (SEQ ID NO:1561), Ceres CLONE ID no. 1792942 (SEQ ID NO:1563), Public GI ID no. 77548772 (SEQ ID NO:1565), Public GI ID no. 84453182 (SEQ ID NO:1567), Public GI ID no. 31746344 (SEQ ID NO:1541), Ceres CLONE ID no. 1926640 (SEQ ID NO:1545), Ceres ANNOT ID no. 1475125 (SEQ ID NO:1549), Ceres ANNOT ID no. 1439653 (SEQ ID NO:1551), Ceres ANNOT ID no. 1461995 (SEQ ID NO:1553), Public GI ID no. 13877517 (SEQ ID NO:1554), Public GI ID no. 7239157 (SEQ ID NO:1555), Public GI ID no. 22652125 (SEQ ID NO:1557), Public GI ID no. 22652115 (SEQ ID NO:1558), Public GI ID no. 22652117 (SEQ ID NO:1559), Public GI ID no. 125535858 (SEQ ID NO:1564), Public GI ID no. 125578581 (SEQ ID NO:1566), Public GI ID no. 13752407 (SEQ ID NO:1568), Ceres ANNOT ID no. 6098817 (SEQ ID NO:1570), Ceres ANNOT ID no. 6039430 (SEQ ID NO:1572), Ceres ANNOT ID no. 6068141 (SEQ ID NO:1574), Ceres ANNOT ID no. 6033916 (SEQ ID NO:1576), Ceres ANNOT ID no. 6034399 (SEQ ID NO:1578), Ceres ANNOT ID no. 6068617 (SEQ ID NO:1580), Ceres ANNOT ID no. 6026318 (SEQ ID NO:1582), Ceres ANNOT ID no. 6107650 (SEQ ID NO:1584), and sequences identified as functional homologs of the sequences of FIG. 21, as set forth in the sequence listing.

Polypeptides are shown in the sequence listing that have HMM bit scores greater than 1340 when fitted to an HMM generated from the amino acid sequences set forth in FIG. 22. Such polypeptides include At1g04400 (SEQ ID NO:538), Public GI ID no. 5731739 (SEQ ID NO:539), Ceres ANNOT ID no. 1538045 (SEQ ID NO:541), Public GI ID no. 29467479 (SEQ ID NO:542), Public GI ID no. 133921974 (SEQ ID NO:543), Public GI ID no. 113197027 (SEQ ID NO:544), Public GI ID no. 92879277 (SEQ ID NO:545), Public GI ID no. 45935260 (SEQ ID NO:546), Public GI ID no. 8101444 (SEQ ID NO:547), Public GI ID no. 78217443 (SEQ ID NO:548), Public GI ID no. 28372347 (SEQ ID NO:549), Public GI ID no. 16416405 (SEQ ID NO:550), Ceres ANNOT ID no. 1484634 (SEQ ID NO:552), Ceres ANNOT ID no. 1451869 (SEQ ID NO:554), Public GI ID no. 25407462 (SEQ ID NO:555), Public GI ID no. 29467481 (SEQ ID NO:556), Public GI ID no. 29467477 (SEQ ID NO:557), Public GI ID no. 45935264 (SEQ ID NO:558), Public GI ID no. 5524201 (SEQ ID NO:559), Public GI ID no. 78217441 (SEQ ID NO:560), Public GI ID no. 3551221 (SEQ ID NO:561), Public GI ID no. 3551219 (SEQ ID NO:562), Public GI ID no. 23954324 (SEQ ID NO:563), Public GI ID no. 125582937 (SEQ ID NO:564), Public GI ID no. 83764373 (SEQ ID NO:565), Ceres ANNOT ID no. 6045327 (SEQ ID NO:567), and sequences identified as functional homologs of the sequences of FIG. 22, as set forth in the sequence listing.

Polypeptides are shown in the sequence listing that have HMM bit scores greater than 80 when fitted to an HMM generated from the amino acid sequences set forth in FIG. 23. Such polypeptides include At3g45610 (SEQ ID NO:606), Public GI ID no. 92873064 (SEQ ID NO:607), Public GI ID no. 37051125 (SEQ ID NO:608), Public GI ID no. 112363376 (SEQ ID NO:609), Ceres CLONE ID no. 1938524 (SEQ ID NO:611), Ceres ANNOT ID no. 1473601 (SEQ ID NO:613), Ceres ANNOT ID no. 1468397 (SEQ ID NO:615), Public GI ID no. 21554185 (SEQ ID NO:616), Public GI ID no. 18424330 (SEQ ID NO:617), Public GI ID no. 8885571 (SEQ ID NO:618), Ceres CLONE ID no. 20852 (SEQ ID NO:620), Public GI ID no. 21553763 (SEQ ID NO:621), Public GI ID no. 18401763 (SEQ ID NO:622), Ceres CLONE ID no. 16423 (SEQ ID NO:624), Public GI ID no. 112363380 (SEQ ID NO:625), Public GI ID no. 6092016 (SEQ ID NO:626), Ceres CLONE ID no. 770468 (SEQ ID NO:628), Public GI ID no. 113205234 (SEQ ID NO:629), Ceres ANNOT ID no. 6094775 (SEQ ID NO:631), and sequences identified as functional homologs of the sequences of FIG. 23, as set forth in the sequence listing.

Polypeptides are shown in the sequence listing that have HMM bit scores greater than 110 when fitted to an HMM generated from the amino acid sequences set forth in FIG. 24. Such polypeptides include At4g08330 (SEQ ID NO:570), Ceres CLONE ID no. 1919714 (SEQ ID NO:572), Ceres ANNOT ID no. 1443290 (SEQ ID NO:574), Ceres CLONE ID no. 1042157 (SEQ ID NO:576), Ceres CLONE ID no. 1384304 (SEQ ID NO:578), Public GI ID no. 115464375 (SEQ ID NO:579), Ceres CLONE ID no. 100028078 (SEQ ID NO:580), Ceres ANNOT ID no. 1452096 (SEQ ID NO:582), Ceres ANNOT ID no. 1503869 (SEQ ID NO:584), Ceres ANNOT ID no. 1525651 (SEQ ID NO:586), Ceres CLONE ID no. 1645639 (SEQ ID NO:588), Ceres CLONE ID no. 603237 (SEQ ID NO:590), Ceres CLONE ID no. 340925 (SEQ ID NO:592), Ceres CLONE ID no. 293238 (SEQ ID NO:594), Ceres CLONE ID no. 483742 (SEQ ID NO:596), Ceres CLONE ID no. 1460255 (SEQ ID NO:598), Ceres CLONE ID no. 1400107 (SEQ ID NO:600), Public GI ID no. 115440865 (SEQ ID NO:601), Ceres ANNOT ID no. 6016008 (SEQ ID NO:603), and sequences identified as functional homologs of the sequences of FIG. 24, asset forth in the sequence listing.

E. Percent Identity

In some embodiments, an SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NO:3, SEQ ID NO:70, SEQ ID NO:129, SEQ ID NO:317, SEQ ID NO:337, SEQ ID NO:456, SEQ ID NO:538, SEQ ID NO:570, SEQ ID NO:606, SEQ ID NO:634, SEQ ID NO:644, SEQ ID NO:850, SEQ ID NO:907, SEQ ID NO:953, SEQ ID NO:1024, SEQ ID NO:1047, SEQ ID NO:1151, SEQ ID NO:1277, SEQ ID NO:1347, SEQ ID NO:1457, SEQ ID NO:1497, SEQ ID NO:1540, SEQ ID NO:1587, SEQ ID NO:1630, and SEQ ID NO:1635. Polypeptides having such a percent sequence identity often have a domain indicative of an SD+EODFR and/or low light-tolerance polypeptide and/or have an HMM bit score that is greater than 20, as discussed above. Amino acid sequences of SD+EODFR and/or low light-tolerance polypeptides having at least 40% sequence identity to one of the amino acid sequences set forth in SEQ ID NO:3, SEQ ID NO:70, SEQ ID NO:129, SEQ ID NO:317, SEQ ID NO:337, SEQ ID NO:456, SEQ ID NO:538, SEQ ID NO:570, SEQ ID NO:606, SEQ ID NO:634, SEQ ID NO:644, SEQ ID NO:850, SEQ ID NO:907, SEQ ID NO:953, SEQ ID NO:1024, SEQ ID NO:1047, SEQ ID NO:1151, SEQ ID NO:1277, SEQ ID NO:1347, SEQ ID NO:1457, SEQ ID NO:1497, SEQ ID NO:1540, SEQ ID NO:1587, and SEQ ID NO:1635 are provided in FIGS. 1-24.

"Percent sequence identity" refers to the degree of sequence identity between any given reference sequence, e.g., SEQ ID NO:3, and a candidate SD+EODFR and/or low light-tolerance sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple sequence alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, an SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3. Amino acid sequences of polypeptides having greater than 40% sequence identity to the polypeptide set forth in SEQ ID NO:3 are provided in FIG. 1. Such polypeptides include Ceres CLONE ID no. 1844057 (SEQ ID NO:7), Ceres ANNOT ID no. 1469148 (SEQ ID NO:22), Public GI ID no. 18390998 (SEQ ID NO:25), Ceres CLONE ID no. 1065656 (SEQ ID NO:32), Ceres CLONE ID no. 1652677 (SEQ ID NO:36), Public GI ID no. 92874556 (SEQ ID NO:49), Ceres CLONE ID no. 1329161 (SEQ ID NO:53), Ceres CLONE ID no. 1030378 (SEQ ID NO:55), Ceres CLONE ID no. 1413787 (SEQ ID NO:57), and Public GI ID no. 125543598 (SEQ ID NO:60).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:70. Amino acid sequences of polypeptides having greater than 40% sequence identity to the polypeptide set forth in SEQ ID NO:70 are provided in FIG. 2. Such polypeptides include Ceres CLONE ID no. 1975934 (SEQ ID NO:72), Ceres ANNOT ID no. 1529913 (SEQ ID NO:80), Ceres CLONE ID no. 977794 (SEQ ID NO:93), Public GI ID no. 42362378 (SEQ ID NO:96), Public GI ID no. 23899378 (SEQ ID NO:99), Public GI ID no. 15963346 (SEQ ID NO:101), Public GI ID no. 15963344+B816 (SEQ ID NO:102), Public GI ID no. 92429657 (SEQ ID NO:103), Ceres CLONE ID no. 746644 (SEQ ID NO:105), Ceres CLONE ID no. 623089 (SEQ ID NO:109), Ceres CLONE ID no. 1913678 (SEQ ID NO:115), and Public GI ID no. 115450609 (SEQ ID NO:119).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:129. Amino acid sequences of polypeptides having greater than 40% sequence identity to the polypeptide set forth in SEQ ID NO:129 are provided in FIG. 3. Such polypeptides include Public GI ID no. 34550779 (SEQ ID NO:133), Ceres CLONE ID no. 1932235 (SEQ ID NO:137), Ceres CLONE ID no. 981738 (SEQ ID NO:201), Ceres CLONE ID no. 565974 (SEQ ID NO:209), Public GI ID no. 1352058 (SEQ ID NO:231), Public GI ID no. 11131101 (SEQ ID NO:234), Public GI ID no. 4887018 (SEQ ID NO:236), Public GI ID no. 4887018 (SEQ ID NO:236), Ceres CLONE ID no. 644455 (SEQ ID NO:247), Ceres CLONE ID no. 1731500 (SEQ ID NO:270), Public GI ID no. 20269063 (SEQ ID NO:300), Public GI ID no. 50404477 (SEQ ID NO:302), and Public GI ID no. 62125392 (SEQ ID NO:303).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:317. Amino acid sequences of polypeptides having greater than 40% sequence identity to the polypeptide set forth in SEQ ID NO:317 are provided in FIG. 4. Such polypeptides include Ceres CLONE ID no. 1842125 (SEQ ID NO:319), Ceres ANNOT ID no. 1461360 (SEQ ID NO:321), Ceres CLONE ID no. 480906 (SEQ ID NO:327), Public GI ID no. 92889352 (SEQ ID NO:330), and Public GI ID no. 56201850 (SEQ ID NO:330).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:337. Amino acid sequences of polypeptides having greater than 40% sequence identity to the polypeptide set forth in SEQ ID NO:337 are provided in FIG. 5. Such polypeptides include At2g04240 Ceres CLONE ID no. 952050 (SEQ ID NO:339), Public GI ID no. 115477050 (SEQ ID NO:349), Public GI ID no. 87162911 (SEQ ID NO:355), Ceres CLONE ID no. 1790901 (SEQ ID NO:357), Ceres CLONE ID no. 1460088 (SEQ ID NO:370), Ceres CLONE ID no. 1734065 (SEQ ID NO:393), Ceres CLONE ID no. 473509 (SEQ ID NO:395), Ceres CLONE ID no. 849918 (SEQ ID NO:401), Ceres CLONE ID no. 633470 (SEQ ID NO:409), Ceres CLONE ID no. 1808334 (SEQ ID NO:417), and Ceres ANNOT ID no. 1525600 (SEQ ID NO:437).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:456. Amino acid sequences of polypeptides having greater than 40% sequence identity to the polypeptide set forth in SEQ ID NO:456 are provided in FIG. 6. Such polypeptides include Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 21655154 (SEQ ID NO:532), Public GI ID no. 90657642 (SEQ ID NO:536), and Ceres CLONE ID no. 1569555 (SEQ ID NO:1842).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:634. Amino acid sequences of polypeptides having greater than 40% sequence identity to the polypeptide set forth in SEQ ID NO:634 are provided in FIG. 7. Such polypeptides include Public GI ID no. 98961985 (SEQ ID NO:637).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:644. Amino acid sequences of polypeptides having greater than 40% sequence identity to the polypeptide set forth in SEQ ID NO:644 are provided in FIG. 8. Such polypeptides include SEQ ID NO:645, Ceres CLONE ID no. 1849479 (SEQ ID NO:767), Public GI ID no. 89275008 (SEQ ID NO:796), Public GI ID no. 120400525 (SEQ ID NO:797), Public GI ID no. 98980426 (SEQ ID NO:804), Public GI ID no. 71983373 (SEQ ID NO:808), Public GI ID no. 41351817 (SEQ ID NO:809), Public GI ID no. 76446191 (SEQ ID NO:811), Public GI ID no. 5616086 (SEQ ID NO:813), Ceres CLONE ID no. 1052602 (SEQ ID NO:826), Public GI ID no. 72068957 (SEQ ID NO:830), Public GI ID no. 71534113 (SEQ ID NO:831), Public GI ID no. 37147896 (SEQ ID NO:832), Public GI ID no. 92918850 (SEQ ID NO:834), Public GI ID no. 40647095 (SEQ ID NO:835), Ceres ANNOT ID no. 1527711 (SEQ ID NO:837), Public GI ID no. 71041116 (SEQ ID NO:838), Public GI ID no. 12003384 (SEQ ID NO:839), Public GI ID no. 18535580 (SEQ ID NO:840), and Public GI ID no. 115353971 (SEQ ID NO:1843).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:850. Amino acid sequences of polypeptides having greater than 40% sequence identity to the polypeptide set forth in SEQ ID NO:850 are provided in FIG. 9. Such polypeptides include Ceres CLONE ID no. 1833093 (SEQ ID NO:853), Ceres ANNOT ID no. 1502190 (SEQ ID NO:857), Ceres CLONE ID no. 565641 (SEQ ID NO:876), Public GI ID no. 87240507 (SEQ ID NO:877), Ceres CLONE ID no. 1325382 (SEQ ID NO:881), Ceres CLONE ID no. 1558265 (SEQ ID NO:885), Ceres CLONE ID no. 1823669 (SEQ ID NO:895), and Public GI ID no. 115464921 (SEQ ID NO:898).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:907. Amino acid sequences of polypeptides having greater than 40% sequence identity to the polypeptide set forth in SEQ ID NO:907 are provided in FIG. 10. Such polypeptides include Ceres CLONE ID no. 1940797 (SEQ ID NO:909), Ceres ANNOT ID no. 1538900 (SEQ ID NO:911), Ceres CLONE ID no. 1126868 (SEQ ID NO:922), Public GI ID no. 89257684 (SEQ ID NO:923), Public GI ID no. 124360460 (SEQ ID NO:929), Public GI ID no. 62865694 (SEQ ID NO:931), Public GI ID no. 62865692 (SEQ ID NO:932), Ceres CLONE ID no. 260368 (SEQ ID NO:936), Ceres CLONE ID no. 1873510 (SEQ ID NO:947), Public GI ID no. 125541662 (SEQ ID NO:948), Public GI ID no. 48716268 (SEQ ID NO:950), and Public GI ID no. 62865696 (SEQ ID NO:1844).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:953. Amino acid sequences of polypeptides having greater than 40% sequence identity to the polypeptide set forth in SEQ ID NO:953 are provided in FIG. 11. Such polypeptides include Ceres CLONE ID no. 1798705 (SEQ ID NO:955), Ceres ANNOT ID no. 1458907 (SEQ ID NO:963), Ceres CLONE ID no. 1090409 (SEQ ID NO:971), Ceres CLONE ID no. 479817 (SEQ ID NO:977), Ceres CLONE ID no. 1041793 (SEQ ID NO:979), Ceres CLONE ID no. 684633 (SEQ ID NO:985), Ceres CLONE ID no. 371815 (SEQ ID NO:991), Ceres CLONE ID no. 1686460 (SEQ ID NO:993), Ceres CLONE ID no. 1448595 (SEQ ID NO:995), Ceres CLONE ID no. 1734477 (SEQ ID NO:999), Ceres CLONE ID no. 1605693 (SEQ ID NO:1005), Ceres CLONE ID no. 1757400 (SEQ ID NO:1009), and Public GI ID no. 115434334 (SEQ ID NO:1015).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1024 Amino acid sequences of polypeptides having greater than 40% sequence identity to the polypeptide set forth in SEQ ID NO:1024 are provided in FIG. 12. Such polypeptides include Ceres ANNOT ID no. 1452905 (SEQ ID NO:1029), Ceres CLONE ID no. 956176 (SEQ ID NO:1039), Public GI ID no. 92870366 (SEQ ID NO:1040), Ceres CLONE ID no. 294166 (SEQ ID NO:1042), and Public GI ID no. 125543067 (SEQ ID NO:1043).

In some cases, an SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1047 Amino acid sequences of polypeptides having greater than 40% sequence identity to the polypeptide set forth in SEQ ID NO:1047 are provided in FIG. 13. Such polypeptides include Ceres CLONE ID no. 1837694 (SEQ ID NO:1053), Ceres ANNOT ID no. 1483367 (SEQ ID NO:1057), Ceres CLONE ID no. 1077781 (SEQ ID NO:1083), Ceres CLONE ID no. 471026 (SEQ ID NO:1085), Public GI ID no. 92888885 (SEQ ID NO:1099), Public GI ID no. 45544873 (SEQ ID NO:1100), Public GI ID no. 45758663 (SEQ ID NO:1101), Ceres CLONE ID no. 772927 (SEQ ID NO:1105), Ceres CLONE ID no. 895080 (SEQ ID NO:1111), Ceres CLONE ID no. 1806128 (SEQ ID NO:1131), Public GI ID no. 115458192 (SEQ ID NO:1134), and Public GI ID no. 82470795 (SEQ ID NO:1139).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1151 Amino acid sequences of polypeptides having greater than 40% sequence identity to the polypeptide set forth in SEQ ID NO:1151 are provided in FIG. 14. Such polypeptides include Ceres CLONE ID no. 1851526 (SEQ ID NO:1155), Ceres ANNOT ID no. 1486769 (SEQ ID NO:1172), Public GI ID no. 83032232 (SEQ ID NO:1209), Ceres CLONE ID no. 1620420 (SEQ ID NO:1211), Public GI ID no. 92892428 (SEQ ID NO:1215), Ceres CLONE ID no. 884742 (SEQ ID NO:1223), Ceres CLONE ID no. 1821559 (SEQ ID NO:1246), Public GI ID no. 51535021 (SEQ ID NO:1258), Public GI ID no. 113205304 (SEQ ID NO:1263), and Public GI ID no. 37719051 (SEQ ID NO:1264).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1277 Amino acid sequences of polypeptides having greater than 40% sequence identity to the polypeptide set forth in SEQ ID NO:1277 are provided in FIG. 15. Such polypeptides include Ceres CLONE ID no. 1926352 (SEQ ID NO:1279), Ceres ANNOT ID no. 1448905 (SEQ ID NO:1285), Public GI ID no. 15236865 (SEQ ID NO:1294), Ceres CLONE ID no. 934771 (SEQ ID NO:1301), Ceres CLONE ID no. 338386 (SEQ ID NO:1303), Ceres CLONE ID no. 1780691 (SEQ ID NO:1317), and Public GI ID no. 115464819 (SEQ ID NO:1326).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1347 Amino acid sequences of polypeptides having greater than 40% sequence identity to the polypeptide set forth in SEQ ID NO:1347 are provided in FIG. 16. Such polypeptides include Ceres CLONE ID no. 285028 (SEQ ID NO:1419), Ceres CLONE ID no. 100969565 (SEQ ID NO:1422), Public GI ID no. 1352057 (SEQ ID NO:1427), Ceres ANNOT ID no. 1453784 (SEQ ID NO:1429), Public GI ID no. 452777 (SEQ ID NO:1430), and Public GI ID no. 92873297 (SEQ ID NO:1431).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1457 Amino acid sequences of polypeptides having greater than 40% sequence identity to the polypeptide set forth in SEQ ID NO:1457 are provided in FIG. 17. Such polypeptides include Ceres CLONE ID no. 1924904 (SEQ ID NO:1460), Ceres ANNOT ID no. 1543346 (SEQ ID NO:1462), Public GI ID no. 18396338 (SEQ ID NO:1467), Ceres CLONE ID no. 833872 (SEQ ID NO:1471), Ceres CLONE ID no. 1579587 (SEQ ID NO:1475), Ceres CLONE ID no. 1786411 (SEQ ID NO:1477), and Public GI ID no. 108864370 (SEQ ID NO:1480).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1497 Amino acid sequences of polypeptides having greater than 40% sequence identity to the polypeptide set forth in SEQ ID NO:1497 are provided in FIG. 18. Such polypeptides include Ceres ANNOT ID no. 1443463 (SEQ ID NO:1499), Public GI ID no. 13605525 (SEQ ID NO:1502), Public GI ID no. 94965681 (SEQ ID NO:1506), and Public GI ID no. 28201254 (SEQ ID NO:1512).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1587 Amino acid sequences of polypeptides having greater than 40% sequence identity to the polypeptide set forth in SEQ ID NO:1587 are provided in FIG. 19. Such polypeptides include Ceres CLONE ID no. 1839577 (SEQ ID NO:1589), Ceres ANNOT ID no. 1491567 (SEQ ID NO:1591), Ceres CLONE ID no. 574505 (SEQ ID NO:1596), Public GI ID no. 56117815 (SEQ ID NO:1597), Public GI ID no. 92874021 (SEQ ID NO:1603), Public GI ID no. 123684 (SEQ ID NO:1605), Public GI ID no. 5821136 (SEQ ID NO:1606), Ceres CLONE ID no. 283366 (SEQ ID NO:1609), Public GI ID no. 16118447 (SEQ ID NO:1612), and Public GI ID no. 125562434 (SEQ ID NO:1614).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1635 Amino acid sequences of polypeptides having greater than 40% sequence identity to the polypeptide set forth in SEQ ID NO:1635 are provided in FIG. 20. Such polypeptides include Ceres ANNOT ID no. 1508307 (SEQ ID NO:1637), Public GI ID no. 1495267 (SEQ ID NO:1642), Public GI ID no. 87241310 (SEQ ID NO:1644), Ceres CLONE ID no. 938390 (SEQ ID NO:1646), Ceres CLONE ID no. 272338 (SEQ ID NO:1648), Ceres CLONE ID no. 1993510 (SEQ ID NO:1650), Public GI ID no. 125563862 (SEQ ID NO:1651), and Public GI ID no. 125605833 (SEQ ID NO:1653).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1540 Amino acid sequences of polypeptides having greater than 40% sequence identity to the polypeptide set forth in SEQ ID NO:1540 are provided in FIG. 21. Such polypeptides include Ceres CLONE ID no. 1943265 (SEQ ID NO:1543), Ceres ANNOT ID no. 1454522 (SEQ ID NO:1547), Public GI ID no. 31323447 (SEQ ID NO:1556), Ceres CLONE ID no. 1583941 (SEQ ID NO:1561), Ceres CLONE ID no. 1792942 (SEQ ID NO:1563), Public GI ID no. 77548772 (SEQ ID NO:1565), and Public GI ID no. 84453182 (SEQ ID NO:1567).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:538. Amino acid sequences of polypeptides having greater than 40% sequence identity to the polypeptide set forth in SEQ ID NO:538 are provided in FIG. 22. Such polypeptides include Public GI ID no. 5731739 (SEQ ID NO:539), Ceres ANNOT ID no. 1538045 (SEQ ID NO:541), Public GI ID no. 29467479 (SEQ ID NO:542), Public GI ID no. 133921974 (SEQ ID NO:543), Public GI ID no. 113197027 (SEQ ID NO:544), Public GI ID no. 92879277 (SEQ ID NO:545), Public GI ID no. 45935260 (SEQ ID NO:546), Public GI ID no. 8101444 (SEQ ID NO:547), Public GI ID no. 78217443 (SEQ ID NO:548), and Public GI ID no. 28372347 (SEQ ID NO:549).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:606. Amino acid sequences of polypeptides having greater than 40% sequence identity to the polypeptide set forth in SEQ ID NO:606 are provided in FIG. 23. Such polypeptides include Public GI ID no. 92873064 (SEQ ID NO:607), Public GI ID no. 37051125 (SEQ ID NO:608), and Public GI ID no. 112363376 (SEQ ID NO:609).

In some cases, a SD+EODFR and/or low light-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:570. Amino acid sequences of polypeptides having greater than 40% sequence identity to the polypeptide set forth in SEQ ID NO:570 are provided in FIG. 24. Such polypeptides include Ceres CLONE ID no. 1919714 (SEQ ID NO:572), Ceres ANNOT ID no. 1443290 (SEQ ID NO:574), Ceres CLONE ID no. 1042157 (SEQ ID NO:576), Ceres CLONE ID no. 1384304 (SEQ ID NO:578), and Public GI ID no. 115464375 (SEQ ID NO:579).

In some cases, a red light specific response pathway polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:456. Amino acid sequences of polypeptides having greater than 40% sequence identity to the polypeptide set forth in SEQ ID NO:456 are provided in FIG. 6. Such polypeptides include Public GI ID no. 58430585 (SEQ ID NO:457), Ceres CLONE ID no. 1842825 (SEQ ID NO:466), Ceres ANNOT ID no. 1449721 (SEQ ID NO:474), Public GI ID no. 41323978 (SEQ ID NO:475), Public GI ID no. 2895186 (SEQ ID NO:478), Public GI ID no. 22854950 (SEQ ID NO:481), Public GI ID no. 116010474 (SEQ ID NO:485), Public GI ID no. 4091804 (SEQ ID NO:488), Public GI ID no. 60459257 (SEQ ID NO:494), Public GI ID no. 45544881 (SEQ ID NO:496), Public GI ID no. 36789802 (SEQ ID NO:498), Public GI ID no. 92875402 (SEQ ID NO:508), Public GI ID no. 118406898 (SEQ ID NO:510), Public GI ID no. 107770485 (SEQ ID NO:511), Public GI ID no. 21655154 (SEQ ID NO:532), Public GI ID no. 90657642 (SEQ ID NO:536), and Ceres CLONE ID no. 1569555 (SEQ ID NO:1842).

In some cases, red light specific response pathway polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:953. Amino acid sequences of polypeptides having greater than 40% sequence identity to the polypeptide set forth in SEQ ID NO:953 are provided in FIG. 11. Such polypeptides include Ceres CLONE ID no. 1798705 (SEQ ID NO:955), Ceres ANNOT ID no. 1458907 (SEQ ID NO:963), Ceres CLONE ID no. 1090409 (SEQ ID NO:971), Ceres CLONE ID no. 479817 (SEQ ID NO:977), Ceres CLONE ID no. 1041793 (SEQ ID NO:979), Ceres CLONE ID no. 684633 (SEQ ID NO:985), Ceres CLONE ID no. 371815 (SEQ ID NO:991), Ceres CLONE ID no. 1686460 (SEQ ID NO:993), Ceres CLONE ID no. 1448595 (SEQ ID NO:995), Ceres CLONE ID no. 1734477 (SEQ ID NO:999), Ceres CLONE ID no. 1605693 (SEQ ID NO:1005), Ceres CLONE ID no. 1757400 (SEQ ID NO:1009), and Public GI ID no. 115434334 (SEQ ID NO:1015).

In some cases, a red light specific response pathway polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1540 Amino acid sequences of polypeptides having greater than 40% sequence identity to the polypeptide set forth in SEQ ID NO:1540 are provided in FIG. 21. Such polypeptides include Ceres CLONE ID no. 1943265 (SEQ ID NO:1543), Ceres ANNOT ID no. 1454522 (SEQ ID NO:1547), Public GI ID no. 31323447 (SEQ ID NO:1556), Ceres CLONE ID no. 1583941 (SEQ ID NO:1561), Ceres CLONE ID no. 1792942 (SEQ ID NO:1563), Public GI ID no. 77548772 (SEQ ID NO:1565), and Public GI ID no. 84453182 (SEQ ID NO:1567).

F. Other Sequences

It should be appreciated that an SD+EODFR and/or low light-tolerance polypeptide and red light specific response pathway polypeptide can include additional amino acids that are not involved in an SD+EODFR and/or low light tolerance, or a red light specific response pathway, and thus such a polypeptide can be longer than would otherwise be the case. For example, an SD+EODFR and/or low light-tolerance polypeptide can include a purification tag, a chloroplast transit peptide, a mitochondrial transit peptide, an amyloplast peptide, or a leader sequence added to the amino or carboxy terminus. In some embodiments, an SD+EODFR and/or low light-tolerance polypeptide includes an amino acid sequence that functions as a reporter, e.g., a green fluorescent protein or yellow fluorescent protein.

III. NUCLEIC ACIDS

Nucleic acids described herein include nucleic acids that are effective to modulate SD+EODFR and/or low light tolerance when transcribed in a plant or plant cell. Such nucleic acids include, without limitation, those that encode an SD+EODFR and/or low light-tolerance polypeptide and those that can be used to inhibit expression of an SD+EODFR and/or low light-tolerance polypeptide or a red light specific response pathway polypeptide via a nucleic acid based method.

A. Nucleic Acids Encoding SD+EODFR and/or Low Light-Tolerance Polypeptides

Nucleic acids encoding SD+EODFR and/or low light-tolerance polypeptides are described herein. Such nucleic acids include SEQ ID NOs:1, 2, 4, 6, 8, 11, 13, 15, 17, 19, 21, 23, 27, 29, 31, 33, 35, 37, 39, 41, 43, 45, 47, 50, 52, 54, 56, 58, 64, 66, 68, 69, 71, 73, 75, 77, 79, 81, 83, 85, 87, 92, 94, 104, 106, 108, 110, 112, 114, 123, 125, 127, 128, 134, 136, 138, 140, 142, 144, 146, 148, 150, 152, 154, 156, 158, 160, 162, 164, 166, 168, 170, 172, 174, 176, 178, 180, 182, 184, 186, 190, 192, 194, 196, 198, 200, 202, 204, 206, 208, 210, 212, 214, 216, 218, 220, 222, 224, 226, 228, 240, 242, 244, 246, 248, 250, 252, 254, 256, 258, 260, 263, 265, 267, 269, 272, 274, 276, 278, 280, 282, 284, 286, 288, 290, 305, 307, 309, 311, 313, 315, 316, 318, 320, 322, 324, 326, 328, 333, 335, 336, 338, 340, 342, 345, 356, 358, 360, 363, 369, 371, 373, 375, 377, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 455, 461, 463, 465, 467, 469, 471, 473, 476, 490, 492, 500, 502, 504, 506, 513, 517, 519, 537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 632, 633, 635, 640, 642, 643, 646, 648, 650, 652, 654, 656, 658, 660, 662, 664, 666, 668, 670, 672, 674, 677, 679, 681, 683, 685, 687, 689, 691, 693, 696, 698, 700, 703, 705, 707, 710, 715, 717, 719, 722, 724, 727, 729, 731, 733, 735, 737, 739, 746, 748, 752, 754, 756, 758, 760, 766, 768, 770, 772, 775, 777, 781, 785, 787, 789, 791, 793, 825, 828, 836, 842, 844, 846, 848, 849, 852, 854, 856, 858, 860, 867, 869, 871, 873, 875, 878, 880, 882, 884, 886, 888, 890, 892, 894, 896, 899, 901, 903, 905, 906, 908, 910, 912, 914, 916, 918, 921, 925, 927, 933, 935, 942, 944, 946, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1019, 1020, 1021, 1022, 1023, 1026, 1028, 1031, 1034, 1036, 1038, 1041, 1045, 1046, 1048, 1050, 1052, 1054, 1056, 1058, 1060, 1062, 1064, 1066, 1070, 1076, 1079, 1082, 1084, 1086, 1088, 1090, 1092, 1094, 1096, 1102, 1104, 1106, 1108, 1110, 1112, 1114, 1116, 1118, 1120, 1122, 1124, 1126, 1128, 1130, 1132, 1140, 1142, 1144, 1146, 1148, 1150, 1152, 1154, 1156, 1158, 1163, 1165, 1167, 1169, 1171, 1173, 1175, 1177, 1179, 1181, 1183, 1185, 1187, 1189, 1191, 1193, 1195, 1197, 1205, 1207, 1210, 1212, 1218, 1220, 1222, 1224, 1226, 1228, 1231, 1233, 1235, 1237, 1239, 1241, 1243, 1245, 1247, 1249, 1251, 1253, 1265, 1267, 1269, 1271, 1273, 1275, 1276, 1278, 1280, 1282, 1284, 1286, 1288, 1290, 1292, 1296, 1300, 1302, 1304, 1306, 1308, 1310, 1312, 1314, 1316, 1318, 1320, 1333, 1335, 1337, 1339, 1341, 1343, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1453, 1454, 1455, 1456, 1459, 1461, 1463, 1465, 1470, 1472, 1474, 1476, 1487, 1489, 1491, 1493, 1495, 1496, 1498, 1500, 1507, 1509, 1517, 1526, 1530, 1537, 1538, 1539, 1542, 1544, 1546, 1548, 1550, 1552, 1560, 1562, 1569, 1571, 1573, 1575, 1577, 1579, 1581, 1583, 1585, 1586, 1588, 1590, 1592, 1595, 1608, 1610, 1622, 1624, 1626, 1627, 1628, 1629, 1633, 1634, 1636, 1638, 1640, 1645, 1647, 1649, 1656, 1658, 1660, 1662, 1664, 1666, 1668, 1670, 1672, 1674, 1676, 1678, 1680, 1683, 1685, 1687, 1689, 1691, 1693, 1695, 1697, 1706, 1708, 1710, 1712, 1714, 1716, 1718, 1724, 1726, 1728, 1731, 1733, 1735, 1737, 1747, 1749, 1753, 1755, 1757, 1759, 1761, 1763, 1765, 1779, 1781, 1783, 1785, 1787, 1789, 1791, 1793, 1795, 1797, 1799, 1801, 1803, 1841, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2068, 2071, 2073, 2075, 2077, 2079, 2082, 2086, 2088, 2090, 2092, 2094, 2096, 2098, 2100, 2102, 2104, 2106, 2108, 2110, 2112, 2122, 2124, 2126, 2128, 2130, 2132, 2134, 2145, 2147, 2149, 2151, 2153, 2155, 2157, 2159, 2161, 2163, 2165, 2167, 2169, 2171, 2173, 2175, 2177, 2179, 2181, 2265, 2267, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2349, 2351, 2353, 2355, 2357, 2359, 2361, 2363, 2365, 2367, 2369, 2371, and 2373 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs:1, 2, 4, 6, 8, 11, 13, 15, 17, 19, 21, 23, 27, 29, 31, 33, 35, 37, 39, 41, 43, 45, 47, 50, 52, 54, 56, 58, 64, 66, 68, 69, 71, 73, 75, 77, 79, 81, 83, 85, 87, 92, 94, 104, 106, 108, 110, 112, 114, 123, 125, 127, 128, 134, 136, 138, 140, 142, 144, 146, 148, 150, 152, 154, 156, 158, 160, 162, 164, 166, 168, 170, 172, 174, 176, 178, 180, 182, 184, 186, 190, 192, 194, 196, 198, 200, 202, 204, 206, 208, 210, 212, 214, 216, 218, 220, 222, 224, 226, 228, 240, 242, 244, 246, 248, 250, 252, 254, 256, 258, 260, 263, 265, 267, 269, 272, 274, 276, 278, 280, 282, 284, 286, 288, 290, 305, 307, 309, 311, 313, 315, 316, 318, 320, 322, 324, 326, 328, 333, 335, 336, 338, 340, 342, 345, 356, 358, 360, 363, 369, 371, 373, 375, 377, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 455, 461, 463, 465, 467, 469, 471, 473, 476, 490, 492, 500, 502, 504, 506, 513, 517, 519, 537, 540, 551, 553, 566, 568, 569, 571, 573, 575, 577, 581, 583, 585, 587, 589, 591, 593, 595, 597, 599, 602, 604, 605, 610, 612, 614, 619, 623, 627, 630, 632, 633, 635, 640, 642, 643, 646, 648, 650, 652, 654, 656, 658, 660, 662, 664, 666, 668, 670, 672, 674, 677, 679, 681, 683, 685, 687, 689, 691, 693, 696, 698, 700, 703, 705, 707, 710, 715, 717, 719, 722, 724, 727, 729, 731, 733, 735, 737, 739, 746, 748, 752, 754, 756, 758, 760, 766, 768, 770, 772, 775, 777, 781, 785, 787, 789, 791, 793, 825, 828, 836, 842, 844, 846, 848, 849, 852, 854, 856, 858, 860, 867, 869, 871, 873, 875, 878, 880, 882, 884, 886, 888, 890, 892, 894, 896, 899, 901, 903, 905, 906, 908, 910, 912, 914, 916, 918, 921, 925, 927, 933, 935, 942, 944, 946, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1019, 1020, 1021, 1022, 1023, 1026, 1028, 1031, 1034, 1036, 1038, 1041, 1045, 1046, 1048, 1050, 1052, 1054, 1056, 1058, 1060, 1062, 1064, 1066, 1070, 1076, 1079, 1082, 1084, 1086, 1088, 1090, 1092, 1094, 1096, 1102, 1104, 1106, 1108, 1110, 1112, 1114, 1116, 1118, 1120, 1122, 1124, 1126, 1128, 1130, 1132, 1140, 1142, 1144, 1146, 1148, 1150, 1152, 1154, 1156, 1158, 1163, 1165, 1167, 1169, 1171, 1173, 1175, 1177, 1179, 1181, 1183, 1185, 1187, 1189, 1191, 1193, 1195, 1197, 1205, 1207, 1210, 1212, 1218, 1220, 1222, 1224, 1226, 1228, 1231, 1233, 1235, 1237, 1239, 1241, 1243, 1245, 1247, 1249, 1251, 1253, 1265, 1267, 1269, 1271, 1273, 1275, 1276, 1278, 1280, 1282, 1284, 1286, 1288, 1290, 1292, 1296, 1300, 1302, 1304, 1306, 1308, 1310, 1312, 1314, 1316, 1318, 1320, 1333, 1335, 1337, 1339, 1341, 1343, 1345, 1346, 1348, 1350, 1354, 1356, 1359, 1361, 1363, 1365, 1369, 1371, 1373, 1376, 1378, 1380, 1382, 1384, 1386, 1388, 1390, 1392, 1394, 1396, 1398, 1400, 1403, 1405, 1407, 1409, 1416, 1418, 1420, 1428, 1432, 1437, 1441, 1443, 1445, 1447, 1449, 1451, 1453, 1454, 1455, 1456, 1459, 1461, 1463, 1465, 1470, 1472, 1474, 1476, 1487, 1489, 1491, 1493, 1495, 1496, 1498, 1500, 1507, 1509, 1517, 1526, 1530, 1537, 1538, 1539, 1542, 1544, 1546, 1548, 1550, 1552, 1560, 1562, 1569, 1571, 1573, 1575, 1577, 1579, 1581, 1583, 1585, 1586, 1588, 1590, 1592, 1595, 1608, 1610, 1622, 1624, 1626, 1627, 1628, 1629, 1633, 1634, 1636, 1638, 1640, 1645, 1647, 1649, 1656, 1658, 1660, 1662, 1664, 1666, 1668, 1670, 1672, 1674, 1676, 1678, 1680, 1683, 1685, 1687, 1689, 1691, 1693, 1695, 1697, 1706, 1708, 1710, 1712, 1714, 1716, 1718, 1724, 1726, 1728, 1731, 1733, 1735, 1737, 1747, 1749, 1753, 1755, 1757, 1759, 1761, 1763, 1765, 1779, 1781, 1783, 1785, 1787, 1789, 1791, 1793, 1795, 1797, 1799, 1801, 1803, 1841, 1849, 1851, 1853, 1855, 1857, 1868, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2068, 2071, 2073, 2075, 2077, 2079, 2082, 2086, 2088, 2090, 2092, 2094, 2096, 2098, 2100, 2102, 2104, 2106, 2108, 2110, 2112, 2122, 2124, 2126, 2128, 2130, 2132, 2134, 2145, 2147, 2149, 2151, 2153, 2155, 2157, 2159, 2161, 2163, 2165, 2167, 2169, 2171, 2173, 2175, 2177, 2179, 2181, 2265, 2267, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2349, 2351, 2353, 2355, 2357, 2359, 2361, 2363, 2365, 2367, 2369, 2371, and 2373.

An SD+EODFR and/or low light-tolerance nucleic acid can comprise the nucleotide sequence set forth in SEQ ID NO:1 or SEQ ID NO:2. Alternatively, an SD+EODFR and/or low light-tolerance nucleic acid can be a variant of the nucleic acid having the nucleotide sequence set forth in SEQ ID NO:1 or SEQ ID NO:2. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1 or SEQ ID NO:2.

An SD+EODFR and/or low light-tolerance nucleic acid can comprise the nucleotide sequence set forth in SEQ ID NO:68 or SEQ ID NO:69. Alternatively, an SD+EODFR and/or low light-tolerance nucleic acid can be a variant of the nucleic acid having the nucleotide sequence set forth in SEQ ID NO:68 or SEQ ID NO:69. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:68 or SEQ ID NO:69.

An SD+EODFR and/or low light-tolerance nucleic acid can comprise the nucleotide sequence set forth in SEQ ID NO:127 or SEQ ID NO:128. Alternatively, an SD+EODFR and/or low light-tolerance nucleic acid can be a variant of the nucleic acid having the nucleotide sequence set forth in SEQ ID NO:127 or SEQ ID NO:128. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:127 or SEQ ID NO:128.

An SD+EODFR and/or low light-tolerance nucleic acid can comprise the nucleotide sequence set forth in SEQ ID NO:315 or SEQ ID NO:316. Alternatively, an SD+EODFR and/or low light-tolerance nucleic acid can be a variant of the nucleic acid having the nucleotide sequence set forth in SEQ ID NO:315 or SEQ ID NO:316. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:315 or SEQ ID NO:316.

An SD+EODFR and/or low light-tolerance nucleic acid can comprise the nucleotide sequence set forth in SEQ ID NO:335 or SEQ ID NO:336. Alternatively, an SD+EODFR and/or low light-tolerance nucleic acid can be a variant of the nucleic acid having the nucleotide sequence set forth in SEQ ID NO:335 or SEQ ID NO:336. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:335 or SEQ ID NO:336.

An SD+EODFR and/or low light-tolerance nucleic acid can comprise the nucleotide sequence set forth in SEQ ID NO:454 or SEQ ID NO:455. Alternatively, an SD+EODFR and/or low light-tolerance nucleic acid can be a variant of the nucleic acid having the nucleotide sequence set forth in SEQ ID NO:454 or SEQ ID NO:455. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:454 or SEQ ID NO:455.

An SD+EODFR and/or low light-tolerance nucleic acid can comprise the nucleotide sequence set forth in SEQ ID NO:537. Alternatively, an SD+EODFR and/or low light-tolerance nucleic acid can be a variant of the nucleic acid having the nucleotide sequence set forth in SEQ ID NO:537. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:537.

An SD+EODFR and/or low light-tolerance nucleic acid can comprise the nucleotide sequence set forth in SEQ ID NO:568 or SEQ ID NO:569. Alternatively, an SD+EODFR and/or low light-tolerance nucleic acid can be a variant of the nucleic acid having the nucleotide sequence set forth in SEQ ID NO:568 or SEQ ID NO:569. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:568 or SEQ ID NO:569.

An SD+EODFR and/or low light-tolerance nucleic acid can comprise the nucleotide sequence set forth in SEQ ID NO:604 or SEQ ID NO:605. Alternatively, an SD+EODFR and/or low light-tolerance nucleic acid can be a variant of the nucleic acid having the nucleotide sequence set forth in SEQ ID NO:604 or SEQ ID NO:605. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:604 or SEQ ID NO:605.

An SD+EODFR and/or low light-tolerance nucleic acid can comprise the nucleotide sequence set forth in SEQ ID NO:632 or SEQ ID NO:633. Alternatively, an SD+EODFR and/or low light-tolerance nucleic acid can be a variant of the nucleic acid having the nucleotide sequence set forth in SEQ ID NO:632 or SEQ ID NO:633. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:632 or SEQ ID NO:633.

An SD+EODFR and/or low light-tolerance nucleic acid can comprise the nucleotide sequence set forth in SEQ ID NO:642 or SEQ ID NO:643. Alternatively, an SD+EODFR and/or low light-tolerance nucleic acid can be a variant of the nucleic acid having the nucleotide sequence set forth in SEQ ID NO:642 or SEQ ID NO:643. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:642 or SEQ ID NO:643.

An SD+EODFR and/or low light-tolerance nucleic acid can comprise the nucleotide sequence set forth in SEQ ID NO:848 or SEQ ID NO:849. Alternatively, an SD+EODFR and/or low light-tolerance nucleic acid can be a variant of the nucleic acid having the nucleotide sequence set forth in SEQ ID NO:848 or SEQ ID NO:849. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:848 or SEQ ID NO:849.

An SD+EODFR and/or low light-tolerance nucleic acid can comprise the nucleotide sequence set forth in SEQ ID NO:905 or SEQ ID NO:906. Alternatively, an SD+EODFR and/or low light-tolerance nucleic acid can be a variant of the nucleic acid having the nucleotide sequence set forth in SEQ ID NO:905 or SEQ ID NO:906. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:905 or SEQ ID NO:906.

An SD+EODFR and/or low light-tolerance nucleic acid can comprise the nucleotide sequence set forth in SEQ ID NO:951 or SEQ ID NO:952. Alternatively, an SD+EODFR and/or low light-tolerance nucleic acid can be a variant of the nucleic acid having the nucleotide sequence set forth in SEQ ID NO:951 or SEQ ID NO:952. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:951 or SEQ ID NO:952.

An SD+EODFR and/or low light-tolerance nucleic acid can comprise the nucleotide sequence set forth in SEQ ID NO:1019, SEQ ID NO:1020, SEQ ID NO:1021, SEQ ID NO:1022, or SEQ ID NO:1023. Alternatively, an SD+EODFR and/or low light-tolerance nucleic acid can be a variant of the nucleic acid having the nucleotide sequence set forth in SEQ ID NO:1019, SEQ ID NO:1020, SEQ ID NO:1021, SEQ ID NO:1022, or SEQ ID NO:1023. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1019, SEQ ID NO:1020, SEQ ID NO:1021, SEQ ID NO:1022, or SEQ ID NO:1023.

An SD+EODFR and/or low light-tolerance nucleic acid can comprise the nucleotide sequence set forth in SEQ ID NO:1045 or SEQ ID NO:1046. Alternatively, an SD+EODFR and/or low light-tolerance nucleic acid can be a variant of the nucleic acid having the nucleotide sequence set forth in SEQ ID NO:1045 or SEQ ID NO:1046. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1045 or SEQ ID NO:1046.

An SD+EODFR and/or low light-tolerance nucleic acid can comprise the nucleotide sequence set forth in SEQ ID NO:1150. Alternatively, an SD+EODFR and/or low light-tolerance nucleic acid can be a variant of the nucleic acid having the nucleotide sequence set forth in SEQ ID NO:1150. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1150.

An SD+EODFR and/or low light-tolerance nucleic acid can comprise the nucleotide sequence set forth in SEQ ID NO:1275 or SEQ ID NO:1276. Alternatively, an SD+EODFR and/or low light-tolerance nucleic acid can be a variant of the nucleic acid having the nucleotide sequence set forth in SEQ ID NO:1275 or SEQ ID NO:1276. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1275 or SEQ ID NO:1276.

An SD+EODFR and/or low light-tolerance nucleic acid can comprise the nucleotide sequence set forth in SEQ ID NO:1345 or SEQ ID NO:1346. Alternatively, an SD+EODFR and/or low light-tolerance nucleic acid can be a variant of the nucleic acid having the nucleotide sequence set forth in SEQ ID NO:1345 or SEQ ID NO:1346. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1345 or SEQ ID NO:1346.

An SD+EODFR and/or low light-tolerance nucleic acid can comprise the nucleotide sequence set forth in SEQ ID NO:1453, SEQ ID NO:1454, SEQ ID NO:1455, or SEQ ID NO:1456. Alternatively, an SD+EODFR and/or low light-tolerance nucleic acid can be a variant of the nucleic acid having the nucleotide sequence set forth in SEQ ID NO:1453, SEQ ID NO:1454, SEQ ID NO:1455, or SEQ ID NO:1456. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1453, SEQ ID NO:1454, SEQ ID NO:1455, or SEQ ID NO:1456.

An SD+EODFR and/or low light-tolerance nucleic acid can comprise the nucleotide sequence set forth in SEQ ID NO:1495 or SEQ ID NO:1496. Alternatively, an SD+EODFR and/or low light-tolerance nucleic acid can be a variant of the nucleic acid having the nucleotide sequence set forth in SEQ ID NO:1495 or SEQ ID NO:1496. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1495 or SEQ ID NO:1496.

An SD+EODFR and/or low light-tolerance nucleic acid can comprise the nucleotide sequence set forth in SEQ ID NO:1537, SEQ ID NO:1538, or SEQ ID NO:1539. Alternatively, an SD+EODFR and/or low light-tolerance nucleic acid can be a variant of the nucleic acid having the nucleotide sequence set forth in SEQ ID NO:1537, SEQ ID NO:1538, or SEQ ID NO:1539. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1537, SEQ ID NO:1538, or SEQ ID NO:1539.

An SD+EODFR and/or low light-tolerance nucleic acid can comprise the nucleotide sequence set forth in SEQ ID NO:1585 or SEQ ID NO:1586. Alternatively, an SD+EODFR and/or low light-tolerance nucleic acid can be a variant of the nucleic acid having the nucleotide sequence set forth in SEQ ID NO:1585 or SEQ ID NO:1586. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1585 or SEQ ID NO:1586.

An SD+EODFR and/or low light-tolerance nucleic acid can comprise the nucleotide sequence set forth in SEQ ID NO:1626, SEQ ID NO:1627, SEQ ID NO:1628, or SEQ ID NO:1629. Alternatively, an SD+EODFR and/or low light-tolerance nucleic acid can be a variant of the nucleic acid having the nucleotide sequence set forth in SEQ ID NO:1626, SEQ ID NO:1627, SEQ ID NO:1628, or SEQ ID NO:1629. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1626, SEQ ID NO:1627, SEQ ID NO:1628, or SEQ ID NO:1629.

An SD+EODFR and/or low light-tolerance nucleic acid can comprise the nucleotide sequence set forth in SEQ ID NO:1633 or SEQ ID NO:1634. Alternatively, an SD+EODFR and/or low light-tolerance nucleic acid can be a variant of the nucleic acid having the nucleotide sequence set forth in SEQ ID NO:1633 or SEQ ID NO:1634. For example, an SD+EODFR and/or low light-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1633 or SEQ ID NO:1634.

B. Nucleic Acids Encoding Red Light Specific Response Pathway Polypeptides

Nucleic acids encoding red light specific response pathway polypeptides are described herein. Such nucleic acids include SEQ ID NOs: 454, 455, 461, 463, 465, 467, 469, 471, 473, 476, 490, 492, 500, 502, 504, 506, 513, 517, 519, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1537, 1538, 1539, 1542, 1544, 1546, 1548, 1550, 1552, 1560, 1562, 1569, 1571, 1573, 1575, 1577, 1579, 1581, 1583, 1660, 1662, 1664, 1666, 1668, 1670, 1672, 1674, 1676, 1779, 1781, 1783, 1785, 1787, 1789, 1791, 1793, 1795, 1797, 1799, 1801, 1803, 1841, and 2267 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 454, 455, 461, 463, 465, 467, 469, 471, 473, 476, 490, 492, 500, 502, 504, 506, 513, 517, 519, 951, 952, 954, 956, 958, 960, 962, 964, 968, 970, 972, 974, 976, 978, 980, 982, 984, 986, 988, 990, 992, 994, 996, 998, 1000, 1002, 1004, 1006, 1008, 1010, 1012, 1017, 1537, 1538, 1539, 1542, 1544, 1546, 1548, 1550, 1552, 1560, 1562, 1569, 1571, 1573, 1575, 1577, 1579, 1581, 1583, 1660, 1662, 1664, 1666, 1668, 1670, 1672, 1674, 1676, 1779, 1781, 1783, 1785, 1787, 1789, 1791, 1793, 1795, 1797, 1799, 1801, 1803, 1841, and 2267.

A red light specific response pathway nucleic acid can comprise the nucleotide sequence set forth in SEQ ID NO:454 or SEQ ID NO:455. Alternatively, a red light specific response pathway nucleic acid can be a variant of the nucleic acid having the nucleotide sequence set forth in SEQ ID NO:454 or SEQ ID NO:455. For example, a red light specific response pathway nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:454 or SEQ ID NO:455.

A red light specific response pathway nucleic acid can comprise the nucleotide sequence set forth in SEQ ID NO:951 or SEQ ID NO:952. Alternatively, a red light specific response pathway nucleic acid can be a variant of the nucleic acid having the nucleotide sequence set forth in SEQ ID NO:951 or SEQ ID NO:952. For example, a red light specific response pathway nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:951 or SEQ ID NO:952.

A red light specific response pathway nucleic acid can comprise the nucleotide sequence set forth in SEQ ID NO:1537, SEQ ID NO:1538, or SEQ ID NO:1539. Alternatively, a red light specific response pathway nucleic acid can be a variant of the nucleic acid having the nucleotide sequence set forth in SEQ ID NO:1537, SEQ ID NO:1538, or SEQ ID NO:1539. For example, a red light specific response pathway nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1537, SEQ ID NO:1538, or SEQ ID NO:1539.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

C. Use of Nucleic Acids to Modulate Expression of Polypeptides Expression of an SD+EODFR and/or Low Light-Tolerance Polypeptide A nucleic acid encoding one of the SD+EODFR and/or low light-tolerance polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular SD+EODFR and/or low light-tolerance polypeptide; i.e., for many amino acids, there is more than one nucleotide triplet that serves as the codon for the amino acid.

Thus, codons in the coding sequence for a given SD+EODFR and/or low light-tolerance polypeptide can be modified such that optimal expression in a particular plant species is obtained, using appropriate codon bias tables for that species.

In some cases, expression of an SD+EODFR and/or low light-tolerance polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

D. Use of Nucleic Acids to Inhibit Expression of a Red Light Specific Response Pathway Polypeptide Polynucleotides and recombinant constructs described herein can be used to inhibit expression of a red light specific response pathway polypeptide in a plant species of interest. See, e.g., Matzke and Birchler, *Nature Reviews Genetics*, 6:24-35 (2005); Akashi et al., *Nature Reviews Mol. Cell Biology*, 6:413-422 (2005); Mittal, *Nature Reviews Genetics*, 5:355-365 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding red light specific response pathway polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5 '-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, NJ. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a red light specific response pathway polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the red light specific response pathway polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a red light specific response pathway polypeptide, and the other strand of the stem portion of the double stranded RNA comprises a sequence that is similar or identical to the sequence that is complementary to the 3' or 5' untranslated region, respectively, or a fragment thereof, of the mRNA encoding the red light specific response pathway polypeptide. In other embodiments, one strand of the stem portion of a double stranded RNA comprises a sequence that is similar or identical to the sequence of an intron, or a fragment thereof, in the pre-mRNA encoding a red light specific response pathway polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a red light specific response pathway polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a red light specific response pathway polypeptide, or a fragment of such sequences. In some embodiments, the sense or antisense sequence is identical or complementary to a sequence of the regulatory region that drives transcription of the gene encoding a red light specific response pathway polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a red light specific response pathway polypeptide described herein. The sense sequence complementary to the antisense sequence can be a sequence present within the mRNA of the red light specific response pathway polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

E. Constructs/Vectors

Recombinant constructs provided herein can be used to transform plants or plant cells in order to modulate SD+EODFR, low light tolerance, and/or red light specific response pathways. A recombinant nucleic acid construct can comprise a nucleic acid encoding an SD+EODFR and/or low light-tolerance polypeptide as described herein, operably linked to a regulatory region suitable for expressing the SD+EODFR and/or low light-tolerance polypeptide in the plant or cell. Thus, a nucleic acid can comprise a coding sequence that encodes any of the SD+EODFR and/or low light-tolerance polypeptides as set forth in SEQ ID NOs:3, 5, 7, 9, 10, 12, 14, 16, 18, 20, 22, 24, 25, 26, 28, 30, 32, 34, 36, 38, 40, 42, 44, 46, 48, 49, 51, 53, 55, 57, 59, 60, 61, 62, 63, 65, 67, 70, 72, 74, 76, 78, 80, 82, 84, 86, 88, 89, 90, 91, 93, 95, 96, 97, 98, 99, 100, 101, 102, 103, 105, 107, 109, 111, 113, 115, 116, 117, 118, 119, 120, 121, 122, 124, 126, 129, 130, 131, 132, 133, 135, 137, 139, 141, 143, 145, 147, 149, 151, 153, 155, 157, 159, 161, 163, 165, 167, 169, 171, 173, 175, 177, 179, 181, 183, 185, 187, 188, 189, 191, 193, 195, 197, 199, 201, 203, 205, 207, 209, 211, 213, 215, 217, 219, 221, 223, 225, 227, 229, 230, 231, 232, 233, 234, 235, 236, 237, 238, 239, 241, 243, 245, 247, 249, 251, 253, 255, 257, 259, 261, 262, 264, 266, 268, 270, 271, 273, 275, 277, 279, 281, 283, 285, 287, 289, 291, 292, 293, 294, 295, 296, 297, 298, 299, 300, 301, 302, 303, 304, 306, 308, 310, 312, 314, 317, 319, 321, 323, 325, 327, 329, 330, 331, 332, 334, 337, 339, 341, 343, 344, 346, 347, 348, 349, 350, 351, 352, 353, 354, 355, 357, 359, 361, 362, 364, 365, 366, 367, 368, 370, 372, 374, 376, 378, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 456, 457, 458, 459, 460, 462, 464, 466, 468, 470, 472, 474, 475, 477, 478, 479, 480, 481, 482, 483, 484, 485, 486, 487, 488, 489, 491, 493, 494, 495, 496, 497, 498, 499, 501, 503, 505, 507, 508, 509, 510, 511, 512, 514, 515, 516, 518, 520, 521, 522, 523, 524, 525, 526, 527, 528, 529, 530, 531, 532, 533, 534, 535, 536, 538, 539, 541, 542, 543, 544, 545, 546, 547, 548, 549, 550, 552, 554, 555, 556, 557, 558, 559, 560, 561, 562, 563, 564, 565, 567, 570, 572, 574, 576, 578, 579, 580, 582, 584, 586, 588, 590, 592, 594, 596, 598, 600, 601, 603, 606, 607, 608, 609, 611, 613, 615, 616, 617, 618, 620, 621, 622, 624, 625, 626, 628, 629, 631, 634, 636, 637, 638, 639, 641, 644, 645, 647, 649, 651, 653, 655, 657, 659, 661, 663, 665, 667, 669, 671, 673, 675, 676, 678, 680, 682, 684, 686, 688, 690, 692, 694, 695, 697, 699, 701, 702, 704, 706, 708, 709, 711, 712, 713, 714, 716, 718, 720, 721, 723, 725, 726, 728, 730, 732, 734, 736, 738, 740, 741, 742, 743, 744, 745, 747, 749, 750, 751, 753, 755, 757, 759, 761, 762, 763, 764, 765, 767, 769, 771, 773, 774, 776, 778, 779, 780, 782, 783, 784, 786, 788, 790, 792, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 826, 827, 829, 830, 831, 832, 833, 834, 835, 837, 838, 839, 840, 841, 843, 845, 847, 850, 851, 853, 855, 857, 859, 861, 862, 863, 864, 865, 866, 868, 870, 872, 874, 876, 877, 879, 881, 883, 885, 887, 889, 891, 893, 895, 897, 898, 900, 902, 904, 907, 909, 911, 913, 915, 917, 919, 920, 922, 923, 924, 926, 928, 929, 930, 931, 932, 934, 936, 937, 938, 939, 940, 941, 943, 945, 947, 948, 949, 950, 953, 955, 957, 959, 961, 963, 965, 966, 967, 969, 971, 973, 975, 977, 979, 981, 983, 985, 987, 989, 991, 993, 995, 997, 999, 1001, 1003, 1005, 1007, 1009, 1011, 1013, 1014, 1015, 1016, 1018, 1024, 1025, 1027, 1029, 1030, 1032, 1033, 1035, 1037, 1039, 1040, 1042, 1043, 1044, 1047, 1049, 1051, 1053, 1055, 1057, 1059, 1061, 1063, 1065, 1067, 1068, 1069, 1071, 1072, 1073, 1074, 1075, 1077, 1078, 1080, 1081, 1083, 1085, 1087, 1089, 1091, 1093, 1095, 1097, 1098, 1099, 1100, 1101, 1103, 1105, 1107, 1109, 1111, 1113, 1115, 1117, 1119, 1121, 1123, 1125, 1127, 1129, 1131, 1133, 1134, 1135, 1136, 1137, 1138, 1139, 1141, 1143, 1145, 1147, 1149, 1151, 1153, 1155, 1157, 1159, 1160, 1161, 1162, 1164, 1166, 1168, 1170, 1172, 1174, 1176, 1178, 1180, 1182, 1184, 1186, 1188, 1190, 1192, 1194, 1196, 1198, 1199, 1200, 1201, 1202, 1203, 1204, 1206, 1208, 1209, 1211, 1213, 1214, 1215, 1216, 1217, 1219, 1221, 1223, 1225, 1227, 1229, 1230, 1232, 1234, 1236, 1238, 1240, 1242, 1244, 1246, 1248, 1250, 1252, 1254, 1255, 1256, 1257, 1258, 1259, 1260, 1261, 1262, 1263, 1264, 1266, 1268, 1270, 1272, 1274, 1277, 1279, 1281, 1283, 1285, 1287, 1289, 1291, 1293, 1294, 1295, 1297, 1298, 1299, 1301, 1303, 1305, 1307, 1309, 1311, 1313, 1315, 1317, 1319, 1321, 1322, 1323, 1324, 1325, 1326, 1327, 1328, 1329, 1330, 1331, 1332, 1334, 1336, 1338, 1340, 1342, 1344, 1347, 1349, 1351, 1352, 1353, 1355, 1357, 1358, 1360, 1362, 1364, 1366, 1367, 1368, 1370, 1372, 1374, 1375, 1377, 1379, 1381, 1383, 1385, 1387, 1389, 1391, 1393, 1395, 1397, 1399, 1401, 1402, 1404, 1406, 1408, 1410, 1411, 1412, 1413, 1414, 1415, 1417, 1419, 1421, 1422, 1423, 1424, 1425, 1426, 1427, 1429, 1430, 1431, 1433, 1434, 1435, 1436, 1438, 1439, 1440, 1442, 1444, 1446, 1448, 1450, 1452, 1457, 1458, 1460, 1462, 1464, 1466, 1467, 1468, 1469, 1471, 1473, 1475, 1477, 1478, 1479, 1480, 1481, 1482, 1483, 1484, 1485, 1486, 1488, 1490, 1492, 1494, 1497, 1499, 1501, 1502, 1503, 1504, 1505, 1506, 1508, 1510, 1511, 1512, 1513, 1514, 1515, 1516, 1518, 1519, 1520, 1521, 1522, 1523, 1524, 1525, 1527, 1528, 1529, 1531, 1532, 1533, 1534, 1535, 1536, 1540, 1541, 1543, 1545, 1547, 1549, 1551, 1553, 1554, 1555, 1556, 1557, 1558, 1559, 1561, 1563, 1564, 1565, 1566, 1567, 1568, 1570, 1572, 1574, 1576, 1578, 1580, 1582, 1584, 1587, 1589, 1591, 1593, 1594, 1596, 1597, 1598, 1599, 1600, 1601, 1602, 1603, 1604, 1605, 1606, 1607, 1609, 1611, 1612, 1613, 1614, 1615, 1616, 1617, 1618, 1619, 1620, 1621, 1623, 1625, 1630, 1631, 1632, 1635, 1637, 1639, 1641, 1642, 1643, 1644, 1646, 1648, 1650, 1651, 1652, 1653, 1654, 1655, 1657, 1659, 1661, 1663, 1665, 1667, 1669, 1671, 1673, 1675, 1677, 1679, 1681, 1682, 1684, 1686, 1688, 1690, 1692, 1694, 1696, 1698, 1699, 1700, 1701, 1702, 1703, 1704, 1705, 1707, 1709, 1711, 1713, 1715, 1717, 1719, 1720, 1721, 1722, 1723, 1725, 1727, 1729, 1730, 1732, 1734, 1736, 1738, 1739, 1740, 1741, 1742, 1743, 1744, 1745, 1746, 1748, 1750, 1751, 1752, 1754, 1756, 1758, 1760, 1762, 1764, 1766, 1767, 1768, 1769, 1770, 1771, 1772, 1773, 1774, 1775, 1776, 1777, 1778, 1780, 1782, 1784, 1786, 1788, 1790, 1792, 1794, 1796, 1798, 1800, 1802, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1842, 1843, 1844, 1845, 1846, 1847, 1848, 1850, 1852, 1854, 1856, 1858, 1859, 1860, 1861, 1862, 1863, 1864, 1865, 1866, 1867, 1869, 1870, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2069, 2070, 2072, 2074, 2076, 2078, 2080, 2081, 2083, 2084, 2085, 2087, 2089, 2091, 2093, 2095, 2097, 2099, 2101, 2103, 2105, 2107, 2109, 2111, 2113, 2114, 2115, 2116, 2117, 2118, 2119, 2120, 2121, 2123, 2125, 2127, 2129, 2131, 2133, 2135, 2136, 2137, 2138, 2139, 2140, 2141, 2142, 2143, 2144, 2146, 2148, 2150, 2152, 2154, 2156, 2158, 2160, 2162, 2164, 2166, 2168, 2170, 2172, 2174, 2176, 2178, 2180, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2266, 2268, 2269, 2270, 2271, 2272, 2273, 2274, 2275, 2276, 2277, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2350, 2352, 2354, 2356, 2358, 2360, 2362, 2364, 2366, 2368, 2370, 2372, 2374, 2375, 2376, 2377, 2378, 2379, 2380, 2381. Examples of nucleic acids encoding SD+EODFR and/or low light-tolerance polypeptides are described herein. The SD+EODFR and/or low light-tolerance polypeptide encoded by a recombinant nucleic acid can be a native SD+EODFR and/or low light-tolerance polypeptide, or can be heterologous to the cell. In some cases, the recombinant construct contains a nucleic acid that inhibits expression of an SD+EODFR and/or low light-tolerance polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

F. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/

62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6):609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean a' subunit of β-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the Commelina yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding an SD+EODFR and/or low light-tolerance polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous SD+EODFR and/or low light-tolerance polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of an SD+EODFR and/or low light-tolerance polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level SD+EODFR and/or low light tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in SD+EODFR and/or low light tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Cathauranthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species include *Panicum* spp. or hybrids thereof, *Sorghum* spp. or hybrids thereof, sudangrass, *Miscanthus* spp. or hybrids thereof, *Saccharum* spp. or hybrids thereof, *Erianthus* spp., *Populus* spp., *Andropogon gerardii* (big bluestem), *Pennisetum purpureum* (elephant grass) or hybrids thereof (e.g., *Pennisetum purpureum*×*Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrids thereof, *Secale cereale* (rye), *Salix* spp. (willow), *Eucalyptus* spp. (eucalyptus), Triticosecale (triticum—wheat X rye) and bamboo.

In some embodiments, a suitable species can be a wild, weedy, or cultivated sorghum species such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum*×*almum, Sorghum*×sudangrass or *Sorghum*×*drummondii*.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea*

(broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum* annum (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (*petunia*) and *Poinsettia pulcherrima* (poinsettia). Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledenous plants and plant cell systems, wherein such plants are hybrids of different species or varieties of a specific species (e.g., *Saccharum* sp.× *Miscanthus* sp., *Panicum virgatum*×*Panicum amarum, Panicum virgatum*×*Panicum amarulum*, and *Pennisetum purpureum*×*Pennisetum typhoidum*).

D. Transgenic Plant Phenotypes

The light in shady environments is enriched in FR wavelengths relative to the light in non-shady environments. Red wavelengths typically range from a photon irradiance of about 630 nm to a photon irradiance of about 700 nm. Far-red wavelengths typically range from a photon irradiance of about 700 nm to a photon irradiance of about 750 nm.

In some embodiments, a plant in which expression of an SD+EODFR and/or low light-tolerance polypeptide is modulated can have increased SD+EODFR and/or low light tolerance. The phenotype of a transgenic plant in which expression of an SD+EODFR and/or low light-tolerance polypeptide is modulated and a corresponding control plant that either lacks the transgene or does not express the transgene can be evaluated under particular environmental conditions that are useful for simulating shade, i.e., Short Day plus End-of-Day Far-Red (SD+EODFR) conditions. SD+EODFR conditions consist of a light period followed by a pulse of far-red-enriched light conditions followed by a 14 hour dark period. The light period is from about 9.0 to about 9.6 hours with a red:far-red ratio of about 5.5, with the following fluence rates: $blue_{450}=12$ $\mu mol/m^2/s$, red $633=22$ $\mu mol/m^2/S$, far-$red_{740}=4$ $\mu mol/m^2/s$, $PPFD_{400-700}=55$ $\mu mol/m^2/s$. The pulse of far-red-enriched light conditions is from about 0.4 to about 1.0 hours with a red:far-red ratio of about 0.14 with the following fluence rates: $blue_{450}=0.004$ $\mu mol/m^2/s$, red $633=10$ $\mu mol/m^2/s$, far-$red_{740}=70$ $\mu mol/m^2/s$, $PPFD_{400-700}=8$ $\mu mol/m^2/s$. Sources of lighting equipment appropriate for producing and maintaining SD+EODFR conditions are known to those in art.

The phenotype of a transgenic plant in which expression of an SD+EODFR and/or low light-tolerance polypeptide is modulated and a corresponding control plant can also be evaluated under conditions of low light irradiance. Low light conditions are conditions under which a plant is exposed to an irradiance of about 0.01 $\mu mol/m^2/s$ of light to about 20 $\mu mol/m^2/s$ of light at room temperature and about 70% relative humidity. For example, conditions under which a plant is exposed to 0.01, 1, 5, 10, 15, or 20 $\mu mol/m^2/s$ of light are low light conditions. Sources of lighting and other equipment appropriate for controlling light conditions are known to those in art.

Low light conditions typically have light of a combination of wavelengths, such as white light. White light can be supplied, e.g., by 32 watt fluorescent bulbs (Sylvania, $F_{O32/841}$/ECO, Danvers, MA), providing a red:far-red ratio of 13:1. Red wavelengths typically range from a photon irradiance of about 630 to about 700 nm. Far-red wavelengths typically range from a photon irradiance of about 700 to about 750 nm.

In some embodiments, the phenotype of a transgenic plant is assayed under low light conditions in which there is continuous low light during the light period of a light/dark cycle. Continuous low light conditions can be, for example, 16 hours of irradiance with 0.01 to 20 $\mu mol/m^2/s$ of light alternating with 8 hours of darkness. The phenotype of a transgenic plant is assayed once the plant has been exposed to continuous low light conditions during the light period of the light/dark cycle for seven days.

In some embodiments, the phenotype of a transgenic plant is assayed under red light conditions in which there is continuous red light. Continuous red light conditions can be, for example, continuous irradiance with about ~15 $\mu mol/m^2/s$ of light with a red light to far-red light ratio (R:FR) of about 80. Continuous red light can be supplied by a LED array that can be used to activate and deactivate the plant photoreceptor phytochrome (e.g., SNAP-LITE™ Quantum Devices, WI). The phenotype of a transgenic plant is assayed once the plant has been exposed to continuous red light conditions for about five days.

In some embodiments, the phenotype of a transgenic plant is assayed under far-red light conditions in which there is continuous far-red light. Continuous far-red light conditions can be, for example, continuous irradiance with about 5 µmol/m²/s of light with a R:FR of about 0.10. Continuous far-red light can be supplied by a LED array that can be used to activate and deactivate the plant photoreceptor phytochrome (e.g., SNAP-LITE™ Quantum Devices, WI). The phenotype of a transgenic plant is assayed once the plant has been exposed to continuous far-red light conditions for about five days.

In some embodiments, the phenotype of a transgenic plant is assayed under natural daylight or other broad spectrum light conditions. Natural daylight conditions, can be, for example, full sun or other natural irradiation of green house or field grown transgenic plants. Broad spectrum conditions can be irradiation supplied by a fluorescent lamp with continuous fluence rates of about 12 µmol/m²/s of blue 450 light, 22 µmol/m²/s of red 633 light, 4 µmol/m²/s far-red 740 light, and photosynthetically active radiation ($PAR_{400-700}$) of about 55 µmol/m²/s, with a R:FR of about 5. Other broad spectrum conditions can be, for example, continuous broad-spectrum light during the light period of a light/dark photocycle. In some cases, continuous broad spectrum light can be 16 hours of irradiance of about 15 to 55 µmol/m²/s $PAR_{400-700}$, alternating with 8 hours of darkness, with a dark period of 8 hours, for example. In some cases, continuous broad spectrum light can be 12 hours of irradiance of about to 55 µmol/m²/s $PAR_{400-700}$, alternating with 12 hours of darkness, for example. The phenotype of a transgenic plant is assayed during maturation and/or once the plant has reached maturity.

As compared to a control plant that does not express an SD+EODFR and/or low light-tolerance polypeptide grown under SD+EODFR conditions or low light conditions, a transgenic plant expressing an SD+EODFR and/or low light-tolerance polypeptide can exhibit one or more of the following phenotypes under SD+EODFR conditions or low light conditions: decreases in extension growth, acceleration in leaf development, decreased apical dominance, increased chloroplast development, alterations in flowering and seed/fruit production, and an increase in storage organ deposition.

As compared to a control plant that does not overexpress a red specific light response pathway polypeptide grown under continuous red light or far-red light conditions, a transgenic plant overexpressing a red light specific response pathway polypeptide can exhibit decreases in hypocotyl length under continuous red light or natural daylight conditions, but has similar hypocotyl length under continuous far-red light or dark conditions.

Typically, a difference (e.g., an increase or a decrease) in a morphological feature in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the dimensions of any individual morphological feature is statistically significant at $p<0.01$, $p<0.005$, or $p<0.001$. A statistically significant difference in, for example, a morphological feature in a transgenic plant compared to the corresponding morphological feature a control plant indicates that expression of the recombinant nucleic acid present in the transgenic plant confers the alteration in the morphological feature.

Examples of a decrease in extension growth include, without limitation, decreased petiole length, decreased hypocotyl length, decreased internode spacing, and decreased leaf elongation in cereals, when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. A decrease in extension growth can be a decrease of from about 0.25% to about 90%, e.g., from about 0.25% to about 15%, from about 5% to about 50%, from about 5% to about 10%, from about 25% to about 50%, from about 1% to about 30%, from about 50% to about 90%, from about 20% to about 40%, from about 1% to about 5%, from about 0.5% to about 2%, from about 15% to about 50%, about 20%, about 25%, about 30%, about 35%, about 40%, about 45%, about 50%, about 55%, about 60%, about 65%, about 70%, about 75%, or about 80%.

One suitable phenotype to measure is hypocotyl length. When wild-type seedlings are grown under SD+EODFR conditions or low light conditions, the hypocotyl length is typically significantly increased relative to the hypocotyl length found in wild-type seedlings grown under control light conditions. Thus, seedlings of a transgenic plant and seedlings of a corresponding control plant that either lacks the transgene or does not express the transgene can be grown under SD+EODFR conditions or low light conditions and at the appropriate time, hypocotyl lengths from seedlings of each group can be measured. Under SD+EODFR conditions or low light conditions, a seedling in which the expression of an SD+EODFR and/or low light-tolerance polypeptide is increased can have a statistically significantly shorter hypocotyl length than a seedling of a corresponding control plant that either lacks the transgene or does not express the transgene. The hypocotyl length can be shorter by at least 20 percent, e.g., 20, 25, 30, 35, 40, 45, 50, 55, 60, 65, 70, 75, or 80 percent, as compared to the hypocotyl length in a corresponding control plant that does not express the transgene.

When wild-type seedlings are grown under continuous red-light conditions, the hypocotyl length is typically significantly decreased relative to the hypocotyl length found in wild-type seedlings grown under continuous far-red light conditions. Thus, seedlings of a transgenic plant and seedlings of a corresponding control plant that either lacks the transgene or does not express the transgene can be grown under continuous red-light conditions or far-red light conditions and at the appropriate time, hypocotyl lengths from seedlings of each group can be measured. Under red light conditions, a seedling in which the expression of a red light specific response pathway polypeptide is increased can have a statistically significantly shorter hypocotyl length than a seedling of a corresponding control plant that either lacks the transgene or does not express the transgene. The hypocotyl length can be shorter by at least 20 percent, e.g., 20, 25, 30, 35, 40, 45, 50, 55, 60, 65, 70, 75, or 80 percent, as compared to the hypocotyl length in a corresponding control plant that does not express the transgene. Under far-red conditions, a seedling in which the expression of a red light specific response pathway polypeptide is increased can have a hypocotyl of similar length to a corresponding control plant that either lacks the transgene or does not express the transgene.

In contrast, a seedling in which the expression of a red light specific response pathway polypeptide is decreased can have a statistically significantly longer hypocotyl length than a seedling of a corresponding control plant that either lacks the transgene or does not express the transgene. The hypocotyl length can be longer by at least 20 percent, e.g., 20, 25, 30, 35, 40, 45, 50, 55, 60, 65, 70, 75, or 80 percent, as compared to the hypocotyl length in a corresponding control plant that does not express the transgene. Under far-red conditions, a seedling in which the expression of a red light specific response pathway polypeptide is decreased can have a hypocotyl of similar length to a corresponding control plant that either lacks the transgene or does not express the transgene.

Another suitable phenotype can be overall plant height of mature plants. When wild-type plants are grown under natural light or other broad spectrum light conditions, the plant height at maturity can be significantly decreased relative to the plant height found in wild-type plants grown under low light conditions. Thus, the transgenic plant and a corresponding control plant that either lacks the transgene or does not express the transgene can be grown under natural light conditions or low light conditions and at maturity, the height of the plants from each group can be measured. Under natural light or other broad spectrum light conditions, a mature plant in which the expression of a red light specific response pathway polypeptide is decreased can have a statistically significantly taller plant than a mature plant of a corresponding control plant that either lacks the transgene or does not express the transgene. The plant height can be taller by at least 20 percent, e.g., 20, 25, 30, 35, 40, 45, 50, 55, 60, 65, 70, or 75 percent, as compared to the height in a corresponding control plant that does not express the transgene.

Another suitable phenotype can be rate of plant growth. The rate of plant growth can be determined by measuring differences in fresh weight (T/acre), or differences in sub-apical cell expansion, over a period of time, for example. When wild-type plants are grown under natural light or other broad spectrum light conditions, the rate of plant growth can be significantly slower relative to the rate of plant growth found in wild-type plants grown under low light conditions. Thus, the transgenic plant and a corresponding control plant that either lacks the transgene or does not express the transgene can be grown under natural light conditions or low light conditions and during maturation, the rate of plant growth for plants from each group can be measured. Under natural light or other broad spectrum light conditions, a plant in which the expression of a red light specific response pathway polypeptide is decreased can have a statistically significantly increased rate of plant growth, than a plant of a corresponding control plant that either lacks the transgene or does not express the transgene. The rate of growth can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. Another suitable phenotype to measure can be dry matter yield of stem parts, or above ground parts, excluding inflorescence and seed parts of a plant. When wild-type plants are grown under natural light or other broad spectrum light conditions, the dry matter yield can be significantly decreased relative to the dry matter yield found in wild-type plants grown under low light conditions. Thus, the transgenic plant and a corresponding control plant that either lacks the transgene or does not express the transgene can be grown under natural light conditions or low light conditions and at harvest, the dry matter yield of the plants from each group can be measured. Under natural light or other broad spectrum light conditions, a mature plant in which the expression of a red light specific response pathway polypeptide is decreased can have a statistically significantly greater dry matter yield than a mature plant of a corresponding control plant that either lacks the transgene or does not express the transgene. Dry matter yield (DMY) yield is calculated using the fresh matter weight (FMW) and a measurement of weight percent moisture (M) in the following equation. $DMY=((100-M)/100)*FMW$. For example, the dry matter yield can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the dry matter yield level in a corresponding control plant that does not express the transgene.

Another suitable phenotype to measure is petiole length. When wild-type seedlings are grown under SD+EODFR conditions or low light conditions, the petiole length is typically significantly increased relative to the petiole length found in wild-type seedlings grown under control light conditions. Thus, seedlings of a transgenic plant and seedlings of a corresponding control plant that either lacks the transgene or does not express the transgene can be grown under SD+EODFR conditions or low light conditions and at the appropriate time, petiole lengths from seedlings of each group can be measured. Under SD+EODFR conditions or low light conditions, a seedling in which the expression of an SD+EODFR and/or low light-tolerance polypeptide is increased can have a statistically significantly shorter petiole length than a seedling of a corresponding control plant that either lacks the transgene or does not express the transgene. The petiole length can be shorter by at least 20 percent, e.g., 20, 25, 30, 35, 40, 45, 50, 55, 60, 65, 70, or 75 percent, as compared to the petiole length in a corresponding control plant that does not express the transgene.

Examples of acceleration in leaf development include, without limitation, increased leaf thickness and increased leaf area growth when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. Leaf thickness or leaf area growth can be increased by about 0.25% to about 200% (e.g., about 0.25% to about 2%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions.

Examples of decreased apical dominance include, without limitation, increased branching and increased tillering when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. Branching and tillering can be increased by about 0.25% to about 200% (e.g., about 0.25% to about 2%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions.

Examples of increased apical dominance include, without limitation, decreased branching and decreased tillering when comparing a transgenic plant in which a red light specific response pathway polypeptide is down-regulated to a control plant that either lacks the transgene or does not express the transgene grown natural light or other broad spectrum light conditions. Branching and tillering can be decreased by about 0.25% to about 200% (e.g., about 0.25% to about 2%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) in a transgenic plant in which a red light specific response pathway polypeptide is down-regulated grown under natural light or other broad spectrum light conditions as compared to a control plant that either lacks the transgene or does not express the transgene grown natural light or other broad spectrum light conditions.

Examples of increased chloroplast development include, without limitation, increased chlorophyll synthesis and a change in the chlorophyll a:b ratio when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. Chlorophyll synthesis and/or the chlorophyll a:b ratio can be about 0.25% to about 200% (e.g., about 0.25% to about 2%, 0.25% to about 0.5%, about 0.25% to about 1.5%, about 0.5% to about 1%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) greater in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions.

Examples of alterations in flowering and seed/fruit production include, without limitation, a decreased rate of flowering, an increase in seed set, and an increase of fruit development when comparing a transgenic plant expressing an SD+EODFR and/or low light-tolerance polypeptide grown under SD+EODFR conditions or low light conditions to a control plant that does not express an SD+EODFR and/or low light-tolerance polypeptide grown under SD+EODFR conditions or low light conditions. The rate of flowering can be a decreased from about 0.25% to about 90% (e.g., from about 0.25% to about 15%, from about 5% to about 50%, from about 5% to about 10%, from about 25% to about 50%, from about 1% to about 30%, from about 50% to about 90%, from about 20% to about 40%, from about 1% to about 5%, from about 0.5% to about 2%, from about 15% to about 50%, about 20%, about 25%, about 30%, about 35%, about 40%, about 45%, about 50%, about 55%, about 60%, about 65%, about 70%, about 75%, or about 80%) in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions. Seed or fruit weight can be increased by about 0.25% to about 200% (e.g., about 0.25% to about 2%, about 0.5% to about 5%, about 0.5% to about 15%, about 2% to about 10%, about 5% to about 35%, about 10% to about 25%, about 20% to about 80%, about 50% to about 200%, about 100% to about 200%, about 100% to about 150%, about 5%, about 10%, about 20%, about 35%, about 50%, about 70%, about 90%, about 120%, about 180%, or about 200%) in a transgenic plant expressing an SD+EODFR and/or low light-tolerance polypeptide grown under SD+EODFR conditions or low light conditions as compared to a control plant that does not express an SD+EODFR and/or low light-tolerance polypeptide grown under SD+EODFR conditions or low light conditions.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, 51 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. PLANT BREEDING

Genetic polymorphisms are discrete allelic sequence differences in a population. Typically, an allele that is present at 1% or greater is considered to be a genetic polymorphism. The discovery that polypeptides disclosed herein can modulate SD+EODFR and/or low light tolerance is useful in plant breeding, because genetic polymorphisms exhibiting a degree of linkage with loci for such polypeptides are more likely to be correlated with variation in SD+EODFR and/or low light tolerance. For example, genetic polymorphisms linked to the loci for such polypeptides are more likely to be useful in marker-assisted breeding programs to create lines having SD+EODFR and/or low light tolerance.

Thus, one aspect of the invention includes methods of identifying whether one or more genetic polymorphisms are associated with variation in SD+EODFR and/or low light tolerance. Such methods involve determining whether genetic polymorphisms in a given population exhibit linkage with the locus for one of the polypeptides depicted in FIGS. 1-24 and/or a functional homolog thereof. The correlation is measured between variation in SD+EODFR and/or low light tolerance in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in SD+EODFR and/or low light tolerance, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al., (1997) Electrophoresis 18: 1519. The identification of RFLPs is discussed, for example, in Alonso-Blanco et al. (Methods in Molecular Biology, vol. 82, "Arabidopsis Protocols", pp. 137-146, J. M. Martinez-Zapater and J. Salinas, eds., c. 1998 by Humana Press, Totowa, NJ); Burr ("Mapping Genes with Recombinant Inbreds", pp. 249-254, in Freeling, M. and V. Walbot (Ed.), The Maize Handbook, c. 1994 by Springer-Verlag New York, Inc.: New York, NY, USA; Berlin Germany; Burr et al. Genetics (1998) 118: 519; and Gardiner, J. et al., (1993) Genetics 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in SD+EODFR and/or low light tolerance. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. ARTICLES OF MANUFACTURE

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of low light conditions and/or SD+EODFR conditions. Thus, such transgenic plants can be used to provide yield stability under environmentally stressful conditions such as low light conditions and/or SD+EODFR conditions. By providing higher yields under environmentally stressful conditions such as low light conditions and/or SD+EODFR conditions, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

VII. OTHER POLYPEPTIDES, NUCLEIC ACIDS, PLANT CELLS, PLANTS, AND METHODS

In some cases, this document provides methods and materials involved in plant UV-B tolerance. For example, this document provides seeds and plants having cells comprising an exogenous nucleic acid encoding a polypeptide having UV-B tolerance activity as described in U.S. Patent Application Publication No. 2010-0192261 (U.S. patent application Ser. No. 12/373,134), which is incorporated by reference herein in its entirety. In some cases, a plant can include a polypeptide or nucleic acid or can be made to include a polypeptide or nucleic acid such that the sequence of such a polypeptide or nucleic acid is as set forth in one of the identified sequences of U.S. Patent Application Publication No. 2010-0192261 (U.S. patent application Ser. No. 12/373,134) (e.g., SEQ ID NOs:1-119 of U.S. Patent Application Publication No. 2010-0192261 (U.S. patent application Ser. No. 12/373,134)), or is a homolog or ortholog thereof as described in U.S. Patent Application Publication No. 2010-0192261 (U.S. patent application Ser. No. 12/373, 134), or has at least 80% sequence identity (e.g., at least 80%, 85%, 90%, 95%, 97%, 98%, or 99% sequence identity) to an identified sequence of U.S. Patent Application Publication No. 2010-0192261 (U.S. patent application Ser. No. 12/373,134), as set forth in U.S. Patent Application Publication No. 2010-0192261 (U.S. patent application Ser.

No. 12/373,134). SEQ ID NOs:1-119 of U.S. Patent Application Publication No. 2010-0192261 (U.S. patent application Ser. No. 12/373,134), together with the identified activities for each of SEQ ID NOs:1-119, the described homologs and orthologs of SEQ ID NOs:1-119 and their associated activities, the sequences having at least 80% sequence identity (e.g., at least 80%, 85%, 90%, 95%, 97%, 98%, or 99% sequence identity) to SEQ ID NOs:1-119 and their associated activities, the phenotypes of plants containing any one of SEQ ID NOs:1-119 or the described homologs of SEQ ID NOs:1-119 or the described orthologs of SEQ ID NOs:1-119 or the described sequences having at least 80% sequence identity to any one of SEQ ID NOs:1-119, and the working examples and data set forth in Examples 1-6 of U.S. Patent Application Publication No. 2010-0192261 (U.S. patent application Ser. No. 12/373,134) are incorporated by reference herein.

In some cases, this document provides methods and materials involved in tolerance of plants to low light conditions. For example, this document provides transgenic plants and seeds comprising nucleic acids encoding polypeptides that confer tolerance to conditions of low light irradiance as described in U.S. Patent Application Publication No. 2010-0205688 (U.S. Patent Application Ser. No. 12/513,086), which is incorporated by reference herein in its entirety. In some cases, a plant can include a polypeptide or nucleic acid or can be made to include a polypeptide or nucleic acid such that the sequence of such a polypeptide or nucleic acid is as set forth in one of the identified sequences of U.S. Patent Application Publication No. 2010-0205688 (U.S. Patent Application Ser. No. 12/513,086) (e.g., SEQ ID NOs:1-149 of U.S. Patent Application Publication No. 2010-0205688 (U.S. patent application Ser. No. 12/513,086)), or is a homolog or ortholog thereof as described in U.S. Patent Application Publication No. 2010-0205688 (U.S. patent application Ser. No. 12/513,086), or has at least 80% sequence identity (e.g., at least 80%, 85%, 90%, 95%, 97%, 98%, or 99% sequence identity) to an identified sequence of U.S. Patent Application Publication No. 2010-0205688 (U.S. patent application Ser. No. 12/513,086), as set forth in U.S. Patent Application Publication No. 2010-0205688 (U.S. patent application Ser. No. 12/513,086). SEQ ID NOs:1-149 of U.S. Patent Application Publication No. 2010-0205688 (U.S. patent application Ser. No. 12/513,086), together with the identified activities for each of SEQ ID NOs:1-149, the described homologs and orthologs of SEQ ID NOs:1-149 and their associated activities, the sequences having at least 80% sequence identity (e.g., at least 80%, 85%, 90%, 95%, 97%, 98%, or 99% sequence identity) to SEQ ID NOs:1-149 and their associated activities, the phenotypes of plants containing any one of SEQ ID NOs:1-149 or the described homologs of SEQ ID NOs:1-149 or the described orthologs of SEQ ID NOs:1-149 or the described sequences having at least 80% sequence identity to any one of SEQ ID NOs:1-149, and the working examples and data set forth in Examples 1-8 of U.S. Patent Application Publication No. 2010-0205688 (U.S. Patent Application Ser. No. 12/513,086) are incorporated by reference herein.

In some cases, this document provides methods and materials involved in shade tolerance in plants. For example, this document provides plants having increased shade tolerance as well as materials and methods for making plants having increased shade tolerance and plant products derived from plants having increased shade tolerance as described in U.S. Patent Application Publication No. 2010-0199378 (U.S. patent application Ser. No. 12/515,687), which is incorporated by reference herein in its entirety. In some cases, a plant can include a polypeptide or nucleic acid or can be made to include a polypeptide or nucleic acid such that the sequence of such a polypeptide or nucleic acid is as set forth in one of the identified sequences of U.S. Patent Application Publication No. 2010-0199378 (U.S. patent application Ser. No. 12/515,687) (e.g., SEQ ID NOs:1-171 of U.S. Patent Application Publication No. 2010-0199378 (U.S. Patent Application Ser. No. 12/515,687)), or is a homolog or ortholog thereof as described in U.S. Patent Application Publication No. 2010-0199378 (U.S. Patent Application Ser. No. 12/515,687), or has at least 80% sequence identity (e.g., at least 80%, 85%, 90%, 95%, 97%, 98%, or 99% sequence identity) to an identified sequence of U.S. Patent Application Publication No. 2010-0199378 (U.S. patent application Ser. No. 12/515,687), as set forth in U.S. Patent Application Publication No. 2010-0199378 (U.S. patent application Ser. No. 12/515,687). SEQ ID NOs:1-171 of U.S. Patent Application Publication No. 2010-0199378 (U.S. Patent Application Ser. No. 12/515,687), together with the identified activities for each of SEQ ID NOs:1-171, the described homologs and orthologs of SEQ ID NOs:1-171 and their associated activities, the sequences having at least 80% sequence identity (e.g., at least 80%, 85%, 90%, 95%, 97%, 98%, or 99% sequence identity) to SEQ ID NOs:1-171 and their associated activities, the phenotypes of plants containing any one of SEQ ID NOs:1-171 or the described homologs of SEQ ID NOs:1-171 or the described orthologs of SEQ ID NOs:1-171 or the described sequences having at least 80% sequence identity to any one of SEQ ID NOs:1-171, and the working examples and data set forth in Examples 1-11 of U.S. Patent Application Publication No. 2010-0199378 (U.S. Patent Application Ser. No. 12/515,687) are incorporated by reference herein.

In some cases, this document provides methods and materials involved in tolerance of plants to low light conditions. For example, this document provides transgenic plants and seeds comprising nucleic acids encoding polypeptides that confer tolerance to conditions of low light irradiance as described in U.S. Patent Application Publication No. 2010-0119688 (U.S. patent application Ser. No. 12/307,561), which is incorporated by reference herein in its entirety. In some cases, a plant can include a polypeptide or nucleic acid or can be made to include a polypeptide or nucleic acid such that the sequence of such a polypeptide or nucleic acid is as set forth in one of the identified sequences of U.S. Patent Application Publication No. 2010-0119688 (U.S. patent application Ser. No. 12/307,561) (e.g., SEQ ID NOs:1-146 of U.S. Patent Application Publication No. 2010-0119688 (U.S. patent application Ser. No. 12/307,561)), or is a homolog or ortholog thereof as described in U.S. Patent Application Publication No. 2010-0119688 (U.S. patent application Ser. No. 12/307,561), or has at least 80% sequence identity (e.g., at least 80%, 85%, 90%, 95%, 97%, 98%, or 99% sequence identity) to an identified sequence of U.S. Patent Application Publication No. 2010-0119688 (U.S. patent application Ser. No. 12/307,561), as set forth in U.S. Patent Application Publication No. 2010-0119688 (U.S. patent application Ser. No. 12/307,561). SEQ ID NOs:1-146 of U.S. Patent Application Publication No. 2010-0119688 (U.S. patent application Ser. No. 12/307,561), together with the identified activities for each of SEQ ID NOs:1-146, the described homologs and orthologs of SEQ ID NOs:1-146 and their associated activities, the sequences having at least 80% sequence identity (e.g., at least 80%, 85%, 90%, 95%, 97%, 98%, or 99% sequence identity) to SEQ ID NOs:1-146 and their associated activities, the phenotypes of plants containing any one of SEQ ID NOs: 1-146 or the described homologs of SEQ ID NOs:1-146 or the described orthologs of SEQ ID NOs:1-146 or the described sequences having at least 80% sequence identity to any one of SEQ ID NOs:1-146, and the working examples and data set forth in Examples 1-22 of U.S. Patent Application Publication No. 2010-0119688 (U.S. patent application Ser. No. 12/307,561) are incorporated by reference herein.

In some cases, this document provides methods and materials involved in modulating biomass levels in plants. For example, this document provides plants having increased biomass levels as well as materials and methods for making plants and plant products having increased biomass levels as described in International Patent Application Publication No. WO 2010/033564 and U.S. patent application Ser. No. 13/119,572, which are incorporated by reference herein in their entireties. In some cases, a plant can include a polypeptide or nucleic acid or can be made to include a polypeptide or nucleic acid such that the sequence of such a polypeptide or nucleic acid is as set forth in one of the identified sequences of International Patent Application Publication No. WO 2010/033564 and U.S. patent application Ser. No. 13/119,572 (e.g., SEQ ID NOs:1-638 of International Patent Application Publication No. WO 2010/033564 and U.S. patent application Ser. No. 13/119,572), or is a homolog or ortholog thereof as described in International Patent Application Publication No. WO 2010/033564 and U.S. patent application Ser. No. 13/119,572, or has at least 80% sequence identity (e.g., at least 80%, 85%, 90%, 95%, 97%, 98%, or 99% sequence identity) to an identified sequence of International Patent Application Publication No. WO 2010/033564 and U.S. patent application Ser. No. 13/119,572, as set forth in International Patent Application Publication No. WO 2010/033564 and U.S. patent application Ser. No. 13/119,572. SEQ ID NOs:1-638 of International Patent Application Publication No. WO 2010/033564 and U.S. patent application Ser. No. 13/119,572, together with the identified activities for each of SEQ ID NOs:1-638, the described homologs and orthologs of SEQ ID NOs:1-638 and their associated activities, the sequences having at least 80% sequence identity (e.g., at least 80%, 85%, 90%, 95%, 97%, 98%, or 99% sequence identity) to SEQ ID NOs:1-638 and their associated activities, the phenotypes of plants containing any one of SEQ ID NOs:1-638 or the described homologs of SEQ ID NOs:1-638 or the described orthologs of SEQ ID NOs:1-638 or the described sequences having at least 80% sequence identity to any one of SEQ ID NOs:1-638, and the working examples and data set forth in Examples 1-11 of International Patent Application Publication No. WO 2010/033564 and U.S. patent application Ser. No. 13/119,572 are incorporated by reference herein.

The invention will be further described in the following examples, which do not limit the scope of the invention described in the claims.

VIII. EXAMPLES

Example 1—Transgenic *Arabidopsis* Plants

The following symbols are used in the Examples with respect to *Arabidopsis* transformation: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

Nucleic acids were isolated from *Arabidopsis thaliana* plants, and cloned into a Ti plasmid vector, CRS338 or CRS 811, under the control of a 35S promoter. Each construct contained a phosphinothricin acetyltransferase gene which confers Finale™ resistance to transformed plants. Wild-type *Arabidopsis thaliana* ecotype Wassilewskija (Ws) plants were transformed separately with each construct. The transformations were performed essentially as described in Bechtold et al., *C.R. Acad. Sci. Paris*, 316:1194-1199 (1993).

Transgenic *Arabidopsis* lines containing SEQ ID NO:1, SEQ ID NO:69, SEQ ID NO:127, SEQ ID NO:315, SEQ ID NO:335, SEQ ID NO:454, SEQ ID NO:537, SEQ ID NO:568, SEQ ID NO:604, SEQ ID NO:632, SEQ ID NO:642, SEQ ID NO:848, SEQ ID NO:905, SEQ ID NO:951, SEQ ID NO:1023, SEQ ID NO:1045, SEQ ID NO:1150, SEQ ID NO:1276, SEQ ID NO:1345, SEQ ID NO:1456, SEQ ID NO:1496, SEQ ID NO:1539, SEQ ID NO:1586, SEQ ID NO:1629, or SEQ ID NO:1634 were designated, ME05268, ME06120, ME09503, ME10007, ME10852, ME11939, ME12006, ME12596, ME12899, ME13456, ME15935, ME16594, ME16597, ME16630, ME17128, ME17578, ME18158, ME18314, ME18408, ME19304, ME19738, ME19971, ME20871, ME21199, or ME21508, respectively. The presence of each vector containing a nucleic acid described above in the respective transgenic *Arabidopsis* line transformed with the vector was confirmed by Finale™ resistance, PCR amplification from green leaf tissue extract, and/or sequencing of PCR products.

Example 2—Identification of Transgenic Plants Tolerant to Low Light Conditions

Wild-type and transgenic seeds were sterilized, plated on solid 0.5× MS medium containing 5 g/L sucrose, and stratified at 4° C. in the dark for three days. After stratification, plates containing the seeds were allowed to reach room temperature. The plates were then transferred to a Conviron walk-in growth chamber (Controlled Environments Inc., Pambina, ND) at 22° C. and 70% humidity with a 16:8 hour light:dark cycle. Lighting was supplied by 32 watt fluorescent bulbs (Sylvania, F032/841/ECO, Danvers, MA), providing a red:far-red ratio of 13:1. The plates were covered with three layers of shade cloth (New York wire, charcoal fiberglass screen, 857650; Home Depot, Atlanta, GA) such that the irradiance was about 10 μmol/m²/s. The plates were rotated daily and monitored for changes in hypocotyl elongation. After 48 hours, the plates were scored for late germinators, which were eliminated from consideration as candidate plants having reduced hypocotyl elongation under low light conditions. Each seedling was transplanted to an 8×8 cm well of a flat containing a total of 18 wells (three wells by six wells) and measuring 24 cm by 48 cm in size.

Seedlings maintained under conditions of irradiance with about 10 pimol/m² ls of light fbr seven days at 22° C. were analyzed for hypocotyl length. The hypocotyls of individual seedlings were determined to be "long" or "short" based on qualitative observation.

Example 3—Identification of Transgenic Plants Tolerant to Short Day Plus End-of-Day-Far-Red (SD+EODFR) Conditions A Short Day plus End-of-Day-Far-Red (SD+EODFR) assay was carried out on seedlings in order to evaluate the effect of SD+EODFR conditions on hypocotyl length. For the SD+EODFR assay, seeds were plated on 0.5% sucrose, 1×MS media (PhytoTech) agar plates, cold-treated for 3-4 days at 4° C., then germinated for 2 days under continuous white light at about 60 µmol/m$^2$/s in walk-in Conviron growth chambers. Seedlings were then exposed to SD+EODFR conditions for 4 days. SD+EODFR conditions were 9.5 hours light, followed by a 30 minute pulse of far-red light at the end of each light cycle, alternating with 14 hours of darkness. Two Gro-Lux (Sylvania, 24660) and two Cool White (Phillips) lights at about 60 µmol/m$^2$/s PPFD, with a red: far-red ratio of about 5.5, were used for the light cycle; the fluence rates under these conditions were: blue$_{450}$=12 µmol/m$^2$/s, red 633=22 µmol/m$^2$/s, far-red$_{740}$=4 µmol/m$^2$/s, PPFD$_{400-700}$=55 µmol/m$^2$/s. The far-red pulse was generated by 3 SNAP-LITE Far-red light boxes (Quantum devices, SL1515-670-735) at about 8 µmol/m$^2$/s PPFD, with a red: far-red ratio of about 0.14; the fluence rates under these conditions were: blue$_{450}$=0.004 µmol/m$^2$/s, red$_{633}$=ss, far-red$_{740}$=70 µmol/m$^2$/s, PPFD$_{400-700}$=8 µmol/m$^2$/s. Control seedlings were cultured exactly as above except that they did not receive the far-red pulse; that is, following germination, they were exposed for two days to a cycle of 10 hours of light alternating with 14 hours of darkness under 2 Gro-Lux and 2 Cool white lights at about 60 µmol/m$^2$/s PPFD, with a red: far-red ratio of about 5.5. Plates were rotated on the third day after plating and hypocotyl length was characterized on the fourth day after plating. The hypocotyls of individual seedlings were determined to be "long" or "short" based on qualitative observation.

Seedlings were then sprayed with sterile Finale® (concentration=0.63%), on two subsequent days, then allowed to grow for 24 hours before chlorophyll fluorescence imaging was done to determine the Finale® resistant:Finale® sensitive ratio. Finale® sensitivity was determined by placing plates of Finale® treated seedlings in a chlorophyll fluorescence imager (CF Imager, Technologica Limited, UK). Finale® resistant seedlings appeared red and Finale® sensitive seedlings appeared blue. Hypocotyl lengths from Finale® resistant seedlings and Finale® sensitive seedlings were then subjected to a Chi-squared analysis to determine statistical significance.

Example 4—Results for ME05268, ME06120, ME09503, ME10007, ME10852, ME11939, ME13456, ME15935, ME16594, ME16597, ME16630, ME17128, ME17578, ME18158, ME18314, ME19304, ME19738, ME20871, ME21199, and ME21508 Events T$_3$ and T$_4$ seed from event -03 of ME05268, T$_2$ and T$_3$ seed from event -04 of ME05268, T$_2$ and T$_3$ seed from events -11 and -12 of ME06120, T$_2$ and T$_3$ seed from events -03 and -07 of ME09503, T$_2$ and T$_3$ seed from events -02 and -05 of ME10007, T$_2$ and T$_3$ seed from events -03 and -04 of ME10852, T$_2$ and T$_3$ seed from events -01, -02, and -03 of ME11939, T$_2$ and T$_3$ seed from events -02 and -05 of ME13456, T$_2$ and T$_3$ seed from events -03 and -04 of ME15935, T$_3$ and T$_4$ seed from events -02 and -05 of ME16594, T$_2$ and T$_3$ seed from events -01, -04, and -06 of ME16597, T$_2$ and T$_3$ seed from events -01, -02, and -04 of ME16630, T$_2$ and T$_3$ seed from events -02, -03, and -03 of ME17128, T$_2$ and T$_3$ seed from events -01 and -03 of ME17578, T$_2$ and T$_3$ seed from events -01, -03, and -04 of ME18158, T$_2$ and T$_3$ seed from events -01, -02, -03, and -04 of ME18314, T$_2$ and T$_3$ seed from events -07 and -08 of ME19304, T$_2$ and T$_3$ seed from events -02 and -05 of ME19738, T$_2$ and T$_3$ seed from events -03, -05, and -10 of ME20871, T$_2$ and T$_3$ seed from events -01, -03 and -05 of ME21199, T$_2$ and T$_3$ seed from events -01 and -05 of ME21508 was grown under low light conditions and evaluated for hypocotyl length as described in Example 2.

A Chi-square test was performed to compare transgenic seedlings and corresponding non-transgenic segregants having a short or a long hypocotyl. A hypocotyl having a length similar to the hypocotyl length typically exhibited by wild-type *Arabidopsis* seedlings grown under normal light conditions (e.g., about 100 mmol/m$^2$/s of white light) was considered a short hypocotyl, whereas a hypocotyl having a length similar to that typically exhibited by wild-type *Arabidopsis* seedlings grown under low light conditions (e.g., about 10 mmol/m$^2$/s of white light) was considered a long hypocotyl. Wild-type *Arabidopsis* seeds grown for seven days at 22° C. under conditions of irradiance with about 100 mmol/m$^2$/s of white light and a 16:8 hour light:dark cycle typically form hypocotyls that are about 1-3 mm in length. Under conditions of irradiance with about 10 mmol/m$^2$/s of white light, the hypocotyls typically are about 5-7 mm in length.

Seedlings from event -03 of ME05268; event -04 of ME05268; events -11 and -12 of ME06120; events -03 and -07 of ME09503; events -02 and -05 of ME10007; events -03 and -04 of ME10852; events -01, -02, and -03 of ME11939; events -02 and -05 of ME13456; events -03 and -04 of ME15935; events -02 and -05 of ME16594; events -01, -04, and -06 of ME16597; events -01, -02, and -04 of ME16630; events -02, -03, and -03 of ME17128; events -01 and -03 of ME17578; events -01, -03, and -04 of ME18158; events -01, -02, -03, and -04 of ME18314; events -07 and -08 of ME19304; events -02 and -05 of ME19738; events -03, -05, and -10 of ME20871; events -01, -03 and -05 of ME21199; and events -01 and -05 of ME21508 displayed a short hypocotyl under low light conditions in both the T$_2$ and T$_3$ generations, and the transgene was linked to the short hypocotyl phenotype with a confidence level of p<0.05 (Tables 1-23).

T$_3$ or T$_4$ data designated with -99 are data obtained from seed pooled from multiple individual plants of the indicated generation and event.

TABLE 1

| Hypocotyl length in seedlings from ME05268 | | | | |
|---|---|---|---|---|
| Plants | Short Hypocotyl | Long Hypocotyl | Chi-Square | p-value |
| T$_3$ seedlings from event -03-99 of ME05268 | 32 | 6 | 54.35 | 1.68E−13 |
| T$_3$ non-transgenic segregants of event -03-99 of ME05268 | 0 | 37 | | |
| T$_4$ seedlings from event -03-99-99 of ME05268 | 69 | 3 | 53.00 | 1.68E−13 |
| T$_4$ non-transgenic segregants of event -03-99-99 of ME05268 | 0 | 7 | | |
| T$_2$ seedlings from event -04 of ME05268 | 55 | 9 | 17.98 | 2.23E−05 |
| T$_2$ non-transgenic segregants of event -04 of ME05268 | 0 | 4 | | |
| T$_3$ seedlings from event -04-99 of ME05268 | 52 | 8 | 40.81 | 1.68E−10 |
| T$_3$ non-transgenic segregants of event -04-99 of ME05268 | 0 | 14 | | |

TABLE 2

Hypocotyl length in seedlings from ME06120

| Plants | Short Hypocotyl | Long Hypocotyl | Chi-Square | p-value |
|---|---|---|---|---|
| T$_2$ seedlings from event -11 of ME06120 | 26 | 4 | 16.89 | 3.96E−05 |
| T$_2$ non-transgenic segregants of event -11 of ME05268 | 1 | 7 | | |
| T$_3$ seedlings from event -11-99 of ME06120 | 52 | 3 | 37.89 | 7.48E−10 |
| T$_3$ non-transgenic segregants of event -11-99 of ME06120 | 4 | 13 | | |
| T$_2$ seedlings from event -12 of ME06120 | 27 | 2 | 14.43 | 1.45E−04 |
| T$_2$ non-transgenic segregants of event -12 of ME06120 | 0 | 2 | | |
| T$_3$ seedlings from event -12-99 of ME ME06120 | 46 | 0 | 39.93 | 2.63E−10 |
| T$_3$ non-transgenic segregants of event -12-99 of ME ME06120 | 1 | 4 | | |

TABLE 3

Hypocotyl length in seedlings from ME09503

| Plants | Short Hypocotyl | Long Hypocotyl | Chi-Square | p-value |
|---|---|---|---|---|
| T$_2$ seedlings from event -03 of ME09503 | 34 | 4 | 35.47 | 2.59E−09 |
| T$_2$ non-transgenic segregants of event -03 of ME09503 | 1 | 16 | | |
| T$_3$ seedlings from event -03-99 of ME09503 | 55 | 0 | 68.85 | 1.06E−16 |
| T$_3$ non-transgenic segregants of event -03-99 of ME09503 | 1 | 18 | | |
| T$_2$ seedlings from event -07 of ME09503 | 46 | 1 | 44.94 | 2.03E−11 |
| T$_2$ non-transgenic segregants of event -07 of ME09503 | 2 | 12 | | |
| T$_3$ seedlings from event -07-99 of ME09503 | 72 | 1 | 56.91 | 4.56E−14 |
| T$_3$ non-transgenic segregants of event -07-99 of ME09503 | 1 | 6 | | |

TABLE 4

Hypocotyl length in seedlings from ME10007

| Plants | Short Hypocotyl | Long Hypocotyl | Chi-Square | p-value |
|---|---|---|---|---|
| T$_2$ seedlings from event -02 of ME10007 | 57 | 3 | 42.15 | 8.45E−11 |
| T$_2$ non-transgenic segregants of event -02 of ME10007 | 5 | 15 | | |
| T$_3$ seedlings from event -02-99 of ME10007 | 50 | 8 | 40.30 | 2.18E−10 |
| T$_3$ non-transgenic segregants of event -02-99 of ME10007 | 2 | 19 | | |
| T$_2$ seedlings from event -05 of ME10007 | 58 | 0 | 37.14 | 1.10E−09 |
| T$_2$ non-transgenic segregants of event -05 of ME10007 | 9 | 11 | | |
| T$_3$ seedlings from event -05-99 of ME10007 | 49 | 6 | 39.36 | 3.53E−10 |
| T$_3$ non-transgenic segregants of event -05-99 of ME10007 | 3 | 18 | | |

TABLE 5

Hypocotyl length in seedlings from ME10852

| Plants | Short Hypocotyl | Long Hypocotyl | Chi-Square | p-value |
|---|---|---|---|---|
| T$_2$ seedlings from event -03 of ME10852 | 57 | 1 | 48.97 | 2.59E−12 |
| T$_2$ non-transgenic segregants of event -03 of ME10852 | 5 | 15 | | |
| T$_3$ seedlings from event -03-99 of ME10852 | 55 | 0 | 35.66 | 2.59E−09 |
| T$_3$ non-transgenic segregants of event -03-99 of ME10852 | 11 | 13 | | |
| T$_2$ seedlings from event -04 of ME10852 | 57 | 0 | 71.00 | 3.57E−17 |
| T$_2$ non-transgenic segregants of event -04 of ME10852 | 0 | 14 | | |
| T$_3$ seedlings from event -04-99 of ME10852 | 63 | 3 | 57.75 | 2.97E−14 |
| T$_3$ non-transgenic segregants of event -04-99 of ME10852 | 0 | 11 | | |

TABLE 6

Hypocotyl length in seedlings from ME11939

| Plants | Short Hypocotyl | Long Hypocotyl | Chi-Square | p-value |
|---|---|---|---|---|
| T$_2$ seedlings from event -01 of ME13 | 32 | 6 | 29.39 | 5.93E−08 |
| T$_2$ non-transgenic segregants of event -01 of ME11939 | 0 | 13 | | |
| T$_3$ seedlings from event -01-99 of ME11939 | 47 | 0 | 52.88 | 3.55E−13 |
| T$_3$ non-transgenic segregants of event -01-99 of ME11939 | 2 | 14 | | |
| T$_2$ seedlings from event -02 of ME11939 | 42 | 5 | 23.34 | 1.35E−06 |
| T$_2$ non-transgenic segregants of event -02 of ME11939 | 4 | 11 | | |
| T$_3$ seedlings from event -02-99 of ME11939 | 46 | 2 | 44.94 | 2.03E−11 |
| T$_3$ non-transgenic segregants of event -02-99 of ME11939 | 1 | 12 | | |
| T$_2$ seedlings from event -05 of ME11939 | 45 | 8 | 27.72 | 1.40E−07 |
| T$_2$ non-transgenic segregants of event -05 of ME11939 | 4 | 16 | | |
| T$_3$ seedlings from event -05-99 of ME11939 | 33 | 0 | 27.59 | 1.50E−07 |
| T$_3$ non-transgenic segregants of event -05-99 of ME11939 | 3 | 7 | | |

TABLE 7

Hypocotyl length in seedlings from ME13456

| Plants | Short Hypocotyl | Long Hypocotyl | Chi-Square | p-value |
|---|---|---|---|---|
| T$_2$ seedlings from event -02 of ME13456 | 18 | 1 | 12.28 | 4.58E−04 |
| T$_2$ non-transgenic segregants of event -02 of ME13456 | 3 | 6 | | |
| T$_3$ seedlings from event -02-99 of ME13456 | 47 | 3 | 34.55 | 4.16E−09 |
| T$_3$ non-transgenic segregants of event -02-99 of ME13456 | 1 | 8 | | |
| T$_2$ seedlings from event -05 of ME13456 | 14 | 2 | 13.13 | 2.91E−04 |
| T$_2$ non-transgenic segregants of event -05 of ME13456 | 0 | 5 | | |

TABLE 7-continued

Hypocotyl length in seedlings from ME13456

| Plants | Short Hypocotyl | Long Hypocotyl | Chi-Square | p-value |
|---|---|---|---|---|
| $T_3$ seedlings from event -05-99 of ME13456 | 21 | 3 | 23.42 | 1.30E−06 |
| $T_3$ non-transgenic segregants of event -05-99 of ME13456 | 1 | 13 | | |

TABLE 8

Hypocotyl length in seedlings from ME15935

| Plants | Short Hypocotyl | Long Hypocotyl | Chi-Square | p-value |
|---|---|---|---|---|
| $T_2$ seedlings from event -03 of ME15935 | 44 | 2 | 33.90 | 5.81E−09 |
| $T_2$ non-transgenic segregants of event -03 of ME15935 | 2 | 12 | | |
| $T_3$ seedlings from event -03-99 of ME15935 | 53 | 3 | 51.86 | 5.97E−13 |
| $T_3$ non-transgenic segregants of event -03-99 of ME15935 | 1 | 15 | | |
| $T_2$ seedlings from event -04 of ME15935 | 23 | 0 | 33.00 | 9.22E−09 |
| $T_2$ non-transgenic segregants of event -04 of ME15935 | 0 | 10 | | |
| $T_3$ seedlings from event -04-99 of ME15935 | 58 | 0 | 41.24 | 1.34E−10 |
| $T_3$ non-transgenic segregants of event -04-99 of ME15935 | 2 | 4 | | |

TABLE 9

Hypocotyl length in seedlings from ME16594

| Plants | Short Hypocotyl | Long Hypocotyl | Chi-Square | p-value |
|---|---|---|---|---|
| $T_2$ seedlings from event -02 of ME16594 | 16 | 0 | 37.14 | 1.10E−09 |
| $T_2$ non-transgenic segregants of event -02 of ME16594 | 12 | 52 | | |
| $T_3$ seedlings from event -02-99 of ME16594 | 46 | 10 | 10.18 | 1.42E−03 |
| $T_3$ non-transgenic segregants of event -02-99 of ME16594 | 4 | 7 | | |
| $T_2$ seedlings from event -05 of ME16594 | 35 | 2 | 52.10 | 5.28E−13 |
| $T_2$ non-transgenic segregants of event -05 of ME16594 | 4 | 33 | | |
| $T_3$ seedlings from event -05-99 of ME16594 | 41 | 11 | 5.14 | 2.34E−02 |
| $T_3$ non-transgenic segregants of event -05-99 of ME16594 | 5 | 6 | | |

TABLE 10

Hypocotyl length in seedlings from ME16597

| Plants | Short Hypocotyl | Long Hypocotyl | Chi-Square | p-value |
|---|---|---|---|---|
| $T_2$ seedlings from event -01 of ME16597 | 18 | 6 | 16.99 | 3.77E−05 |
| $T_2$ non-transgenic segregants of event -01 of ME16597 | 0 | 11 | | |
| $T_3$ seedlings from event -01-99 of ME16597 | 69 | 3 | 55.76 | 8.20E−04 |
| $T_3$ non-transgenic segregants of event -01-99 of ME16597 | 0 | 8 | | |
| $T_2$ seedlings from event -04 of ME16597 | 25 | 3 | 21.88 | 2.91E−06 |
| $T_2$ non-transgenic segregants of event -04 of ME16597 | 0 | 7 | | |
| $T_3$ seedlings from event -04-99 of ME16597 | 54 | 5 | 32.49 | 1.20E−08 |
| $T_3$ non-transgenic segregants of event -04-99 of ME16597 | 3 | 11 | | |
| $T_2$ seedlings from event -04 of ME16597 | 44 | 5 | 34.14 | 5.12E−09 |
| $T_2$ non-transgenic segregants of event -04 of ME16597 | 4 | 17 | | |
| $T_3$ seedlings from event -04-99 of ME16597 | 49 | 4 | 43.99 | 3.30E−11 |
| $T_3$ non-transgenic segregants of event -04-99 of ME16597 | 3 | 18 | | |

TABLE 11

Hypocotyl length in seedlings from ME16630

| Plants | Short Hypocotyl | Long Hypocotyl | Chi-Square | p-value |
|---|---|---|---|---|
| $T_2$ seedlings from event -01 of ME16630 | 49 | 7 | 49.26 | 2.24E−12 |
| $T_2$ non-transgenic segregants of event -01 of ME16630 | 0 | 20 | | |
| $T_3$ seedlings from event -01-99 of ME16630 | 59 | 1 | 55.63 | 8.75E−14 |
| $T_3$ non-transgenic segregants of event -01-99 of ME16630 | 0 | 6 | | |
| $T_2$ seedlings from event -02 of ME16630 | 32 | 9 | 25.13 | 5.36E−07 |
| $T_2$ non-transgenic segregants of event -02 of ME16630 | 4 | 22 | | |
| $T_3$ seedlings from event -02-99 of ME16630 | 43 | 6 | 33.59 | 6.79E−09 |
| $T_3$ non-transgenic segregants of event -02-99 of ME16630 | 2 | 15 | | |
| $T_2$ seedlings from event -04 of ME16630 | 60 | 9 | 19.53 | 9.89E−06 |
| $T_2$ non-transgenic segregants of event -04 of ME16630 | 0 | 4 | | |
| $T_3$ seedlings from event -04-99 of ME16630 | 65 | 9 | 12.14 | 4.94E−04 |
| $T_3$ non-transgenic segregants of event -04-99 of ME16630 | 0 | 2 | | |

TABLE 12

Hypocotyl length in seedlings from ME17128

| Plants | Short Hypocotyl | Long Hypocotyl | Chi-Square | p-value |
|---|---|---|---|---|
| $T_2$ seedlings from event -02 of ME17128 | 31 | 0 | 38.00 | 7.07E−10 |
| $T_2$ non-transgenic segregants of event -02 of ME17128 | 0 | 7 | | |

TABLE 12-continued

Hypocotyl length in seedlings from ME17128

| Plants | Short Hypocotyl | Long Hypocotyl | Chi-Square | p-value |
|---|---|---|---|---|
| $T_3$ seedlings from event -02-99 of ME17128 | 68 | 0 | 70.78 | 4.00E−17 |
| $T_3$ non-transgenic segregants of event -02-99 of ME17128 | 1 | 10 | | |
| $T_2$ seedlings from event -03 of ME17128 | 21 | 11 | 11.05 | 8.86E−04 |
| $T_2$ non-transgenic segregants of event -03 of ME17128 | 0 | 8 | | |
| $T_3$ seedlings from event -03-99 of ME17128 | 74 | 0 | 80.00 | 3.74E−19 |
| $T_3$ non-transgenic segregants of event -03-99 of ME17128 | 0 | 6 | | |
| $T_2$ seedlings from event -04 of ME17128 | 28 | 4 | 18.06 | 2.14E−05 |
| $T_2$ non-transgenic segregants of event -04 of ME17128 | 1 | 7 | | |
| $T_3$ seedlings from event -04-99 of ME17128 | 62 | 0 | 39.42 | 3.41E−10 |
| $T_3$ non-transgenic segregants of event -04-99 of ME17128 | 7 | 9 | | |

TABLE 13

Hypocotyl length in seedlings from ME17578

| Plants | Short Hypocotyl | Long Hypocotyl | Chi-Square | p-value |
|---|---|---|---|---|
| $T_2$ seedlings from event-01 of ME17578 | 32 | 1 | 32.42 | 1.24E−08 |
| $T_2$ non-transgenic segregants of event-01 of ME17578 | 0 | 6 | | |
| $T_3$ seedlings from event-01-99 of ME17578 | 63 | 0 | 69.06 | 9.56E−17 |
| $T_3$ non-transgenic segregants of event-01-99 of ME17578 | 1 | 12 | | |
| $T_2$ seedlings from event-03 of ME17578 | 20 | 0 | 30.00 | 4.32E−08 |
| $T_2$ non-transgenic segregants of event-03 of ME17578 | 0 | 10 | | |
| $T_3$ seedlings from event-03-99 of ME17578 | 29 | 4 | 19.26 | 1.14E−05 |
| $T_3$ non-transgenic segregants of event-03-99 of ME17578 | 14 | 24 | | |

TABLE 14

Hypocotyl length in seedlings from ME18158

| Plants | Short Hypocotyl | Long Hypocotyl | Chi-Square | p-value |
|---|---|---|---|---|
| $T_2$ seedlings from event-01 of ME18158 | 23 | 2 | 22.31 | 2.33E−06 |
| $T_2$ non-transgenic segregants of event-01 of ME18158 | 2 | 11 | | |
| $T_3$ seedlings from event-01-99 of ME18158 | 61 | 0 | 54.93 | 1.25E−13 |
| $T_3$ non-transgenic segregants of event-01-99 of ME18158 | 1 | 5 | | |
| $T_2$ seedlings from event-02 of ME18158 | 25 | 5 | 7.62 | 5.78E−03 |
| $T_2$ non-transgenic segregants of event-02 of ME18158 | 0 | 2 | | |
| $T_3$ seedlings from event-02-99 of ME18158 | 70 | 0 | 7.88 | 5.01E−03 |
| $T_3$ non-transgenic segregants of event-02-99 of ME18158 | 8 | 1 | | |
| $T_2$ seedlings from event-04 of ME18158 | 22 | 3 | 27.17 | 1.86E−07 |
| $T_2$ non-transgenic segregants of event-04 of ME18158 | 0 | 13 | | |
| $T_3$ seedlings from event-04-99 of ME18158 | 22 | 3 | 49.13 | 2.40E−12 |
| $T_3$ non-transgenic segregants of event-04-99 of ME18158 | 0 | 13 | | |

TABLE 15

Hypocotyl length in seedlings from ME18314

| Plants | Short Hypocotyl | Long Hypocotyl | Chi-Square | p-value |
|---|---|---|---|---|
| $T_2$ seedlings from event-01 of ME18314 | 13 | 14 | 5.72 | 1.67E−02 |
| $T_2$ non-transgenic segregants of event-01 of ME18314 | 1 | 11 | | |
| $T_3$ seedlings from event-01-99 of ME18314 | 62 | 0 | 47.75 | 4.85E−12 |
| $T_3$ non-transgenic segregants of event-01-99 of ME18314 | 2 | 5 | | |
| $T_2$ seedlings from event-02 of ME18314 | 16 | 9 | 4.48 | 3.43E−02 |
| $T_2$ non-transgenic segregants of event-02 of ME18314 | 0 | 3 | | |
| $T_3$ seedlings from event-02-99 of ME18314 | 56 | 0 | 46.67 | 8.41E−12 |
| $T_3$ non-transgenic segregants of event-02-99 of ME18314 | 4 | 10 | | |
| $T_2$ seedlings from event-03 of ME18314 | 18 | 6 | 4.78 | 2.88E−02 |
| $T_2$ non-transgenic segregants of event-03 of ME18314 | 6 | 9 | | |
| $T_3$ seedlings from event-03-99 of ME18314 | 37 | 0 | 42.00 | 9.13E−11 |
| $T_3$ non-transgenic segregants of event-03-99 of ME18314 | 0 | 5 | | |
| $T_2$ seedlings from event-04 of ME18314 | 24 | 3 | 20.84 | 4.99E−06 |
| $T_2$ non-transgenic segregants of event-04 of ME18314 | 2 | 11 | | |
| $T_3$ seedlings from event-04-99 of ME18314 | 67 | 0 | 79.00 | 6.21E−19 |
| $T_3$ non-transgenic segregants of event-04-99 of ME18314 | 0 | 12 | | |

TABLE 16

Hypocotyl length in seedlings from ME19304

| Plants | Short Hypocotyl | Long Hypocotyl | Chi-Square | p-value |
|---|---|---|---|---|
| $T_2$ seedlings from event-07 of ME19304 | 28 | 1 | 29.22 | 6.48E−08 |
| $T_2$ non-transgenic segregants of event-07 of ME19304 | 1 | 9 | | |
| $T_3$ seedlings from event-07-99 of ME19304 | 57 | 0 | 40.51 | 1.95E−10 |
| $T_3$ non-transgenic segregants of event-07-99 of ME19304 | 8 | 12 | | |
| $T_2$ seedlings from event-08 of ME19304 | 18 | 11 | 7.67 | 5.62E−03 |
| $T_2$ non-transgenic segregants of event-08 of ME19304 | 0 | 6 | | |
| $T_3$ seedlings from event-08-99 of ME19304 | 69 | 0 | 63.61 | 1.52E−15 |

TABLE 16-continued

Hypocotyl length in seedlings from ME19304

| Plants | Short Hypocotyl | Long Hypocotyl | Chi-Square | p-value |
|---|---|---|---|---|
| $T_3$ non-transgenic segregants of event-08-99 of ME19304 | 2 | 9 | | |

TABLE 17

Hypocotyl length in seedlings from ME19738

| Plants | Short Hypocotyl | Long Hypocotyl | Chi-Square | p-value |
|---|---|---|---|---|
| $T_2$ seedlings from event-02 of ME19738 | 32 | 0 | 20.84 | 4.99E−06 |
| $T_2$ non-transgenic segregants of event-02 of ME19738 | 0 | 7 | | |
| $T_3$ seedlings from event-02-99 of ME19738 | 68 | 0 | 80.00 | 3.74E−19 |
| $T_3$ non-transgenic segregants of event-02-99 of ME19738 | 0 | 12 | | |
| $T_2$ seedlings from event-05 of ME19738 | 22 | 6 | 15.76 | 7.20E−05 |
| $T_2$ non-transgenic segregants of event-05 of ME19738 | 1 | 10 | | |
| $T_3$ seedlings from event-05-99 of ME19738 | 65 | 1 | 66.48 | 3.54E−16 |
| $T_3$ non-transgenic segregants of event-05-99 of ME19738 | 0 | 9 | | |

TABLE 18

Hypocotyl length in seedlings from ME20871

| Plants | Short Hypocotyl | Long Hypocotyl | Chi-Square | p-value |
|---|---|---|---|---|
| $T_2$ seedlings from event-03 of ME20871 | 27 | 8 | 10.03 | 1.54E−03 |
| $T_2$ non-transgenic segregants of event-03 of ME20871 | 0 | 4 | | |
| $T_3$ seedlings from event-03-99 of ME20871 | 51 | 10 | 12.35 | 4.41E−04 |
| $T_3$ non-transgenic segregants of event-03-99 of ME20871 | 0 | 3 | | |
| $T_2$ seedlings from event-05 of ME20871 | 32 | 0 | 40.00 | 2.54E−10 |
| $T_2$ non-transgenic segregants of event-05 of ME20871 | 0 | 8 | | |
| $T_3$ seedlings from event-05-99 of ME20871 | 61 | 0 | 68.52 | 1.26E−16 |
| $T_3$ non-transgenic segregants of event-05-99 of ME20871 | 1 | 13 | | |
| $T_2$ seedlings from event-10 of ME20871 | 26 | 0 | 27.24 | 1.80E−07 |
| $T_2$ non-transgenic segregants of event-10 of ME20871 | 1 | 6 | | |
| $T_3$ seedlings from event-10-99 of ME20871 | 52 | 1 | 48.91 | 2.68E−12 |
| $T_3$ non-transgenic segregants of event-10-99 of ME20871 | 1 | 9 | | |

TABLE 19

Hypocotyl length in seedlings from ME21199

| Plants | Short Hypocotyl | Long Hypocotyl | Chi-Square | p-value |
|---|---|---|---|---|
| $T_2$ seedlings from event-01 of ME21199 | 29 | 0 | 29.83 | 4.72E−08 |

TABLE 19-continued

Hypocotyl length in seedlings from ME21199

| Plants | Short Hypocotyl | Long Hypocotyl | Chi-Square | p-value |
|---|---|---|---|---|
| $T_2$ non-transgenic segregants of event-01 of ME21199 | 1 | 6 | | |
| $T_3$ seedlings from event-01-99 of ME21199 | 62 | 0 | 78.00 | 1.03E−18 |
| $T_3$ non-transgenic segregants of event-01-99 of ME21199 | 0 | 16 | | |
| $T_2$ seedlings from event-03 of ME21199 | 19 | 0 | 9.44 | 2.12E−03 |
| $T_2$ non-transgenic segregants of event-03 of ME21199 | 7 | 5 | | |
| $T_3$ seedlings from event-03-99 of ME21199 | 68 | 0 | 55.03 | 1.19E−13 |
| $T_3$ non-transgenic segregants of event-03-99 of ME21199 | 3 | 8 | | |
| $T_2$ seedlings from event-05 of ME21199 | 26 | 0 | 20.41 | 6.26E−06 |
| $T_2$ non-transgenic segregants of event-05 of ME21199 | 4 | 7 | | |
| $T_3$ seedlings from event-05-99 of ME21199 | 31 | 1 | 17.88 | 2.35E−05 |
| $T_3$ non-transgenic segregants of event-05-99 of ME21199 | 5 | 7 | | |

TABLE 20

Hypocotyl length in seedlings from ME21508

| Plants | Short Hypocotyl | Long Hypocotyl | Chi-Square | p-value |
|---|---|---|---|---|
| $T_2$ seedlings from event-01 of ME21508 | 20 | 5 | 15.76 | 7.19E−05 |
| $T_2$ non-transgenic segregants of event-01 of ME21508 | 2 | 12 | | |
| $T_3$ seedlings from event-01-99 of ME21508 | 74 | 0 | 80.00 | 3.74E−19 |
| $T_3$ non-transgenic segregants of event-01-99 of ME21508 | 0 | 6 | | |
| $T_2$ seedlings from event-05 of ME21508 | 23 | 8 | 15.71 | 7.85E−05 |
| $T_2$ non-transgenic segregants of event-05 of ME21508 | 0 | 9 | | |
| $T_3$ seedlings from event-05-99 of ME21508 | 65 | 0 | 78.00 | 1.03E−18 |
| $T_3$ non-transgenic segregants of event-05-99 of ME21508 | 0 | 13 | | |

There were no observable or statistically significant differences between $T_2$ ME05268, ME06120, ME09503, ME10007, ME10852, ME11939, ME13456, ME15935, ME16594, ME16597, ME16630, ME17128, ME17578, ME18158, ME18314, ME19304, ME19738, ME20871, ME21199, and ME21508 plants and control plants in germination, onset of flowering, rosette area, fertility, and general morphology/architecture.

Example 5—Results for ME12006, ME12596, and ME12899 Events $T_2$ and $T_3$ seed from events −03, −02, and −03 of ME12006, $T_2$ and $T_3$ seed from events −08 and −09 of ME12596, and $T_2$ and $T_3$ seed from events −05 and −06 of ME12899 was grown under SD+EODFR conditions and evaluated for hypocotyl length as described in Example 3.

Seedlings from events −03, −02, and −03 of ME12006; events −08 and −09 of ME12596; and events −05 and −06 of ME12899 displayed a short hypocotyl under SD+EODFR conditions in both the $T_2$ and $T_3$ generations, and the transgene was linked to the short hypocotyl phenotype with a confidence level of $p<0.05$ (Tables 21-23).

TABLE 21

Hypocotyl length in seedlings from ME12006

| Plants | Short Hypocotyl | Long Hypocotyl | Chi-Square | p-value |
|---|---|---|---|---|
| $T_2$ seedlings from event-01 of ME12006 | 22 | 2 | 8.89 | 2.87E−03 |
| $T_2$ non-transgenic segregants of event-01 of ME12006 | 8 | 8 | | |
| $T_3$ seedlings from event-01-03 of ME12006 | 27 | 3 | 7.50 | 6.17E−03 |
| $T_3$ non-transgenic segregants of event-01-03 of ME12006 | 5 | 5 | | |
| $T_2$ seedlings from event-02 of ME12006 | 20 | 20 | 12.23 | 4.70E−04 |
| $T_2$ non-transgenic segregants of event-02 of ME12006 | 6 | 10 | | |
| $T_3$ seedlings from event-02-01 of ME12006 | 23 | 4 | 12.61 | 3.84E−04 |
| $T_3$ non-transgenic segregants of event-02-01 of ME12006 | 2 | 7 | | |
| $T_2$ seedlings from event-03 of ME12006 | 24 | 4 | 7.94 | 4.83E−03 |
| $T_2$ non-transgenic segregants of event-03 of ME12006 | 4 | 6 | | |
| $T_3$ seedlings from event-03-04 of ME12006 | 19 | 2 | 8.82 | 2.99E−03 |
| $T_3$ non-transgenic segregants of event-03-04 of ME12006 | 2 | 4 | | |

TABLE 22

Hypocotyl length in seedlings from ME12596

| Plants | Short Hypocotyl | Long Hypocotyl | Chi-Square | p-value |
|---|---|---|---|---|
| $T_2$ seedlings from event-08 of ME12596 | 22 | 4 | 18.75 | 1.487E−05 |
| $T_2$ non-transgenic segregants of event-08 of ME12596 | 2 | 12 | | |
| $T_3$ seedlings from event-08-01 of ME12596 | 18 | 4 | 10.21 | 1.40E−04 |
| $T_3$ non-transgenic segregants of event-08-01 of ME12596 | 4 | 10 | | |
| $T_2$ seedlings from event-09 of ME12596 | 21 | 5 | 8.12 | 4.39E−03 |
| $T_2$ non-transgenic segregants of event-09 of ME12596 | 5 | 9 | | |
| $T_3$ seedlings from event-09-01 of ME12596 | 20 | 4 | 5.08 | 2.42E−02 |
| $T_3$ non-transgenic segregants of event-09-01 of ME12596 | 8 | 8 | | |

TABLE 23

Hypocotyl length in seedlings from ME12899

| Plants | Short Hypocotyl | Long Hypocotyl | Chi-Square | p-value |
|---|---|---|---|---|
| $T_2$ seedlings from event-05 of ME12899 | 24 | 4 | 10.98 | 9.23E−04 |
| $T_2$ non-transgenic segregants of event-05 of ME12899 | 4 | 8 | | |
| $T_3$ seedlings from event-05-99 of ME12899 | 27 | 3 | 7.5 | 6.17E−03 |
| $T_3$ non-transgenic segregants of event-05-99 of ME12899 | 5 | 5 | | |
| $T_2$ seedlings from event-06 of ME12899 | 26 | 2 | 23.22 | 1.445E−06 |
| $T_2$ non-transgenic segregants of event-06 of ME12899 | 2 | 10 | | |
| $T_3$ seedlings from event-06-99 of ME12899 | 21 | 3 | 6.77 | 9.264E−03 |
| $T_3$ non-transgenic segregants of event-06-99 of ME12899 | 8 | 8 | | |

There were no observable or statistically significant differences between $T_2$ ME12006, ME12596, and ME12899 plants and control plants in germination, onset of flowering, rosette area, fertility, and general morphology/architecture.

Example 6—Results for ME18408 and ME19971 Events $T_2$ and $T_3$ seed from events −01, −02, and −03 of ME18408, and $T_2$ and $T_3$ seed from events −01, −02, −03, and −05 of ME19971 was grown under low light conditions and SD+EODFR conditions as described in Examples 2 and 3, respectively, and evaluated for hypocotyl length.

Seedlings from events −01, −02, and −03 of ME18408, and events −01, −02, −03, and −05 of ME19971 displayed a short hypocotyl under SD+EODFR conditions in both the $T_2$ and $T_3$ generations, and the transgene was linked to the short hypocotyl phenotype with a confidence level of $p<0.05$ (Tables 24 and 26). Seedlings from events −01, and −02 of ME18408, and events −01, −02, −03, and −05 of ME19971 displayed a short hypocotyl under SD+EODFR conditions in both the $T_2$ and $T_3$ generations, and the transgene was linked to the short hypocotyl phenotype with a confidence level of $p<0.05$ (Tables 25 and 27).

TABLE 24

Hypocotyl length in seedlings from ME18408 grown under low light conditions

| Plants | Short Hypocotyl | Long Hypocotyl | Chi-Square | p-value |
|---|---|---|---|---|
| $T_2$ seedlings from event-01 of ME18408 | 63 | 2 | 44.58 | 2.44E−11 |
| $T_2$ non-transgenic segregants of event-01 of ME18408 | 0 | 4 | | |
| $T_3$ seedlings from event-01-99 of ME18408 | 40 | 6 | 35.90 | 2.08E−09 |
| $T_3$ non-transgenic segregants of event-01-99 of ME18408 | 1 | 16 | | |
| $T_2$ seedlings from event-02 of ME18408 | 38 | 7 | 28.67 | 8.58E−08 |
| $T_2$ non-transgenic segregants of event-02 of ME18408 | 3 | 17 | | |
| $T_3$ seedlings from event-02-99 of ME18408 | 39 | 17 | 10.98 | 9.20E−04 |
| $T_3$ non-transgenic segregants of event-02-99 of ME18408 | 5 | 14 | | |
| $T_2$ seedlings from event-03 of ME18408 | 30 | 1 | 25.76 | 3.86E−07 |
| $T_2$ non-transgenic segregants of event-03 of ME18408 | 7 | 15 | | |
| $T_3$ seedlings from event-03-99 of ME18408 | 23 | 5 | 21.74 | 3.12E−06 |
| $T_3$ non-transgenic segregants of event-03-99 of ME18408 | 11 | 32 | | |

TABLE 25

Hypocotyl length in seedlings from ME18408 grown under SD + EODFR conditions

| Plants | Short Hypocotyl | Long Hypocotyl | Chi-Square | p-value |
|---|---|---|---|---|
| T$_2$ seedlings from event-01 of ME18408 | 22 | 5 | 6.18 | 1.29E−02 |
| T$_2$ non-transgenic segregants of event-01 of ME18408 | 5 | 7 | | |
| T$_3$ seedlings from event-01-99 of ME18408 | 19 | 8 | 10.71 | 1.06E−03 |
| T$_3$ non-transgenic segregants of event-01-99 of ME18408 | 1 | 9 | | |
| T$_2$ seedlings from event-02 of ME18408 | 25 | 5 | 4.44 | 3.50E−02 |
| T$_2$ non-transgenic segregants of event-02 of ME18408 | 5 | 5 | | |
| T$_3$ seedlings from event-02-99 of ME18408 | 22 | 3 | 6.8 | 9.13E−03 |
| T$_3$ non-transgenic segregants of event-02-99 of ME18408 | 7 | 7 | | |

TABLE 26

Hypocotyl length in seedlings from ME19971 grown under low light conditions

| Plants | Short Hypocotyl | Long Hypocotyl | Chi-Square | p-value |
|---|---|---|---|---|
| T$_2$ seedlings from event-01 of ME19971 | 8 | 0 | 18.00 | 2.21E−05 |
| T$_2$ non-transgenic segregants of event-01 of ME19971 | 0 | 10 | | |
| T$_3$ seedlings from event-01-99 of ME19971 | 37 | 0 | 61.00 | 5.71E−15 |
| T$_3$ non-transgenic segregants of event-01-99 of ME19971 | 0 | 24 | | |
| T$_2$ seedlings from event-02 of ME19971 | 16 | 2 | 19.64 | 9.37E−06 |
| T$_2$ non-transgenic segregants of event-02 of ME19971 | 0 | 9 | | |
| T$_3$ seedlings from event-02-99 of ME19971 | 36 | 0 | 29.19 | 6.56E−08 |
| T$_3$ non-transgenic segregants of event-02-99 of ME19971 | 1 | 3 | | |
| T$_2$ seedlings from event-03 of ME19971 | 14 | 1 | 19.08 | 1.25E−05 |
| T$_2$ non-transgenic segregants of event-03 of ME19971 | 0 | 8 | | |
| T$_3$ seedlings from event-03-99 of ME19971 | 34 | 0 | 46.00 | 1.18E−11 |
| T$_3$ non-transgenic segregants of event-03-99 of ME19971 | 0 | 12 | | |
| T$_2$ seedlings from event-05 of ME19971 | 26 | 0 | 29.00 | 7.24E−08 |
| T$_2$ non-transgenic segregants of event-05 of ME19971 | 0 | 3 | | |
| T$_3$ seedlings from event-05-99 of ME19971 | 42 | 0 | 47.94 | 4.39E−12 |
| T$_3$ non-transgenic segregants of event-05-99 of ME19971 | 3 | 16 | | |

TABLE 27

Hypocotyl length in seedlings from ME19971 grown under SD + EODFR conditions

| Plants | Short Hypocotyl | Long Hypocotyl | Chi-Square | p-value |
|---|---|---|---|---|
| T$_2$ seedlings from event-01 of ME19971 | 30 | 2 | 30.00 | 4.32E−08 |
| T$_2$ non-transgenic segregants of event-01 of ME19971 | 0 | 8 | | |
| T$_3$ seedlings from event-01-04 of ME19971 | 22 | 0 | 32.00 | 1.542E−08 |
| T$_3$ non-transgenic segregants of event-01-04 of ME19971 | 0 | 10 | | |
| T$_2$ seedlings from event-02 of ME19971 | 24 | 4 | 17.60 | 2.721E−05 |
| T$_2$ non-transgenic segregants of event-02 of ME19971 | 2 | 10 | | |
| T$_3$ seedlings from event-02-04 of ME19971 | 22 | 6 | 16.16 | 5.811E−05 |
| T$_3$ non-transgenic segregants of event-02-04 of ME19971 | 0 | 8 | | |
| T$_2$ seedlings from event-03 of ME19971 | 28 | 0 | 40.00 | 2.54E−10 |
| T$_2$ non-transgenic segregants of event-03 of ME19971 | 0 | 12 | | |
| T$_3$ seedlings from event-03-06 of ME19971 | 24 | 0 | 17.49 | 2.895E−05 |
| T$_3$ non-transgenic segregants of event-03-06 of ME19971 | 4 | 6 | | |
| T$_2$ seedlings from event-05 of ME19971 | 24 | 2 | 24.35 | 8.034E−07 |
| T$_2$ non-transgenic segregants of event-05 of ME19971 | 2 | 12 | | |
| T$_3$ seedlings from event-05-02 of ME19971 | 25 | 4 | 6.13 | 1.33E−02 |
| T$_3$ non-transgenic segregants of event-05-02 of ME19971 | 3 | 4 | | |

There were no observable or statistically significant differences between T$_2$ ME18408 and ME19971 plants and control plants in germination, onset of flowering, rosette area, fertility, and general morphology/architecture.

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO:3, SEQ ID NO:70, SEQ ID NO:129, SEQ ID NO:317, SEQ ID NO:337, SEQ ID NO:456, SEQ ID NO:538, SEQ ID NO:570, SEQ ID NO:606, SEQ ID NO:634, SEQ ID NO:644, SEQ ID NO:850, SEQ ID NO:907, SEQ ID NO:953, SEQ ID NO:1024, SEQ ID NO:1047, SEQ ID NO:1151, SEQ ID NO:1277, SEQ ID NO:1347, SEQ ID NO:1457, SEQ ID NO:1497, SEQ ID NO:1540, SEQ ID NO:1587, SEQ ID NO:1630, and SEQ ID NO:1635 are shown in FIGS. 1-24, respectively.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO:3.

The procedure above was repeated and an HMM was generated for each group of sequences shown in FIGS. 2-24, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

Example 9—Identification of Transgenic Plants Exhibiting a Red Light-Specific Short Hypocotyl Phenotype Wild type and transgenic seeds were surface-sterilized, plated on solid 0.5× MS medium containing 5 g/L sucrose, 0.5 g/L MES, 7 g/L Agar (adjusted to pH 5.7), and stratified at 4° C. in the dark for three to four days. After stratification, plates were acclimated to room temperature, wrapped in micropore tape, and exposed to continuous white light having a fluence rate of ~60 mmol/m²/s PAR, and a red:far-red ratio (R:FR) of ~5.3. After 24 hours, plates from wild type controls and transgenic lines were moved to one of three light conditions: (1) white light conditions at a lower fluence rate (~15 mmol/m²/s PAR, R:FR=~5.0), (2) red-light conditions (SNAP-LITE™ Red/Far-Red light box (Quantum Devices), at ~15 μmol/m²/s PAR, R:FR=~80), or (3) far-red conditions (SNAP-LITE™ Red/Far-red light box, at ~15 μmol/m²/s PAR, R:FR=~0.10). Seedlings were maintained under continuous light conditions for five days. The hypocotyls of individual seedlings were determined to be "tall" or "short" based on qualitative observation.

A hypocotyl having a length similar to the hypocotyl length typically exhibited by wild-type *Arabidopsis* seedlings grown under the same light conditions was considered a tall hypocotyl. A hypocotyl having reduced length relative to the hypocotyl length typically exhibited by wild-type *Arabidopsis* seedlings grown under the same light conditions was considered a short hypocotyl. Transgenic seedlings from ten Ceres SEEDLINE ID nos. failed to germinate, or germinated poorly, under continuous red light (ME10007, ME10852, ME11961, ME15935, ME17128, ME18158, ME18314, ME19304, ME20871, and ME21508).

Transgenic seedlings from eight Ceres SEEDLINE ID nos. (ME11939, ME16630, ME19971, ME05268, ME13456, ME13629, ME16597, and ME17578) exhibited short hypocotyls when grown under continuous red light. Transgenic seedlings from three of these (ME11939, ME16630, and ME19971) exhibited tall hypocotyls under continuous far-red light exposure, indicating that the short hypocotyl phenotype was red-light specific in these three seed lines. In contrast, the other five seedlings (ME05268, ME13456, ME13629, ME16597, and ME17578) exhibited a short-hypocotyl phenotype when grown under far-red light, indicating that the short-hypocotyl phenotype exhibited by ME05268, ME13456, ME13629, ME16597, and ME17578 was not red-light specific (See, e.g., Parks and Spaulding, Proc. Natl. Acad. Sci., 96: 14142-14146 (1999) describing different molecular mechanisms for suppression of hypocotyl elongation under continuous red and far-red light conditions).

A similar red light-dependent short hypocotyl phenotype has been observed in transgenic plants overexpressing the photochemically and biologically functional photoreceptor, Phytochrome B (Phy B) (Wagner et al., Plant Cell, 3: 1275-1288 (1991)). Phy B null mutants exhibit a long hypocotyl seedling phenotype and increased plant height (Kebrom and Brutnell, *J Exp. Bot.*, 58: 3079-3089 (2007)). These observations suggest that transgene modulation of light response pathways can produce plants exhibiting either increased grain yield, or increased biomass. See Pennell et al., U.S. Pat. App. Ser. No. 61/097,789, "Transgenic Plants Having Increased Biomass," filed Sep. 17, 2008, incorporated by reference herein. Thus, transgenic plants comprising nucleic acid sequences that down-regulate expression of a At5g14370 polypeptide (SEQ ID NO: 456) (FIG. 6), a At1g13360 polypeptide (SEQ ID NO: 953) (FIG. 11), a At2g35940 polypeptide (SEQ ID NO: 1540) (FIG. 21), and sequences identified as functional homologs of these sequences (see FIGS. 6, 11, 21 and sequence listing) are predicted to exhibit a tall hypocotyl phenotype under conditions of normal or low light.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12385057B2). An electronic copy of the sequence listing will also be available from the USPTO upon request and payment of the fee set forth in 37 CFR 1.19(b)(3).

What is claimed is:

1. A method of modulating a trait in a dicotyledonous plant, said method comprising
   introducing into a dicotyledonous plant cell an exogenous nucleic acid, said exogenous nucleic acid comprising a nucleotide sequence encoding a polypeptide having 95 percent or greater sequence identity to the amino acid sequence of SEQ ID NO:1635, wherein the nucleotide sequence is operably linked to a heterologous regulatory region;
   producing a dicotyledonous plant from said dicotyledonous plant cell; and
   selecting a dicotyledonous plant for increased low light tolerance or SD+EODFR tolerance as compared to a control plant that does not comprise said nucleic acid.

2. A dicotyledonous plant cell comprising an exogenous nucleic acid, said exogenous nucleic acid comprising a nucleotide sequence encoding a polypeptide having 95 percent or greater sequence identity to the amino acid sequence of SEQ ID NO:1635;
   wherein the nucleotide sequence is operably linked to a heterologous regulatory region;
   wherein a dicotyledonous plant produced from said cell has increased low light tolerance or SD+EODFR tolerance as compared to a control plant that does not comprise said nucleic acid.

3. A dicotyledonous plant comprising an exogenous nucleic acid, said exogenous nucleic acid comprising:
   a nucleotide sequence encoding a polypeptide having 95 percent or greater sequence identity to the amino acid of SEQ ID NO: 1635;
   wherein the nucleotide sequence is operably linked to a heterologous regulatory region;
   wherein the dicotyledonous plant has increased low light tolerance or SD+EODFR tolerance as compared to a control plant that does not comprise said nucleic acid.

4. The method of claim 1, wherein said polypeptide has 97 percent or greater sequence identity to the amino acid sequence of SEQ ID NO:1635.

5. The method of claim 1, wherein said polypeptide sequence comprises the amino sequence of SEQ ID NO:1635.

6. The method of claim 1, wherein said nucleotide sequence comprises the polynucleotide sequence of SEQ ID NO:1633 or SEQ ID NO:1634.

7. The dicotyledonous plant of claim 3, wherein said polypeptide has 97 percent or greater sequence identity to the amino acid sequence of SEQ ID NO: 1635.

8. The dicotyledonous plant of claim 3, wherein said polypeptide sequence comprises the amino acid sequence of SEQ ID NO:1635.

9. The dicotyledonous plant of claim 3, wherein said nucleotide sequence comprises the polynucleotide sequence of SEQ ID NO:1633 or SEQ ID NO:1634.

10. The dicotyledonous plant of claim 3, wherein the plant is selected for having increased low light tolerance.

11. The dicotyledonous plant of claim 3, wherein the plant is selected for having increased SD+EODFR tolerance.

* * * * *